(12) United States Patent
Shelton, IV et al.

(10) Patent No.: US 10,973,520 B2
(45) Date of Patent: Apr. 13, 2021

(54) SURGICAL STAPLE CARTRIDGE WITH FIRING MEMBER DRIVEN CAMMING ASSEMBLY THAT HAS AN ONBOARD TISSUE CUTTING FEATURE

(71) Applicant: Ethicon LLC, Guaynabo, PR (US)

(72) Inventors: Frederick E. Shelton, IV, Hillsboro, OH (US); Jason L. Harris, Lebanon, OH (US); Gregory J. Bakos, Mason, OH (US)

(73) Assignee: Ethicon LLC, Guaynabo, PR (US)

(*) Notice: Subject to any disclaimer, the term of this patent is extended or adjusted under 35 U.S.C. 154(b) by 117 days.

(21) Appl. No.: 16/281,660

(22) Filed: Feb. 21, 2019

(65) Prior Publication Data

US 2019/0298351 A1 Oct. 3, 2019

Related U.S. Application Data

(60) Provisional application No. 62/807,310, filed on Feb. 19, 2019, provisional application No. 62/807,319, (Continued)

(51) Int. Cl.
*A61B 17/115* (2006.01)
*A61B 17/072* (2006.01)
(Continued)

(52) U.S. Cl.
CPC ............... *A61B 17/07207* (2013.01); *A61B 2017/00017* (2013.01); *A61B 2017/0046* (2013.01);
(Continued)

(58) Field of Classification Search
CPC .... A61B 17/07207; A61B 2017/07278; A61B 2017/07285
See application file for complete search history.

(56) References Cited

U.S. PATENT DOCUMENTS 3,082,426 A 3/1963 Miles
3,503,396 A 3/1970 Pierie et al.
(Continued)

FOREIGN PATENT DOCUMENTS

AU 2015201140 A1 3/2015
CA 2795323 A1 5/2014
(Continued)

OTHER PUBLICATIONS

US 10,504,709 B2, 12/2019, Karancsi et al. (withdrawn)
(Continued)

*Primary Examiner* — Andrew M Tecco
*Assistant Examiner* — Eyamindae C Jallow

(57) ABSTRACT

A surgical staple cartridge configured for use with a surgical stapler including a firing member that is configured to progressively axially engage an anvil and channel of the stapler. The cartridge includes a cam assembly that is configured to operably interface with the firing member such that axial movement of the firing member in a distal direction drives the cam assembly from a starting position to an ending position. A cutting member is movably supported by the cam assembly between a deployed position wherein at least a portion of the cutting member extends above the deck surface and a recessed position wherein the cutting member is below the deck surface.

21 Claims, 92 Drawing Sheets

Related U.S. Application Data filed on Feb. 19, 2019, provisional application No. 62/807,309, filed on Feb. 19, 2019, provisional application No. 62/650,887, filed on Mar. 30, 2018, provisional application No. 62/649,302, filed on Mar. 28, 2018, provisional application No. 62/649,294, filed on Mar. 28, 2018, provisional application No. 62/649,300, filed on Mar. 28, 2018, provisional application No. 62/649,309, filed on Mar. 28, 2018, provisional application No. 62/649,310, filed on Mar. 28, 2018, provisional application No. 62/649,291, filed on Mar. 28, 2018, provisional application No. 62/649,296, filed on Mar. 28, 2018, provisional application No. 62/649,333, filed on Mar. 28, 2018, provisional application No. 62/649,327, filed on Mar. 28, 2018, provisional application No. 62/649,315, filed on Mar. 28, 2018, provisional application No. 62/649,313, filed on Mar. 28, 2018, provisional application No. 62/649,320, filed on Mar. 28, 2018, provisional application No. 62/649,307, filed on Mar. 28, 2018, provisional application No. 62/649,323, filed on Mar. 28, 2018.

(51) Int. Cl.
A61B 17/00 (2006.01)
A61B 17/29 (2006.01)
A61B 90/00 (2016.01)

(52) U.S. Cl.
CPC .............. *A61B 2017/00398* (2013.01); *A61B 2017/00477* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2903* (2013.01); *A61B 2017/2927* (2013.01); *A61B 2017/2929* (2013.01); *A61B 2017/2933* (2013.01); *A61B 2017/2939* (2013.01); *A61B 2017/2946* (2013.01); *A61B 2090/034* (2016.02); *A61B 2090/037* (2016.02); *A61B 2090/0801* (2016.02); *A61B 2090/0814* (2016.02)

(56) References Cited

U.S. PATENT DOCUMENTS

| | | |
|---|---|---|
| 3,584,628 A | 6/1971 | Green |
| 3,759,017 A | 9/1973 | Young |
| 4,448,193 A | 5/1984 | Ivanov |
| 4,523,695 A | 6/1985 | Braun et al. |
| 4,608,160 A | 8/1986 | Zoch |
| 4,701,193 A | 10/1987 | Robertson et al. |
| 4,735,603 A | 4/1988 | Goodson et al. |
| 4,788,977 A | 12/1988 | Farin et al. |
| 5,042,460 A | 8/1991 | Sakurai et al. |
| 5,084,057 A | 1/1992 | Green et al. |
| 5,100,402 A | 3/1992 | Fan |
| 5,151,102 A | 9/1992 | Kamiyama et al. |
| 5,156,315 A | 10/1992 | Green et al. |
| 5,158,585 A | 10/1992 | Saho et al. |
| 5,197,962 A | 3/1993 | Sansom et al. |
| 5,242,474 A | 9/1993 | Herbst et al. |
| 5,253,793 A | 10/1993 | Green et al. |
| RE34,519 E | 1/1994 | Fox et al. |
| 5,318,516 A | 6/1994 | Cosmescu |
| 5,322,055 A | 6/1994 | Davison et al. |
| 5,342,349 A | 8/1994 | Kaufman |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,417,699 A | 5/1995 | Klein et al. |
| 5,439,468 A | 8/1995 | Schulze et al. |
| 5,445,304 A | 8/1995 | Plyley et al. |
| 5,465,895 A | 11/1995 | Knodel et al. |
| 5,467,911 A | 11/1995 | Tsuruta et al. |
| 5,474,566 A | 12/1995 | Alesi et al. |
| 5,496,315 A | 3/1996 | Weaver et al. |
| 5,503,320 A | 4/1996 | Webster et al. |
| 5,531,743 A | 7/1996 | Nettekoven et al. |
| 5,545,148 A | 8/1996 | Wurster |
| 5,610,379 A | 3/1997 | Muz et al. |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,725,536 A * | 3/1998 | Oberlin ............ A61B 17/07207 606/139 |
| 5,725,542 A | 3/1998 | Yoon |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A * | 5/1998 | Bolanos ............ A61B 17/07207 227/176.1 |
| 5,762,255 A * | 6/1998 | Chrisman ........ A61B 17/07207 227/175.2 |
| 5,766,186 A | 6/1998 | Faraz et al. |
| 5,769,791 A | 6/1998 | Benaron et al. |
| 5,797,537 A * | 8/1998 | Oberlin ............ A61B 17/07207 227/176.1 |
| D399,561 S | 10/1998 | Ellingson |
| 5,817,093 A | 10/1998 | Williamson, IV et al. |
| 5,820,009 A * | 10/1998 | Melling ........... A61B 17/07207 227/176.1 |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A * | 3/1999 | Bittner ............. A61B 17/07207 227/175.4 |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,997,528 A | 12/1999 | Bisch et al. |
| 6,010,054 A * | 1/2000 | Johnson ........... A61B 17/07207 227/176.1 |
| 6,030,437 A | 2/2000 | Gourrier et al. |
| 6,036,637 A | 3/2000 | Kudo |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,155,473 A | 12/2000 | Tompkins et al. |
| 6,214,000 B1 | 4/2001 | Fleenor et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,443,973 B1 | 9/2002 | Whitman |
| 6,461,352 B2 | 10/2002 | Morgan et al. |

(56) References Cited

U.S. PATENT DOCUMENTS

| | | |
|---|---|---|
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,773,444 B2 | 8/2004 | Messerly |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,852,219 B2 | 2/2005 | Hammond |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,118,564 B2 | 10/2006 | Ritchie et al. |
| 7,121,460 B1 | 10/2006 | Parsons et al. |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 * | 10/2007 | Green ............. A61B 17/07207 227/176.1 |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,575,144 B2 | 8/2009 | Ortiz et al. |
| 7,621,192 B2 | 11/2009 | Conti et al. |
| 7,621,898 B2 | 11/2009 | Lalomia et al. |
| 7,637,410 B2 | 12/2009 | Marczyk |
| 7,641,092 B2 | 1/2010 | Kruszynski et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,736,357 B2 | 6/2010 | Lee, Jr. et al. |
| 7,742,176 B2 | 6/2010 | Braunecker et al. |
| 7,753,245 B2 | 7/2010 | Boudreaux et al. |
| 7,766,905 B2 | 8/2010 | Paterson et al. |
| 7,770,773 B2 | 8/2010 | Whitman et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,818,041 B2 | 10/2010 | Kim et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,862,560 B2 | 1/2011 | Marion |
| 7,862,579 B2 | 1/2011 | Ortiz et al. |
| 7,892,337 B2 | 2/2011 | Palmerton et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,955,322 B2 | 6/2011 | Devengenzo et al. |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,043,560 B2 | 10/2011 | Okumoto et al. |
| 8,054,184 B2 | 11/2011 | Cline et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,096,459 B2 | 1/2012 | Ortiz et al. |
| 8,120,301 B2 | 2/2012 | Goldberg et al. |
| 8,123,764 B2 | 2/2012 | Meade et al. |
| 8,131,565 B2 | 3/2012 | Dicks et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,210,411 B2 | 7/2012 | Yates et al. |
| 8,214,007 B2 | 7/2012 | Baker et al. |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,888 B2 | 10/2012 | Whitman |

(56) References Cited

U.S. PATENT DOCUMENTS

| | | |
|---|---|---|
| 8,308,040 B2 | 11/2012 | Huang et al. |
| 8,321,581 B2 | 11/2012 | Katis et al. |
| 8,328,065 B2 | 12/2012 | Shah |
| 8,335,590 B2 | 12/2012 | Costa et al. |
| 8,346,392 B2 | 1/2013 | Walser et al. |
| 8,364,222 B2 | 1/2013 | Cook et al. |
| 8,365,975 B1 * | 2/2013 | Manoux ............ A61B 17/07207 227/180.1 |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,365 B2 | 8/2013 | Wiener et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,573,459 B2 | 11/2013 | Smith et al. |
| 8,573,465 B2 | 11/2013 | Shelton, IV |
| 8,591,536 B2 | 11/2013 | Robertson |
| 8,595,607 B2 | 11/2013 | Nekoomaram et al. |
| 8,596,513 B2 | 12/2013 | Olson et al. |
| 8,608,044 B2 | 12/2013 | Hueil et al. |
| 8,608,045 B2 | 12/2013 | Smith et al. |
| 8,616,431 B2 * | 12/2013 | Timm ............... A61B 17/00234 227/178.1 |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,632,525 B2 | 1/2014 | Kerr et al. |
| 8,652,086 B2 | 2/2014 | Gerg et al. |
| 8,652,128 B2 | 2/2014 | Ward |
| 8,657,176 B2 | 2/2014 | Shelton, IV et al. |
| 8,657,177 B2 * | 2/2014 | Scirica ............. A61B 17/07207 227/180.1 |
| 8,663,220 B2 | 3/2014 | Wiener et al. |
| 8,666,544 B2 | 3/2014 | Moll et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,701,962 B2 | 4/2014 | Kostrzewski |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,986,302 B2 | 3/2015 | Aldridge et al. |
| 8,989,903 B2 | 3/2015 | Weir et al. |
| 8,992,565 B2 | 3/2015 | Brisson et al. |
| 8,998,797 B2 | 4/2015 | Omori |
| 9,002,518 B2 | 4/2015 | Manzo et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |

(56) References Cited

U.S. PATENT DOCUMENTS

| | | |
|---|---|---|
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,114,494 B1 | 8/2015 | Mah |
| 9,116,597 B1 | 8/2015 | Gulasky |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,149,322 B2 | 10/2015 | Knowlton |
| 9,161,803 B2 | 10/2015 | Yates et al. |
| 9,168,054 B2 | 10/2015 | Turner et al. |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,226,689 B2 | 1/2016 | Jacobsen et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,241,728 B2 | 1/2016 | Price et al. |
| 9,241,731 B2 | 1/2016 | Boudreaux et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,736 B2 | 9/2016 | Olson |
| 9,445,764 B2 | 9/2016 | Gross et al. |
| 9,450,701 B2 | 9/2016 | Do et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,566,708 B2 | 2/2017 | Kurnianto |
| 9,572,592 B2 | 2/2017 | Price et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,808 B2 | 4/2017 | Beller et al. |
| 9,629,560 B2 | 4/2017 | Joseph |
| 9,629,623 B2 | 4/2017 | Lytle, IV et al. |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,675,264 B2 | 6/2017 | Acquista et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,706,993 B2 | 7/2017 | Hessler et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |

(56) References Cited

U.S. PATENT DOCUMENTS

| | | |
|---|---|---|
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,522 B2 | 9/2017 | Scheib et al. |
| 9,750,523 B2 | 9/2017 | Tsubuku |
| 9,753,135 B2 | 9/2017 | Bosch |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 * | 9/2017 | Ogilvie .................. A61F 5/024 |
| 9,764,164 B2 | 9/2017 | Wiener et al. |
| 9,770,541 B2 | 9/2017 | Carr et al. |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,914 B2 | 2/2018 | Martin et al. |
| 9,888,919 B2 | 2/2018 | Leimbach et al. |
| 9,888,921 B2 | 2/2018 | Williams et al. |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,778 B2 | 5/2018 | Ohline et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| D826,405 S | 8/2018 | Shelton, IV et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,054,441 B2 | 8/2018 | Schorr et al. |
| 10,076,326 B2 | 9/2018 | Yates et al. |
| 10,080,618 B2 | 9/2018 | Marshall et al. |
| 10,085,748 B2 | 10/2018 | Morgan et al. |
| 10,085,749 B2 | 10/2018 | Cappola et al. |
| 10,095,942 B2 | 10/2018 | Mentese et al. |

(56) References Cited

U.S. PATENT DOCUMENTS

| | | |
|---|---|---|
| 10,098,527 B2 | 10/2018 | Weisenburgh, II et al. |
| 10,098,635 B2 | 10/2018 | Burbank |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,949 B2 | 11/2018 | Felder et al. |
| 10,143,526 B2 | 12/2018 | Walker et al. |
| 10,143,948 B2 | 12/2018 | Bonifas et al. |
| 10,149,680 B2 | 12/2018 | Parihar et al. |
| 10,152,789 B2 | 12/2018 | Carnes et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,194,907 B2 | 2/2019 | Marczyk et al. |
| 10,194,913 B2 | 2/2019 | Nalagatla et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,285,698 B2 | 5/2019 | Cappola et al. |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,299,792 B2 | 5/2019 | Huitema et al. |
| 10,299,870 B2 | 5/2019 | Connolly et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,227 B2 | 7/2019 | Heard |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,433,837 B2 | 10/2019 | Worthington et al. |
| 10,433,844 B2 | 10/2019 | Shelton, IV et al. |

(56) References Cited

U.S. PATENT DOCUMENTS

| | | |
|---|---|---|
| 10,433,849 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 * | 4/2020 | Wellman .......... A61B 17/07207 |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,414 B2 | 4/2020 | Shelton, IV et al. |
| 10,617,484 B2 | 4/2020 | Kilroy et al. |
| 10,624,635 B2 | 4/2020 | Harris et al. |
| 10,624,691 B2 | 4/2020 | Wiener et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,709,446 B2 | 7/2020 | Harris et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,729,458 B2 | 8/2020 | Stoddard et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,651 B2 | 9/2020 | Shelton, IV et al. |
| 10,772,688 B2 | 9/2020 | Peine et al. |
| 10,779,818 B2 | 9/2020 | Zemlok et al. |

(56) References Cited

U.S. PATENT DOCUMENTS

| | | |
|---|---|---|
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,327 B2 | 9/2020 | Anderson et al. |
| 10,792,118 B2 | 10/2020 | Prpa et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 2002/0049551 A1 | 4/2002 | Friedman et al. |
| 2003/0093503 A1 | 5/2003 | Yamaki et al. |
| 2003/0223877 A1 | 12/2003 | Anstine et al. |
| 2004/0078236 A1 | 4/2004 | Stoodley et al. |
| 2004/0199180 A1* | 10/2004 | Knodel ............ A61B 17/07207 606/139 |
| 2004/0199659 A1 | 10/2004 | Ishikawa et al. |
| 2004/0243148 A1 | 12/2004 | Wasielewski |
| 2004/0243435 A1 | 12/2004 | Williams |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0149001 A1 | 7/2005 | Uchikubo et al. |
| 2005/0149356 A1 | 7/2005 | Cyr et al. |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0116908 A1 | 6/2006 | Dew et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0175955 A1 | 8/2007 | Shelton et al. |
| 2007/0225556 A1 | 9/2007 | Ortiz et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0255413 A1 | 10/2008 | Zemlok et al. |
| 2008/0262654 A1 | 10/2008 | Omori et al. |
| 2008/0281678 A1 | 11/2008 | Keuls et al. |
| 2008/0296346 A1 | 12/2008 | Shelton, IV et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0070417 A1 | 3/2010 | Flynn et al. |
| 2010/0132334 A1 | 6/2010 | Duclos et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0256634 A1* | 10/2010 | Voegele ............ A61B 17/07207 606/45 |
| 2010/0292535 A1 | 11/2010 | Paskar |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0237883 A1 | 9/2011 | Chun |
| 2011/0306840 A1 | 12/2011 | Allen et al. |
| 2012/0116381 A1 | 5/2012 | Houser et al. |
| 2012/0130217 A1 | 5/2012 | Kauphusman et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0105552 A1* | 5/2013 | Weir .................. A61B 34/37 227/180.1 |
| 2013/0116218 A1 | 5/2013 | Kaplan et al. |
| 2013/0123822 A1* | 5/2013 | Wellman ............ A61B 17/072 606/170 |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331875 A1 | 12/2013 | Ross et al. |
| 2014/0001234 A1 | 1/2014 | Shelton, IV et al. |
| 2014/0006132 A1 | 1/2014 | Barker |
| 2014/0006943 A1 | 1/2014 | Robbins et al. |
| 2014/0029411 A1 | 1/2014 | Nayak et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108983 A1 | 4/2014 | William R et al. |
| 2014/0183244 A1* | 7/2014 | Duque ............ A61B 17/07207 227/180.1 |
| 2014/0187856 A1 | 7/2014 | Holoien et al. |
| 2014/0204190 A1 | 7/2014 | Rosenblatt, III et al. |
| 2014/0246475 A1 | 9/2014 | Hall et al. |
| 2014/0249557 A1 | 9/2014 | Koch et al. |
| 2014/0252064 A1* | 9/2014 | Mozdzierz ............ A61B 17/068 227/176.1 |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |

(56) References Cited

U.S. PATENT DOCUMENTS

| | | |
|---|---|---|
| 2015/0199109 A1 | 7/2015 | Lee |
| 2015/0209030 A1* | 7/2015 | Kostrzewski .... A61B 17/07207 227/177.1 |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0058450 A1* | 3/2016 | Shelton, IV ..... A61B 17/07207 227/176.1 |
| 2016/0066913 A1 | 3/2016 | Swayze et al. |
| 2016/0106934 A1 | 4/2016 | Hiraga et al. |
| 2016/0180045 A1 | 6/2016 | Syed |
| 2016/0192960 A1 | 7/2016 | Bueno et al. |
| 2016/0206202 A1 | 7/2016 | Frangioni |
| 2016/0235303 A1 | 8/2016 | Fleming et al. |
| 2016/0249910 A1 | 9/2016 | Shelton, IV et al. |
| 2016/0256160 A1 | 9/2016 | Shelton, IV et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342916 A1 | 11/2016 | Arceneaux et al. |
| 2016/0350490 A1 | 12/2016 | Martinez et al. |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196637 A1 | 7/2017 | Shelton, IV et al. |
| 2017/0202591 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0249432 A1 | 8/2017 | Grantcharov |
| 2017/0262604 A1 | 9/2017 | Francois |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0290586 A1 | 10/2017 | Wellman |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303419 A1 | 10/2017 | Collins et al. |
| 2017/0303984 A1 | 10/2017 | Malackowski |
| 2017/0304020 A1 | 10/2017 | Ng et al. |
| 2017/0325813 A1 | 11/2017 | Aranyi et al. |
| 2017/0360438 A1 | 12/2017 | Cappola |
| 2017/0360439 A1 | 12/2017 | Chen et al. |
| 2017/0360499 A1 | 12/2017 | Greep et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2018/0008359 A1 | 1/2018 | Randle |
| 2018/0014848 A1 | 1/2018 | Messerly et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168621 A1 | 6/2018 | Shelton, IV et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0199995 A1 | 7/2018 | Odermatt et al. |
| 2018/0207307 A1 | 7/2018 | Schwartz et al. |
| 2018/0214025 A1 | 8/2018 | Homyk et al. |
| 2018/0221598 A1 | 8/2018 | Silver |

(56) References Cited

U.S. PATENT DOCUMENTS

| | | |
|---|---|---|
| 2018/0228557 A1 | 8/2018 | Darisse et al. |
| 2018/0242967 A1 | 8/2018 | Meade |
| 2018/0250084 A1 | 9/2018 | Kopp et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271603 A1 | 9/2018 | Nir et al. |
| 2018/0296286 A1 | 10/2018 | Peine et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0317826 A1 | 11/2018 | Muhsin et al. |
| 2018/0317915 A1 | 11/2018 | McDonald, II |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0029712 A1 | 1/2019 | Stoddard et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069962 A1 | 3/2019 | Tabandeh et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0090969 A1 | 3/2019 | Jarc et al. |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125381 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |

(56) References Cited

U.S. PATENT DOCUMENTS

| | | |
|---|---|---|
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0254759 A1 | 8/2019 | Azizian |
| 2019/0269476 A1 | 9/2019 | Bowling et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0314015 A1 | 10/2019 | Shelton, IV et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0100830 A1 | 4/2020 | Henderson et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-2007137304 A2 | 11/2007 |

(56) References Cited

FOREIGN PATENT DOCUMENTS

| | | |
|---|---|---|
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016206015 A1 | 12/2016 |
| WO | WO-2017011382 A1 | 1/2017 |
| WO | WO-2017011646 A1 | 1/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Slocinski et al., "Distance measure for impedance spectra for quantified evaluations," Lecture Notes on Impedance Spectroscopy, vol. 3, Taylor and Francis Group (Jul. 2012)—Book Not Attached.
Zoccali, Bruno, "A Method for Approximating Component Temperatures at Altitude Conditions Based on CFD Analysis at Sea Level Conditions," (white paper), www.tdmginc.com, Dec. 6, 2018 (9 pages).
Flores et al., "Large-scale Offloading in the Internet of Things," 2017 IEEE International Conference on Pervasive Computing and Communications Workshops (PERCOM Workshops), IEEE, pp. 479-484, Mar. 13, 2017.
Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.
Yuyi Mao et al., "A Survey on Mobile Edge Computing: The Communication Perspective," IEEE Communications Surveys & Tutorials, pp. 2322-2358, Jun. 13, 2017.
Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey, " Artificial Intelligence in Medicine, vol. 39, No. 1, pp. 1-24 (2006).
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode," Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UIdQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

(56) References Cited

OTHER PUBLICATIONS

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.

\* cited by examiner

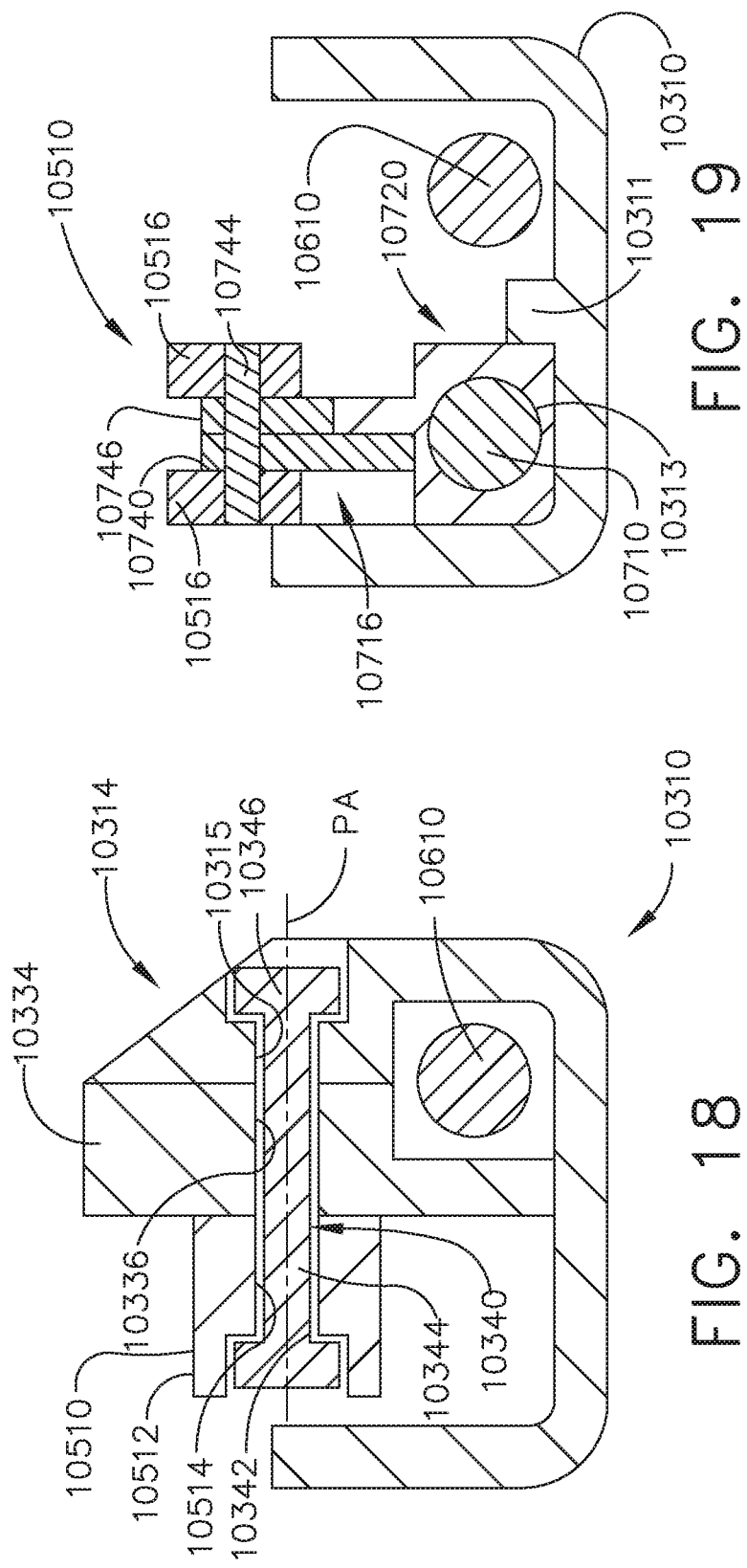

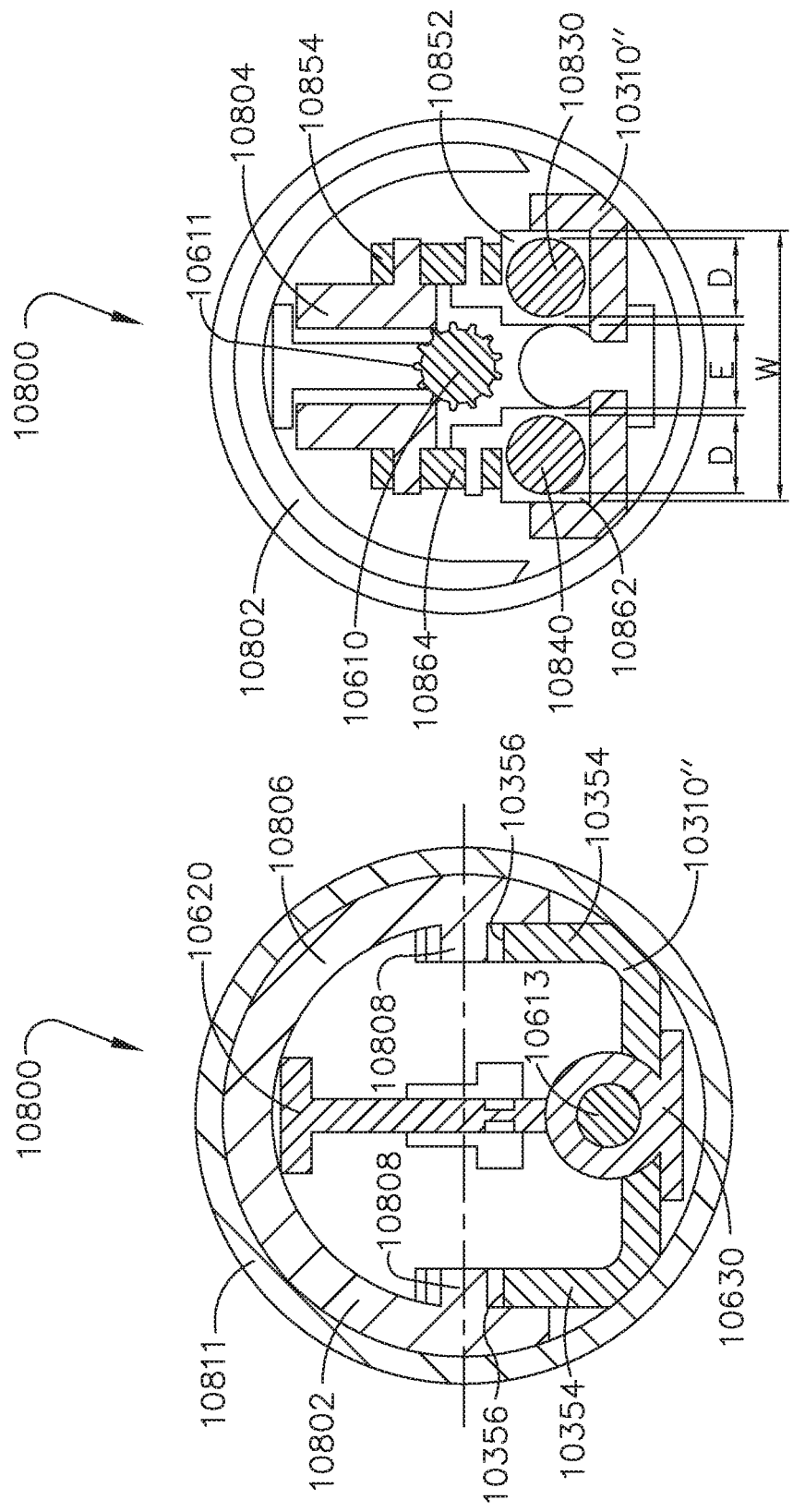

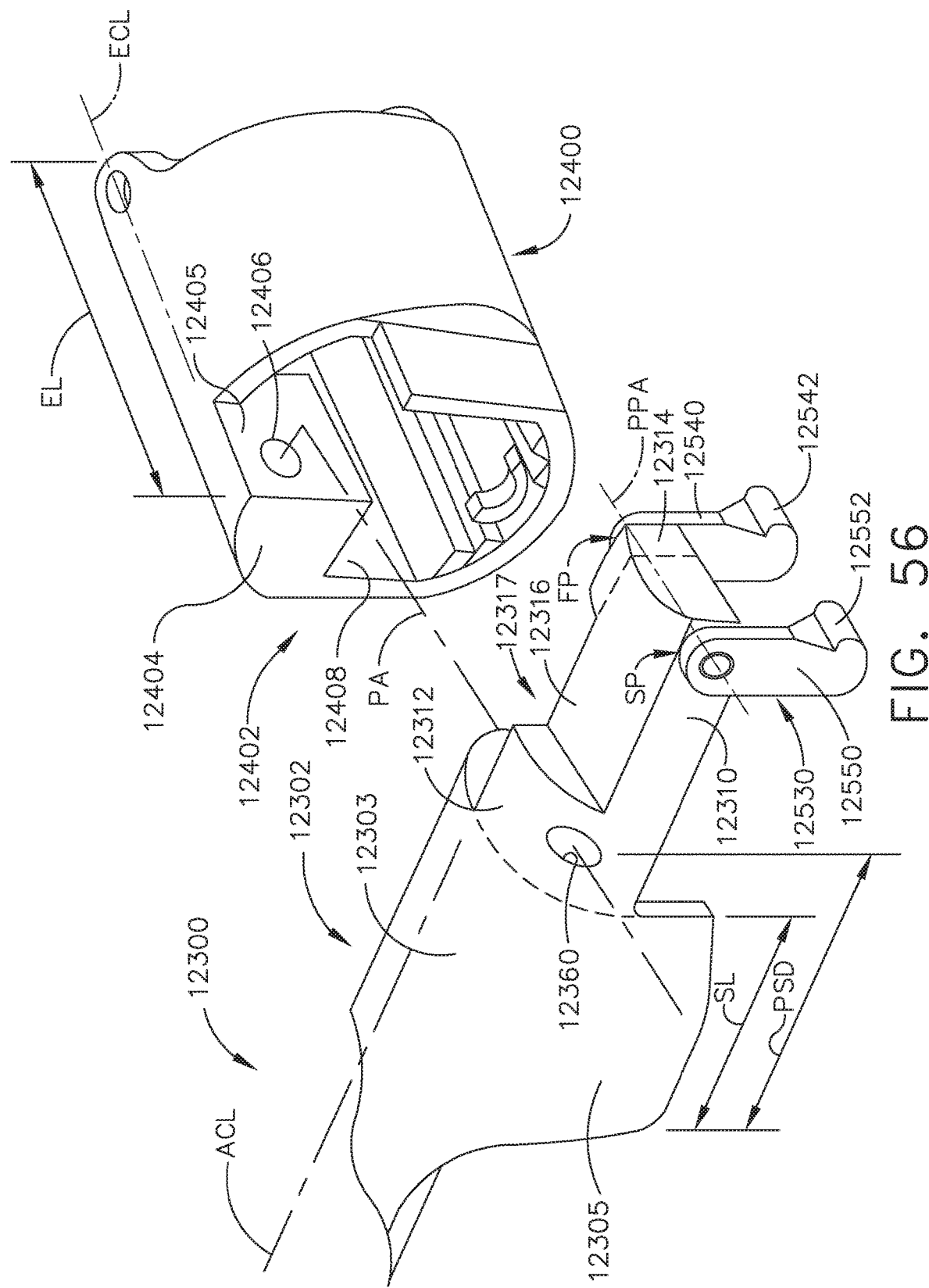

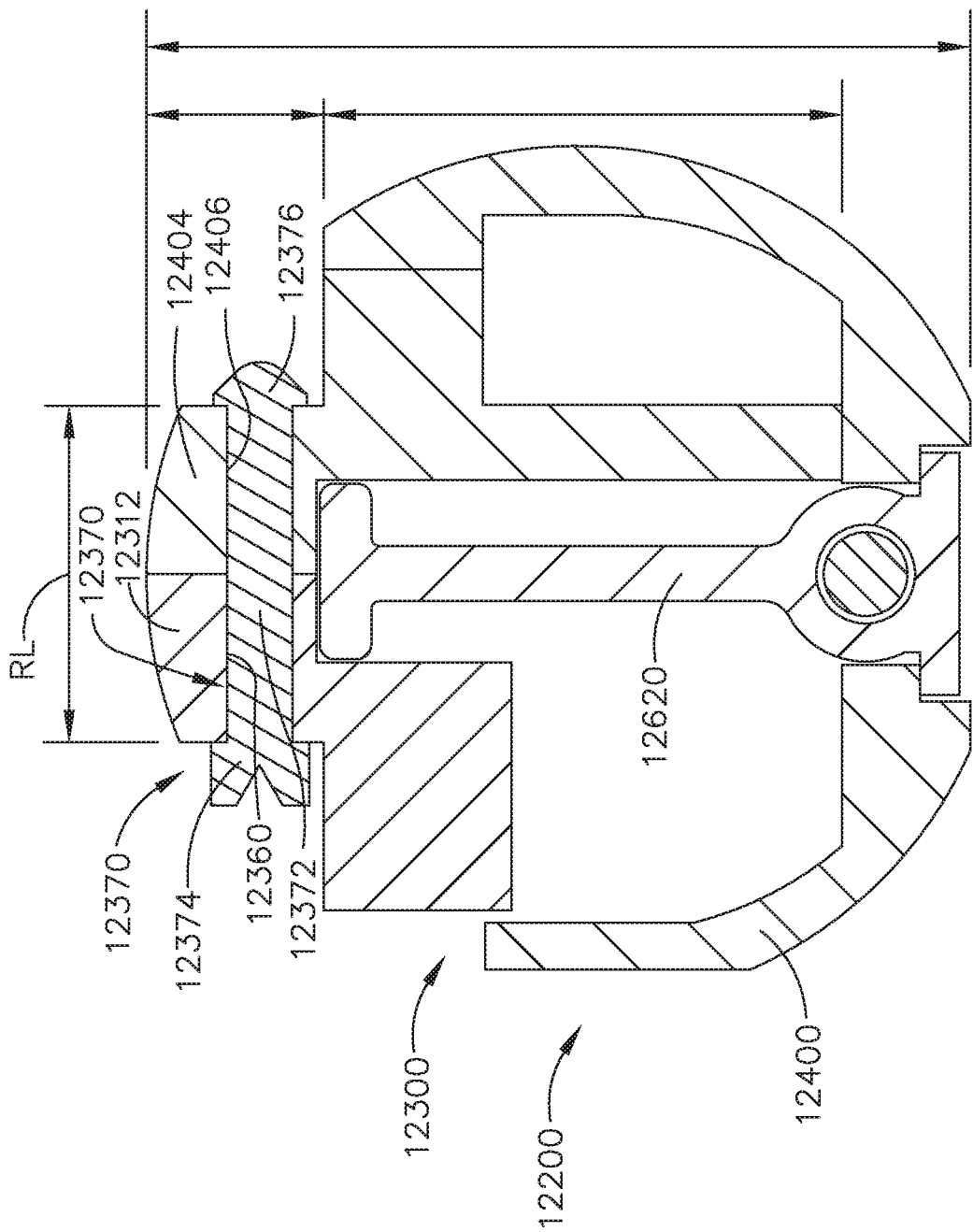

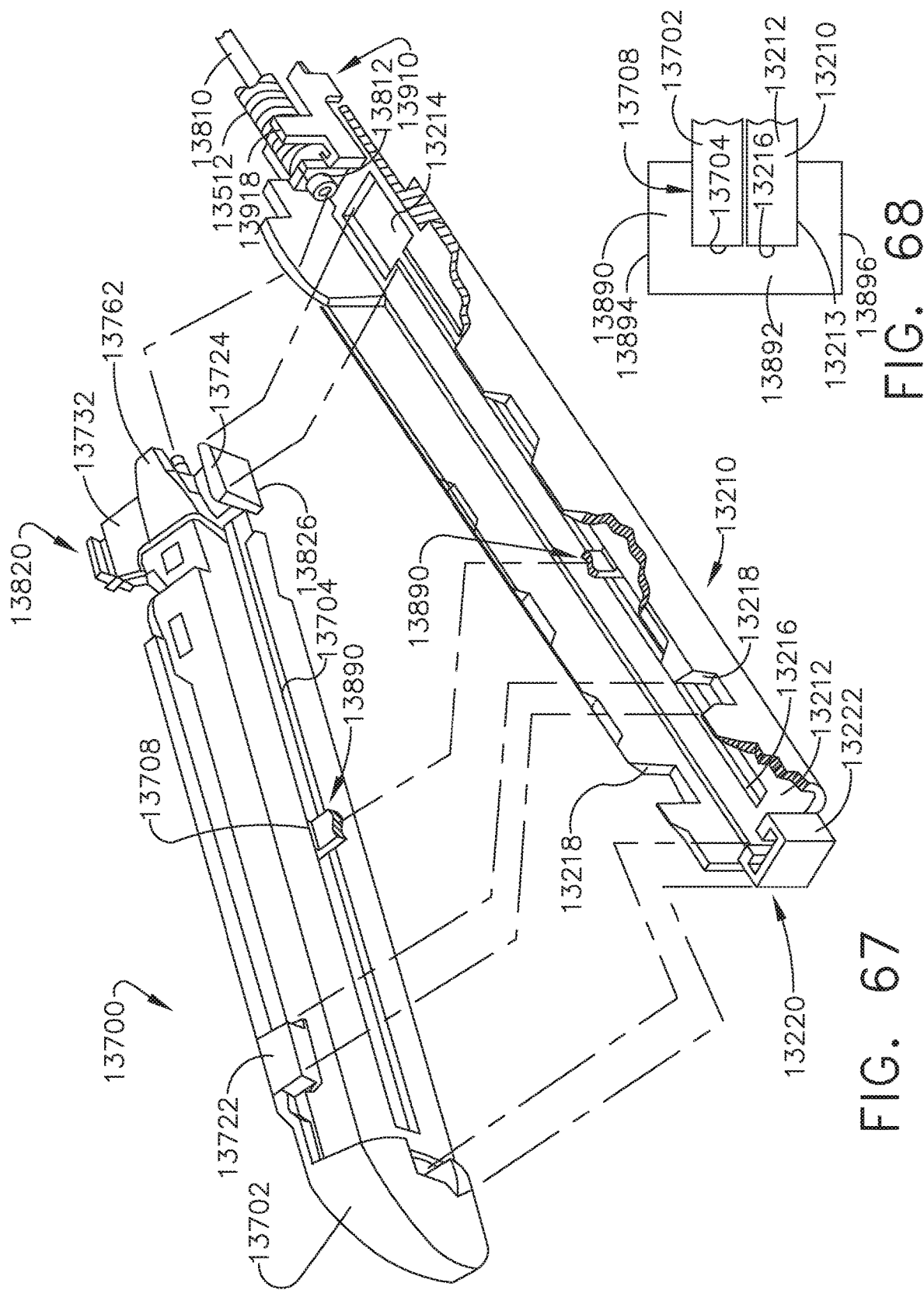

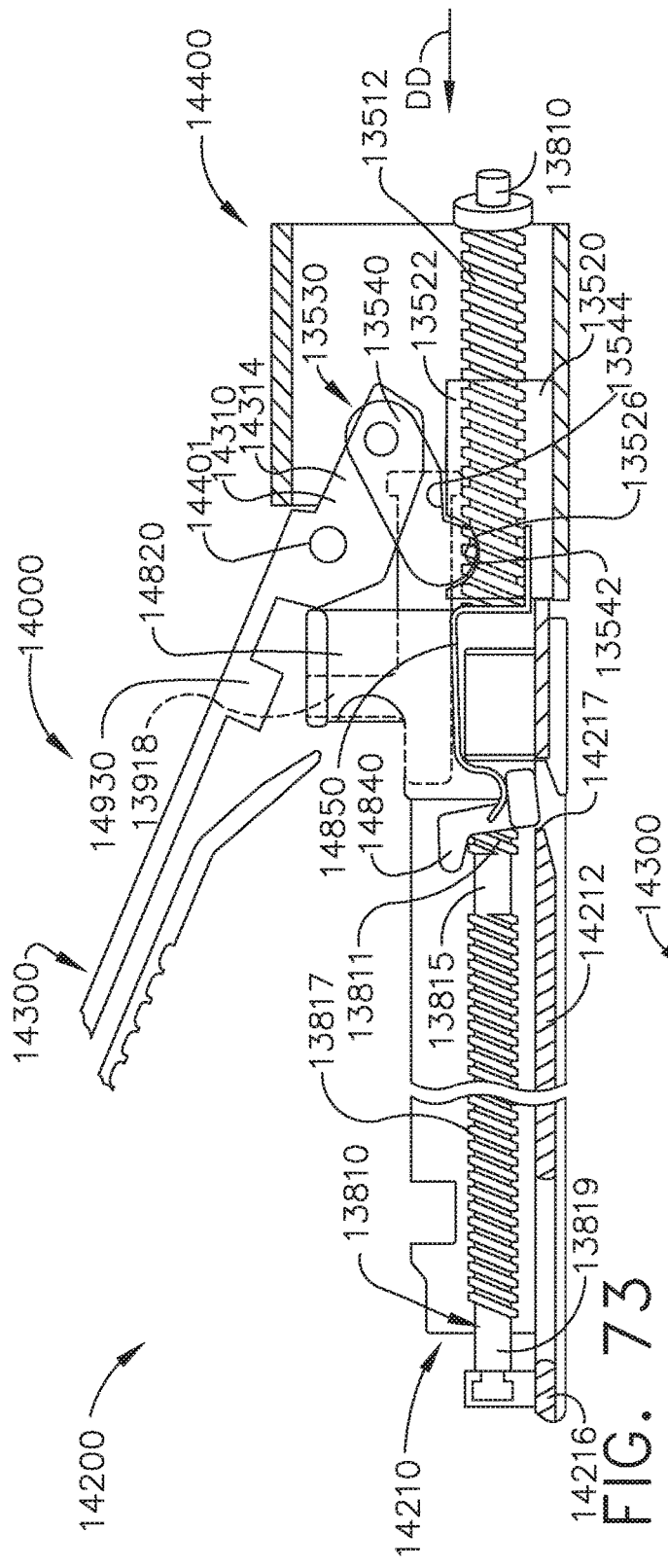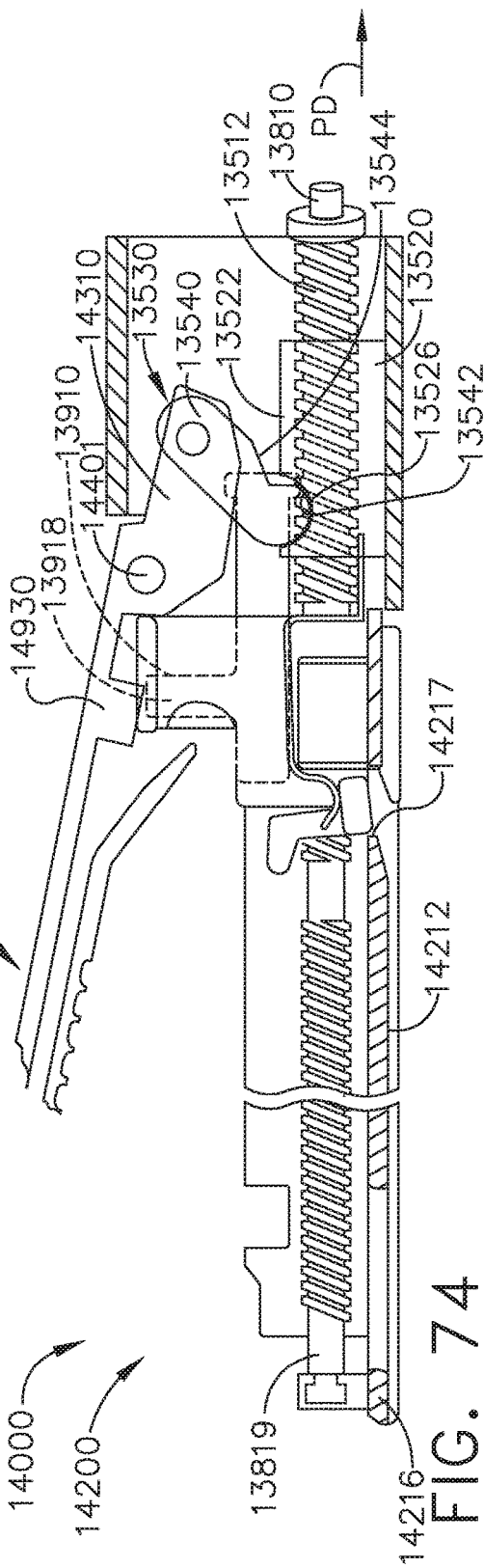

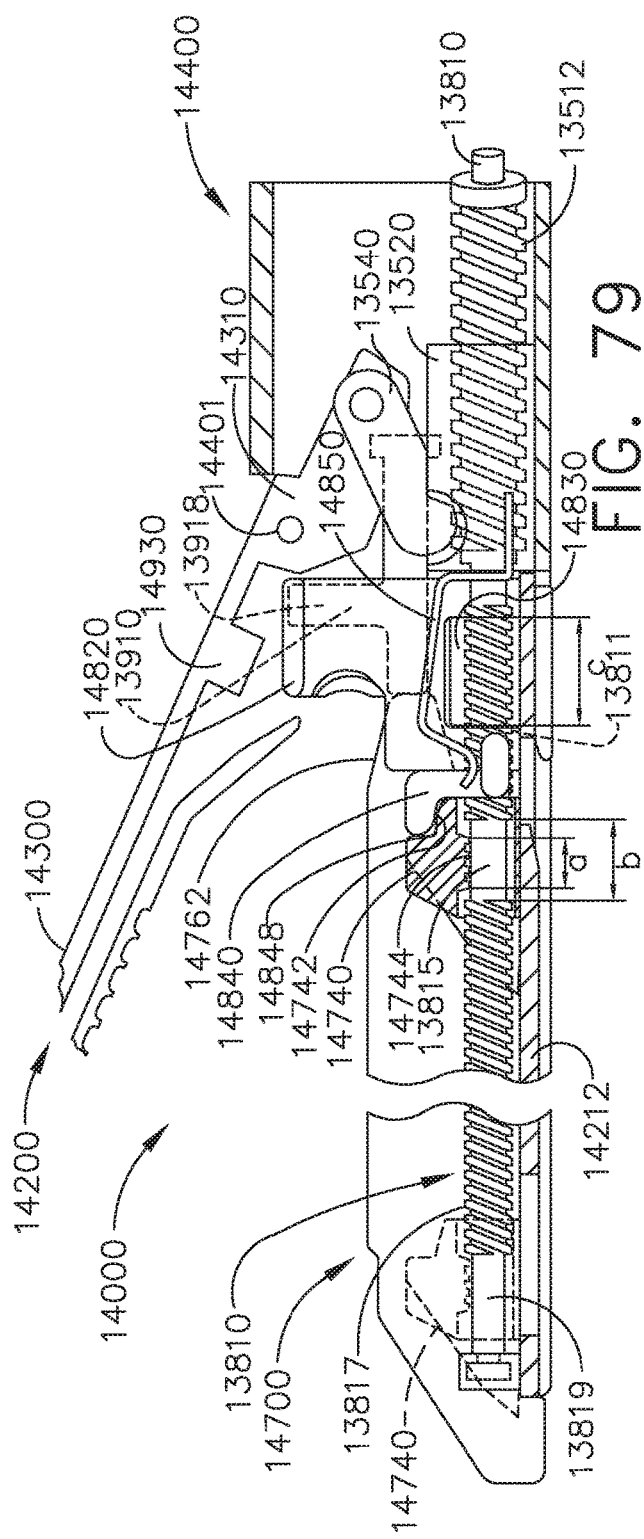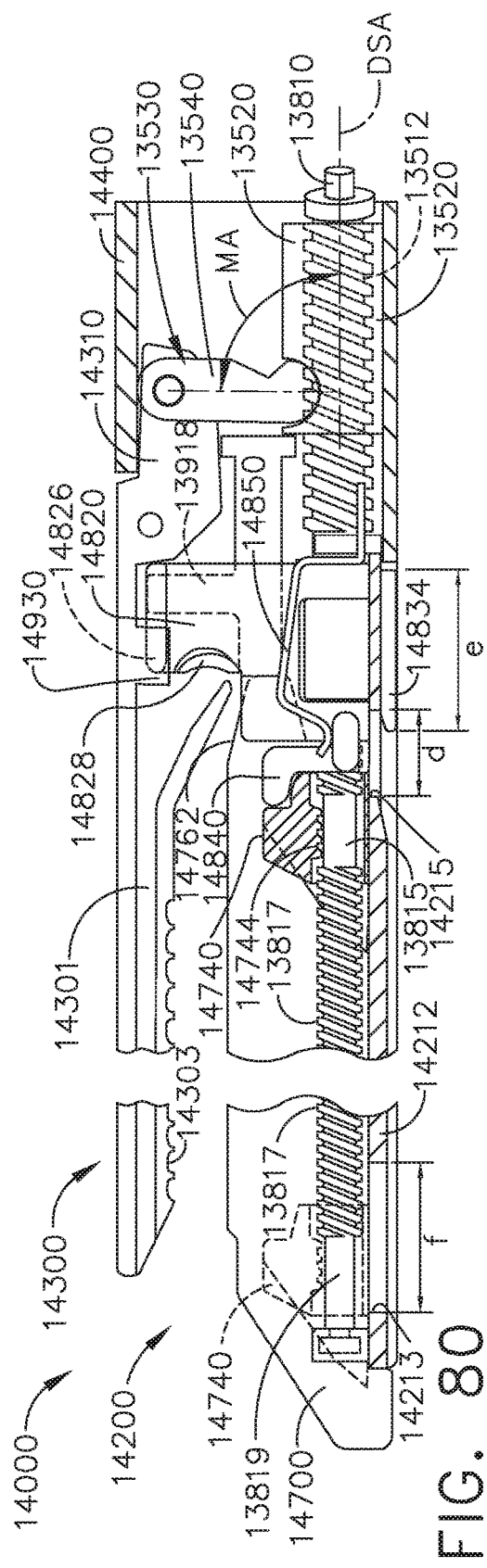

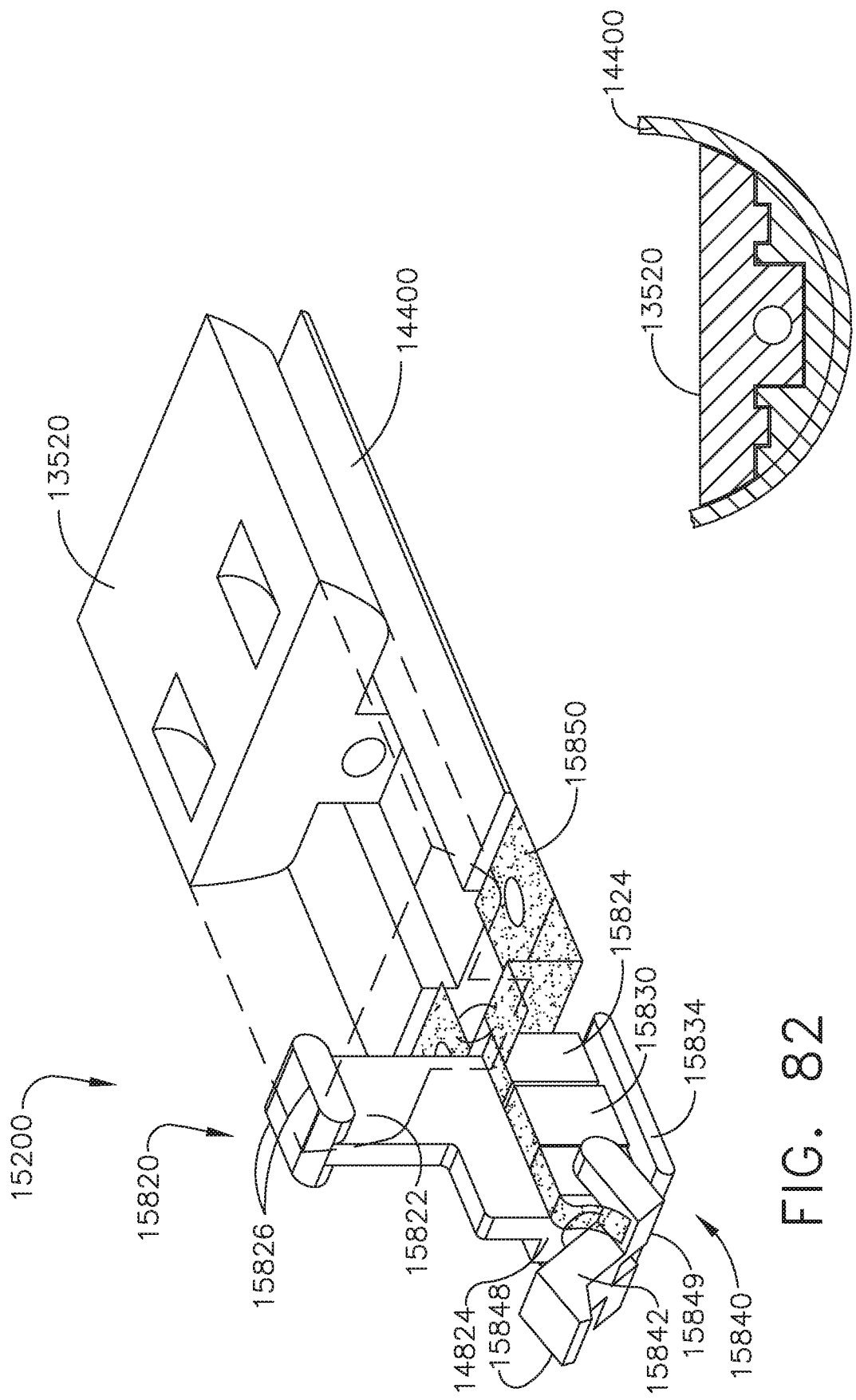

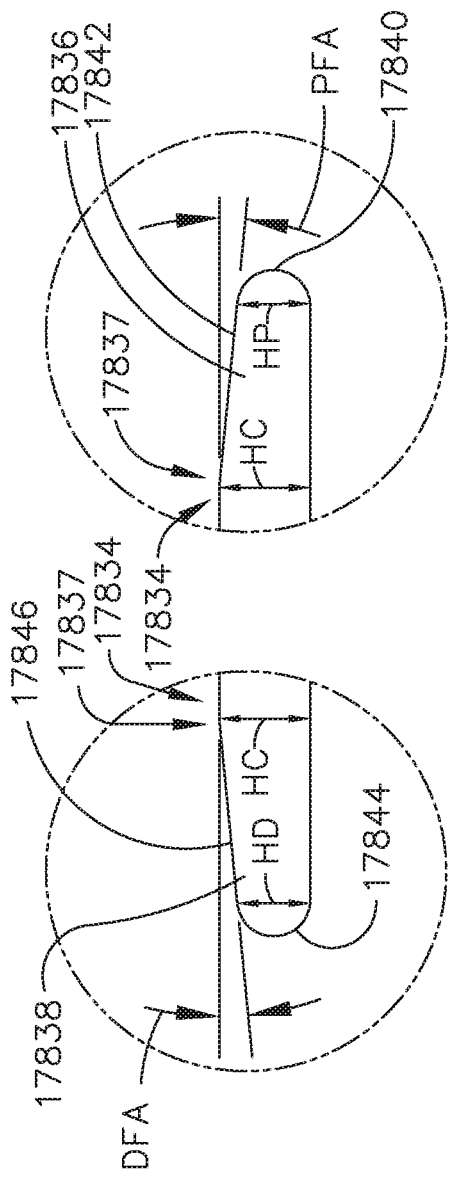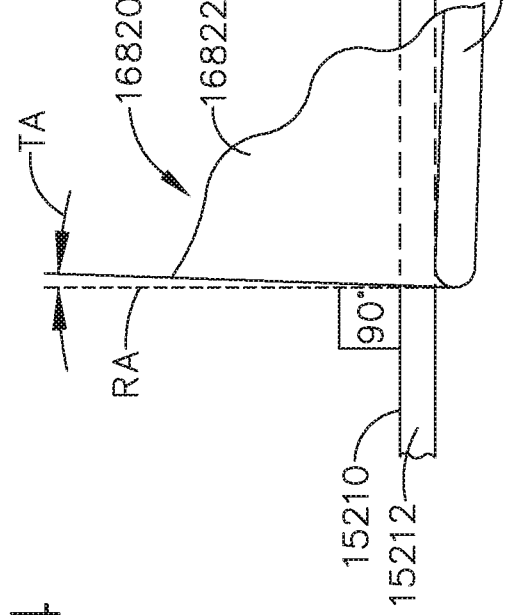
FIG. 92
FIG. 94
FIG. 95

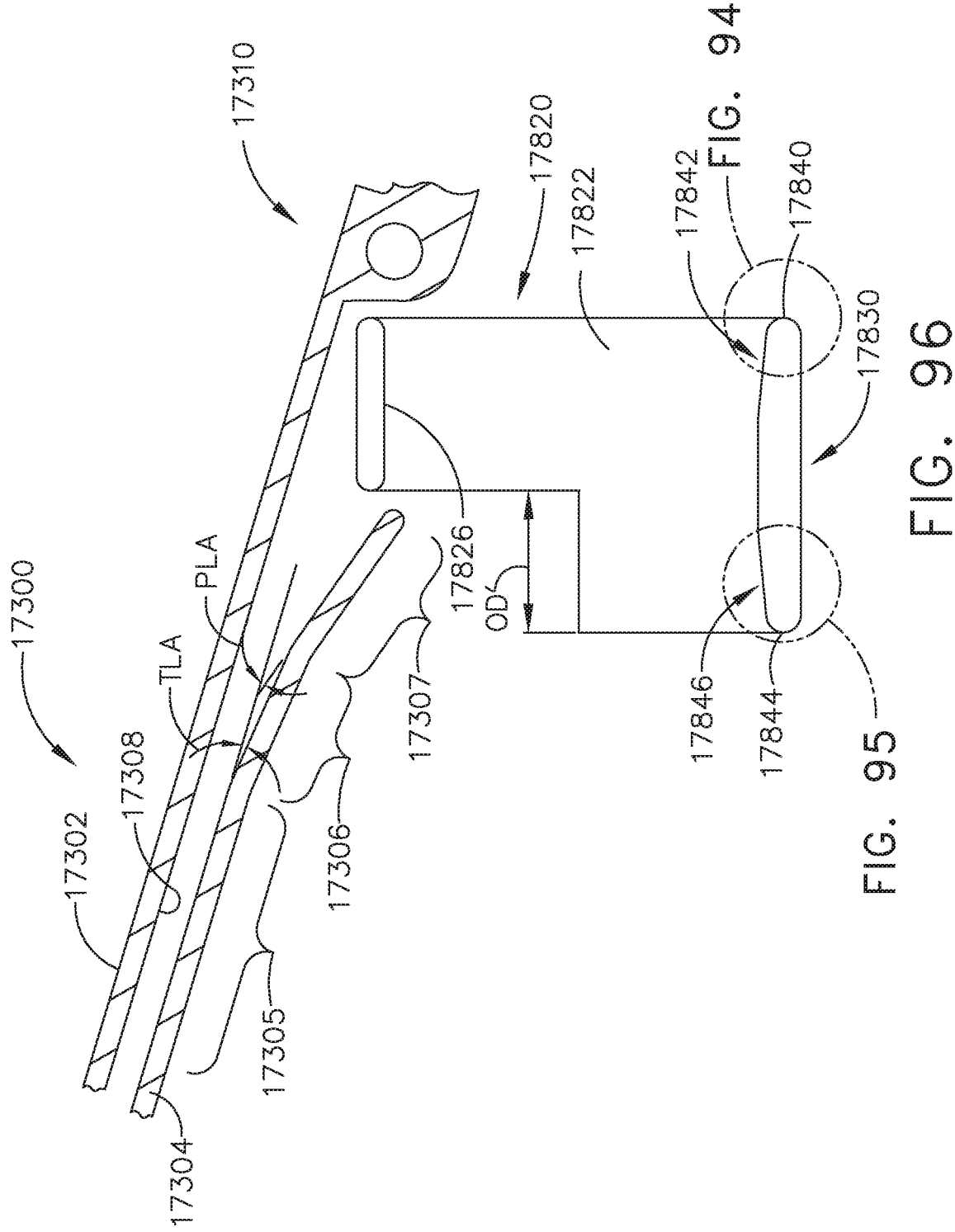

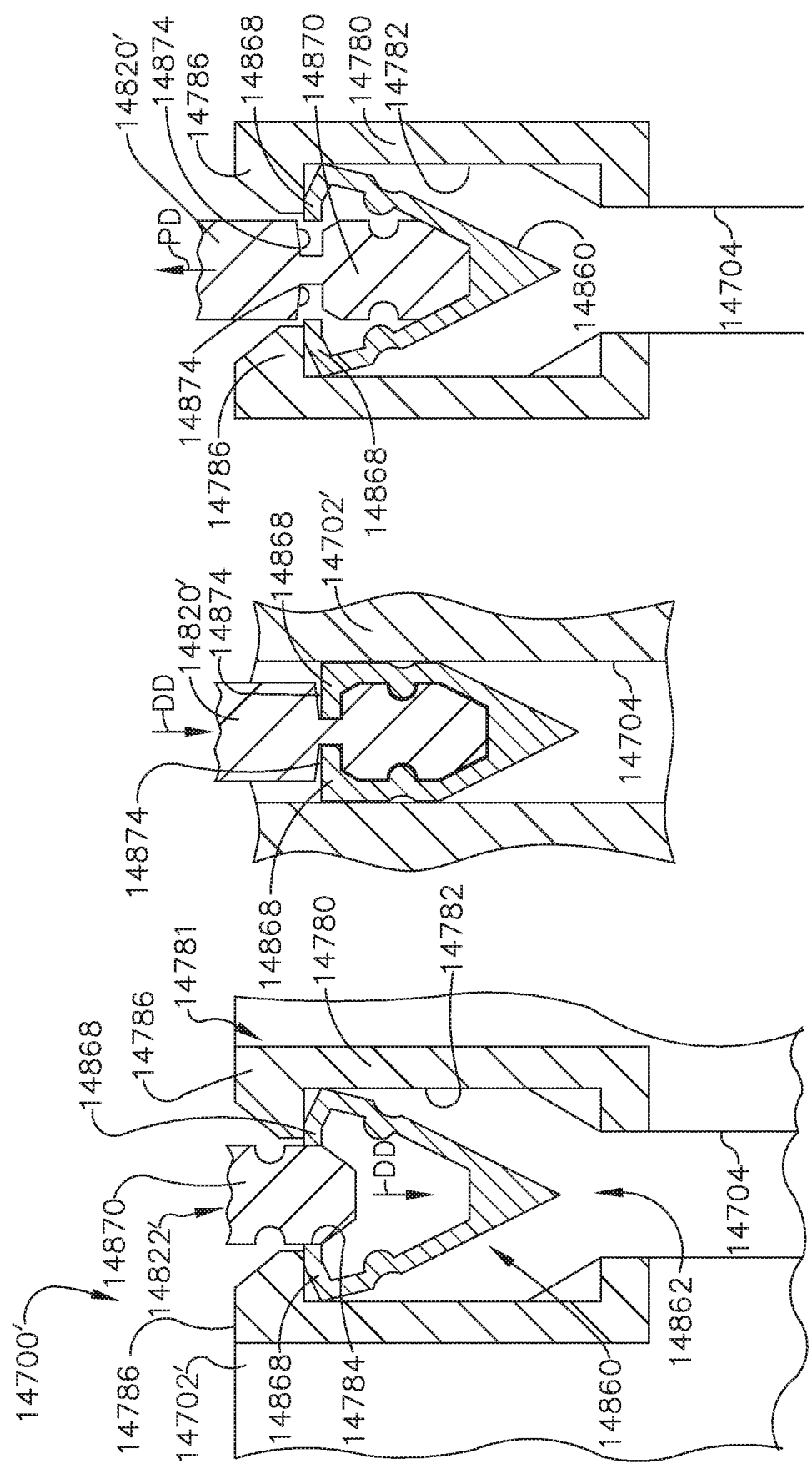

SURGICAL STAPLE CARTRIDGE WITH FIRING MEMBER DRIVEN CAMMING ASSEMBLY THAT HAS AN ONBOARD TISSUE CUTTING FEATURE

CROSS-REFERENCE TO RELATED APPLICATIONS

This application claims the benefit of U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS, filed Feb. 19, 2019, of U.S. Provisional Patent Application Ser. No. 62/807,319, entitled SURGICAL STAPLING DEVICES WITH IMPROVED LOCKOUT SYSTEMS, filed Feb. 19, 2019, and of U.S. Provisional Patent Application Ser. No. 62/807,309, entitled SURGICAL STAPLING DEVICES WITH IMPROVED ROTARY DRIVEN CLOSURE SYSTEMS, filed Feb. 19, 2019, the disclosures of which are incorporated by reference herein in their entireties. This application claims the benefit of U.S. Provisional Patent Application Ser. No. 62/650,887, entitled SURGICAL SYSTEMS WITH OPTIMIZED SENSING CAPABILITIES, filed Mar. 30, 2018, the disclosure of which is incorporated by reference herein in its entirety. This application claims the benefit of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, and of U.S. Provisional Patent Application Ser. No. 62/649,323, entitled SENSING ARRANGEMENTS FOR ROBOT-ASSISTED SURGICAL PLATFORMS, filed Mar. 28, 2018, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 18 is a cross-sectional view of the anvil and end effector of FIG. 17 taken along line 18-18 in FIG. 17;

FIG. 19 is another cross-sectional view of the anvil and end effector of FIG. 17 taken along line 19-19 in FIG. 17;

FIG. 26 is a cross-sectional end view of the rotary powered surgical end effector of FIG. 24;

FIG. 27 is another cross-sectional end view of the rotary powered surgical end effector of FIG. 24;

FIG. 56 is a partial exploded assembly view of an anvil and end cap portion of the surgical end effector of the surgical instrument of FIG. 53;

FIG. 57 is a partial cross-sectional end view of the surgical end effector of the surgical instrument of FIG. 53;

FIG. 67 is partial perspective assembly view of an elongate channel portion of the surgical end effector of FIG. 65 and a bottom perspective view of the surgical staple cartridge of FIG. 66;

FIG. 68 is a side elevational view of a clip of the surgical staple cartridge of FIG. 67 in engagement with a portion of the elongate channel of FIG. 67 when the staple cartridge has been operably installed in the elongate channel;

FIG. 73 is a partial cross-sectional side view of another surgical end effector with an anvil thereof in an open position and prior to installation of a surgical staple cartridge therein;

FIG. 74 is another partial cross-sectional side view of the surgical end effector of FIG. 73 after the anvil has started to close;

FIG. 79 is a cross-sectional side view of the surgical end effector of FIG. 73 with a surgical staple cartridge installed therein and the anvil thereof in an open position;

FIG. 80 is another cross-sectional side view of the surgical end effector of FIG. 73, with the anvil thereof in a closed position;

FIG. 82 is a perspective view of a portion of a firing member and a closure system of the surgical end effector of FIG. 81;

FIG. 83 is a cross-sectional end view of a portion of an elongate channel and closure shuttle of the surgical end effector of FIG. 81;

FIG. 92 is a side view of a portion of the firing member of FIG. 90 in relation to a portion of an elongate channel of a surgical end effector;

FIG. 94 is a partial side elevational view of a portion of a proximal segment of a flange assembly of the firing member of FIG. 93;

FIG. 95 is a partial side elevational view of a portion of a distal segment of the flange assembly of FIG. 94;

FIG. 96 is a side elevational view of the firing member of FIG. 93 in relation to an anvil of a surgical end effector with the anvil in an open position and shown in cross-section;

FIG. 119 is a perspective view of a distal end of the surgical staple cartridge of FIG. 112, with a portion omitted to expose the camming assembly thereof in an ending position and the tissue cutting member thereof in a stored position;

FIG. 120 is another perspective view of the surgical staple cartridge of FIG. 119;

FIG. 121 is a partial side elevational view of a surgical end effector during installation of a surgical staple cartridge therein with portions of the end effector and cartridge omitted for clarity;

FIG. 122 is another partial side elevational view of the surgical end effector and staple cartridge of FIG. 121 with a firing member of the end effector in operable engagement with a camming assembly of the cartridge prior to commencement of a firing process;

FIG. 123 is another partial side elevational view of the surgical end effector and staple cartridge of FIG. 121 after completion of the firing process and during retraction of the firing member in a proximal direction;

FIG. 124 is a perspective view of another surgical staple cartridge and a portion of a firing member of a powered surgical end effector;

FIG. 125 is another perspective view of a portion of the firing member of FIG. 124 and a removable blade structure of the surgical staple cartridge of FIG. 124;

FIG. 126 is a perspective view of the removable blade structure of FIG. 125;

FIG. 127 is a partial cross-sectional top view showing the positions of the blade structure of the staple cartridge and firing member of FIG. 124 during the initial installation of the surgical staple cartridge;

FIG. 128 is another top cross-sectional view of a portion of the surgical staple cartridge and firing member of FIG. 124 during the distal advancement of the firing member through the staple cartridge;

FIG. 129 is another top cross-sectional view of a portion of the surgical staple cartridge and firing member of FIG. 124 during the retraction of the firing member back to a starting position;

FIG. 130 is a perspective view of another removable blade structure;

Figure 131:
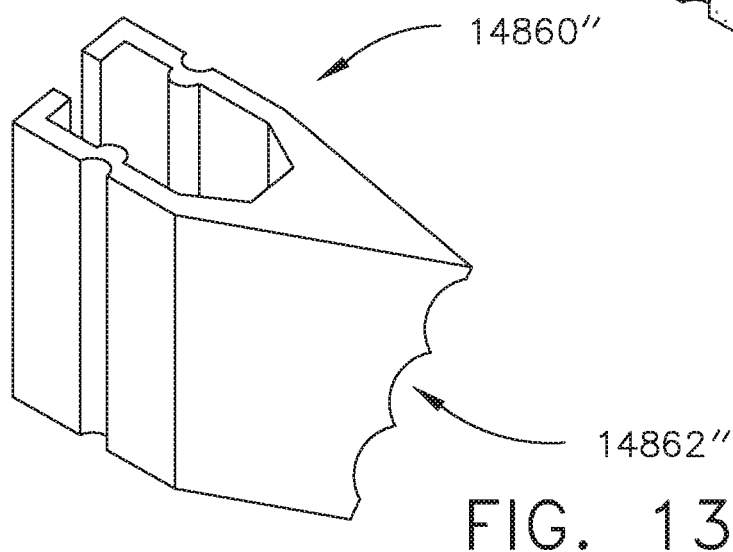

FIG. 131 is a perspective view of another removable blade structure; and

Figure 132:
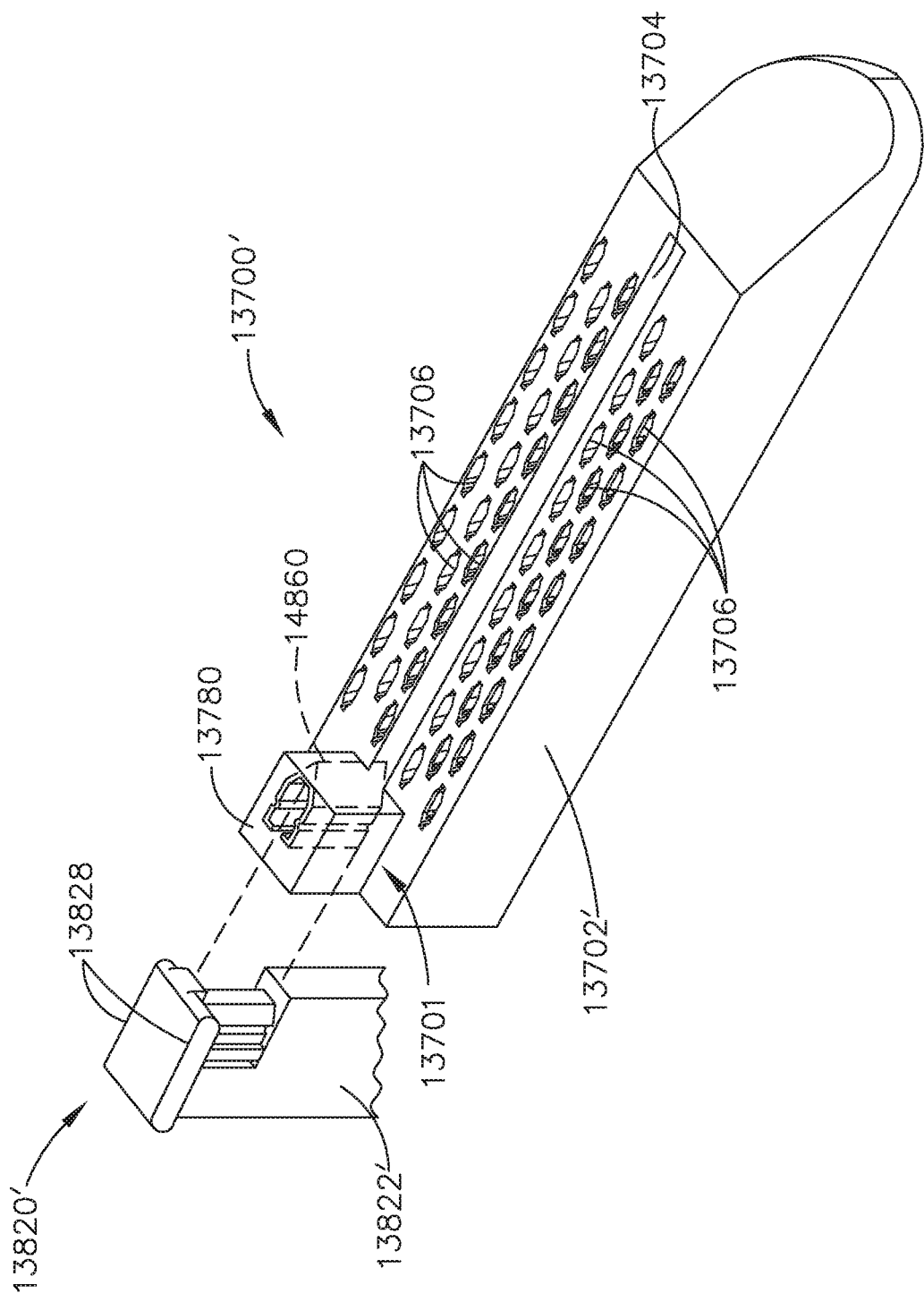

FIG. 132 is a perspective view of another surgical staple cartridge and firing member of another powered surgical instrument.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. Patent Applications that were filed on Feb. 12, 2019 and which are each herein incorporated by reference in their respective entireties:

U.S. Patent Application entitled METHODS FOR CONTROLLING A POWERED SURGICAL STAPLER THAT HAS SEPARATE ROTARY CLOSURE AND FIRING SYSTEMS, Ser. No. 16/281,658, now U.S. Patent Application Publication No. 2019-0298350;

U.S. Patent Application entitled STAPLE CARTRIDGE COMPRISING A LOCKOUT KEY CONFIGURED TO LIFT A FIRING MEMBER, Ser. No. 16/281,670, now U.S. Patent Application Publication No. 2019-0298340;

U.S. Patent Application entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, Ser. No. 16/281,675, now U.S. Patent Application Publication No. 2019-0298354;

U.S. Patent Application entitled SURGICAL INSTRUMENT COMPRISING CO-OPERATING LOCKOUT FEATURES, Ser. No. 16/281,685, now U.S. Patent Application Publication No. 2019-0298341;

U.S. Patent Application entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, Ser. No. 16/281,693, now U.S. Patent Application Publication No. 2019-0298342;

U.S. Patent Application entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, Ser. No. 16/281,704, now U.S. Patent Application Publication No. 2019-0257578;

U.S. Patent Application entitled STAPLING INSTRUMENT COMPRISING A DEACTIVATABLE LOCKOUT, Ser. No. 16/281,707, now U.S. Patent Application Publication No. 2019-0298347;

U.S. Patent Application entitled SURGICAL INSTRUMENT COMPRISING A JAW CLOSURE LOCKOUT, Ser. No. 16/281,741, now U.S. Patent Application Publication No. 2019-0298357;

U.S. Patent Application entitled SURGICAL STAPLING DEVICES WITH CARTRIDGE COMPATIBLE CLOSURE AND FIRING LOCKOUT ARRANGEMENTS, Ser. No. 16/281,762, now U.S. Patent Application Publication No. 2019-0298343;

U.S. Patent Application entitled SURGICAL STAPLING DEVICES WITH IMPROVED ROTARY DRIVEN CLOSURE SYSTEMS, Ser. No. 16/281,666, now U.S. Patent Application Publication No. 2019-0298352;

U.S. Patent Application entitled SURGICAL STAPLING DEVICES WITH ASYMMETRIC CLOSURE FEATURES, Ser. No. 16/281,762, now U.S. Patent Application Publication No. 2019-0298343;

U.S. Patent Application entitled ROTARY DRIVEN FIRING MEMBERS WITH DIFFERENT ANVIL AND CHANNEL ENGAGEMENT FEATURES, Ser. No. 16/281,678, now U.S. Patent Application Publication No. 2019-0298355; and U.S. Patent Application entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, Ser. No. 16/281,682, now U.S. Patent Application Publication No. 2019-0298346.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. patent application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. patent applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. patent applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. patent applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVERDRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. patent applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Patent Application Publication No. 2017/0281163;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. patent applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;

U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and U.S. patent application Ser. No. 14/984,552, entitled SURGICAL INSTRUMENTS WITH SEPARABLE MOTORS AND MOTOR CONTROL CIRCUITS, now U.S. Patent Application Publication No. 2017/0189020.

Applicant of the present application also owns the U.S. patent applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Patent Application Publication No. 2017/0224333;

U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;

U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Patent Application Publication No. 2017/0224336;

U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. patent applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Patent Application Publication No. 2017/0231623;

U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Patent Application Publication No. 2016/0367256;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Pat. No. 9,993,258; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
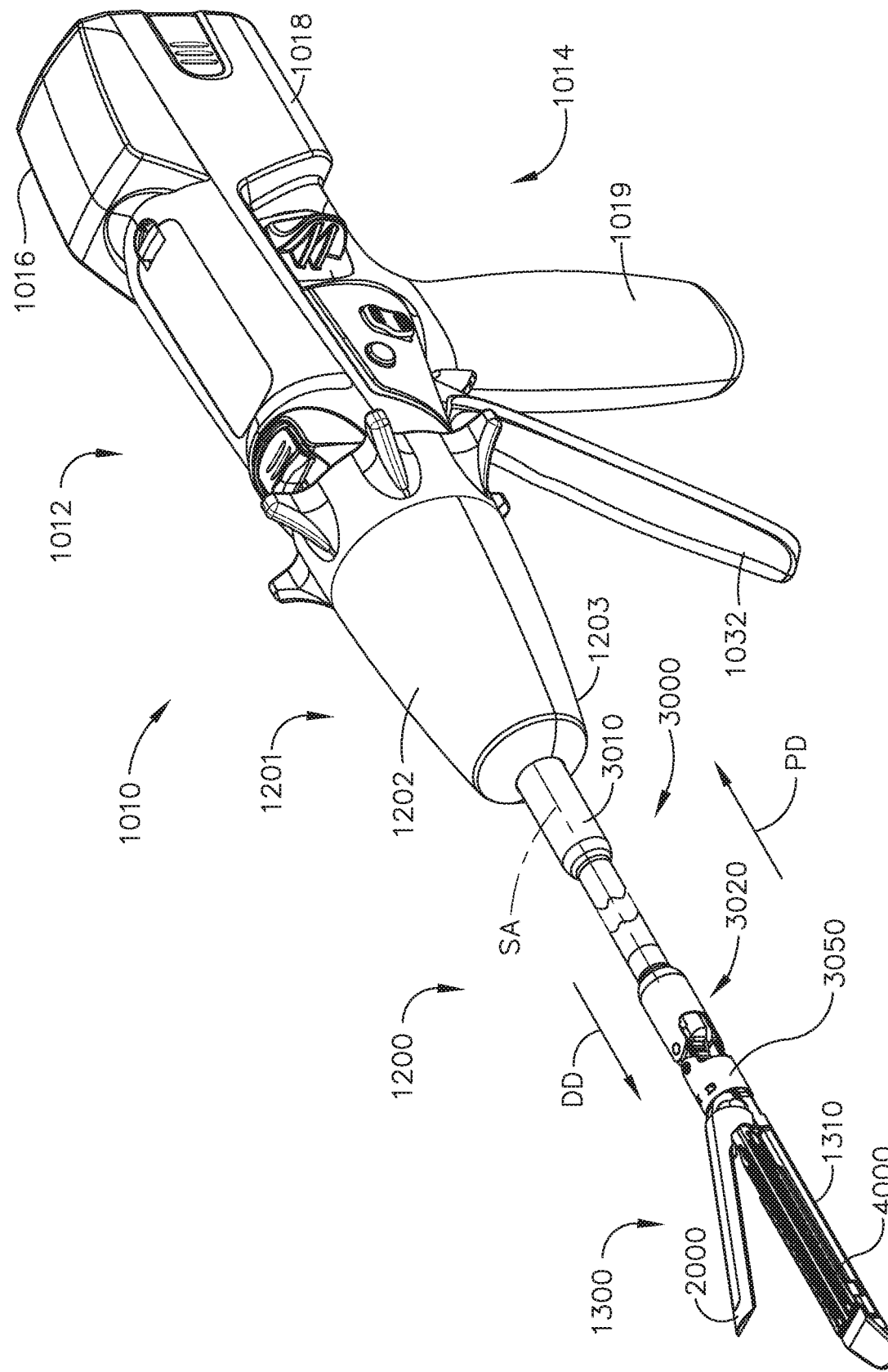
FIG. 1 is a perspective view of a powered surgical stapling system.
Figure 2:
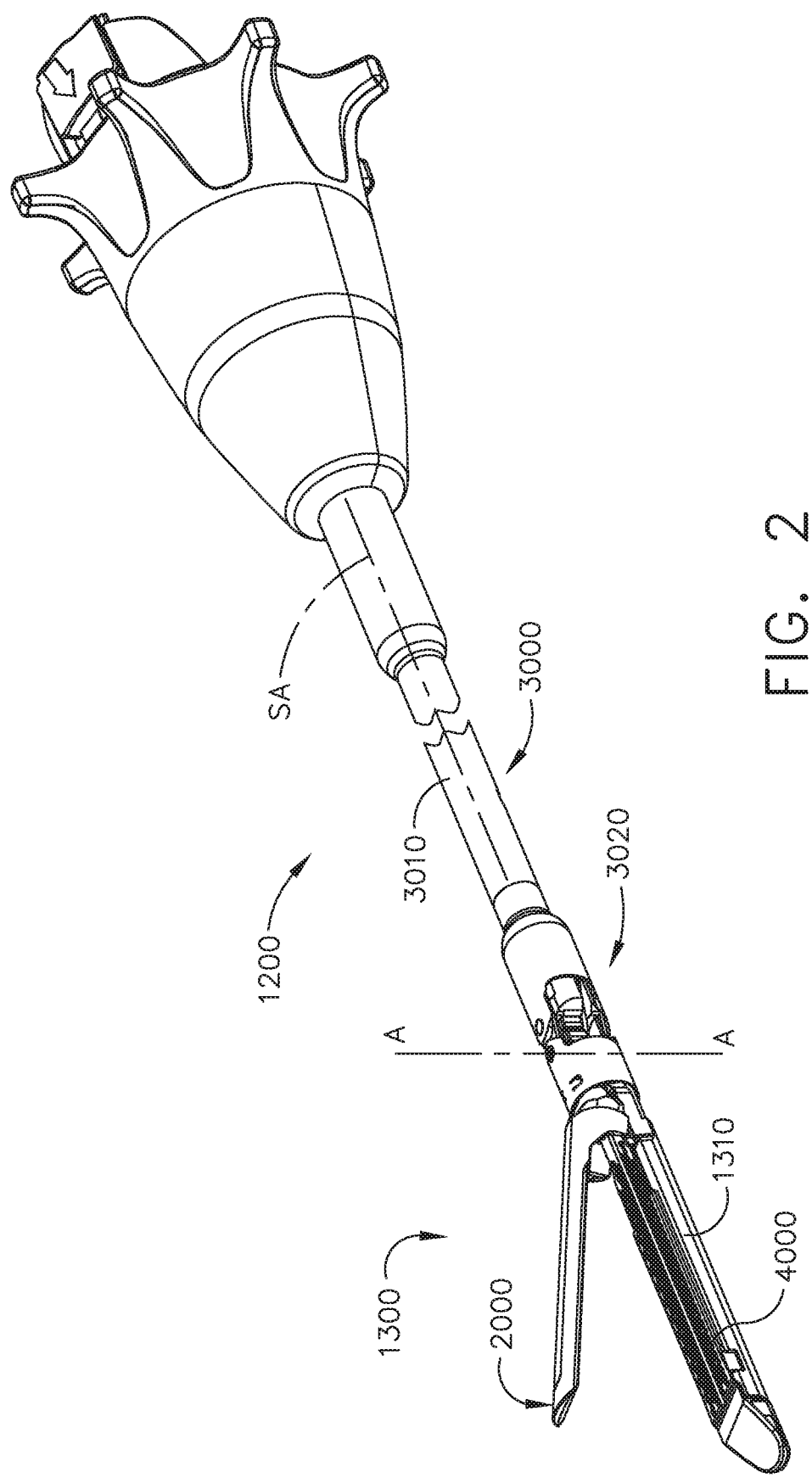
FIG. 2 is a perspective view of an interchangeable surgical shaft assembly of the powered surgical stapling system of FIG. 1.
Figure 3:
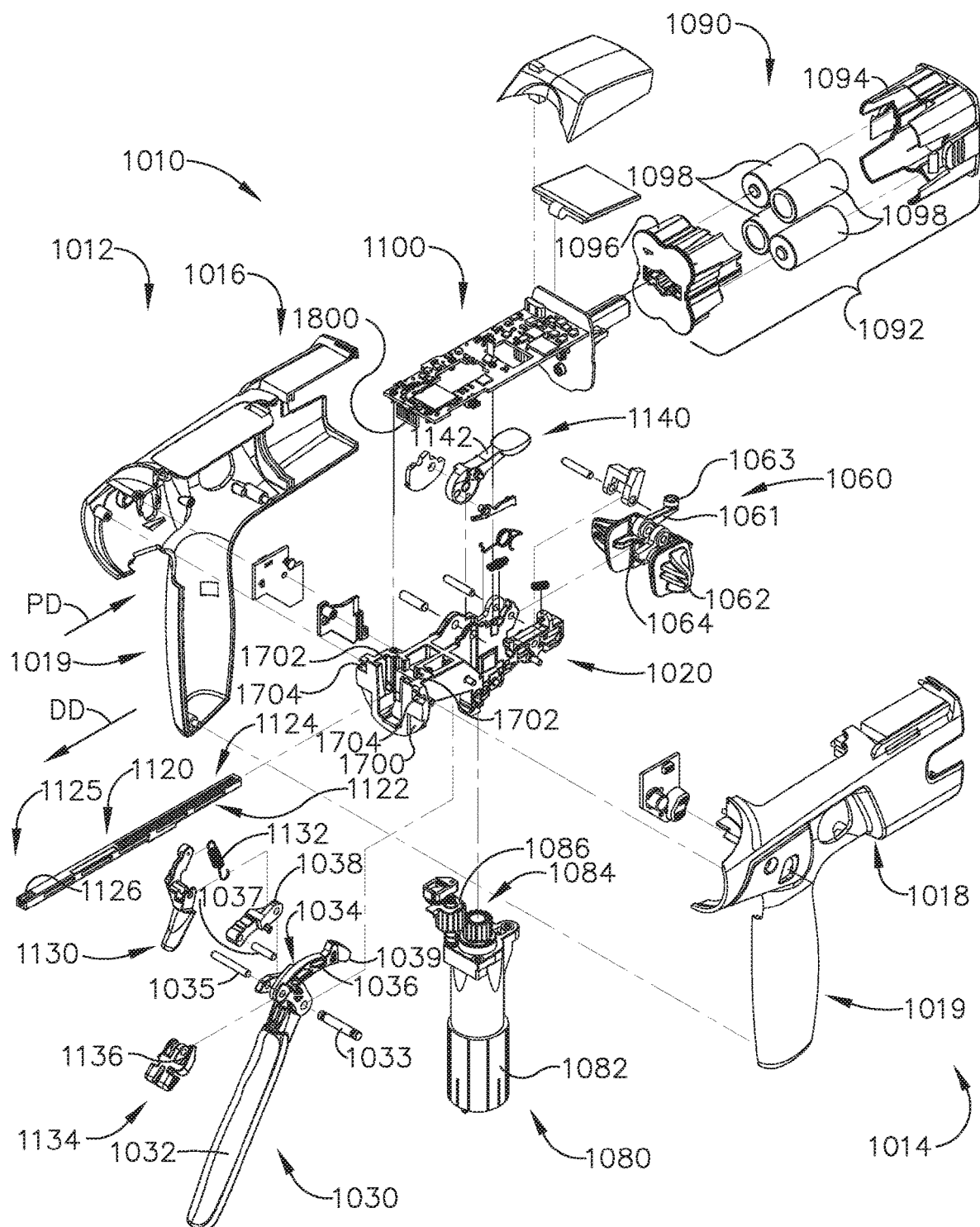
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a previous housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The previous housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 4000 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button 1062. A magnetic element 1063, such as a permanent magnet, for example, may be mounted to the arm 1061. When the closure release button 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
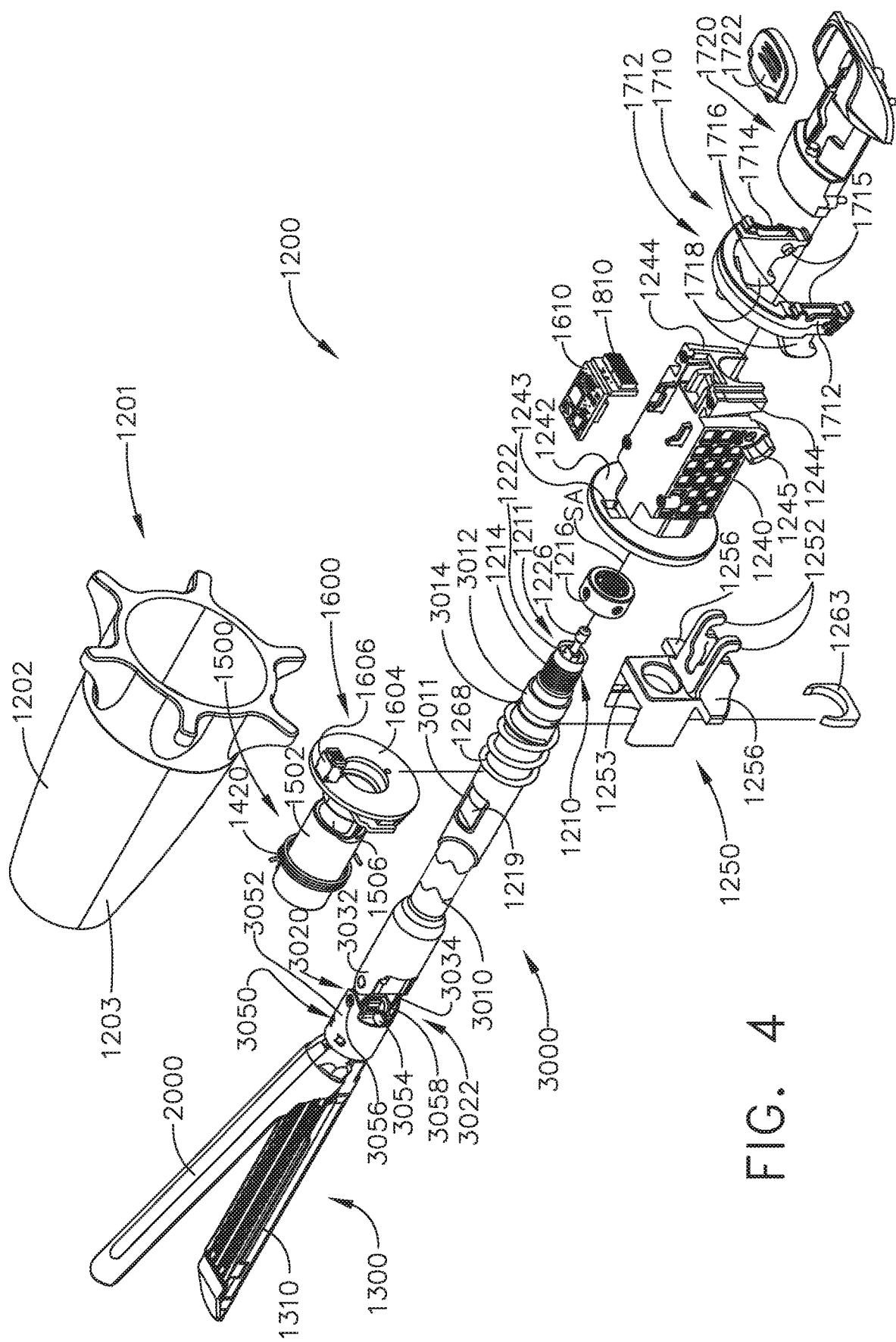
FIG. 4 is an exploded assembly view of the interchangeable surgical shaft assembly of FIG. 2.
Figure 5:
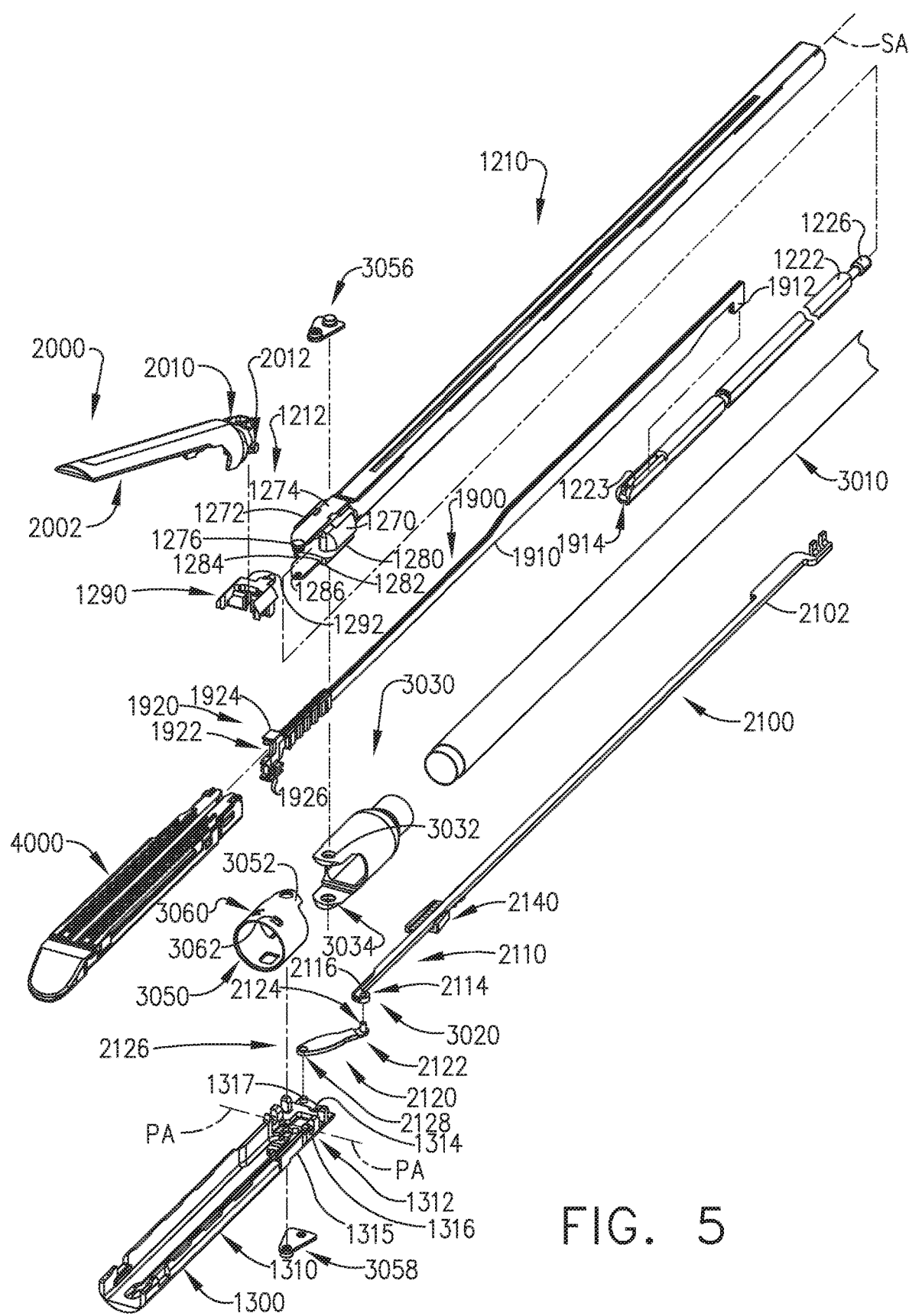
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 4000 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 4000 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the handle control board 1100. Further details regaining the circuitry and control systems may be found in U.S. patent application Ser. No. 13/803,086, now U.S. Patent Application Publication No. 2014/0263541, and U.S. patent application Ser. No. 14/226,142, now U.S. Pat. No. 9,913,642, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
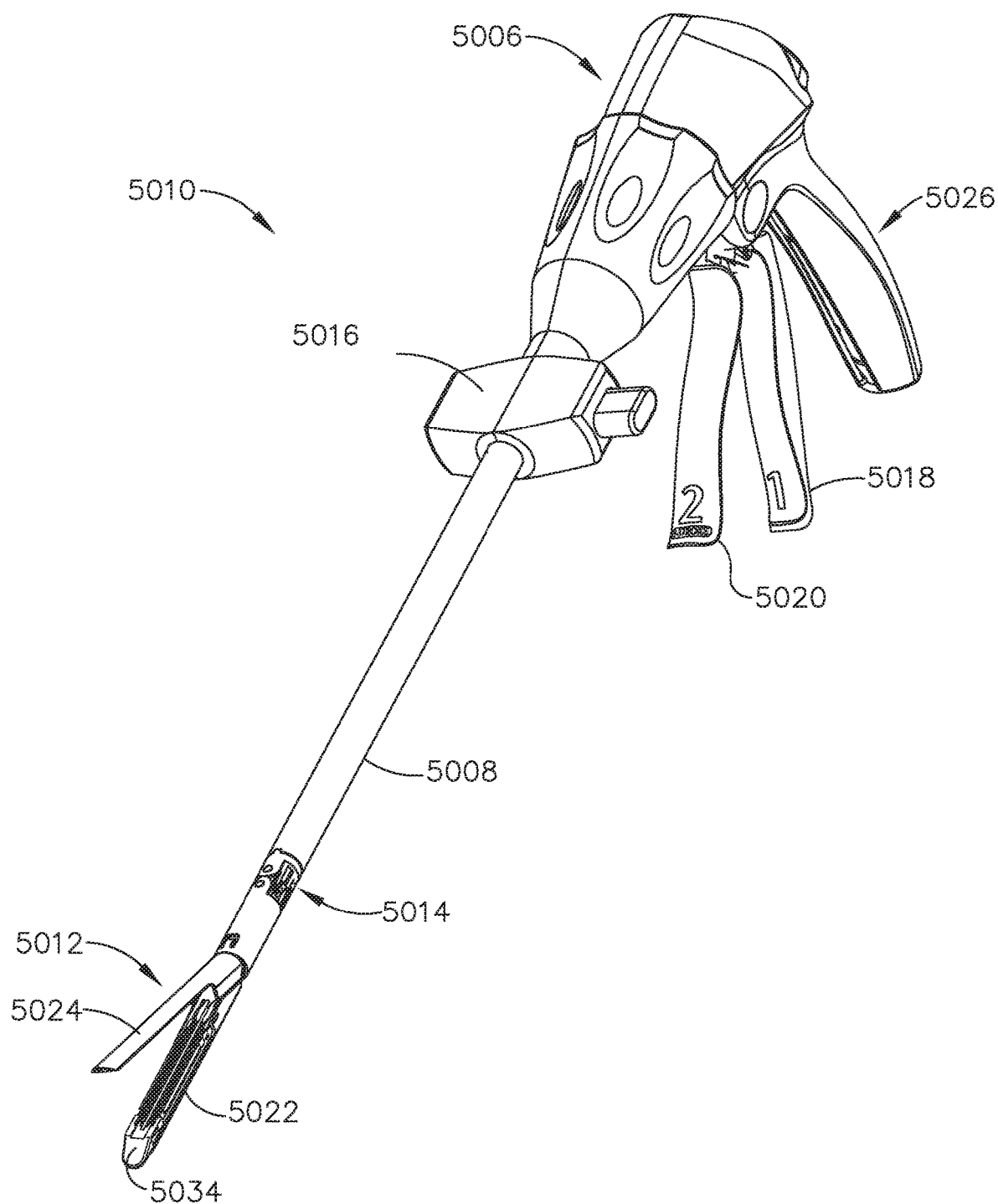
FIG. 6 is a perspective view of another powered surgical stapling system.
Figure 7:
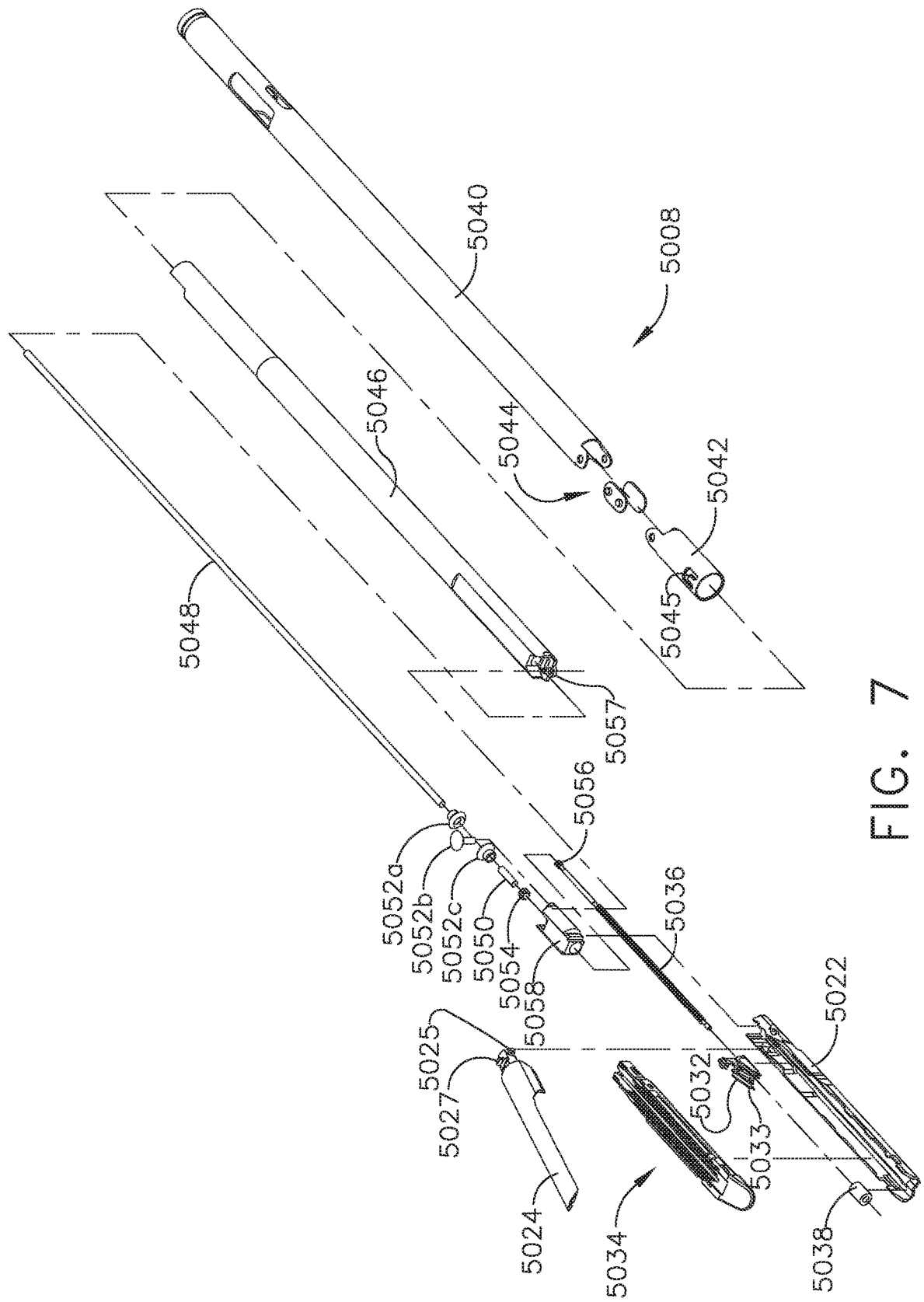
FIG. 7 is an exploded assembly view of portion of a shaft assembly of the power surgical stapling system of FIG. 6.
Figure 8:
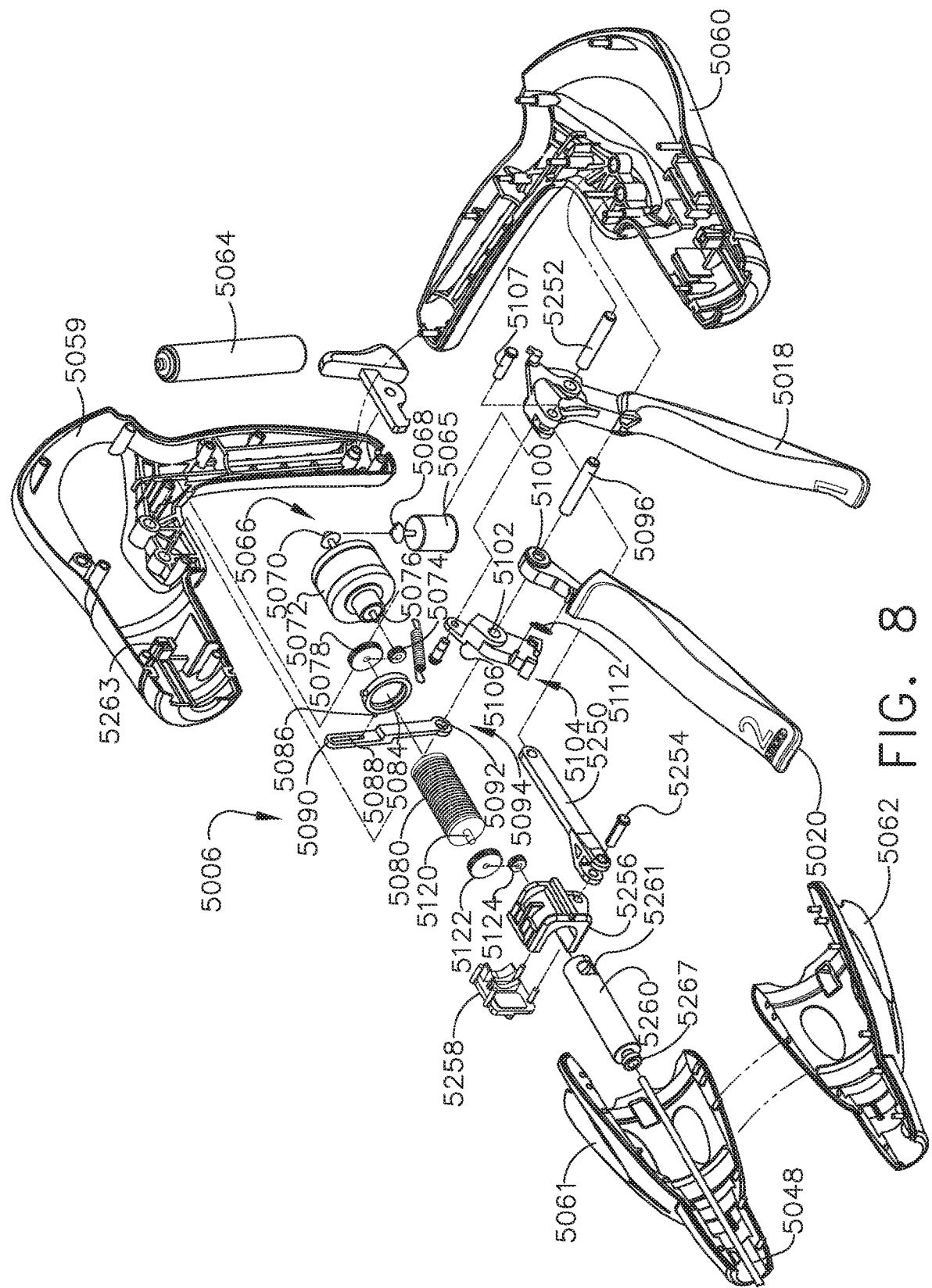
FIG. 8 is an exploded assembly view of portions of a handle assembly of the powered surgical stapling system of FIG. 6.

FIGS. 6-8 depict a previous surgical cutting and fastening instrument 5010 that is configured to generate rotary drive motions for operating a surgical end effector 5012. The endoscopic surgical instrument 5010 comprises a handle 5006, a shaft 5008, and an articulating surgical end effector 5012 pivotally connected to the shaft 5008 at an articulation pivot 5014. An articulation control 5016 may be provided adjacent to the handle 5006 to effect rotation of the end effector 5012 about the articulation pivot 5014. It will be appreciated that various embodiments may include a non-pivoting end effector, and therefore may not have an articulation pivot 5014 or articulation control 5016.

The handle 5006 of the instrument 5010 may include a closure trigger 5018 and a firing trigger 5020 for actuating the end effector 5012. It will be appreciated that instruments having end effectors directed to different surgical tasks may have different numbers or types of triggers or other suitable controls for operating the end effector 5012. In one embodiment, a clinician or operator of the instrument 5010 may articulate the end effector 5012 relative to the shaft 5008 by utilizing the articulation control 5016, as described in more detail in pending U.S. Pat. No. 7,670,334, entitled SURGICAL INSTRUMENT HAVING AN ARTICULATING END EFFECTOR, the entire disclosure of which is incorporated herein by reference. The end effector 5012 includes in this example, among other things, a staple channel 5022 and a pivotally translatable clamping member, such as an anvil 5024, which are maintained at a spacing that assures effective stapling and severing of tissue clamped in the end effector 5012. The handle 5006 includes a pistol grip 5026 toward which the closure trigger 5018 is pivotally drawn by the clinician to cause clamping or closing of the anvil 5024 towards the staple channel 5022 of the end effector 5012 to thereby clamp tissue positioned between the anvil 5024 and channel 5022.

In the arrangement depicted in FIG. 7, the end effector 5012 includes, in addition to the previously-mentioned channel 5022 and anvil 5024, a cutting instrument 5032, a sled 5033, a staple cartridge 5034 that is removably seated in the channel 5022, and a helical screw shaft 5036. The cutting instrument 5032 may be, for example, a knife. The anvil 5024 includes pivot pins 5025 that are movably supported in corresponding slots in the channel 5022. In one arrangement, the anvil 5024 includes a tab 5027 at its proximate end that is inserted into a component of the mechanical closure system (described further below) to open and close the anvil 5024.

Still referring to FIG. 7, the shaft 5008 includes a proximal closure tube 5040 and a distal closure tube 5042 pivotably linked by a pivot link 5044. The distal closure tube 5042 includes an opening 5045 into which the tab 5027 on the anvil 5024 is inserted in order to open and close the anvil 5024, as further described below. Disposed inside the closure tubes 5040, 5042 may be a proximate spine tube 5046. Disposed inside the proximate spine tube 5046 may be a main rotational (or proximate) drive shaft 5048 that communicates with a secondary (or distal) drive shaft 5050 via a bevel gear assembly 5052*a-c*. The secondary drive shaft 5050 is connected to a drive gear 5054 that engages a proximate drive gear 5056 of the helical screw shaft 5036. The vertical bevel gear 5052*b* may sit and pivot in an opening 5057 in the distal end of the proximate spine tube 5046. A distal spine tube 5058 may be used to enclose the secondary drive shaft 5050 and the drive gears 5054, 5056. Collectively, the main drive shaft 5048, the secondary drive shaft 5050, and the articulation assembly (e.g., the bevel gear assembly 5052*a-c*) are sometimes referred to herein as the "main drive shaft assembly."

A bearing 5038, positioned at a distal end of the staple channel 5022, receives the helical screw shaft 5036, allowing the helical screw shaft 5036 to freely rotate with respect to the channel 5022. The helical screw shaft 5036 may interface a threaded opening (not shown) of the knife 5032 such that rotation of the helical screw shaft 5036 causes the knife 5032 to translate distally or proximately (depending on the direction of the rotation) through the staple channel 5022.

Turning next to FIG. 8, the handle 5006 includes exterior lower side pieces 5059, 5060 and nozzle pieces 5061, 5062 that fit together to form, in general, the exterior of the handle 5006. A battery 5064, such as a Li ion battery, may be provided in the pistol grip portion 5026 of the handle 5006. The battery 5064 powers a motor 5065 disposed in an upper portion of the pistol grip portion 5026 of the handle 5006. The motor 5065 may drive a 90° bevel gear assembly 5066 comprising a first bevel gear 5068 and a second bevel gear 5070. The bevel gear assembly 5066 may drive a planetary gear assembly 5072. The planetary gear assembly 5072 may include a pinion gear 5074 connected to a drive shaft 5076. The pinion gear 5074 may drive a mating ring gear 5078 that drives a helical gear drum 5080 via a drive shaft. A ring 5084 may be threaded on the helical gear drum 5080. Thus, when the motor 5065 rotates, the ring 5084 is caused to travel along the helical gear drum 5080 by means of the interposed bevel gear assembly 5066, planetary gear assembly 5072 and ring gear 5078.

The handle 5006 may include a middle handle piece 5104 adjacent to the upper portion of the firing trigger 5020. The handle 5006 also may comprise a bias spring 5112 connected between posts on the middle handle piece 5104 and the firing trigger 5020. The bias spring 5112 may bias the firing trigger 5020 to its fully open position. In that way, when the operator releases the firing trigger 5020, the bias spring 5112 will pull the firing trigger 5020 to its open position. The distal end of the helical gear drum 5080 includes a distal drive shaft 5120 that drives a ring gear 5122, which mates with a pinion gear 5124. The pinion gear 5124 is connected to the main drive shaft 5048 of the main drive shaft assembly. In that way, rotation of the motor 5065 causes the main drive shaft assembly to rotate, which causes actuation of the end effector 5012. The ring 5084 threaded on the helical gear drum 5080 may include a post 5086 that is disposed within a slot 5088 of a slotted arm 5090. The slotted arm 5090 has an opening 5092 in its opposite end 5094 that receives a pivot pin 5096 that is connected between the handle exterior side pieces 5059, 5060. The pivot pin 5096 is also disposed through an opening 5100 in the firing trigger 5020 and an opening 5102 in the middle handle piece 5104.

The middle handle piece 5104 includes a backside shoulder 5106 that engages the slotted arm 5090. The middle handle piece 5104 also has a forward motion 5107 stop that engages the firing trigger 5020. The movement of the slotted arm 5090 is controlled by rotation of the motor 5065. When the slotted arm 5090 rotates counter clockwise as the ring 5084 travels from the proximate end of the helical gear drum 5080 to the distal end, the middle handle piece 5104 will be free to rotate counter clockwise. Thus, as the user draws in the firing trigger 5020, the firing trigger 5020 will engage the forward motion stop 5107 of the middle handle piece 5104, causing the middle handle piece 5104 to rotate counter clockwise. Due to the backside shoulder 5106 engaging the slotted arm 5090, however, the middle handle piece 5104 will only be able to rotate counter clockwise as far as the slotted arm 5090 permits. In that way, if the motor 5065 should stop rotating for some reason, the slotted arm 5090 will stop rotating, and the user will not be able to further draw in the firing trigger 5020 because the middle handle piece 5104 will not be free to rotate counter clockwise due to the slotted arm 5090.

Components of an exemplary closure system for closing (or clamping) the anvil 5024 of the end effector 5012 by retracting the closure trigger 5018 are also shown in FIG. 8. In the illustrated embodiment, the closure system includes a yoke 5250 connected to the closure trigger 5018. A pivot pin 5252 is inserted through aligned openings in both the closure trigger 5018 and the yoke 5250 such that they both rotate about the same point. The distal end of the yoke 5250 is connected, via a pin 5254, to a first closure bracket 5256. The first closure bracket 5256 connects to a second closure bracket 5258. Collectively, the closure brackets 5256, 5258 define an opening in which the proximate end of the proximal closure tube 5040 (see FIG. 7) is seated and held such that longitudinal movement of the closure brackets 5256, 5258 causes longitudinal motion by the proximal closure tube 5040. The instrument 5010 also includes a closure drive shaft 5260 disposed inside the proximal closure tube 5040. The closure drive shaft 5260 may include a window 5261 into which a post 5263 on one of the handle exterior pieces, such as exterior lower side piece 5059 in the illustrated embodiment, is disposed to fixedly connect the closure drive shaft 5260 to the handle 5006. In that way, the proximal closure tube 5040 is capable of moving longitudinally relative to the closure drive shaft 5260. The closure drive shaft 5260 may also include a distal collar 5267 that fits into a cavity in proximate spine tube 5046 and is retained therein by a cap.

In operation, when the yoke 5250 rotates due to retraction of the closure trigger 5018, the closure brackets 5256, 5258 cause the proximal closure tube 5040 to move distally (i.e., away from the handle end of the instrument 5010), which causes the distal closure tube 5042 to move distally, which causes the anvil 5024 to rotate about the pivot pins 5025 into the clamped or closed position. When the closure trigger 5018 is unlocked from the locked position, the proximal closure tube 5040 is caused to slide proximately, which causes the distal closure tube 5042 to slide proximately, which, by virtue of the tab 5027 being inserted in the opening 5045 of the distal closure tube 5042, causes the anvil 5024 to pivot about the pivot pins 5025 into the open or unclamped position. In that way, by retracting and locking the closure trigger 5018, an operator may clamp tissue between the anvil 5024 and channel 5022, and may unclamp the tissue following the cutting/stapling operation by unlocking the closure trigger 5018 from the locked position. Further details concerning the construction and operation of the existing surgical instrument 5010 may be found in U.S. Pat. No. 7,845,537, entitled SURGICAL INSTRUMENT HAVING RECORDING CAPABILITIES, the entire disclosure of which is hereby incorporated by reference herein. Other rotary drive arrangements configured for use with various forms of robotic systems are disclosed in U.S. Patent Application Publication No. 2016/0287251, entitled STAPLING END EFFECTOR CONFIGURED TO COMPENSATE FOR AN UNEVEN GAP BETWEEN A FIRST JAW AND A SECOND JAW, the entire disclosure of which is hereby incorporated by reference herein.

Figure 9:
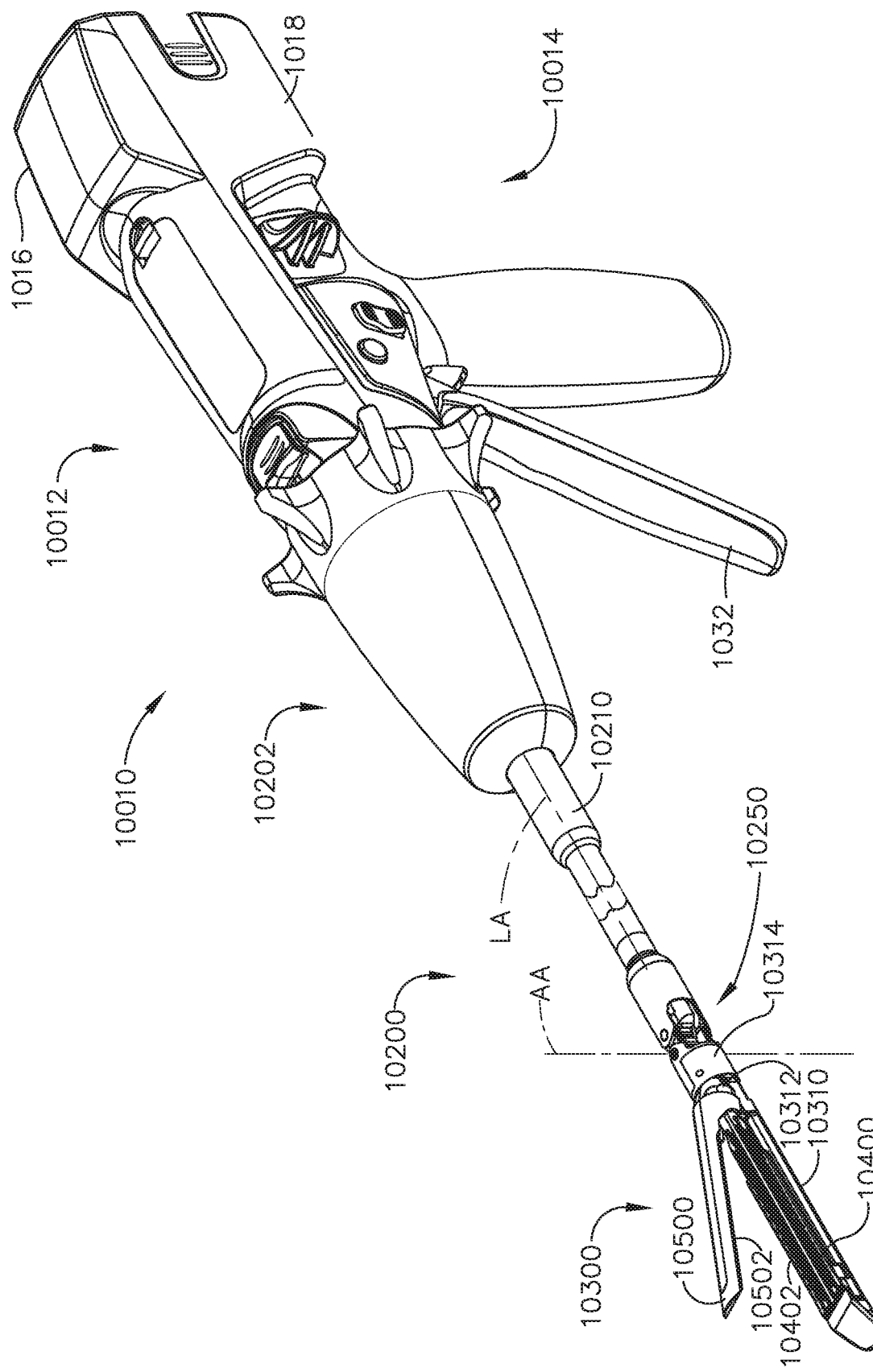
FIG. 9 is a perspective view of another powered surgical stapling system.
Figure 10:
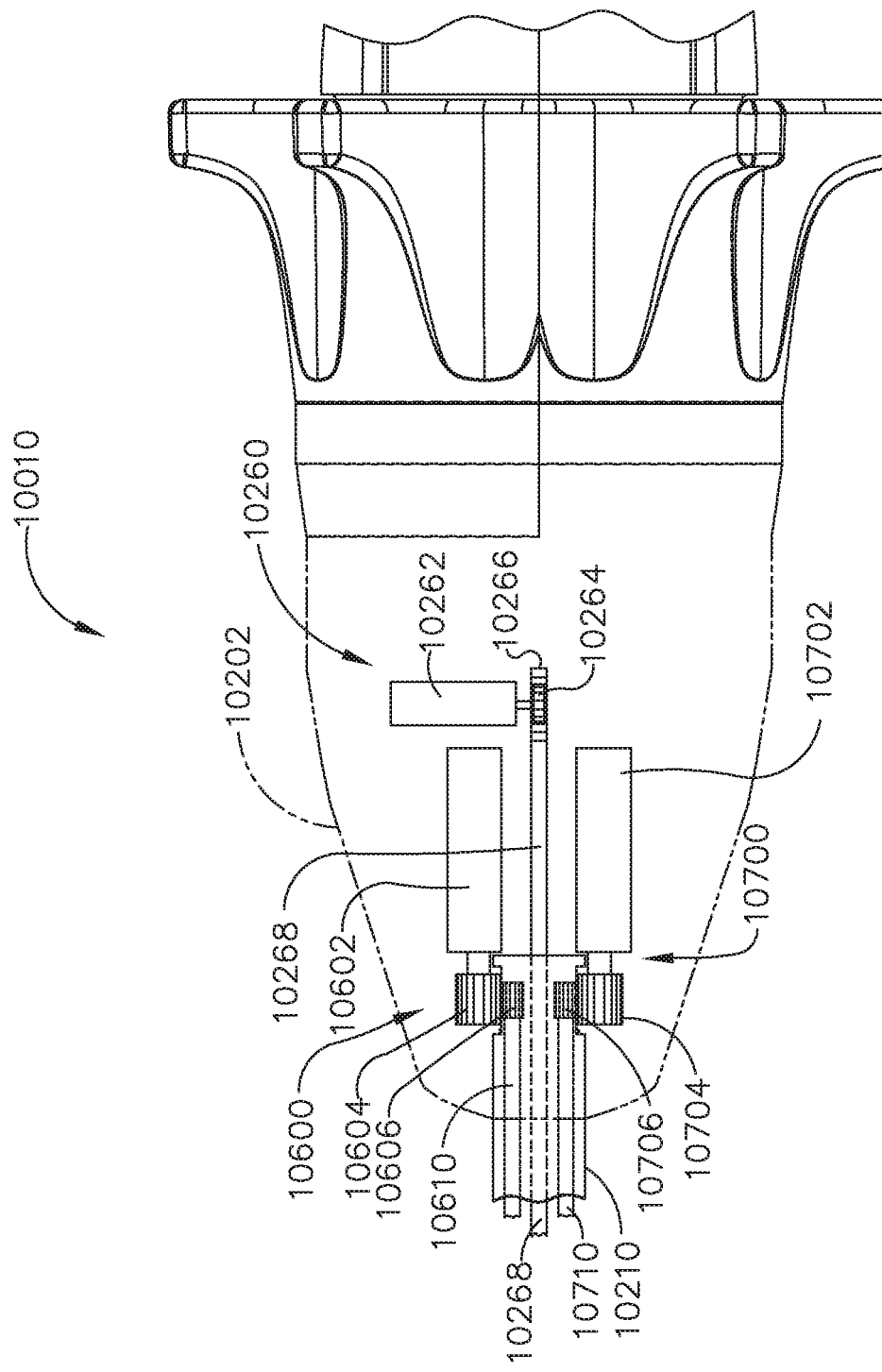
FIG. 10 is a top view of a portion of the powered surgical stapling system of FIG. 9.

Turning next to FIGS. 9 and 10, another motor-driven surgical cutting and fastening instrument 10010 that may or may not be reused is depicted. In the illustrated embodiment, the instrument 10010 includes a housing 10012 that comprises a handle 10014 that is configured to be grasped, manipulated and actuated by the clinician. As can be seen in FIG. 9 for example, the instrument 10010 includes a shaft assembly 10200 that has a surgical end effector 10300 operably coupled thereto that is configured to perform one or more surgical tasks or procedures. In one arrangement, the shaft assembly 10200 comprises an interchangeable shaft assembly that is intended to be removably couplable to the handle assembly 10014 in the various manners disclosed herein. However, the shaft assembly 10200 may also comprise a dedicated shaft assembly that is not intended to be removed from the handle 10014. Only those specific components necessary to understand the functions and operation of the shaft assembly 10200 will be discussed in further detail below.

As can be seen in FIG. 9, for example, the surgical end effector 10300 comprises an elongate channel 10310 that is configured to operably support a staple cartridge 10400 therein. The end effector 10300 also includes an anvil 10500 that is pivotally supported relative to the elongate channel 10310. In one arrangement, for example, the anvil 10500 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. The shaft assembly 10200 may further include an articulation joint 10250 that facilitates articulation of the surgical end effector 10300 about an articulation axis AA that is transverse to a longitudinal shaft axis LA. Other shaft assemblies, however, may not be capable of articulation. In the illustrated example, the shaft assembly 10200 comprises a proximal outer shaft tube or member 10210 that extends distally from a nozzle assembly 10202. A proximal end 10312 of the elongate channel comprises a tubular portion 10314 that is similar in size to the proximal outer shaft tube 10120 and is coupled to the distal end of the proximal outer shaft tube 10210 to form the articulation joint 10250. The articulation joint 10250 includes a double pivot shaft assembly 10252. See FIGS. 11 and 12. According to various forms, the tubular portion 10314 of the elongate channel 10310 includes upper and lower proximally projecting tangs 10316, 10318. See FIG. 11. An upper double pivot link 10320 includes upwardly projecting distal and proximal pivot pins that engage respectively an upper pin hole in the upper proximally projecting tang 10316 and an upper distal pin hole in an upper distally projecting tang 10212 on the proximal outer shaft tube 10210. A lower double pivot link 10322 includes downwardly projecting distal and proximal pivot pins that engage respectively a lower distal pin hole in the lower proximally projecting tang 10318 and a lower proximal pin hole in a lower distally projecting tang 10214 in the proximal outer shaft tube 10210. See FIG. 11. The shaft assembly 10200 also includes an internal spine member 10230 that is pivotally coupled to an insert assembly 10330 that is received within the tubular portion 10314 of the elongate channel 10310 and is attached thereto by, for example, welding, adhesive, fasteners, etc. A proximal end of the internal spine member 10230 may be rotatably coupled to a chassis (not shown) within the nozzle assembly 10202 in the various manners disclosed herein, for example. The distal end of the internal spine member 10230 may be pinned to the insert assembly 10330 to facilitate pivotal travel of the elongate channel 10310 relative to the internal spine member 10230.

Figure 12:
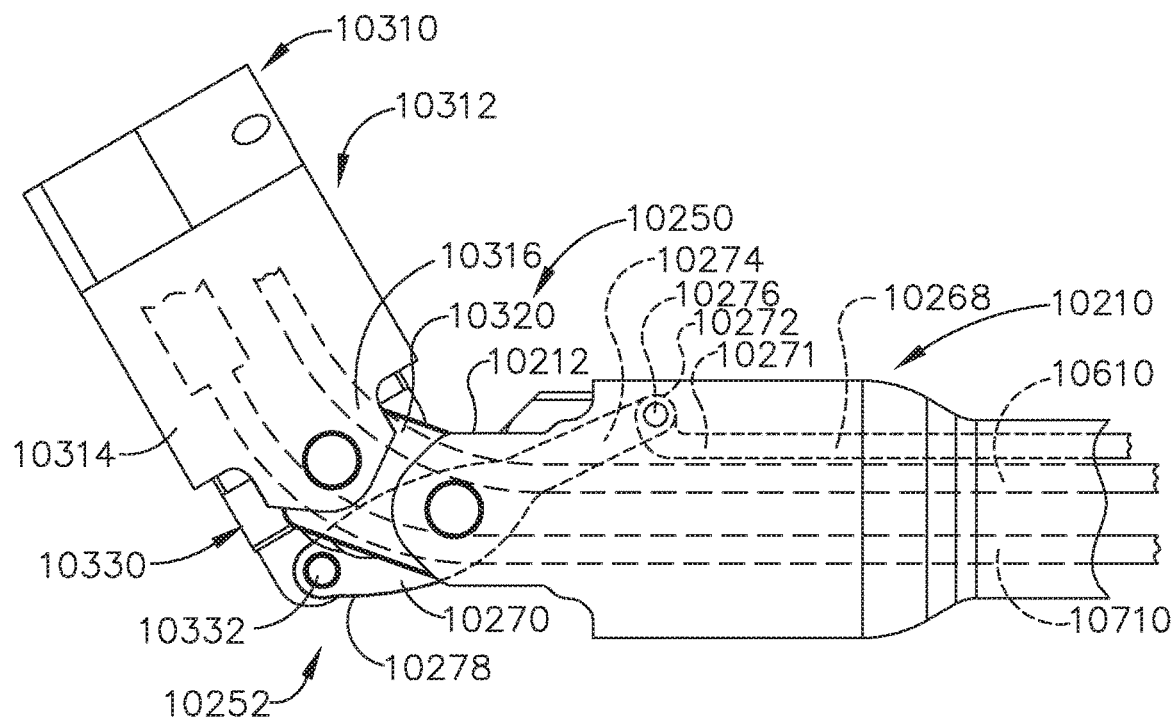
FIG. 12 is a top view of the articulation joint of FIG. 11.

In the illustrated example, the surgical end effector 10300 is selectively articulatable about the articulation axis AA by an articulation system 10260. In one form, the articulation system 10260 includes an articulation motor 10262 that is operably supported in the nozzle assembly 10202, for example. See FIG. 10. In other examples, the articulation motor 10262 may be operably supported in the housing 10012 or handle 10014 or other portion of a robotic system. Referring to FIG. 10, the articulation motor 10262 is coupled to an articulation drive gear 10264 that is in meshing engagement with a drive gear rack 10266 that is attached to or otherwise formed in a proximal articulation driver 10268. A distal end of the proximal articulation driver 10268 is pivotally coupled to a distal articulation link 10270. As can be seen in FIG. 12, an offset attachment lug 10272 is formed on a distal end 10271 of the proximal articulation driver 10268. A pivot hole is formed in the offset attachment lug 10272 and is configured to pivotally receive therein a proximal link pin 10276 formed on the proximal end 10274 of the distal articulation link 10270. A distal end 10278 of the distal articulation link 10270 includes a pivot hole that is configured to pivotally receive therein a channel pin 10332 formed on the insert assembly 10330. Operation of the articulation motor 10262 will cause axial movement of the proximal articulation driver 10268. Axial movement of proximal articulation driver 10268 will apply articulation motions to the elongate channel 10310 to thereby cause the surgical end effector 10300 to articulate about the articulation axis AA relative to the internal spine member 10230. Other articulation systems and arrangements may be employed in the various manners disclosed herein. In other embodiments, the surgical end effector may not be articulatable.

In at least one arrangement, the surgical end effector 10300 includes a firing member that is axially movable within the surgical end effector 10300 between a starting position and an ending position. As will be discussed in further detail below, the firing member may be configured to sever tissue that is clamped between the anvil 10500 and a surgical staple cartridge 10400 that is operably supported in the elongate channel 10310. In one arrangement, the staple cartridge 10400 includes lines of surgical staples or fasteners that are operably supported on corresponding drivers that are movably supported in the cartridge. As the firing member is driven distally, the firing member cooperates with a sled or camming assembly that is supported in the staple cartridge that serves to advance the drivers in a direction toward the closed anvil which causes the staples or fasteners supported thereon to pierce through the clamped tissue into forming contact with the underside of the closed anvil. Once the firing member has been distally advanced from its proximal starting position to its ending position within the end effector, it may be retracted back to its starting position to permit the anvil to be opened to facilitate removal of the cut/stapled tissue from the end effector. In other arrangements, the firing member may be left at the ending position wherein it is permitted to disengage from the anvil to facilitate opening of the anvil.

Figure 11:
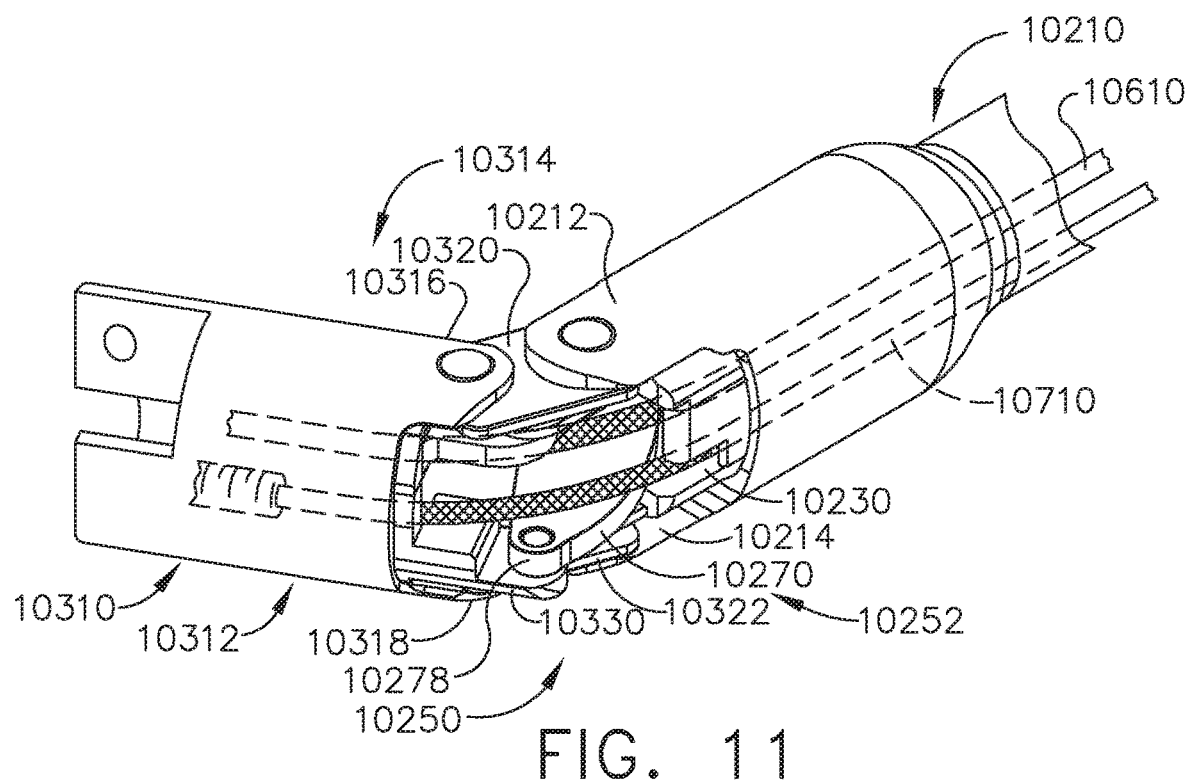
FIG. 11 is a partial perspective view of an articulation joint of the shaft assembly of the surgical stapling system of FIG. 9.

In at least one arrangement, the surgical instrument 10010 also employs a firing system 10600 that is configured to apply rotary drive motions to the firing member to drive the firing member between the starting and end positions. In the example depicted in FIG. 10, the firing system 10600 includes a firing motor 10602 that is operably supported in the nozzle assembly 10202, for example. In other examples, the firing motor 10602 may be operably supported in the housing or handle or other portion of a robotic system. The firing motor 10602 is coupled to a firing drive gear 10604 that is in meshing engagement with a driven gear 10606 that is attached to or otherwise formed in rotary firing drive shaft 10610. As can be seen in FIGS. 11 and 12, the firing drive shaft 10610 may be flexible to permit articulation of the surgical end effector 10300 in the manner described above.

Figure 13:
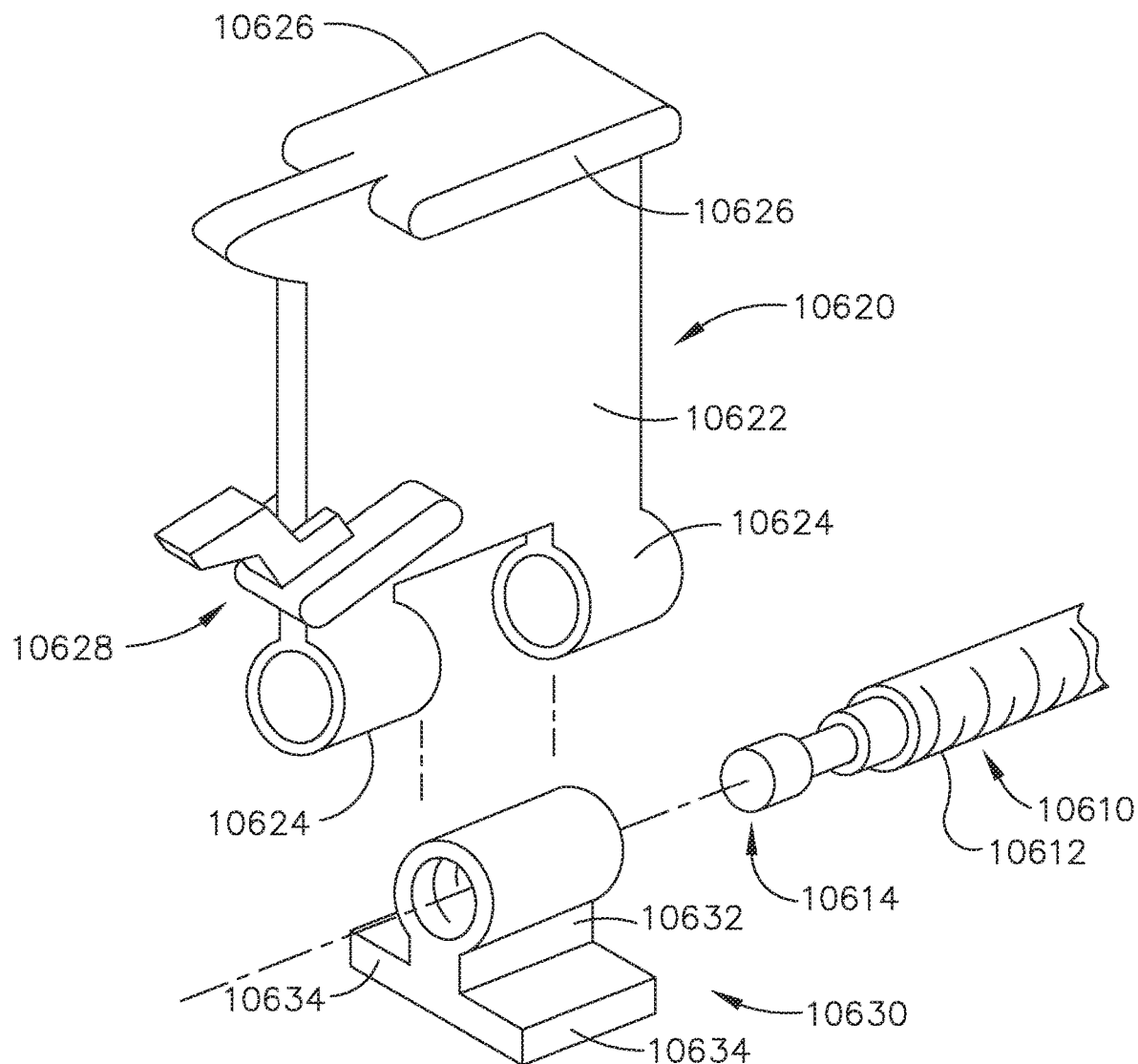
FIG. 13 is a perspective assembly view of a firing member and a firing drive shaft.

FIG. 13 depicts one example of a rotary driven firing member 10620 that may be employed in the surgical end effector 10300. As can be seen in FIG. 13, the firing member 10620 comprises a body portion 10622 that includes two downwardly extending hollow mounting portions 10624 that are unthreaded and spaced from each other to receive a threaded drive nut 10630 therebetween. The threaded drive nut 10630 is threaded onto a threaded portion 10612 of the rotary firing drive shaft 10610. A distal end 10614 of the rotary firing drive shaft 10610 may be configured to be rotatably supported in a bearing (not shown) that is housed within the elongate channel and is configured to rotatably support the rotary firing drive shaft 10610 therein. The drive nut 10630 includes a vertical tab portion 10632 that is sized to extend through an axial slot in the bottom of the elongate channel. Two laterally extending channel engagement flanges 10634 are formed on the threaded drive nut 10630 and are configured to engage the bottom of the elongate channel. In addition, two laterally extending anvil engagement tabs 10626 are formed on the top of the firing member body 10622 and are configured to engage corresponding ledges formed in the anvil 10500 as the firing member 10620 is axially moved within the end effector 10300. In this arrangement, the firing member 10620 includes a camming sled engagement feature 10628 that is configured to operably engage a camming assembly that is movably stored in the staple cartridge. The camming sled or camming assembly (not shown) may include a tissue cutting member or a tissue cutting feature attached to the firing member 10620. The firing member 10620 may be stored within an unfired staple cartridge and is configured to be seated on the threaded drive nut 10630 when the cartridge is operably installed within the elongate channel. However, a variety of other rotary driven firing member arrangements may also be employed. For example, firing and tissue cutting members that are permanently threaded onto the rotary firing drive shaft may also be employed. In various aspects, as the firing member 10620 is distally driven through the surgical staple cartridge 10400, the firing member 10620, through the engagement of the anvil engagement tabs 10626 with the anvil 10500 and the engagement of the channel engagement flanges 10634 with the channel 10310, may serve to maintain a desired amount of tissue gap between a deck surface 10402 on the staple cartridge 10400 and a staple forming undersurface 10502 on the anvil 10500. See FIG. 9.

In the example depicted in FIGS. 10-21, in addition to a rotary driven firing system, the surgical instrument 10010 also includes a rotary driven closure system 10700 that is configured to apply rotary closure motions to the anvil 10500. As can be seen in FIG. 10, for example, in one arrangement, the rotary driven closure system 10700 comprises a closure motor 10702 that is operably supported in the nozzle assembly 10202, for example. In other examples, the closure motor 10702 may be operably supported in the housing or handle or other portion of a robotic system. The closure motor 10702 is coupled to a closure drive gear 10704 that is in meshing engagement with a driven gear 10706 that is attached to or otherwise formed in rotary closure drive shaft 10710. As can be seen in FIGS. 11 and 12, the closure drive shaft 10710 may be flexible to permit articulation of the surgical end effector 10300 in the manner described above.

In the illustrated example, the surgical end effector 10300 includes the anvil 10500 that includes a proximally-extending mounting tab 10510 that is configured to be pivotally attached to a distal insert portion 10334 of the insert assembly 10330. In alternative arrangements, the distal insert portion 10334 may be separate from the insert assembly 10330 and otherwise be attached to the proximal end portion 10312 of the elongate channel 10310 by welding, adhesive, fasteners, etc. In still other arrangements, the distal insert portion 10334 may actually comprise a portion of the elongate channel 10310 and be integrally formed therewith. In the illustrated arrangement, the anvil mounting tab 10510 includes a distal portion 10512 through which a transverse slot 10514 extends therethrough and is aligned with a transverse slot 10336 in the distal insert portion 10334 as well as a slot 10315 in the tubular portion 10314 of the elongate channel 10310. See FIG. 18. The anvil mounting tab 10510 is pivotally attached to the elongate channel 10310 by a rivet 10340. The anvil mounting tab 10510, as well as the distal insert portion 10334, are sufficiently robust to provide a sufficient amount of strength where the rivet 10340 operates which provides the ability to locate the pivoting attachment point above the centerline or midpoint of the end effector and thereby afford sufficient room therein for the firing member components and rotary drive components. Orbit forming of the rivet 10340 pivotally cinches the anvil mounting tab 10510 to the elongate channel 10310 and can remove excessive play or movement (tolerance slop) which serves to place the rivet 10340 in complete or significantly complete shear for resistance against closure loads. In addition, the relatively broad contact between such components may also serve to prevent or minimize twisting between the anvil mounting tab 10510 and the elongate channel 10310.

Figure 14:
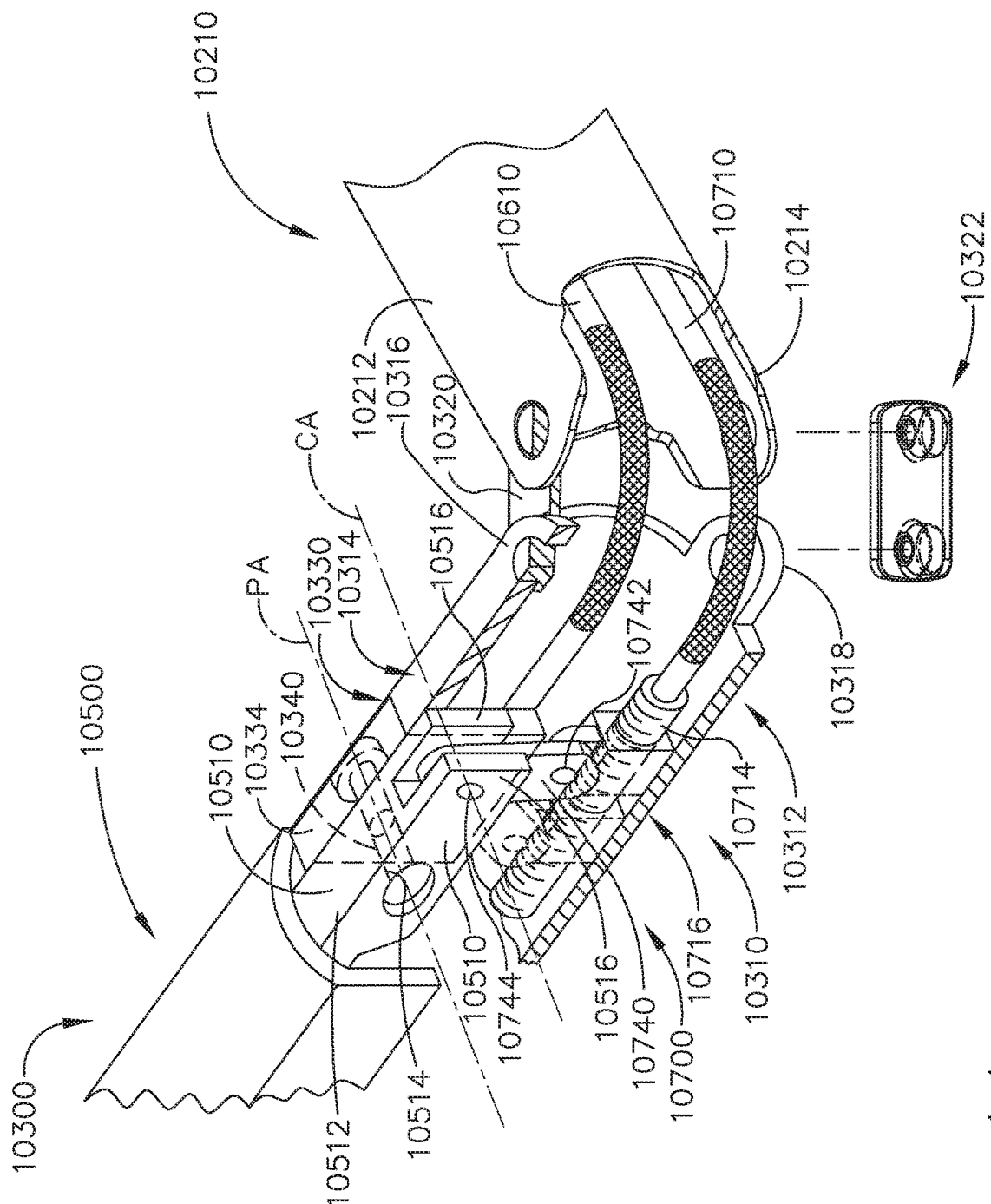
FIG. 14 is a perspective view of portions of an end effector and articulation joint of the powered surgical stapling system of FIG. 9.
Figure 15:
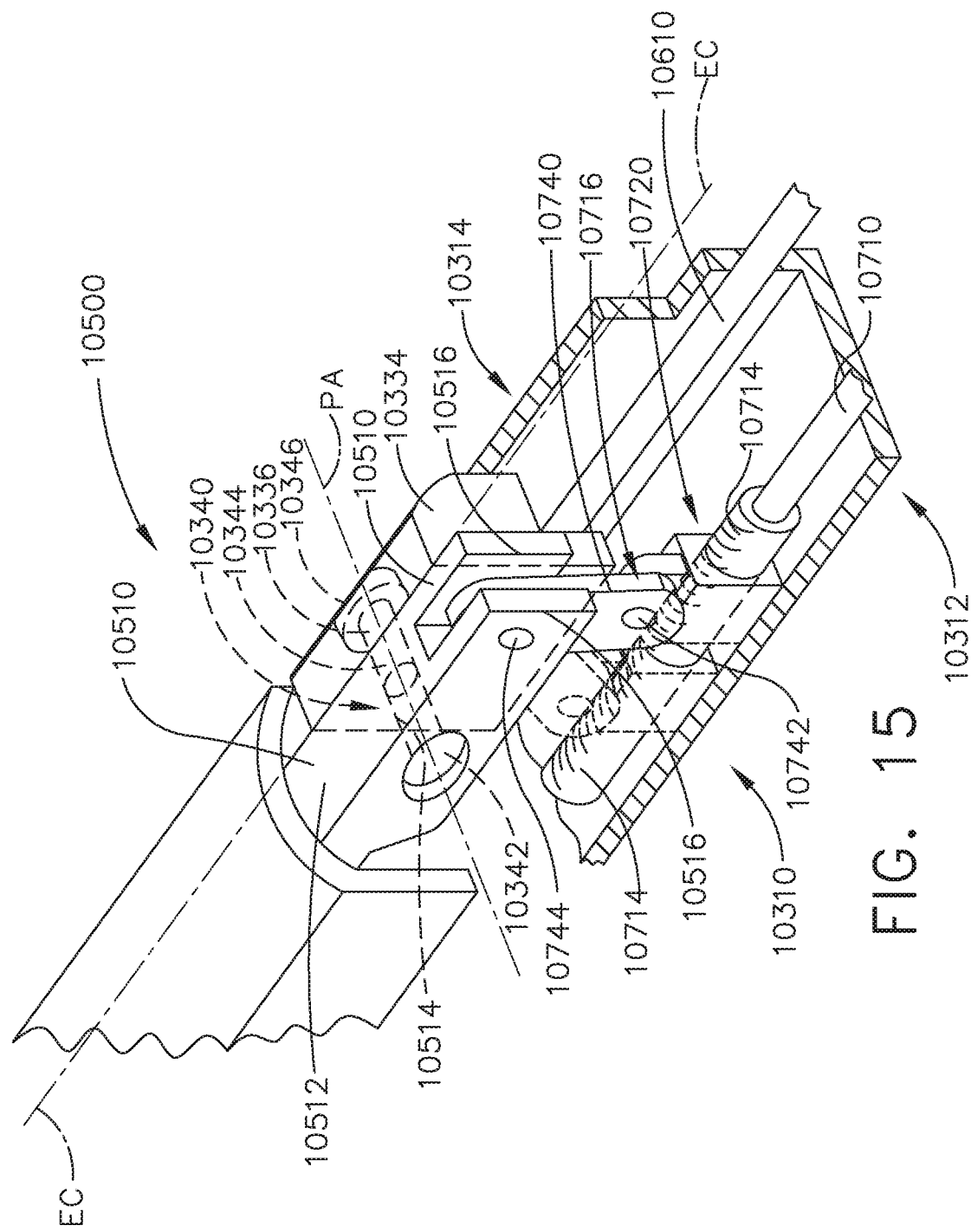
FIG. 15 is another perspective view of the end effector and articulation joint of FIG. 14.
Figure 16:
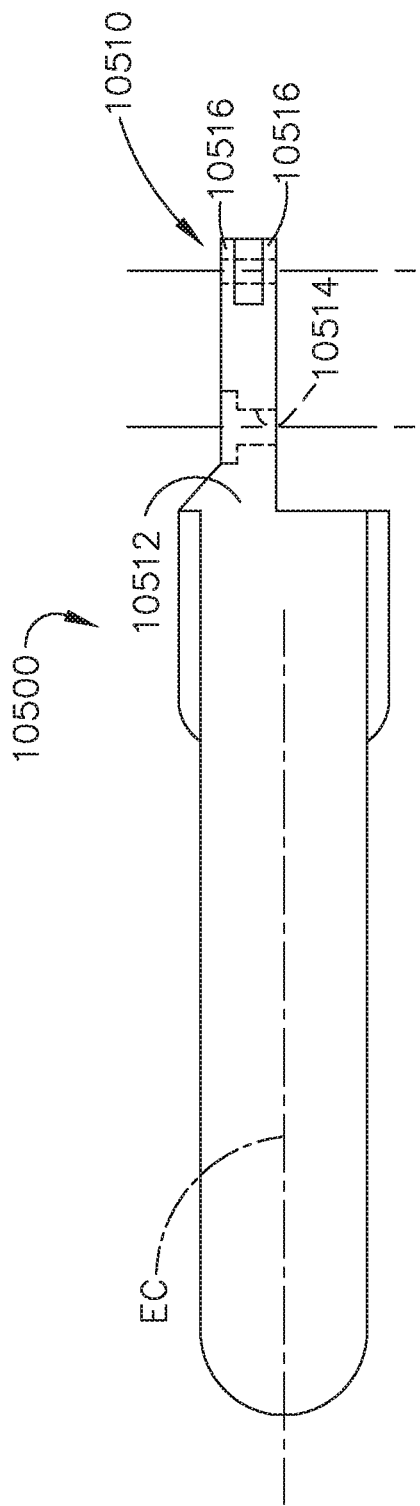
FIG. 16 is a top view of an anvil of the end effector of FIG. 14.
Figure 17:
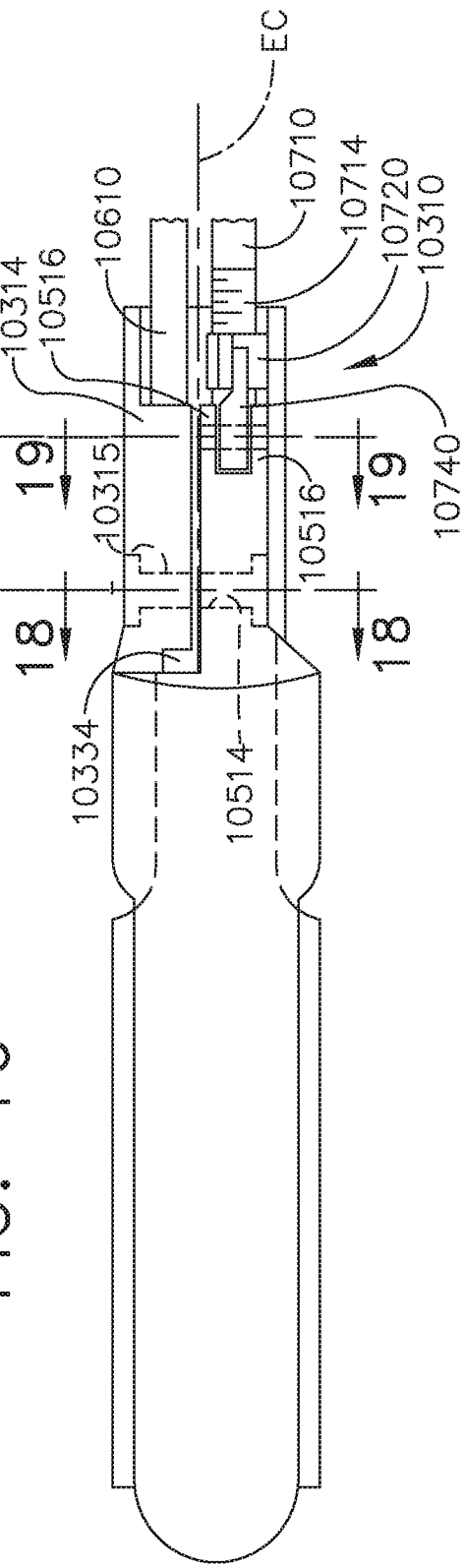
FIG. 17 is another top view of the anvil of FIG. 16 attached to an elongate channel of the end effector of FIG. 14.

As can be seen in FIGS. 14, 15 and 17, the anvil 10500 is asymmetrically coupled to the elongate channel 10310. Stated another way, the location in which the anvil 10500 is attached to the elongate channel 10310 is laterally offset from the end effector centerline EC. In at least one arrangement, the rivet 10340 comprises solid core rivet with a diameter of 0.05"-0.1" and an orbit formed head 10342 on one end of the rivet shank 10344 and a machined head 10346 on the other end of the rivet shank 10344. In one arrangement, the riveting is done in such a way that the rivet 10340 would hold a final formed height that would ensure intimate contact between the anvil mounting tab 10510 and the corresponding attachment portions of the elongate channel 10310. The "orbit formed" head 10342 would swell the rivet shank 10344 on that side of the anvil mounting tab 10510 and elongate channel portions which may prevent the rivet from rotating relative to that part while the other "pre-machined" side 10346 would not have a swelled shank portion which may permit the adjacent components to rotate. In one example, the rivet 10340 is fixed relative to the channel portion to avoid a condition wherein the anvil pivots freely relative to the insert and elongate channel.

Figure 20:
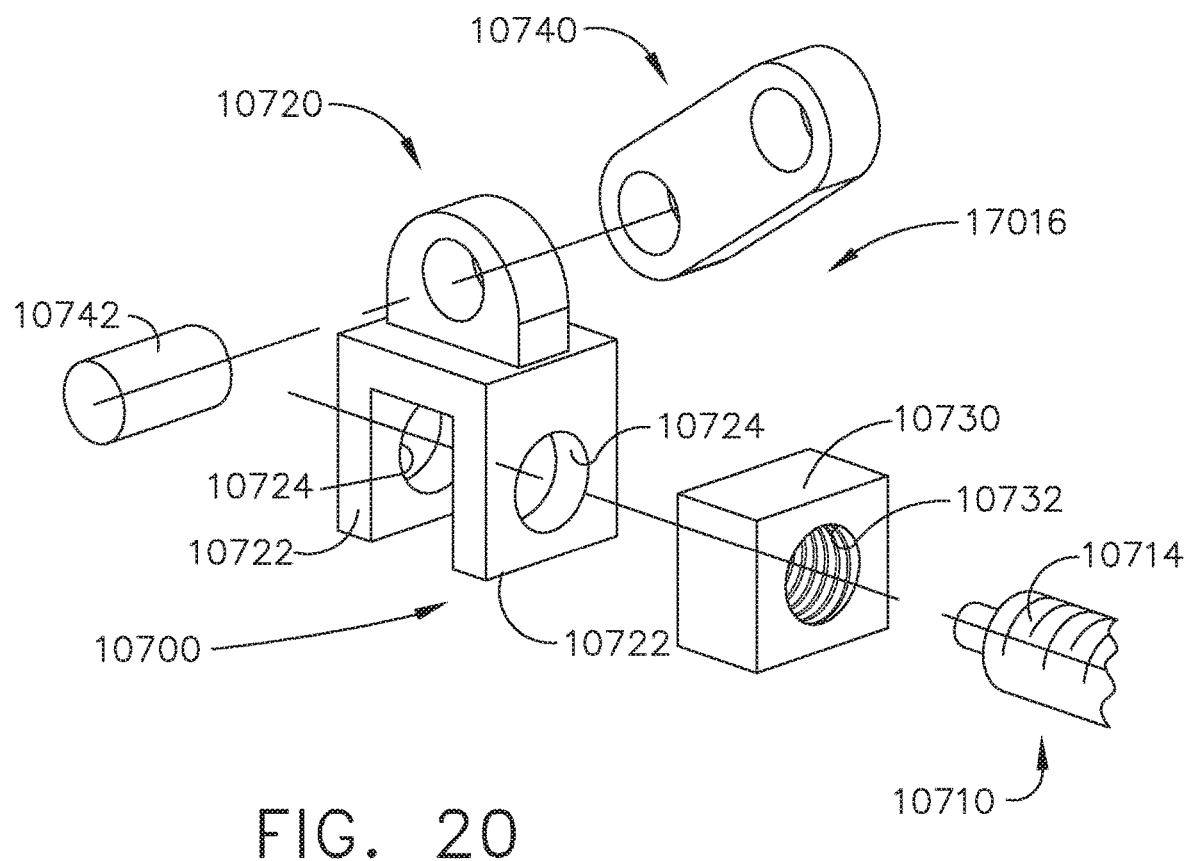
FIG. 20 is an exploded assembly view of a closure linkage assembly of the end effector of FIG. 14 and a closure drive shaft.
Figure 21:
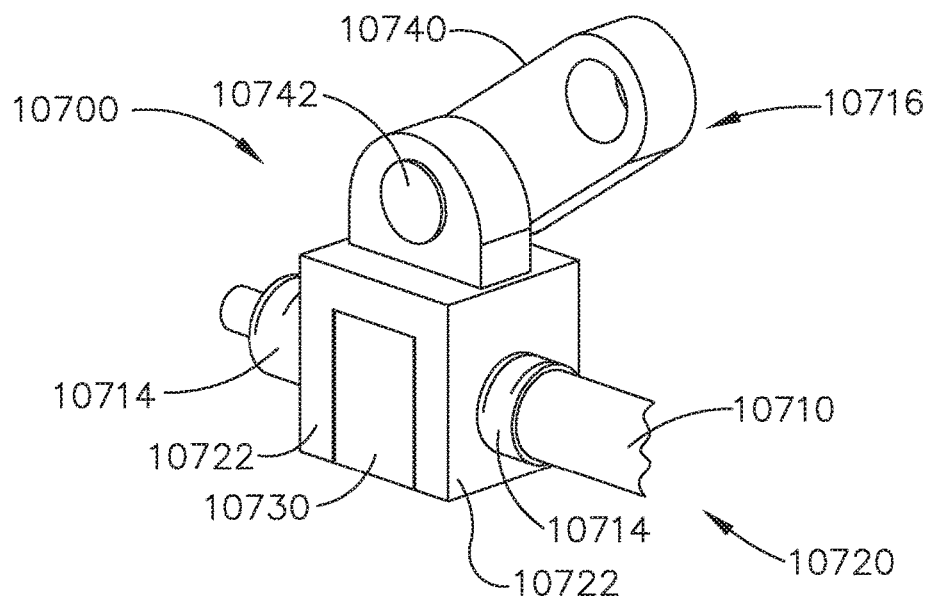
FIG. 21 is a perspective view of the closure linkage assembly and closure drive shaft of FIG. 20.

The example illustrated in FIGS. 10-19 employs a rotary actuated closure system 10700 that is configured to apply opening and closure motions to the anvil 10500. In one arrangement, closure system 10700 comprises a closure linkage assembly 10716 that is pivotally coupled to the anvil mounting tab 10510 for pivotal travel relative thereto about a common closure axis CA. As can be seen in FIGS. 19 and 20, the closure drive shaft 10710 comprises a threaded drive segment 10714 that is configured to threadably engage a drive nut 10730 that is supported by a drive yoke 10720. The drive yoke 10720 includes two yoke arms 10722 that have unthreaded holes 10724 therethrough to permit the closure drive shaft 10710 to pass therethrough. The drive nut 10730 has a threaded hole 10732 therethrough that is threaded onto the threaded drive segment 10714 of the closure drive shaft 10710 and is received between the yoke arms 10722. A closure link 10740 is pivotally coupled to the drive yoke 10720 by a pin 10742. The closure link 10740 is also pivotally attached (pinned) to the anvil mounting tab 10510 by a pin 10744. See FIG. 19. As can be seen in FIG. 19, a spacer member 10746 is provided to fill the space between the closure link 10740 and spaced arms 10516 of the anvil mounting tab 10510. Alternatively, the closure link may be sized and shaped to fill in that space. As can be further seen in FIG. 19, a retainer tab 10311 is formed in the elongate channel 10310 to define an axial trough 10313 for slidably receiving the drive yoke 10720 therein. Rotation of the rotary closure drive shaft 10710 in a first rotary direction will cause the drive yoke 10720 to move distally and cause the closure link 10740 to pull the anvil mounting tab 10510 in an opening direction which causes the anvil 10500 to pivot to an open position about the pivot axis PA. Likewise, rotation of the rotary closure drive shaft 10710 in a second rotary direction will cause the drive yoke 10720 to move proximally and cause the closure link 10740 to push the anvil mounting tab 10510 in a closing direction which causes the anvil 10500 to pivot to a closed position about the pivot axis PA. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 22:
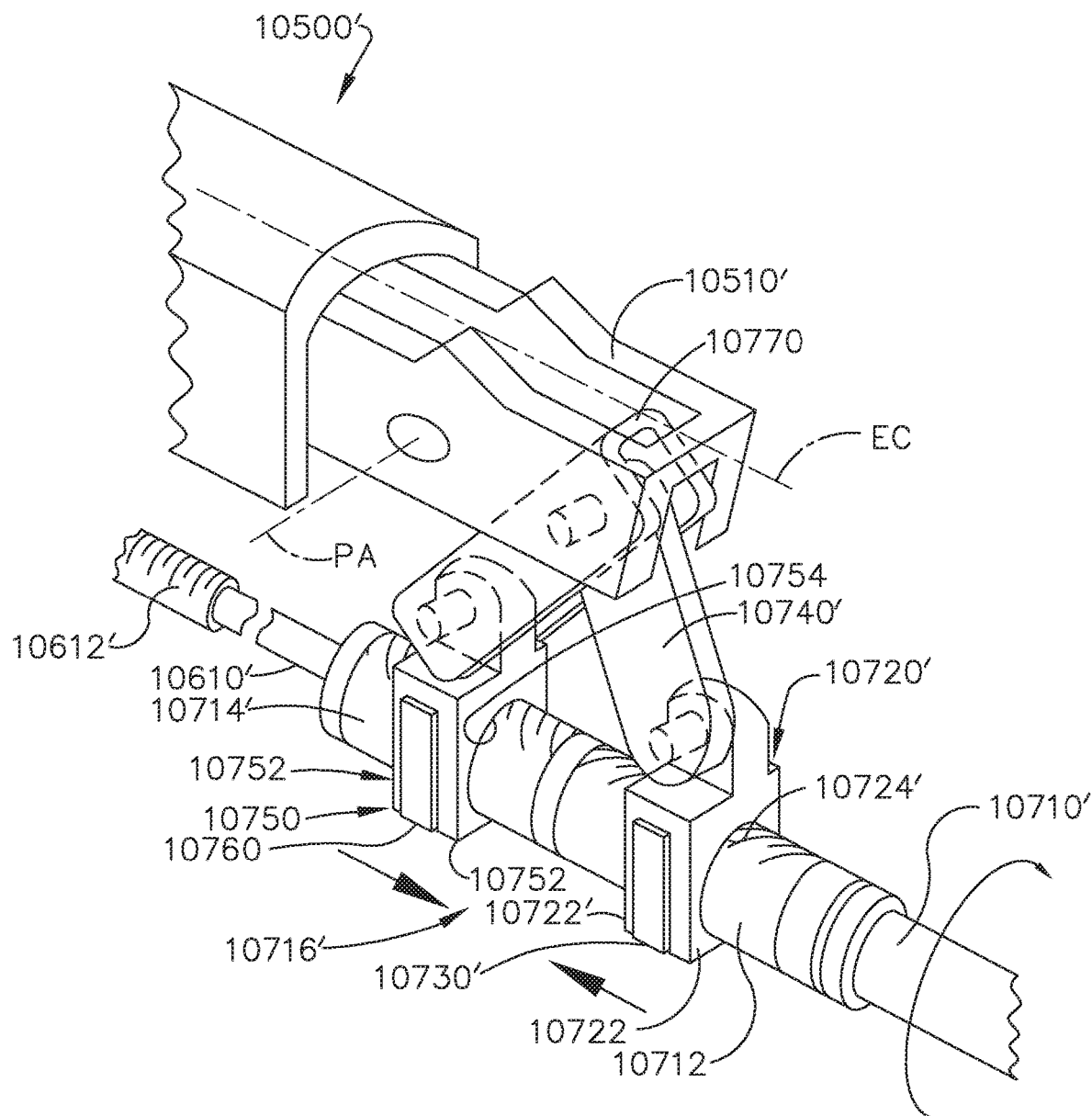
FIG. 22 is a partial perspective view of an anvil, closure linkage assembly, and closure drive shaft of another rotary powered surgical end effector.
Figure 23:
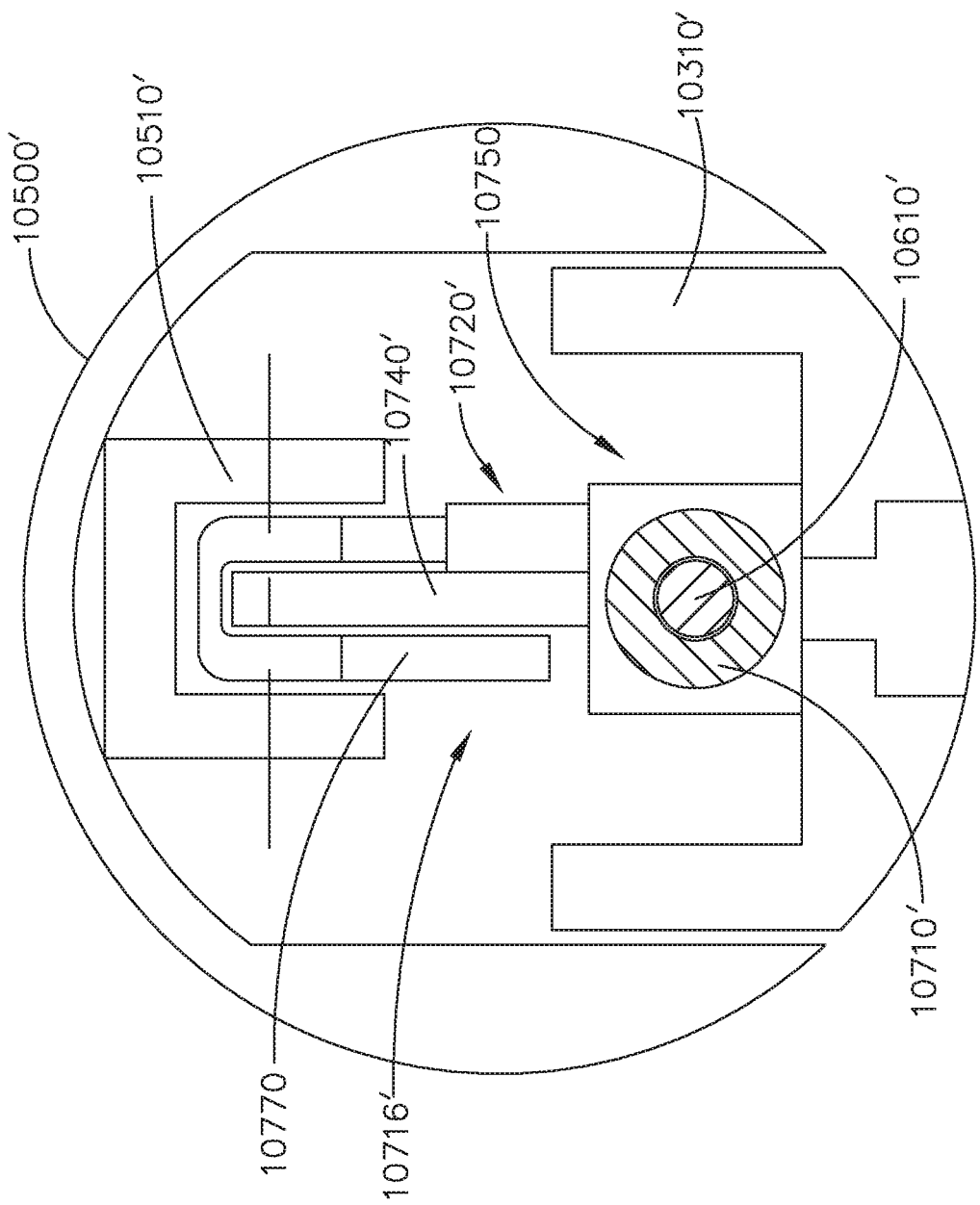
FIG. 23 is a partial end elevational view of the anvil, closure linkage assembly, and closure drive shaft of FIG. 22, with the drive shaft shown in cross-section.

FIGS. 22 and 23 illustrate an alternate closure drive arrangement wherein the anvil mounting tab 10510' of the anvil 10500' is generally centrally supported within the end effector. The anvil mounting portion 10510' may be pivotally coupled to the elongate channel 10310' in the manner described above. In this arrangement, the rotary closure drive shaft 10710' is hollow and concentrically supports the rotary firing shaft 10610' therein. The rotary closure drive shaft 10710' and the rotary firing drive shaft 10610' are centrally disposed within the elongate channel 10310' as can be seen in FIG. 23. The rotary firing drive shaft 10610' rotatably extends through the rotary closure drive shaft 10710' and includes a distal threaded portion 10612' that is configured to threadably drive the firing member 10620 in the manner described above, for example.

The example illustrated in FIGS. 22 and 23 employs a rotary actuated closure linkage assembly 10716' that is configured to apply opening and closure motions to the anvil 10500'. In one arrangement, the closure linkage assembly 10716' comprises a proximal drive yoke assembly 10720' and a distal drive yoke assembly 10750. The proximal drive yoke assembly 10720' includes two spaced yoke arms 10722' that have unthreaded holes 10724' therethrough to permit the closure drive shaft 10710' to pass therethrough. A proximal drive nut 10730' is received between the spaced yoke arms 10722' and includes a threaded hole for threadably engaging a proximal thread segment 10712' on the rotary closure drive shaft 10710'. The proximal drive yoke assembly 10720' is pivotally coupled to a proximal closure link 10740' that is pivotally pinned to the anvil mounting portion 10510'. The distal drive yoke assembly 10750 includes two spaced yoke arms 10752 that have unthreaded holes 10754 therethrough to permit the closure drive shaft 10710' to pass therethrough. A distal drive nut 10760 is received between the spaced yoke arms 10752 and includes a threaded hole for threadably engaging a distal thread segment 10714' on the rotary closure drive shaft 10710'. The proximal threaded segment 10712' and the distal threaded segment 10714' are thread in opposite directions. The distal drive yoke assembly 10750 is pivotally coupled to a U-shaped distal closure link 10770 that is pivotally pinned to the anvil mounting portion 10510'. The U-shaped distal closure link 10770 affords the closure linkage assembly 10716' with a symmetric load bearing arrangement. Rotation of the rotary closure drive shaft 10710' in a first rotary direction will cause the proximal drive yoke 10720' and the distal drive yoke assembly 10750 to axially move away from each other to pull the anvil mounting tab 10510' in an opening direction causing the anvil 10500' to pivot to an open position about the pivot axis PA. Likewise, rotation of the rotary closure drive shaft 10710' in a second rotary direction will cause the proximal drive yoke 10720' and distal drive yoke assembly 10750 to move towards each other and push the anvil mounting tab 10510' in a closing direction causing the anvil 10500' to pivot to a closed position about the pivot axis PA. Such arrangement may serve to apply generally higher closure forces to the anvil 10500'. It will be appreciated that the rotary firing drive shaft 10610' is independently rotatable relative to the rotary closure drive shaft 10710'. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 24:
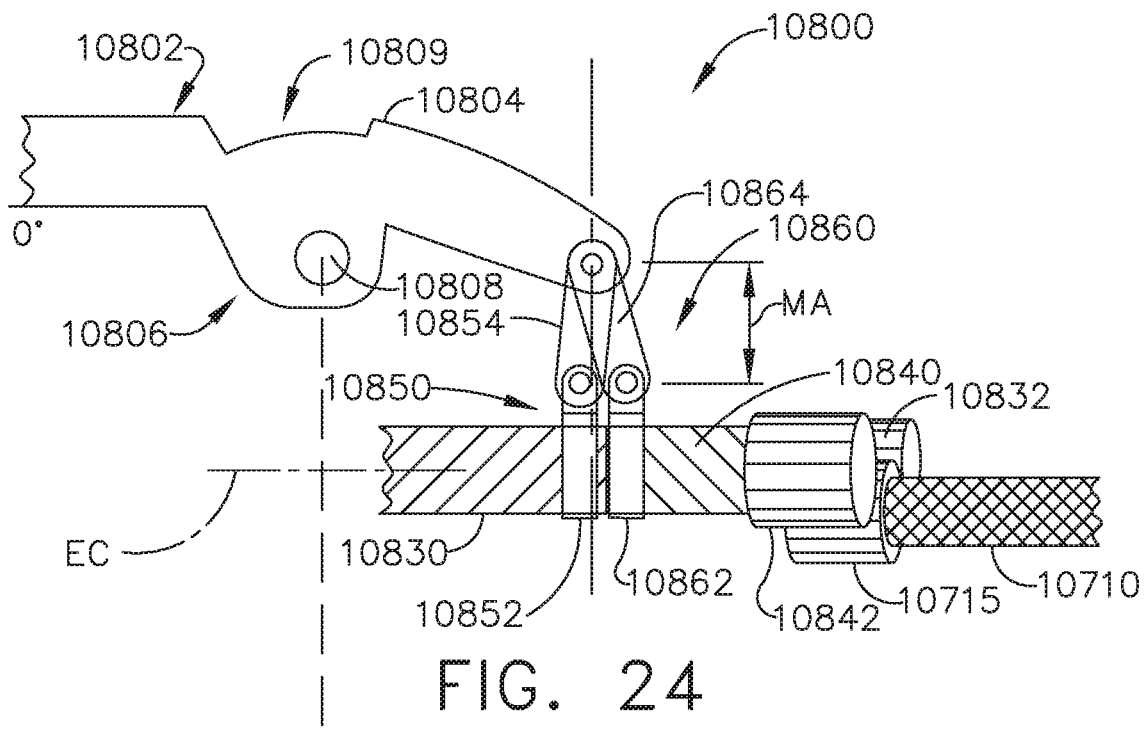
FIG. 24 is a side elevational view of an anvil, closure linkage assembly, rotary firing drive shaft, and closure drive shaft of another rotary powered surgical end effector with an anvil thereof in a closed position.
Figure 25:
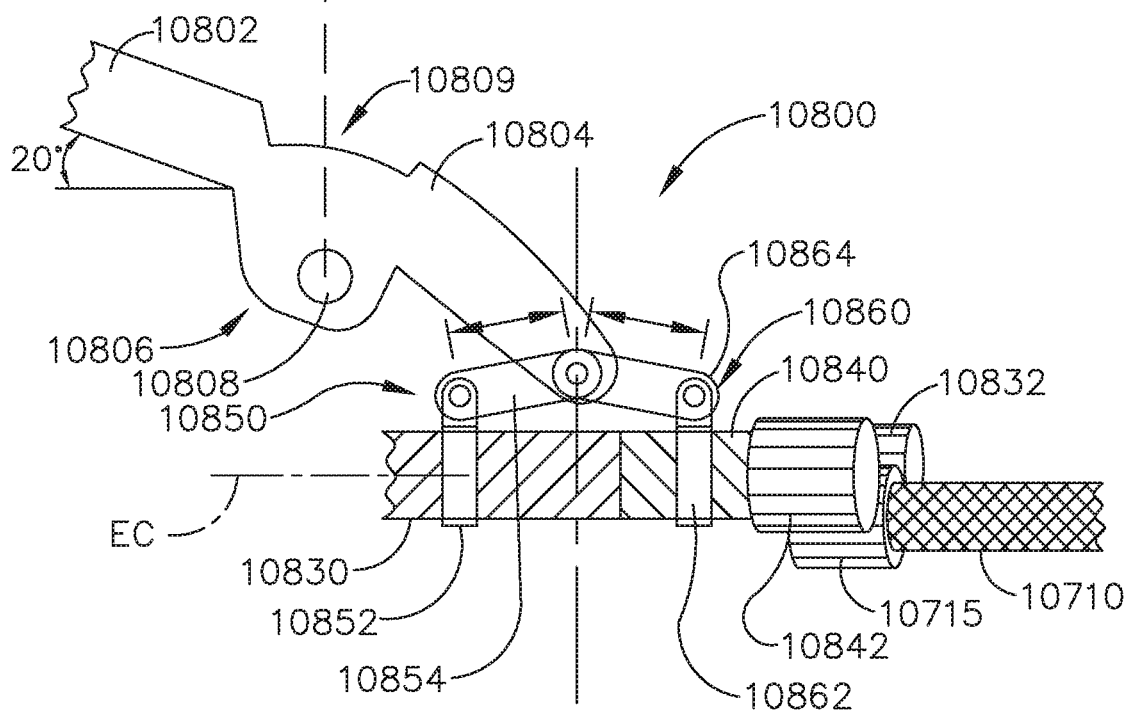
FIG. 25 is another side elevational view of the anvil, closure linkage assembly, rotary firing drive shaft, and closure drive shaft of FIG. 24 with the anvil in an open position.
Figure 28:
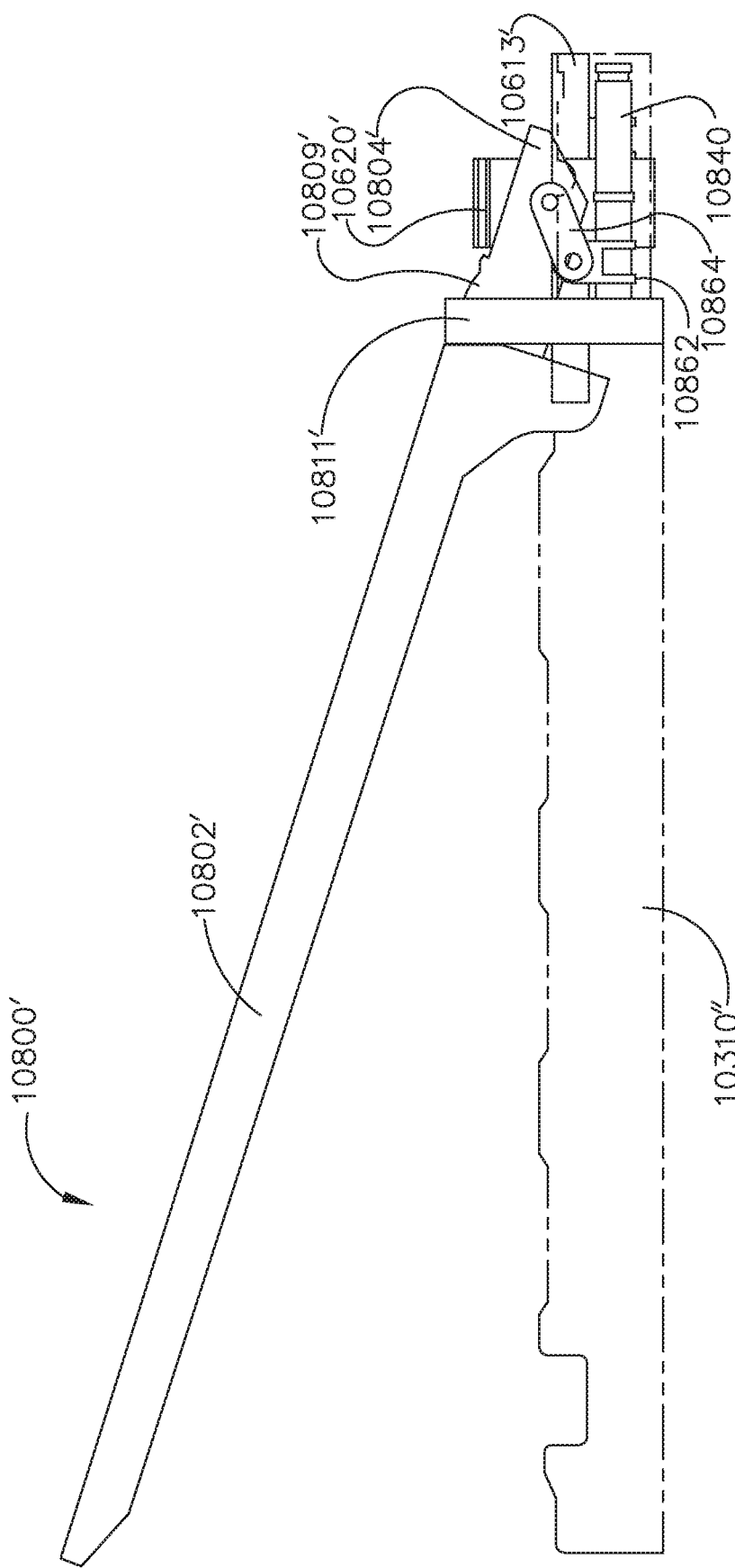
FIG. 28 is a side elevational view of a portion of another rotary powered surgical end effector with an anvil thereof in an open position.
Figure 29:
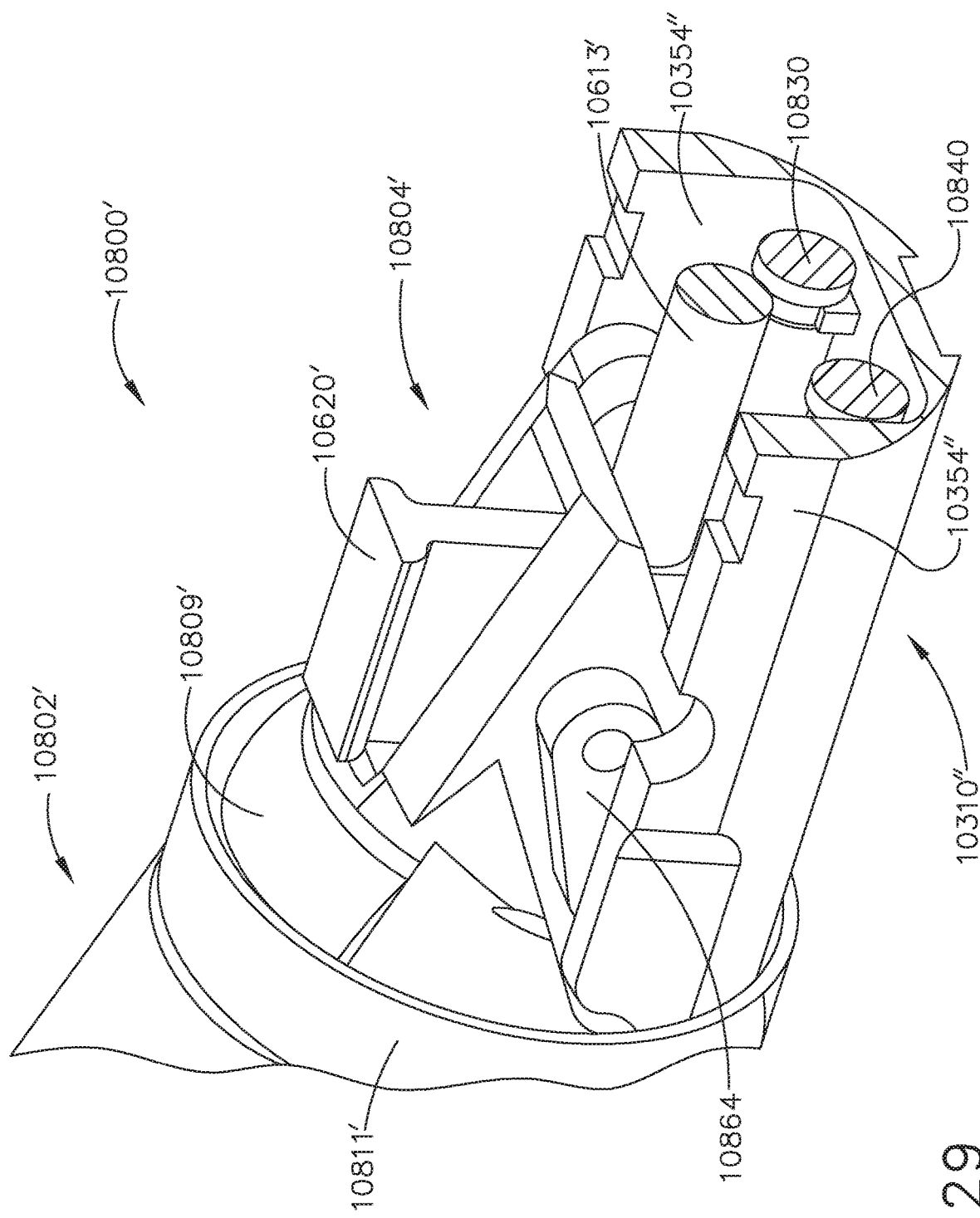
FIG. 29 is an enlarged partial perspective view of a portion of the rotary powered surgical end effector of FIG. 28.

FIGS. 24-27 illustrate an another surgical end effector 10800 that employs a closure drive arrangement wherein an anvil mounting tab 10804 of an anvil 10802 is centrally supported within the end effector 10800 and two rotary closure shafts 10830 and 10840 are employed to apply closure motions to the anvil 10802. In this arrangement, a distal portion 10806 of the anvil mounting tab 10804 includes a pair of laterally extending pivot members 10808 that are adapted to be pivotally cradled in pivot cradles 10356 in upstanding walls 10354 of a distal mounting portion of the elongate channel 10310". See FIG. 27. Thus, the pivot members 10808 are vertically movable or "floatable" within their corresponding pivot cradles 10356. In this arrangement, the rotary firing drive shaft 10610 (FIG. 26) is vertically supported above the rotary closure drive shaft 10710 (FIGS. 24 and 25). In the illustrated example, the rotary firing drive shaft 10610 includes a firing drive gear 10611 that is configured to drivingly engage a driven gear (not shown) on a distal firing drive shaft 10613 that is rotatably supported in the elongate channel 10310" in the various manners described herein. See FIG. 27. A firing member drive nut 10630 is threaded on the distal firing drive shaft 10613 and serves to drive a firing member 10620 within the end effector 10800 as the rotary firing drive shaft 10610 is rotated in the manner described herein.

As can be seen in FIGS. 24 and 25, the rotary closure drive shaft 10710 includes a closure drive gear 10715 that is centrally disposed between a right distal closure shaft 10830 and a left distal closure shaft 10840. The right distal closure shaft 10830 includes a right driven gear 10832 that is in meshing engagement with the closure drive gear 10715 and the left distal closure shaft 10840 includes a left driven gear 10842 that is also in meshing engagement with the closure drive gear 10715. Rotation of the rotary closure drive shaft 10710 will result in the rotation of the right distal closure shaft 10830 in a first rotary direction and the rotation of the left distal closure shaft 10840 in a second rotary direction.

The example illustrated in FIGS. 24-26 employs a rotary actuated right closure linkage assembly 10850 and a rotary actuated left closure linkage assembly 10860 that are configured to apply opening and closure motions to the anvil 10802. In one arrangement, the right closure linkage assembly 10850 comprises a proximal drive nut assembly 10852 that is threaded onto the right distal closure shaft 10830 and is coupled to a right closure link 10854 that is attached to the anvil mounting tab 10804. Likewise, the left closure linkage assembly 10860 comprises a left drive nut assembly 10862 that is threaded onto the left distal closure shaft 10840 and is coupled to a left closure link 10864 that is attached to the anvil mounting tab 10804. In one arrangement, the diameter D of the right distal closure shaft 10830 and the left distal closure shaft 10840 may be approximately 0.078". See FIG. 26. The space "E" between the right drive nut assembly 10852 and the left drive nut assembly 10862 may be approximately 0.093" and the width "W" of the channel 10310" may be approximately 0.256". However, other sizes and shapes of end effector components may be employed. Rotation of the rotary closure drive shaft 10710 in a first rotary direction will cause the right drive nut assembly 10852 and the left drive nut assembly 10862 to move in a synchronized fashion to open the anvil 10802 in a balanced uniform manner. Rotation of the rotary closure drive shaft 10710 in a second rotary direction will cause the right drive nut assembly 10852 and the left drive nut assembly 10862 to move in a synchronized fashion to close the anvil 10802 in a balanced uniform manner and reduce any twisting moment on the anvil 10802 as the anvil 10802 is pivoted closed.

As can also be seen in FIGS. 24 and 25, the anvil mounting tab 10804 includes a domed or spherical distal surface portion 10809. A closure ring 10811 (FIG. 27) is movably journaled on the spherical distal surface portion 10809. As the anvil 10802 is pivoted to the closed position by the right closure linkage assembly 10850 and the left closure linkage assembly 10860, the closure ring 10811 serves to constrain the anvil 10802 to the elongate channel 10310". FIG. 24 illustrates the anvil 10802 in a closed position. As can be seen in FIG. 24, the links 10854 and 10864 are nearly vertical (perpendicular) to the end effector axis EC. Such arrangement establishes a maximum moment arm MA for retaining the anvil 10802 in the closed position. FIG. 25 illustrates the anvil 10802 in an open position. For example, the anvil 10802 is pivoted upward at an angle that is approximately 20° from the horizontal as shown. When in that position, the links 10854 and 10864 are nearly horizontal (relative to each other) which results in the application of a reduced amount of closure force than was established when the anvil was moved to the closed position. In one arrangement, the links 10854 and 10864 may have a length L of approximately 0.150", for example. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

FIGS. 28-31 illustrate another surgical end effector 10800' that employs a closure drive arrangement wherein an anvil mounting tab 10804' of an anvil 10802' is also centrally supported within the end effector 10800' and two rotary closure shafts 10830 and 10840 are employed to apply closure motions to the anvil 10802'. See FIG. 29. In one arrangement, for example, the anvil 10802' may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. In this arrangement, a distal portion 10806' of the anvil mounting tab 10804' includes a pair of laterally extending pivot members 10808' that are adapted to be pivotally cradled in pivot cradles 10356" in upstanding walls 10354" of a distal mounting portion 10352" of the elongate channel 10310". See FIGS. 30 and 31. Thus, the pivot members 10808' are vertically movable or "floatable" within their corresponding pivot cradles 10356". In this arrangement, the rotary firing drive shaft 10610 (similar to that shown in FIG. 26) is vertically supported above the rotary closure drive shaft 10710 (FIGS. 24 and 25) in the elongate shaft. As was discussed above, in the illustrated example, the rotary firing drive shaft (not shown) includes a firing drive gear (not shown) that is configured to drivingly engage a driven gear (not shown) on a distal firing drive shaft 10613' that is rotatably supported in the elongate channel 10310" in the various manners described herein. See FIGS. 28 and 29. The distal firing drive shaft 10613' is configured to threadably drive a firing member 10620' within the end effector

10800' as the rotary firing drive shaft and distal firing drive shaft 10613' are rotated in the manners described herein.

As was described above, the rotary closure drive shaft 10710 includes a closure drive gear 10715 that is centrally disposed between a right distal closure shaft 10830 and a left distal closure shaft 10840. See FIGS. 29-31. The right distal closure shaft 10830 includes a right driven gear that is in meshing engagement with the closure drive gear 10715 and the left distal closure shaft 10840 includes a left driven gear 10842 that is also in meshing engagement with the closure drive gear 10715. Rotation of the rotary closure drive shaft 10710 will result in the rotation of the right distal closure shaft 10830 in a first rotary direction and the rotation of the left distal closure shaft 10840 in a second rotary direction. The example illustrated in FIGS. 30 and 31 employs a rotary actuated right closure linkage assembly 10850 and a rotary actuated left closure linkage assembly 10860 that are configured to apply opening and closure motions to the anvil 10802'. In one arrangement, the right closure linkage assembly 10850 comprises a proximal drive nut assembly 10852 that is threaded onto the right distal closure shaft 10830 and is coupled to a right closure link 10854 that is attached to the anvil mounting tab 10804'. Likewise, the left closure linkage assembly 10860 comprises a left drive nut assembly 10862 that is threaded onto the left distal closure shaft 10840 and is coupled to a left closure link 10864 that is attached to the anvil mounting tab 10804'. Rotation of the rotary closure drive shaft 10710 in a first rotary direction will cause the right drive nut assembly 10852 and the left drive nut assembly 10862 to move in a synchronized fashion to open the anvil 10802' in a balanced uniform manner. Rotation of the rotary closure drive shaft 10710 in a second rotary direction will cause the right drive nut assembly 10852 and the left drive nut assembly 10862 to move in a synchronized fashion to close the anvil 10802' in a balanced uniform manner and reduce any twisting moment on the anvil 10802' as the anvil 10802' is pivoted closed.

Figure 30:
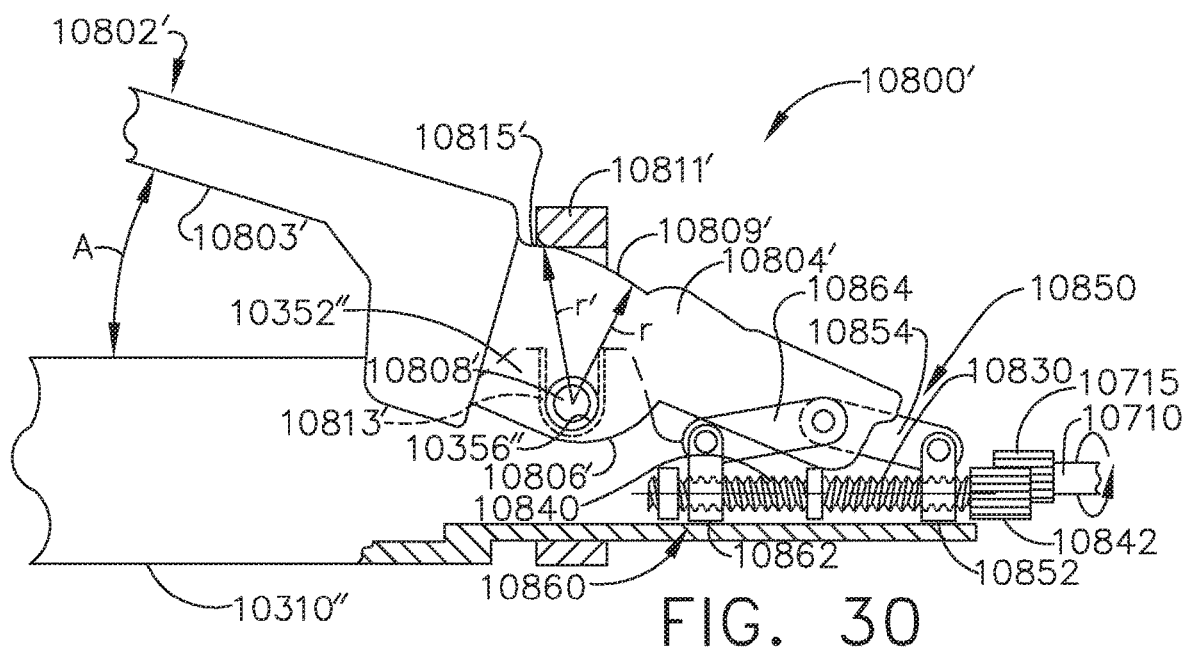
FIG. 30 is a partial side elevational view of portions of the rotary powered surgical end effector of FIGS. 28 and 29, with the anvil thereof in an open position.
Figure 31:
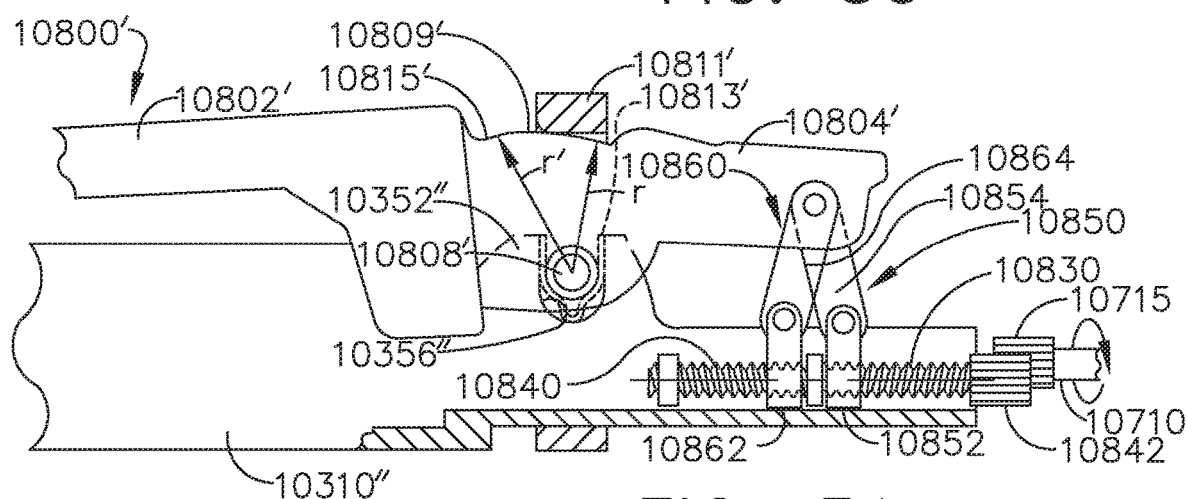
FIG. 31 is another partial side elevational view of portions of the rotary powered surgical end effector of FIG. 30, with the anvil thereof in a closed position.
Figure 32:
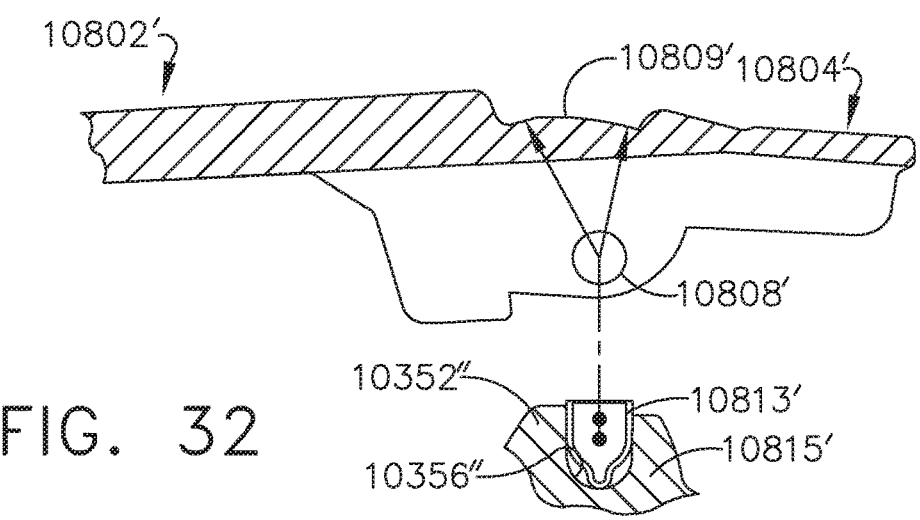
FIG. 32 is a cross-sectional side view of a portion of the anvil and elongate channel of the rotary powered surgical end effector of FIG. 31.

As can be seen in FIGS. 30-32, the anvil mounting tab 10804' includes a domed or spherical distal surface portion 10809'. A closure ring 10811' is movably journaled on the spherical distal surface portion 10809'. As the anvil 10802' is pivoted to the closed position by the right closure linkage assembly 10850 and the left closure linkage assembly 10860, the closure ring 10811' serves to constrain the anvil 10802 to the elongate channel 10310". In the illustrated example, a pivot spring 10813' is seated in each of the cradles 10356" which serves to bias the pivot members 10808' upward in their respective cradles 10356". In at least one arrangement, a distal portion of the spherical surface portion 10809' comprises a shallow notch area 10815' that provides additional clearance for the closure ring 10811' to enable the anvil 10802' to pivot further open, for example, wherein the undersurface 10803' of the anvil 10802' is at least 20° (angle A) from the deck surface of the surgical staple cartridge seated within the channel 10310". See FIG. 30. For example, the radial distance between the center of the pivot members 10808' to the spherical surface 10809' is designated as "r" in FIGS. 30 and 31. The radial distance from the centerline of the pivot members 10808' to the notched area 10815' is designated as "r'", wherein r'>r.

FIG. 30 illustrates the anvil 10802' in a fully open position. As can be seen in FIG. 30, the closure ring 10811' is approximately axially aligned with the pivot members 10808' which serves to drive the pivot members 10808' into the bottom of their respective cradle 10356" and compress the pivot spring 10813' therein. FIG. 31 illustrates the anvil 10802' in the closed position wherein the closure ring 10811' is slightly proximally axially offset from the pivot members 10808' which permits the pivot springs 10813' to bias the pivot members 10808' upward within their respective cradles 10356".

The closure rings in these embodiments essentially encircle the corresponding anvil and elongate channel portions. To facilitate opening of the anvil to a desired opening aperture or angle, the closure ring is permitted to move proximally to distally a small amount (e.g., 0.0"-0.1") while being spring biased to the distal position. The ring does not induce closure but merely constrains the anvil and channel from moving apart vertically allowing a pivoting motion to occur between the two components. Such arrangement facilitates use of a thicker anvil particularly in the anvil mounting area which may improve anvil strength and reliability. This configuration may further enable the jaws (anvil and channel) to pivot in a fashion that improves the moment arm condition of the anvil proximal to the pivot location and facilitate opening of the end effector to greater opening angles. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 33:
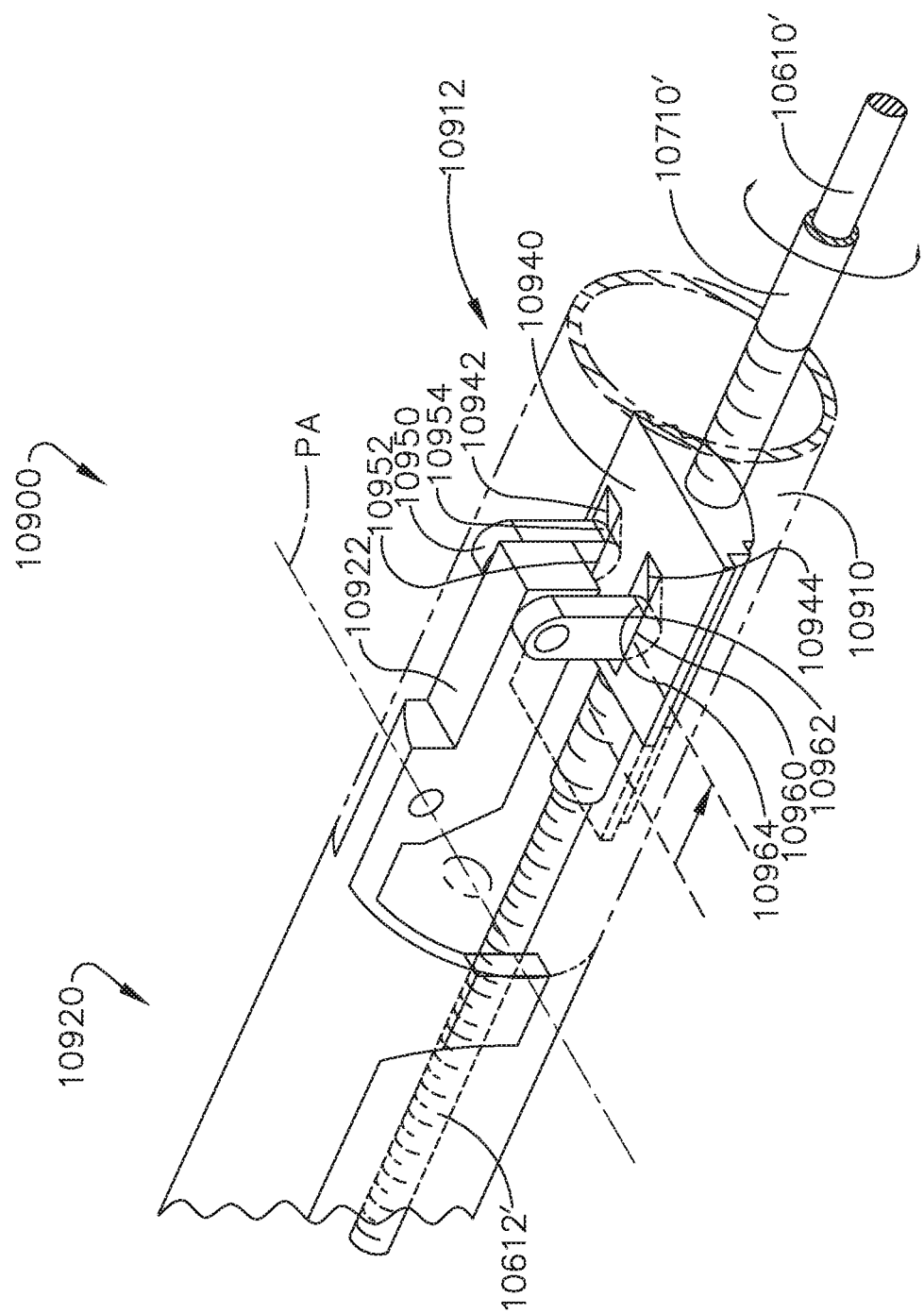
FIG. 33 is a partial perspective view of another rotary powered surgical end effector with an anvil thereof in a closed position.
Figure 34:
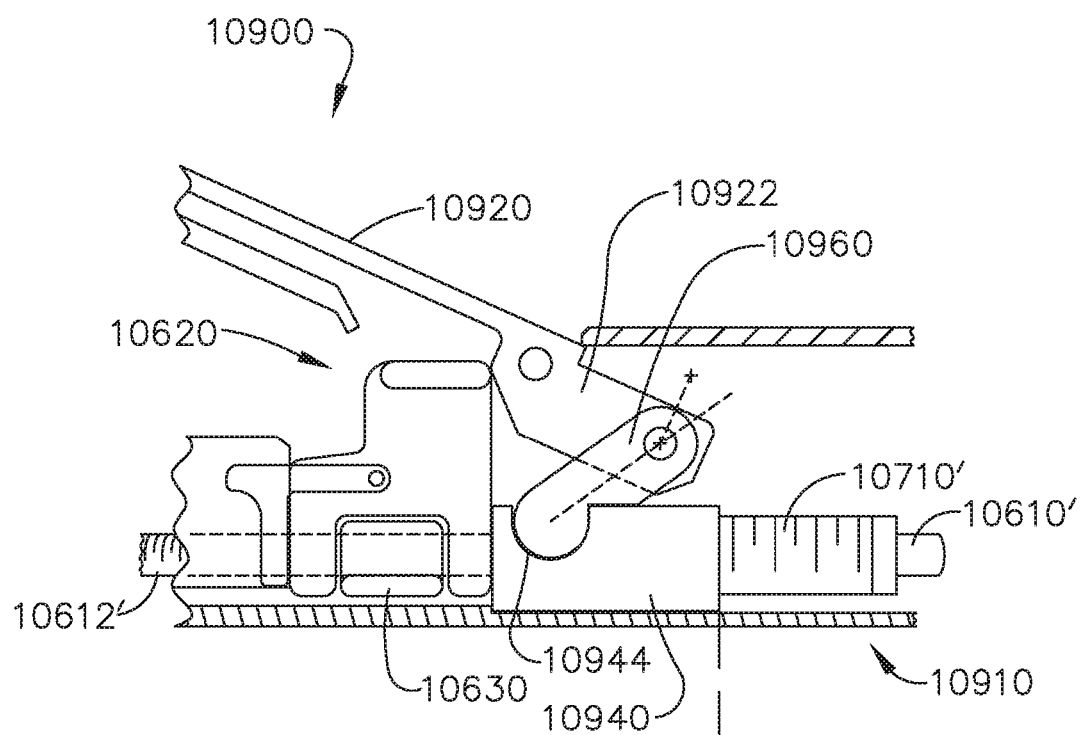
FIG. 34 is a side elevational view of a portion of the rotary powered surgical end effector of FIG. 33 with the anvil in an open position.
Figure 35:
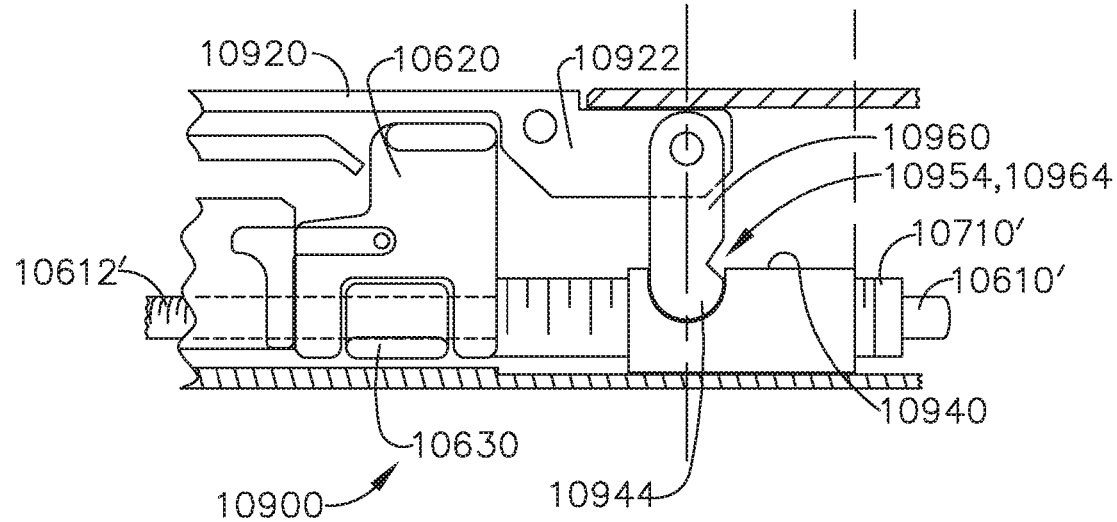
FIG. 35 is another side elevational view of a portion of the rotary powered surgical end effector of FIG. 34 with the anvil in a closed position.

FIGS. 33-35 illustrate another end effector 10900 that employs an alternate closure drive arrangement for opening and closing an anvil 10920 relative to an elongate channel 10910 thereof. The anvil 10920 includes an anvil mounting tab 10922 that protrudes proximally along a centerline of the anvil 10920 and is pivotally coupled to a proximal end 10912 of the elongate channel 10910 in the various manners disclosed herein. In one arrangement, for example, the anvil 10920 may be fabricated using various fabricating techniques described in U.S. patent application Ser. No. 16/105, 101, entitled METHOD FOR FABRICATING SURGICAL STAPLER ANVILS, the entire disclosure of which is hereby incorporated by reference herein. In this arrangement, a rotary closure drive shaft 10710' is hollow and concentrically supports a rotary firing drive shaft 10610' therein. The rotary closure drive shaft 10710' and the rotary firing drive shaft 10610' are centrally disposed within the elongate channel 10910 as can be seen in FIG. 33. The rotary firing drive shaft 10610' rotatably extends through the rotary closure drive shaft 10710' and includes a distal threaded portion 10612' that is configured to threadably drive a firing member 10620 in the manner described above, for example.

Referring to FIG. 33, a closure shuttle 10940 is supported for axial travel within the elongate channel 10910. The closure shuttle 10940 is threadably journaled on the threaded closure drive shaft 10710' such that rotation of the threaded closure drive shaft 10710' in a first direction causes the closure shuttle 10940 to move distally and rotation of the threaded closure drive shaft 10710' in a second rotary direction causes the closure shuttle 10940 to move proximally within the elongate channel 10910. As can be seen in FIG. 33, a right closure link 10950 and a left closure link 10960 are pivotally coupled to the anvil mounting tab 10922. The right closure link 10950 also includes an actuation end 10952 that is received within a corresponding right actuation notch 10942 in the closure shuttle 10940 and the left closure link 10960 includes an actuation end 10962 that is received within a corresponding left actuation notch 10944 in the closure shuttle 10940. Also in the illustrated arrangement, a right drive notch 10954 is provided in the actuation end 10952 of the right closure link 10950 and a left drive notch 10964 is provided in the actuation end 10962 of the left closure link 10960. The drive notches 10954, 10964 are configured to drivingly engage the actuation notches 10942, 10944, respectively.

Figure 36:
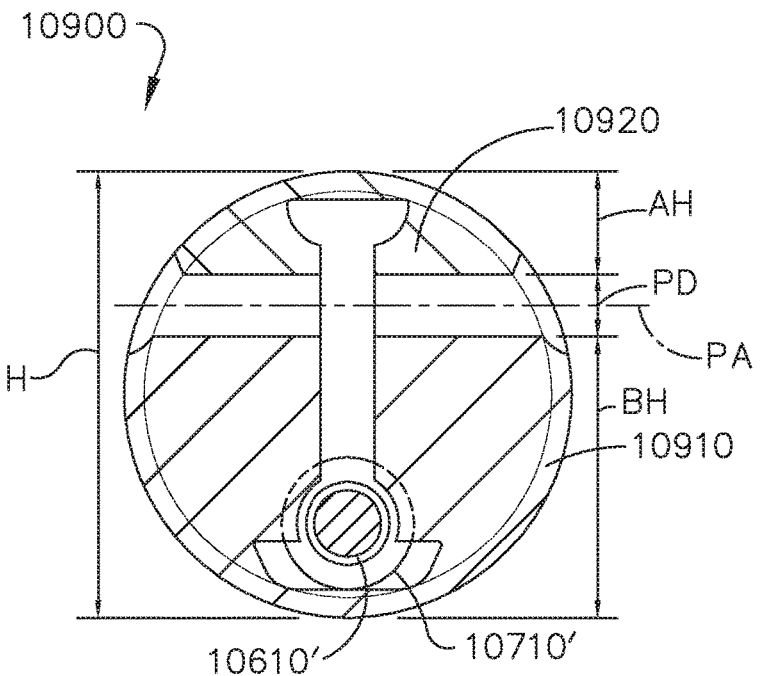
FIG. 36 is a cross-sectional end view of a portion of the rotary powered surgical end effector of FIG. 33.
Figure 37:
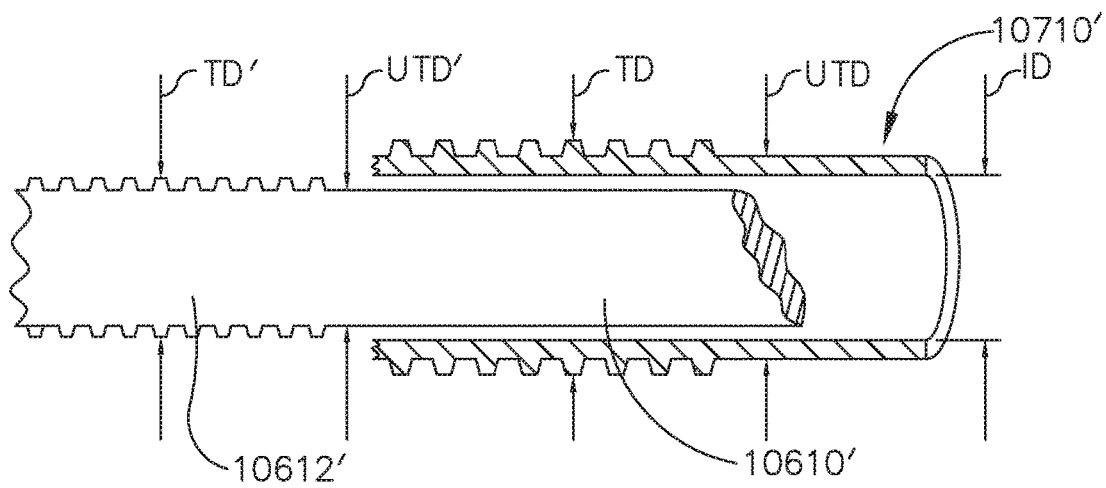
FIG. 37 is a partial cross-sectional side view of a rotary firing drive shaft and a rotary closure drive shaft of the rotary powered surgical end effector of FIG. 33.

FIGS. 33 and 35 illustrate the closure shuttle 10940 in a proximal-most, retracted position. When in that position, the right and left closure links 10950, 10960 push up on the anvil mounting tab 10922 and cause the anvil 10920 to pivot about the pivot axis PA to a closed position. When the closure shuttle 10940 has been moved to its distal-most, extended position, the right and left closure links 10950, 10960 pull the anvil tab 10922 downward and pivot the anvil 10920 to the open position as shown in FIG. 34. FIG. 36 illustrates some exemplary dimensions of various components of the surgical end effector 10900. In one arrangement for example, the overall height "H" may be approximately 0.500". The anvil height "AH" may be approximately 0.120". The rivet passage may have a diameter "PD" of approximately 0.070" and the base height "BH" may be approximately 0.310", for example. Referring to FIG. 37, the hollow closure drive shaft 10710' may have an internal diameter "ID" of approximately 0.100" and an unthreaded outer diameter "UTD" of approximately 0.129" and a threaded outer diameter "TD" of approximately 0.164": The firing drive shaft 10610' may have an unthreaded diameter "UTD'" of approximately 0.0668" and a threaded outer diameter "TD'" of approximately 0.0854", for example. Other diameters, component sizes and dimensions may also be employed.

Figure 39:
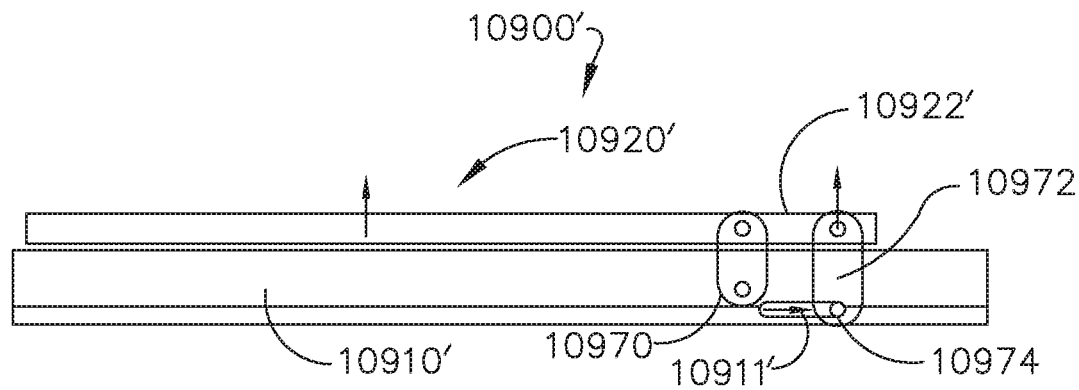
FIG. 39 is another diagrammatical depiction of the end effector of FIG. 38, with the jaws in a closed position.
Figure 38:
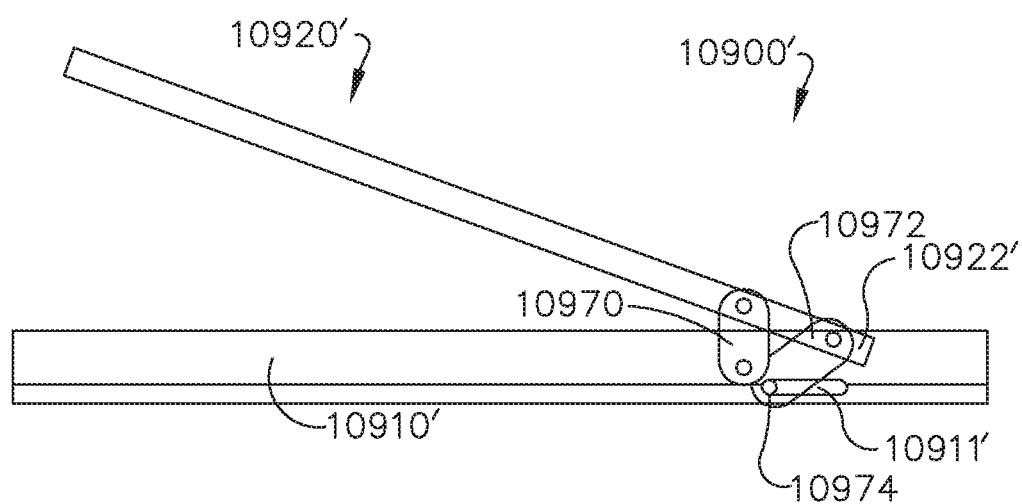
FIG. 38 is a diagrammatical depiction of an end effector that employs a closure link arrangement for opening and closing jaws of the end effector, with the jaws shown in an open position.

FIGS. 38 and 39 are diagrammatical depictions of an end effector 10900' that employs alternative closure link arrangements. As can be seen in those Figures, a distal closure link (or links) 10970 are pivotally pinned or otherwise pivotally coupled to an anvil 10920' and an elongate channel 10910'. In addition, proximal closure links 10972 are attached to an anvil mounting tab portion 10922' and are slidably coupled via a corresponding pin 10974 that is received in a corresponding axial slot 10911' in the elongate channel 10910' or in a closure shuttle or other member (not shown) that is configured to move the proximal closure links 10972 between a first position (FIG. 38) corresponding to an open position of the anvil 10920' and a second position (FIG. 39) corresponding to the closed position of the anvil 10920'.

Figure 41:
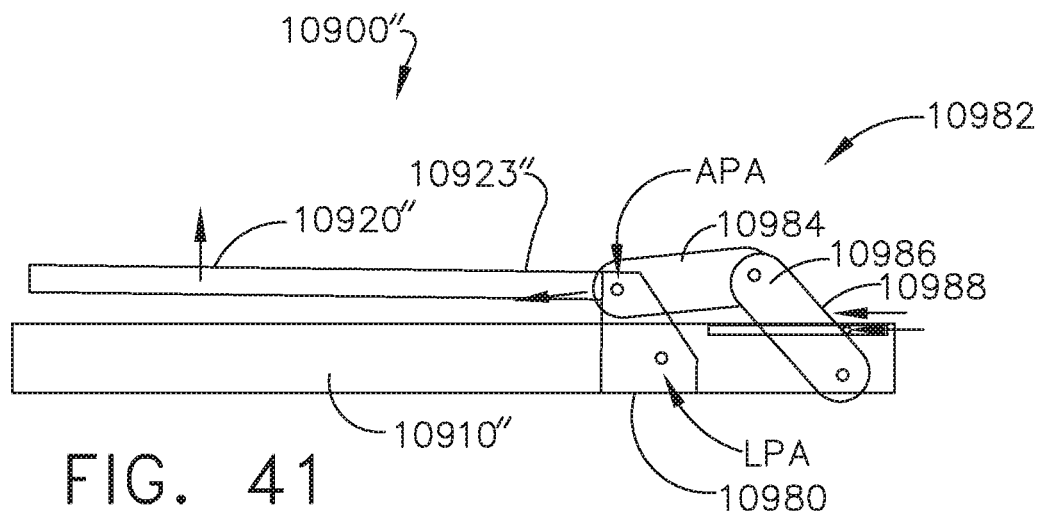
FIG. 41 is another diagrammatical depiction of the end effector of FIG. 40, with the jaws in a closed position.
Figure 40:
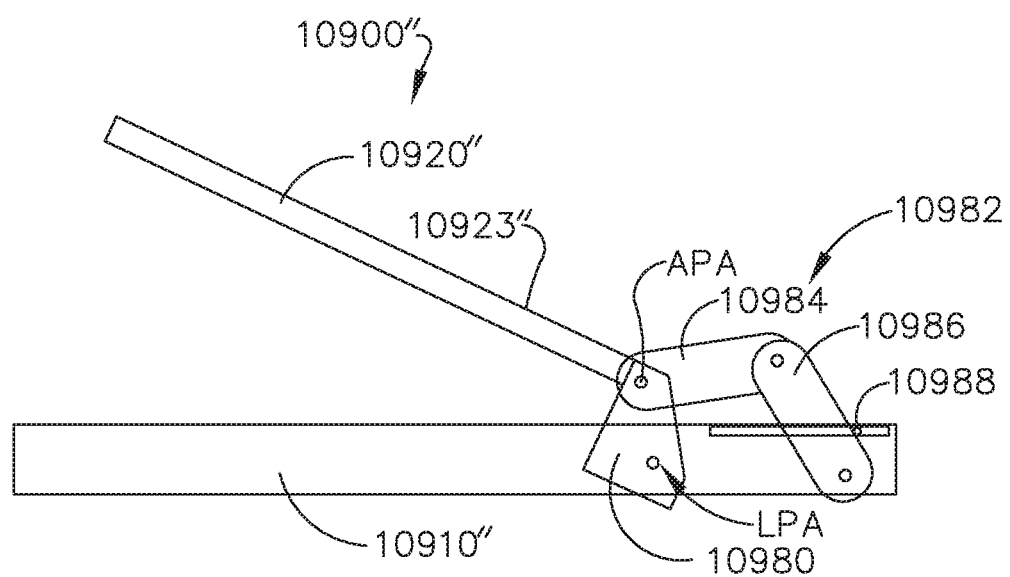
FIG. 40 is a diagrammatical depiction of another end effector that employs a closure link arrangement for opening and closing jaws of the end effector, with the jaws shown in an open position.

FIGS. 40 and 41 are diagrammatical depictions of an end effector 10900" that employs alternative closure link arrangements. As can be seen in those Figures, a proximal end portion 10923" of an anvil 10920" is pivotally coupled to an elongate channel 10910" by proximal mounting links 10980. The proximal mounting links 10980 (only one is shown in the Figures) are pivotally attached to the elongate channel 10910" for pivotal travel relative thereto about a lower pivot axis LPA. The proximal mounting links 10980 are also pivotally coupled to the proximal end portion 10923" for pivotal travel relative thereto about an anvil pivot axis APA. The end effector 10900" further includes a closure linkage assembly 10982 that comprises at least one distal link 10984 and one proximal link 10986. In other arrangements, the closure linkage assembly 10982 comprises a pair of distal links 10984 (one on each side of the elongate channel) and a pair of proximal links 10986 (one on each side of the elongate channel). The distal link(s) 10984 is attached to the anvil 10920" for pivotal travel about the anvil pivot axis APA as well as to the corresponding proximal link(s) 10986. The other end of the proximal link(s) is pivotally attached to the elongate channel 10910". The closure linkage assembly 10982 is actuated by a slider pin or pins 10988 that are constrained to move axially either in the elongate channel or in a closure shuttle or other member (not shown) that is configured to move the pin(s) 10988 between a first position (FIG. 40) corresponding to an open position of the anvil 10920" and a second position (FIG. 41) corresponding to the closed position of the anvil 10920". As indicated, the closure linkage assembly 10982 could comprise a compound set of links. Such arrangement may have interactive surfaces that limit the rotation of one linkage with respect to the second linkage. In this manner, the closure of the anvil 10920" for a given rate of angular rotation could induce first and second closure rate as well establish different mechanical advantages for closing the anvil. For example, a rapid rate of closure may be initially employed for an initial portion of the closure stroke of the closure actuator and then a slower rate of closure may be employed during the remaining portion of the closure stroke which may result in the application of increased closure forces to the anvil.

Figure 43:
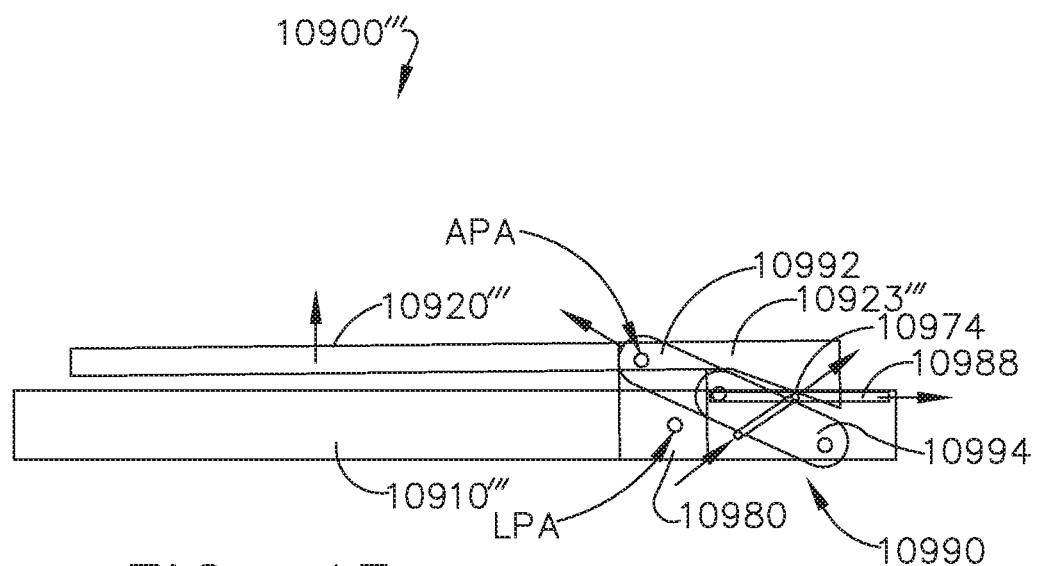
FIG. 43 is another diagrammatical depiction of the end effector of FIG. 42, with the jaws in a closed position.
Figure 42:
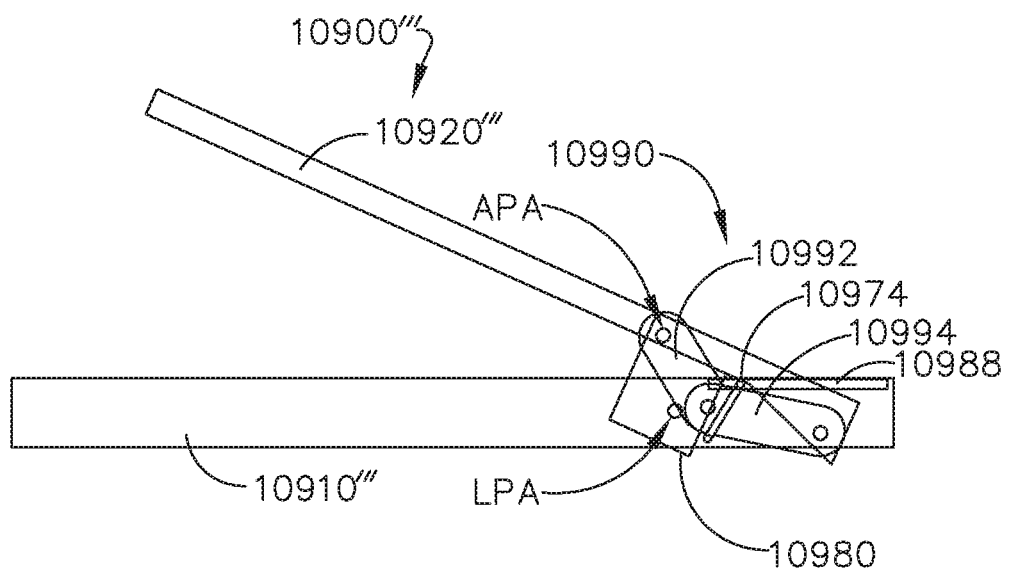
FIG. 42 is a diagrammatical depiction of another end effector that employs a closure link arrangement for opening and closing jaws of the end effector, with the jaws shown in an open position.
Figure 44:
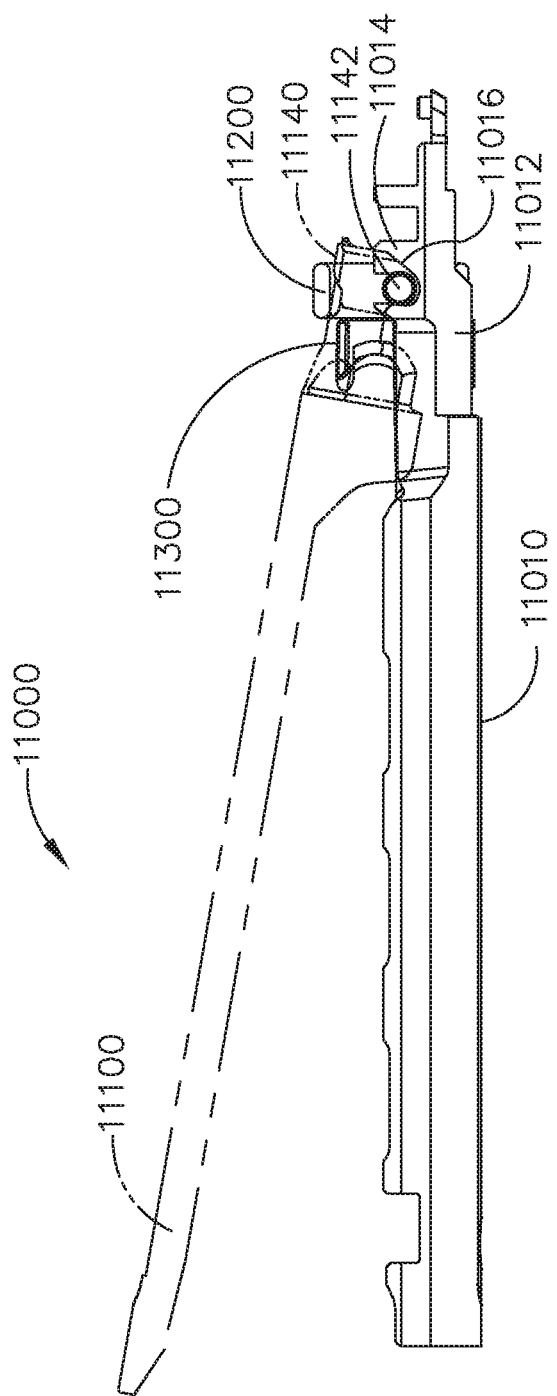
FIG. 44 is a side elevational view of portions of another surgical end effector with an anvil thereof shown in phantom lines in an open position.
Figure 45:
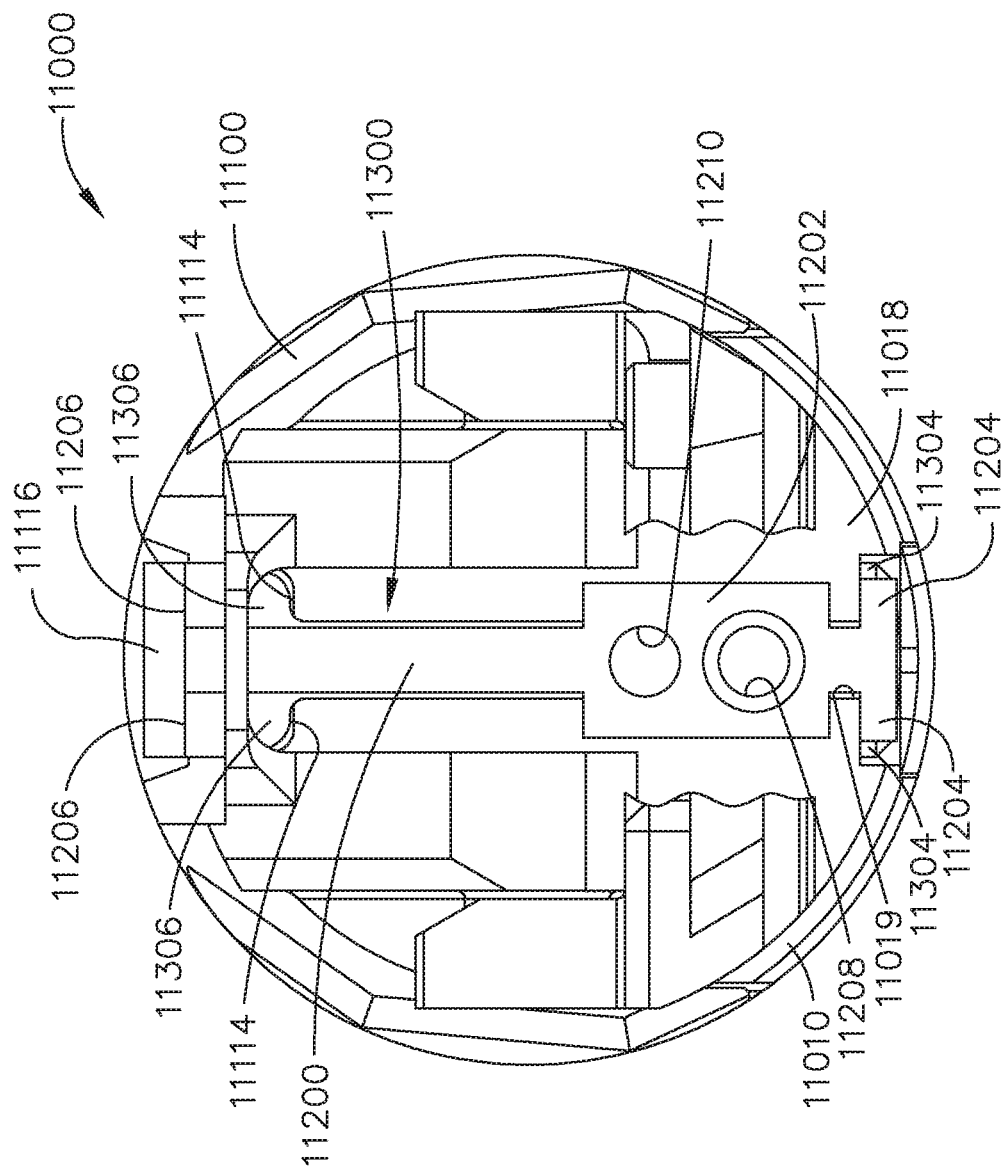
FIG. 45 is an end view of the surgical end effector of FIG. 44.

FIGS. 42 and 43 are diagrammatical depictions of an end effector 10900' that employs alternative closure link arrangements. As can be seen in those Figures, a proximal end portion 10923' end portion of an anvil 10920' is pivotally coupled to the elongate channel 10910' by proximal mounting links 10980. The proximal mounting links 10980 (only one is shown in the Figures) are pivotally attached to the elongate channel 10910' for pivotal travel relative thereto about a lower pivot axis LPA. The proximal mounting links 10980 are also pivotally coupled to the proximal end portion 10923' for pivotal travel relative thereto about an anvil pivot axis APA. The end effector 10900' further includes a closure linkage assembly 10990 that comprises at least one distal link 10992 and one proximal link 10994. In other arrangements, the closure linkage assembly 10990 comprises a pair of distal links 10992 (one on each side of the elongate channel) and a pair of proximal links 10994 (one on each side of the elongate channel). The distal link(s) 10992 is attached to the anvil 10920' for pivotal travel about the anvil pivot axis APA as well as to the corresponding proximal link(s) 10994. The other end of the proximal link(s) is pivotally attached to the elongate channel 10910'. The closure linkage assembly 10990 is actuated by a slider pin or pins 10988 that are constrained to move axially either in a corresponding slot in the elongate channel or in a closure shuttle or other member (not shown) configured to move the pin(s) 10988 between a first position (FIG. 42) corresponding to an open position of the anvil and a second position (FIG. 43) corresponding to the closed position of the anvil. The slider pin(s) 10988 is coupled to the proximal link(s) 10994. In the open state, the slider pin(s) 10988 is in the distal-most position (FIG. 42). To close the anvil 10920', the slider pin(s) 10988 is moved in a proximal direction which pulls the proximal closure link(s) 10994 to the position shown in FIG. 43 wherein the distal closure link(s) 10992 pop over center to retain the anvil 10920' in the closed state. The force vector during closure is provided by the proximal and distal closure links being in compression to thereby resist load generated by the tissue clamped in the end effector during closure.

Turning next to FIGS. 44-52, there is shown another surgical end effector 11000 that includes an anvil 11100 that is pivotally supported on an elongate channel 11010 that is configured to operably support a surgical staple cartridge (not shown) therein. This arrangement also employs two rotary actuation shafts—one for closure (i.e., moving the anvil and elongate channel between open and closed positions) and one for firing (i.e., axially moving a firing member) within the anvil and elongate channel. In the illustrated example, the anvil 11100 includes an elongate anvil body 11110 and an anvil mounting portion 11140. In one arrangement, for example, the anvil 11100 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. A pair of anvil trunnions 11142 protrudes laterally from the anvil mounting portion 11140. Each anvil trunnion is pivotally supported in a corresponding trunnion cradle 11016 that is formed in a corresponding upstanding wall 11014 of a proximal end portion 11012 of the elongate channel 11010. See FIG. 44. The proximal end portion 11012 of the elongate channel 11010 may be pivotally coupled to an elongate shaft assembly 10200 of a surgical instrument 10010 of the type described herein, for example to facilitate articulation of the end effector 11000. In other arrangements, the elongate channel 11010 may not be capable of articulation. The anvil trunnions 11142 may be retained within their respective trunnion cradles 11016 by an anvil retainer (not shown) that may be similar in construction and operation to channel cap or anvil retainer 1290 that was described above.

Figure 47:
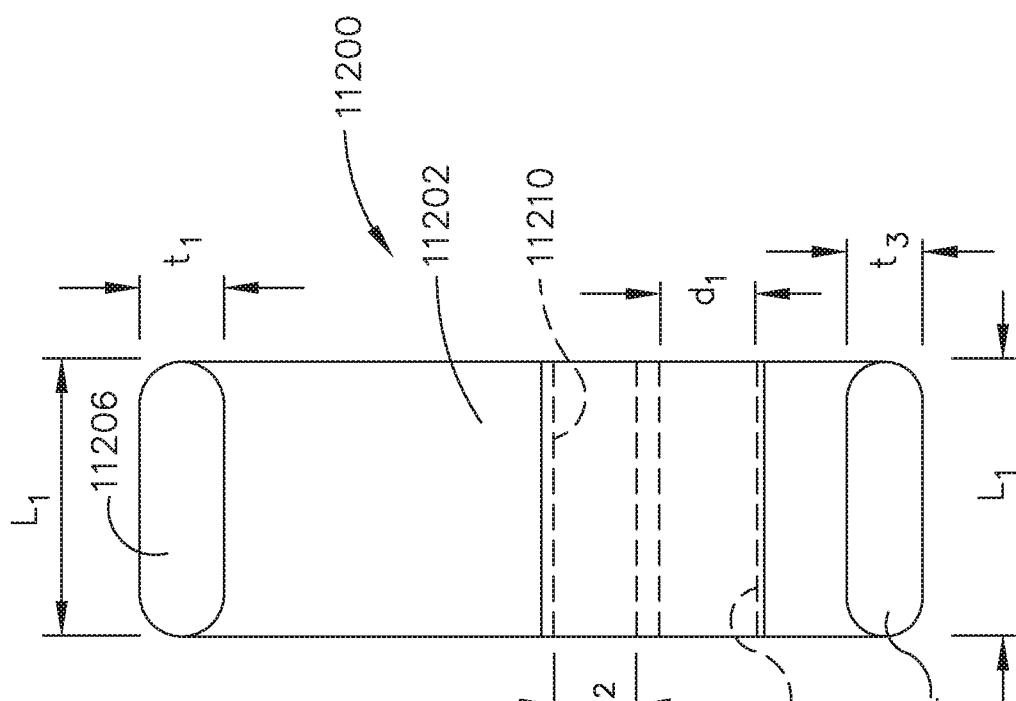
FIG. 47 is a side elevational view of an anvil closure member of the surgical end effector of FIG. 44.

In the illustrated example, the surgical end effector 11000 includes an anvil closure member 11200 and a firing member 11300 that are each independently controlled and axially movable. FIG. 47 illustrates one form of a closure member 11200 that may be employed. As can be seen in FIG. 47, the closure member 11200 includes a vertically extending closure body 11202 that has two bottom channel tabs 10204 laterally protruding therefrom. A portion of the closure body 11202 is configured to extend through a slot 11019 in a bottom surface 11018 of the elongate channel 11010 and channel tabs 11204 extend laterally outward to slidably engage the bottom of the channel 11010. Similarly, a pair of anvil engaging tabs 11206 protrude laterally from the top of the closure body 11202 to slidably engage the anvil 11100. The closure body 11202 includes a threaded through hole 11208 for threadably engaging a threaded portion 10712 of a rotatable closure drive shaft 10710 for axially driving the closure member 11200 in the various manners described herein.

Figure 48:
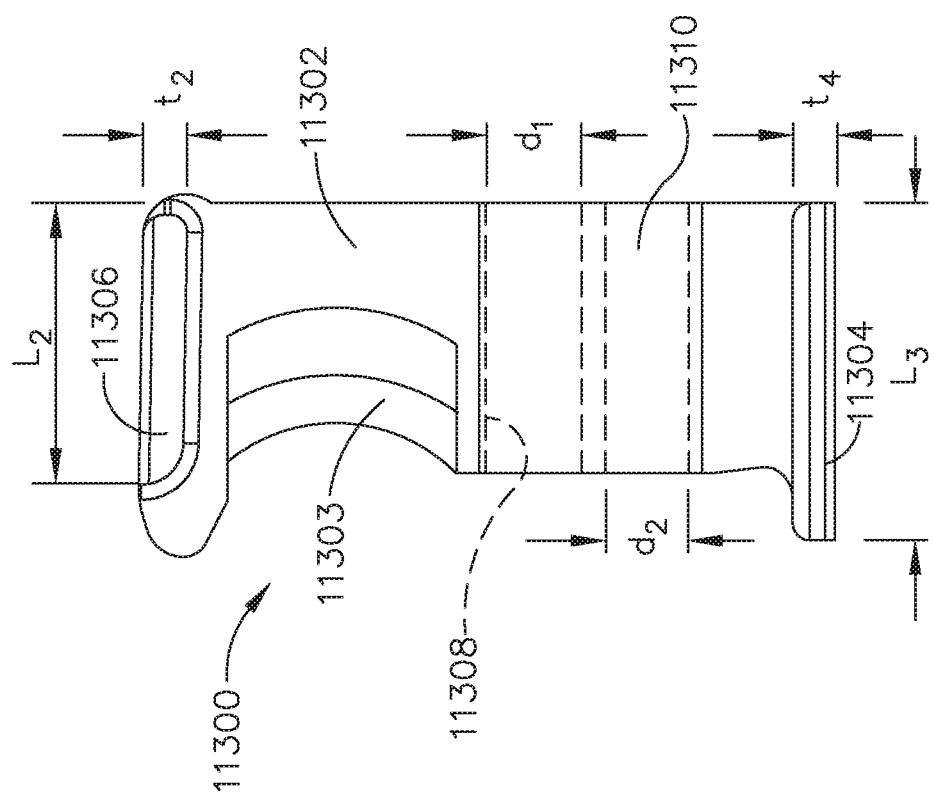
FIG. 48 is a side elevational view of a firing member of the surgical end effector of FIG. 44.

As indicated above, the surgical end effector 11000 further includes an axially movable firing member 11300. FIG. 48 illustrates one form of a firing member 11300 that may be employed. As can be seen in FIG. 48, the firing member 11300 includes a vertically extending firing member body 11302 that has a tissue cutting surface 11303 as well as two bottom channel tabs 11304 laterally protruding therefrom. A portion of the firing member body 11302 is configured to extend through the slot 11019 in the bottom surface 11018 of the elongate channel 11010 and the channel tabs 11304 extend laterally outward to slidably engage the bottom of the channel 11010. See FIG. 45. Similarly, a pair of anvil engaging tabs 11306 protrudes laterally from the top of the firing member body 11302 to slidably engage the anvil 11100. The firing member body 11302 includes a threaded through hole 11308 for threadably engaging a threaded portion of a rotatable firing drive shaft such as a firing drive shaft 10610 described above. The distal firing shaft 10610 passes through an unthreaded clearance hole 11210 in the closure body 11202. See FIG. 47. The firing drive shaft 10610 extends axially down the elongate channel 11010 and is rotatably supported in a distal end portion thereof by a bearing (not shown) or other arrangement. Similarly, the closure drive shaft 10710 may extend axially down the elongate channel 11010 and to be rotatably supported in a distal end portion thereof by a bearing (not shown) or other arrangement. Thus, the firing member body 11302 similarly has an unthreaded clearance hole 11310 therethrough to accommodate the closure drive shaft 10710. It will be appreciated that in such arrangements, the closure drive shaft 10710 and the firing drive shaft 10610 may be supported in a vertical stacked arrangement so that they may be independently rotatable.

Figure 46:
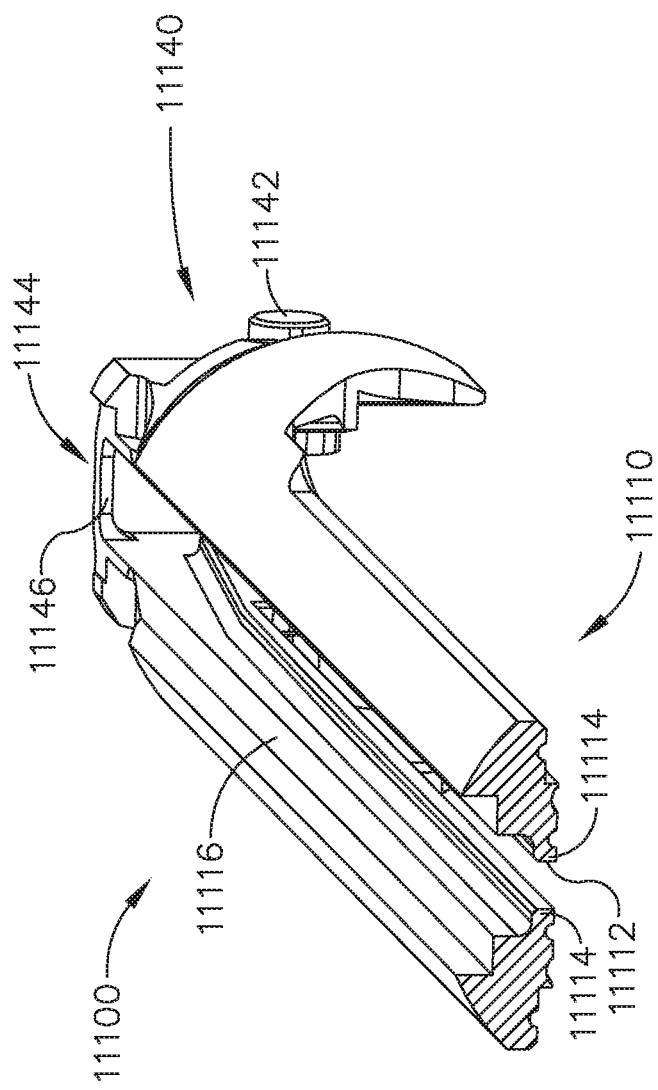
FIG. 46 is a partial cross-sectional perspective view of the anvil of the end effector of FIG. 45.
Figure 49:
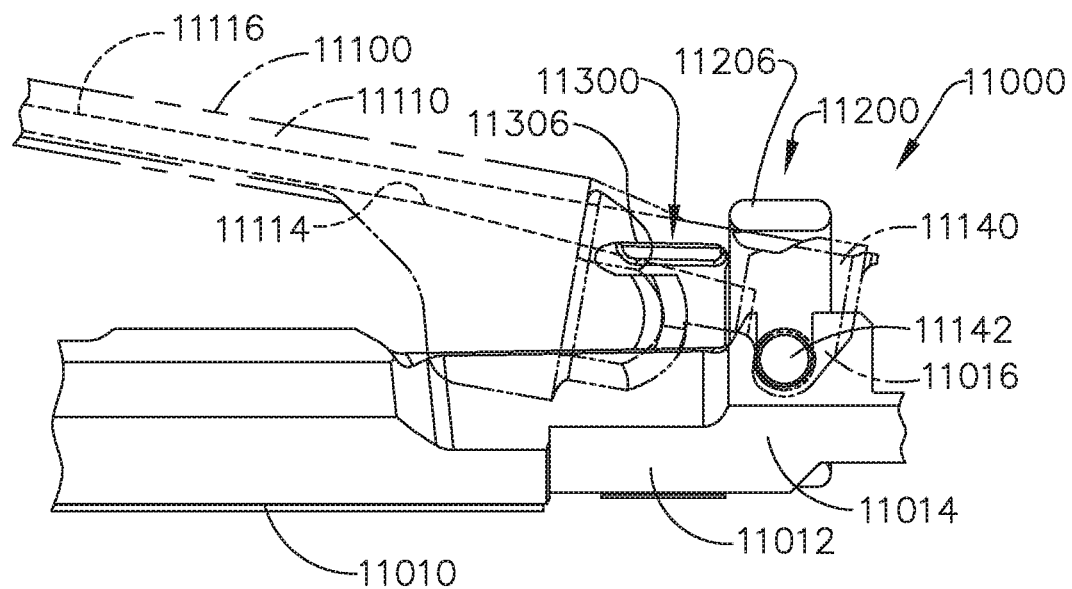
FIG. 49 is a partial side elevational view of the surgical end effector of FIG. 44 with an anvil thereof shown in phantom lines in an open position.
Figure 50:
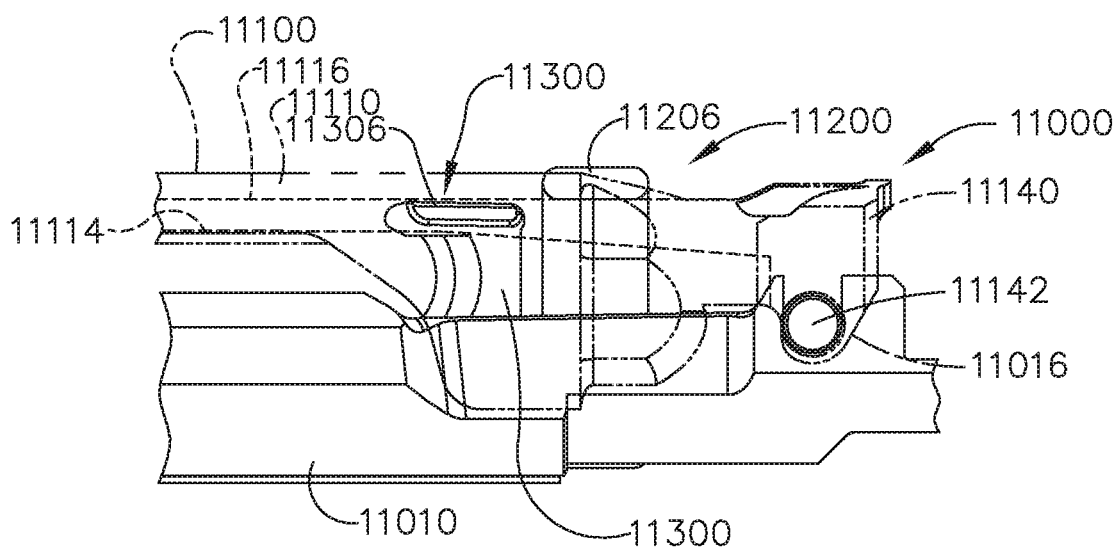
FIG. 50 is another partial side elevational view of the surgical end effector of FIG. 49, with an anvil thereof in a closed position.
Figure 51:
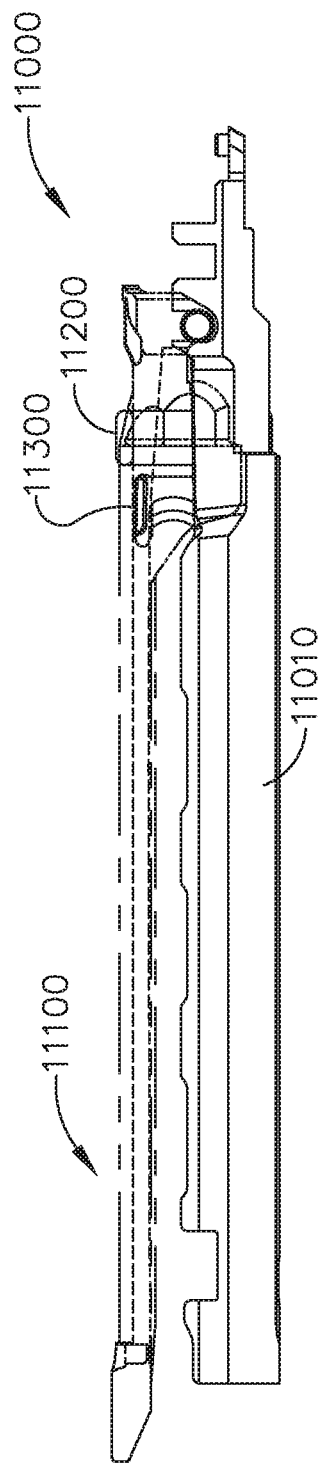
FIG. 51 is another side elevational view of the surgical end effector of FIG. 50 with a firing member thereof beginning a firing process.
Figure 52:
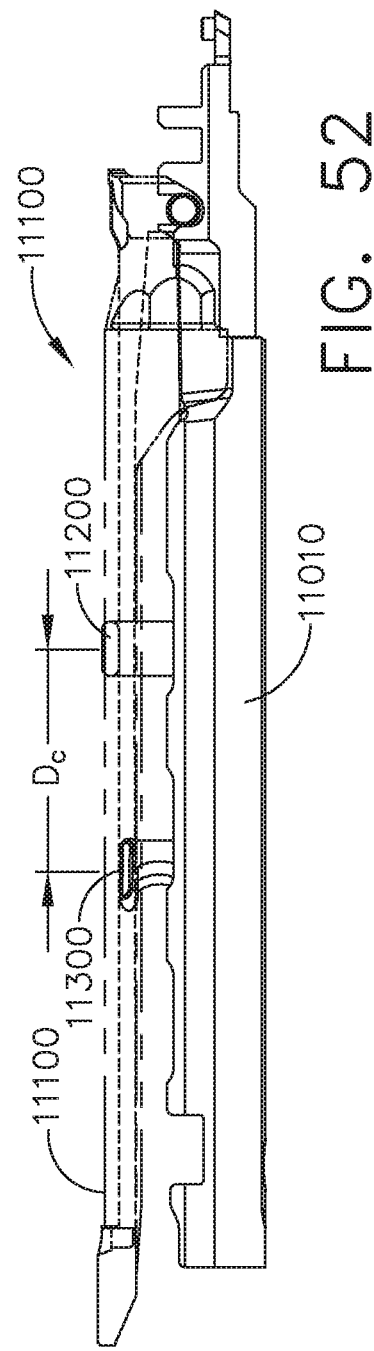
FIG. 52 is another side elevational view of the surgical end effector of FIG. 50 with the anvil closure member and the firing member being partially distally deployed in the end effector.

FIG. 46 illustrates one form of anvil 11100 with portions thereof shown in cross-section. The anvil mounting portion 11140 includes a central cross brace 11144 that serves to define an opening 11146 for accommodating the closure member 11200 therein when the closure member 11200 is in its proximal-most position which corresponds to an open position of the anvil 11100. As can be seen in FIG. 46, the anvil body 11110 defines an elongate slot 11112 for accommodating the firing member body 11302 and closure body 11202 therethrough. The firing member 11300 is located distal to the closure member 11200. The anvil engagement tabs 11306 on the firing member 11302 are configured to slidably engage corresponding first or lower ledges 11114 that are formed on each side of the slot 11112. As can be seen in FIGS. 49 and 50, the lower ledges 11114 taper slightly downward at their proximal ends to accommodate the anvil engagement tabs 11306 on the firing member 11300 when the anvil is pivoted to its open position. The anvil engagement tabs 11206 on the closure member 11200 are configured to slidably engage corresponding second or higher ledges 11116 that are formed on each side of the slot 11112. See FIG. 46. To open the anvil 11100, the closure drive shaft is rotated to threadably drive the closure member 11200 proximally into its proximal-most position (FIG. 49). When the closure member 11200 is in its proximal-most position, the anvil engagement tabs 11206 thereon apply a pivotal opening motion to the anvil 11100 to pivot the anvil open. The firing member 11300 is in its starting position so that the anvil engagement tabs 11306 of the firing member 11300 do not apply a closure motion to the anvil 11100.

To close the anvil 11100, the closure drive shaft 10710 is rotated in an opposite direction to distally advance the closure member 11200 into a closed position. The firing drive shaft 10610 may also be simultaneously rotated to distally advance the firing member 11300 into a starting position. When the closure member 11200 and the firing member 11300 are in those positions, the anvil 11100 is closed and the firing member 11300 is ready to be fired. Thus, assuming that an unspent surgical staple cartridge has been first operably supported in the elongate channel 11010 and the end effector 11000 was manipulated to capture the target tissue between the staple cartridge and the anvil, the user may close the anvil 11100 onto the tissue in the above described manner to ready the end effector to be fired. During this closing process, the firing drive shaft 10610 is rotated to drive the firing member 11300 distally into the clamped tissue to cut the tissue and cause the staples stored in the staple cartridge to be formed into the cut tissue on both sides of the cut. During this process, the closure member 11200 may also be driven distally to apply additional closure motions to the anvil 11100 and elongate channel 11010. Depending upon the amount of resistance experienced by the firing member 11300, for example, the closure member 11200 can be advanced with the firing member 11300, stop and then go again. The closure member 11200 may be advanced distally at a different rate from the firing member's rate of distal advancement. The distance $D_C$ between the closure member 11200 and the firing member 11300 may be controlled to balance the loads experienced during the firing process. See FIG. 52. For example, if the user wanted to decrease an amount of vertical load being experienced by the firing member 11300, the closure member 11200 could be moved closer to the firing member 11300 during advancement. The vertical loads experienced by the firing member 11300 may be increased by increasing the distance between the firing member 11300 and the closure member 11200.

Returning to FIGS. 47 and 48, the thickness $t_1$ of the anvil engagement tabs 11206 on the closure member 11200 is greater than the thickness $t_2$ of the anvil engagement tabs 11306 on the firing member 11300. In one arrangement, the length $L_1$ of the anvil engagement tabs 11206 on the closure member 11200 is slightly less than the length $L_2$ of the anvil engagement tabs 11306 on the firing member 11300. Likewise, the thickness $t_3$ of the channel tabs 11204 on the closure member 11200 is greater than the thickness $t_4$ of the channel tabs 11304 on the firing member 11300. In one arrangement, the length $L_1$ of the channel tabs 11204 on the closure member 11200 are shorter than the length $L_3$ of the channel tabs 11304 on the firing member 11300. In both cases, the diameters $d_1$ of the threaded holes 11208, 11308 may be greater than the diameters $d_2$ of the unthreaded through holes 11210, 11310. In addition, the relative attack angles between the anvil engagement tabs 11206, 11306 and their corresponding anvil ledges and the channel tabs 11204, 11304 and their corresponding channel ledges may be varied, the same or different. In one arrangement, the anvil engagement tabs 11306 on the firing member 11300 are arranged at a slightly higher attack angle relative to their corresponding anvil ledges than the attack angle of the anvil engagement tabs 11206 on the closure member 11200. In one arrangement, the channel tabs 11204 and 11304 ride on the same ledges that are formed in the bottom of the elongate channel 11010. See FIG. 45. The closure member 11200 and the firing member 11300 have separate acting paths which can permit the closure member to be designed to accommodate larger moment arms from the anvil pivot for better firing efficiency.

One advantage that may be experienced when using the foregoing configuration is that the closure member 11200 can be moved away from the firing member 11300 to gain a significant amount of mechanical advantage during closure. The closure member 11200 does not need to travel the complete length of the firing stroke. For example, if the closure member 11200 were to be advanced about half way down the end effector, the relative stiffness of the anvil 11100 would reduce the amount of load being encountered by the firing member 11300. A control system employing sensors (e.g., strain gauges, etc.) for detecting amounts of loads being experienced by the firing system components and closure system components, as well as algorithms, can be used to balance the loads being encountered by both systems. For example, a maximum threshold of vertical load experienced by the firing member 11300 can be set in the controller based on the geometry and composition of that firing member component. When the load approaches that threshold, the algorithm can automatically advance the closure member 11200 so that it absorbs more of the load and reduces the amount of load being experienced by the firing member 11300. In various aspects, as the firing member 11300 is distally driven through the surgical staple cartridge, the firing member 11300, through the engagement of the anvil engagement tabs 11306 with the anvil 11100 and the engagement of the channel engagement tabs 11304 with the channel 11010, may serve to maintain a desired amount of tissue gap between a deck surface on the staple cartridge and a staple forming undersurface on the anvil 11100. Other closure control methods may also be employed in connection with opening and closing the surgical end effector 11000 such as those disclosed in U.S. patent application Ser. No. 16/105,081, entitled METHOD FOR OPERATING A POWERED ARTICULATABLE SURGICAL INSTRUMENT, the entire disclosure of which is hereby incorporated by reference herein.

Figure 53:
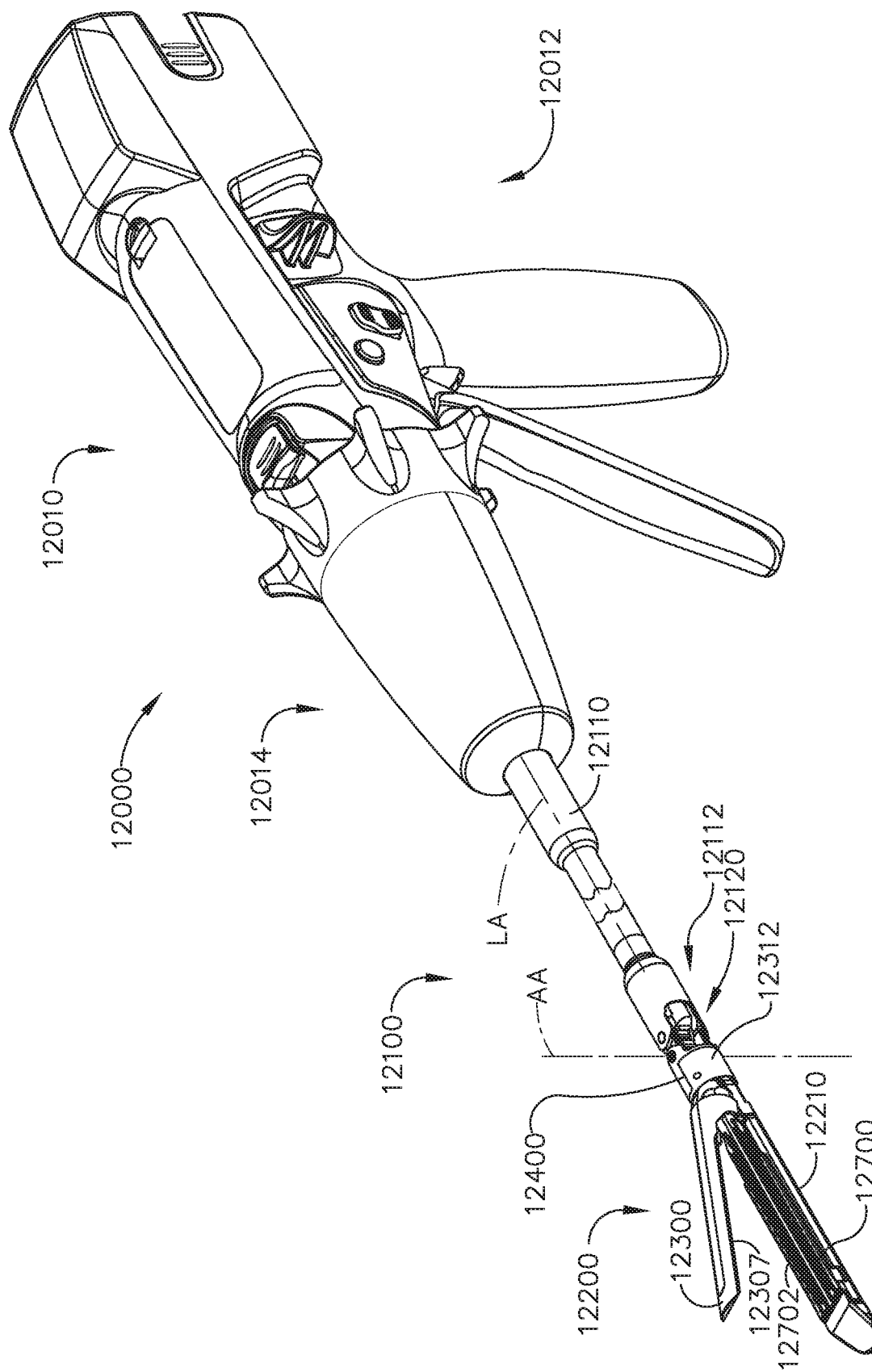
FIG. 53 is a perspective view of another powered surgical instrument.

FIG. 53 depicts a surgical instrument 12000 that may be used to cut and staple tissue. The instrument comprises a housing 12010 that comprises a handle 12012 that is configured to be grasped, manipulated and actuated by the clinician. As can be seen in FIG. 53, for example, the instrument 12000 includes a shaft assembly 12100 that has a surgical end effector 12200 operably coupled thereto that is configured to perform one or more surgical tasks or procedures. The shaft assembly 12100 comprises an interchangeable shaft assembly that is intended to be removably couplable to the handle assembly 12012 in the various manners disclosed herein. However, in other arrangements, the shaft assembly 12100 may comprise a dedicated shaft assembly that is not intended to be removed from the handle 12012. In still other arrangements, the shaft assembly 12100 may be operably coupled to or operably interface with a robotic system that is capable of generating the rotary operating motions necessary to operate the surgical end effector in the various manners disclosed herein. Only those specific components necessary to understand the functions and operation of the shaft assembly 12100 will be discussed in further detail below.

In the illustrated example, the elongate shaft assembly 12100 includes an articulation joint 12120 that facilitates articulation of the surgical end effector 12200 about an articulation axis AA that is transverse to a longitudinal shaft axis LA. Other shaft assemblies, however, may not be capable of articulation. In the illustrated example, the shaft assembly 12100 comprises a proximal outer shaft tube or member 12110 that extends distally from a nozzle assembly 12014 as will be discussed in further detail below, the surgical end effector 12200 is operably attached to an end cap attachment feature 12400. In one arrangement, the end cap attachment feature 12400 comprises a tubular shape body 12402 that is similar in size to the proximal outer shaft tube 12110 and is coupled to the distal end 12112 of the proximal outer shaft tube 12110 to form an articulation joint 12120. The shaft assembly 12100 may also include an internal spine member (not shown) that is pivotally coupled to the end cap 12400. A proximal end of the internal spine member may be rotatably coupled to a chassis (not shown) within the nozzle assembly 12014 in the various manners disclosed herein, for example.

Figure 54:
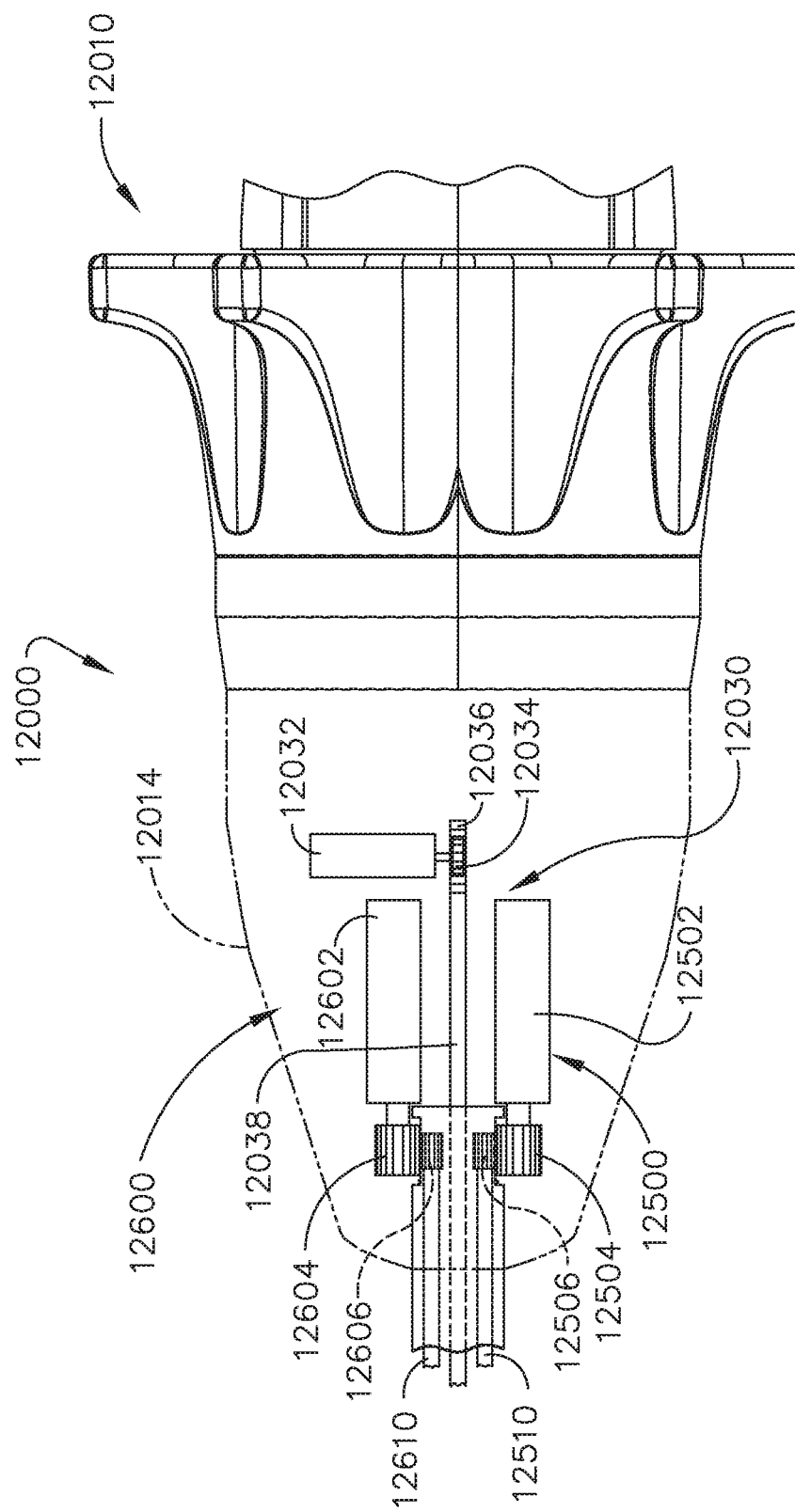
FIG. 54 is a top view of a portion of the powered surgical instrument of FIG. 53.

In the illustrated example, the surgical end effector 12200 is selectively articulatable about the articulation axis AA by an articulation system 12030. In one form, the articulation system 12030 includes an articulation motor 12032 that is operably supported in the nozzle assembly 12014, for example. See FIG. 54. In other examples, the articulation motor may be operably supported in the housing or handle or other portion of a robotic system. Referring to FIG. 54, the articulation motor 12032 is coupled to an articulation drive gear 12034 that is in meshing engagement with a drive gear rack 12036 that is attached to or otherwise formed in a proximal articulation driver 12038. A distal end of the proximal articulation driver 12038 is pivotally coupled to a distal articulation link (not shown) that spans the articulation joint and is coupled to the end cap 12400. Operation of the articulation motor 12032 will cause axial movement of the proximal articulation driver 12038. Axial movement of proximal articulation driver 12038 will apply articulation motions to the end cap 12400 and an elongate channel 12210 attached thereto to thereby cause the surgical end effector 12200 to articulate about the articulation axis AA relative to the shaft assembly 12100. Other articulation systems and arrangements may be employed in the various manners disclosed herein or in other embodiments, the surgical end effector may not be articulatable.

The surgical end effector 12200 further includes an anvil 12300 that is selectively pivotable relative to the elongate channel 12210 between open and closed configurations by a closure system 12500. In one arrangement, for example, the anvil 12300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. In at least one arrangement, the surgical end effector 12200 also includes a firing member 12620 that is axially movable within the surgical end effector 12200 between a starting position and an ending position. See FIG. 55. As will be discussed in further detail below, the firing member 12620 may be configured to sever tissue that is clamped between the anvil 12300 and a surgical staple cartridge 12700 that is operably supported in the elongate channel 12210. In one arrangement, the staple cartridge 12700 includes lines of surgical staples or fasteners (not shown) that are operably supported on corresponding drivers (not shown) that are movably supported in the cartridge. As the firing member 12620 is driven distally, the firing member 12620 cooperates with a sled or camming assembly (not shown) that is supported in the staple cartridge 12700 that serves to cam the drivers in a direction toward the closed anvil 12300 which causes the staples or fasteners supported thereon to pierce through the clamped tissue into forming contact with the underside of the closed anvil. Once the firing member 12620 has been distally advanced from its proximal starting position to its ending position within the end effector 12200, it may be retracted back to its starting position to permit the anvil 12300 to be opened to facilitate removal of the cut/stapled tissue from the end effector 12200. In other arrangements, the firing member 12620 may be left at the ending position wherein it is permitted to disengage from the anvil to facilitate opening of the anvil.

Figure 55:
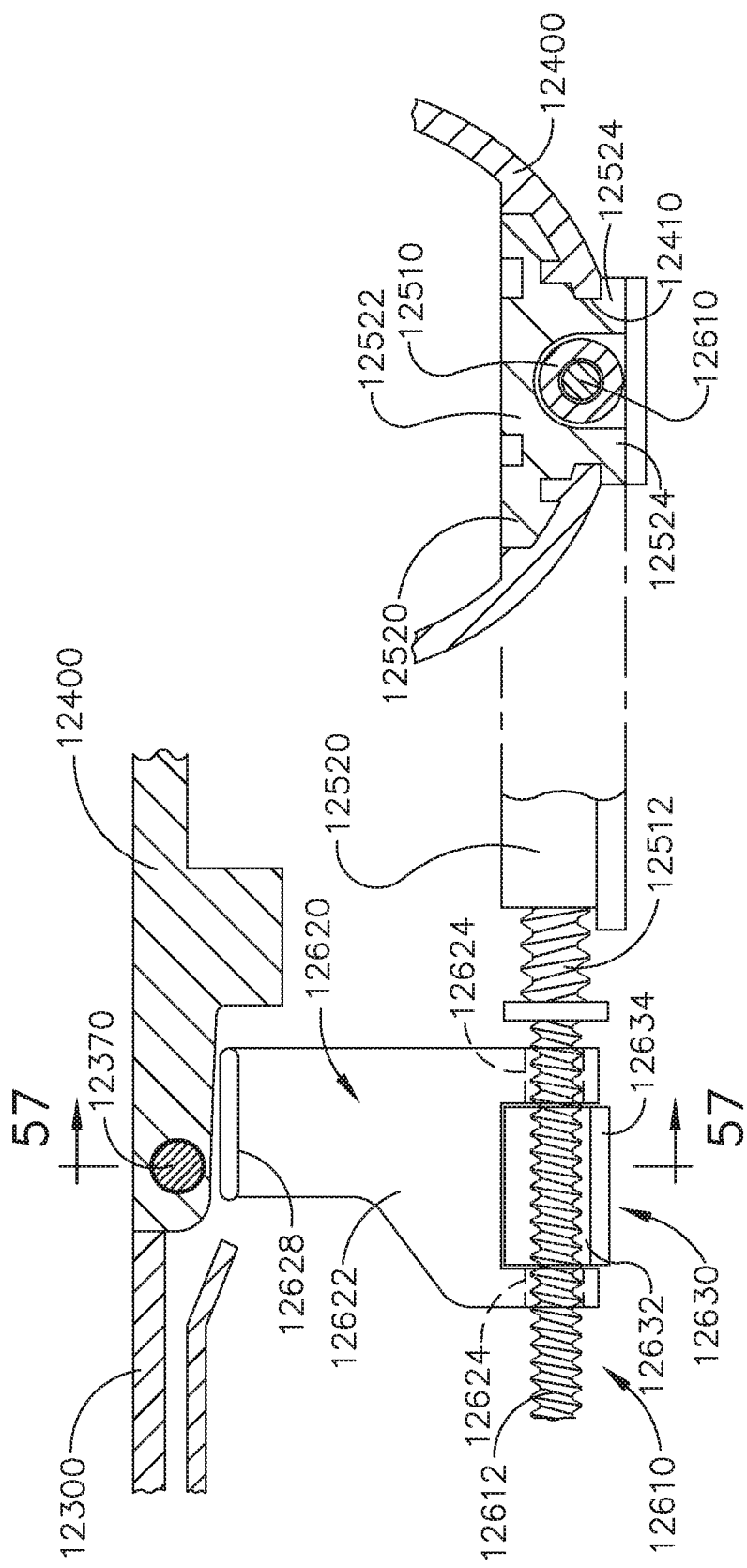
FIG. 55 is a partial cross-sectional view of portions of the surgical end effector of the surgical instrument of FIG. 53.
Figure 62:
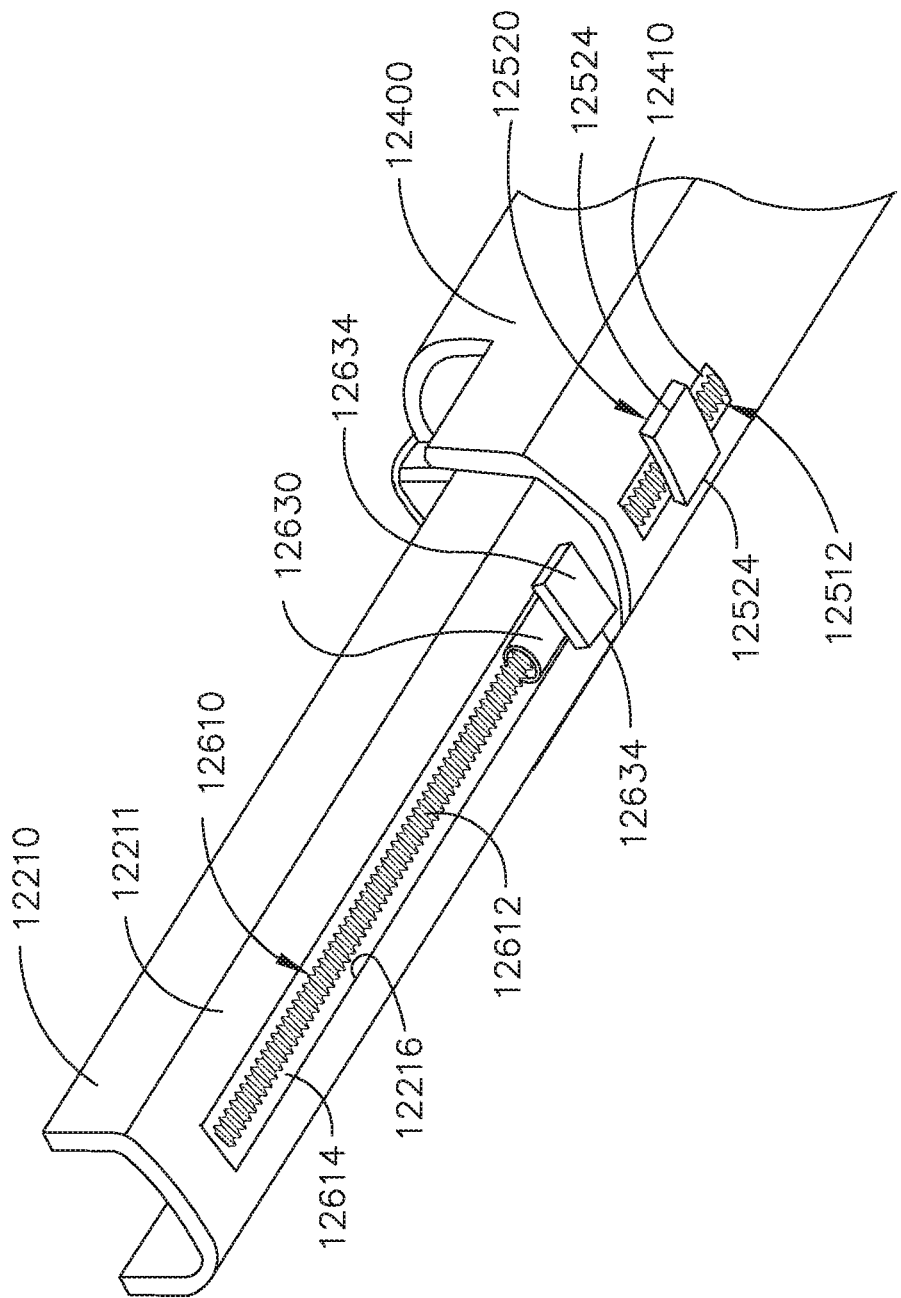
FIG. 62 is a partial bottom perspective view of the elongate channel and firing member of the surgical end effector of FIG. 59.

In at least one arrangement, the surgical instrument 12000 also employs a firing system 12600 that is configured to apply rotary drive motions to the firing member 12620 to drive the firing member between the starting and ending positions. In the example depicted in FIG. 54, the firing system 12600 includes a firing motor 12602 that is operably supported in the nozzle assembly 12014, for example. In other examples, the firing motor 12602 may be operably supported in the housing or handle or other portion of a robotic system. The firing motor 12602 is coupled to a firing drive gear 12604 that is in meshing engagement with a driven gear 12606 that is attached to or otherwise formed in rotary firing drive shaft 12610. The firing drive shaft 12610 may be flexible to permit articulation of the surgical end effector 12200 in the manner described above. As can be seen in FIG. 55, the firing member 12620 comprises a body portion 12622 that includes two downwardly extending hollow mounting portions 12624 that are unthreaded and spaced from each other to receive a threaded drive nut 12630 therebetween. The threaded drive nut 12630 is threaded onto a threaded portion 12612 of the rotary firing drive shaft 12610. A distal end 12614 of the rotary firing drive shaft 12610 may be configured to be rotatably supported in a bearing (not shown) housed within the elongate channel to rotatably support the rotary firing drive shaft 12610 therein. The drive nut 12630 includes a vertical tab portion 12632 that is sized to extend through an axial slot 12216 in the bottom surface 12211 of the elongate channel 12210. See FIG. 62. Two laterally extending retention flanges 12634 are formed on the vertical tab portion 12632 to slidably engage the bottom surface 12211 of the elongate channel 12210. In addition, two laterally extending anvil engagement tabs 12628 are formed on the top of the body portion 12622 of the firing member 12620 and are configured to engage the anvil 12300 as the firing member 12620 is axially moved within the end effector. The threaded drive nut 12630 is threaded onto a threaded portion 12612 of the rotary firing drive shaft 12610. A distal end of the rotary firing drive shaft 12610 may be configured to be rotatably supported in a bearing (not shown) housed within the elongate channel 12210 to rotatably support the rotary firing drive shaft 12610 therein. In various aspects, as the firing member 12620 is distally driven through the surgical staple cartridge 12700, the firing member 12620, through the engagement of the anvil engagement tabs 12628 with the anvil 12300 and the engagement of the laterally extending retention flanges 12634 with the channel 12210, may serve to maintain a desired amount of tissue gap between a deck surface 12702 on the staple cartridge 12700 and a staple forming undersurface 12307 on the anvil 12300. See FIG. 53.

In the illustrated example, in addition, to a rotary driven firing system 12600, the surgical instrument 12000 also includes a rotary driven closure system 12500 that is configured to apply rotary closure motions to the anvil 12300. As can be seen in FIG. 54, for example, in one arrangement, the rotary driven closure system 12500 comprises a closure motor 12502 that is operably supported in the nozzle assembly 12014, for example. In other examples, the closure motor 12502 may be operably supported in the housing or handle or other portion of a robotic system. The closure motor 12502 is coupled to a closure drive gear 12504 that is in meshing engagement with a driven gear 12506 that is attached to or otherwise formed in rotary closure drive shaft 12510. The closure drive shaft 12510 may be flexible to permit articulation of the surgical end effector 12200 in the manner described above.

As can be seen in FIG. 56, the anvil 12300 includes a proximally protruding anvil mounting tab 12310 that is configured to be pivotally coupled to a corresponding pivot lug portion 12404 of the end cap 12400. For example, the pivot lug portion 12404 is formed on a first or right side of the endcap centerline ECL and a corresponding anvil mounting portion 12312 of the anvil mounting tab 12310 is formed on a second or left side of the anvil centerline ACL that corresponds to (aligned with) the endcap centerline ECL when the two components are coupled together. When the anvil 12300 is movably coupled to the end cap 12400, the anvil centerline ACL and the endcap centerline ECL are aligned along an end effector axis or end effector center plane ECP that extends axially through a center of the end effector 12200. Stated another way, the end effector center plane ECP bisects the end effector 12200. See FIGS. 60 and 61. In one aspect, the pivot lug portion 12404 comprises a vertically extending pivot lug attachment face 12405 that is adapted to slidably confront a vertically extending anvil attachment face 12317 formed on a central portion 12316 of the anvil mounting tab 12310. Still referring to FIG. 56, the proximal end 12314 of the anvil mounting tab 12310 is laterally wider than the central portion 12316. When the anvil 12300 is attached to the end cap 12400, the proximal end portion 12314 of the anvil mounting tab 12310 is proximal to the pivot lug portion 12404 and the pivot lug attachment face 12405 and the vertically extending anvil attachment face 12317 movably confront each other along the centrally disposed end effector central plane ECP. See FIG. 60. In the illustrated arrangement, an upper surface 12303 of an anvil body portion 12302 of the anvil 12300 and the anvil mounting portion 12312 of the anvil mounting tab 12310 are rounded to match or at least approximately match the radius of the end cap 12400 to facilitate easy insertion of the surgical end effector and elongate shaft through a trocar, for example.

In one aspect, the anvil 12300 is pivotally coupled to the end cap 12400 by a rivet 12370 that extends through a passage 12360 in the anvil mounting portion 12312 of the anvil mounting tab 12310 and a corresponding passage 12406 in the pivot lug portion 12404 of the end cap 12400. In at least one arrangement, the rivet 12370 comprises a solid core rivet with a shank 12372 having diameter of, for example, 0.05"-0.1" with an orbit formed head 12374 on one end and a machined end 12376 formed on the other end. See FIG. 57. The rivet 12370 may be installed such that it may maintain a final formed height that would ensure intimate contact between the anvil mounting portion 12312 and the pivot lug portion 12404. The orbit formed rivet head 12374 would swell the rivet shank 12372 on that side of the anvil 12300 or end cap 12400 preventing the rivet 12370 from rotating with respect to that component while the machined end 12376 would not have a swelled shank allowing the adjacent part to rotate with respect to the rivet 12370 and the other part (anvil mounting portion 12312 or pivot lug portion 12404). In the example illustrated in FIG. 57, the end of the rivet 12370 that is adjacent to the anvil mounting portion 12312 is orbit formed so that part of the rivet 12370 does not rotate relative to the anvil mounting portion 12312 and the part of the rivet 12370 extending through the end cap 12400 is free to rotate allowing the anvil 12300 to freely pivot relative to the pivot lug portion 12404. As can be seen in FIG. 57, the rivet shank 12372 has a predefined final form length RL that is sized to facilitate such rotational travel. Also, as can be seen in FIG. 56, in one arrangement for example, the end cap 12400 may have a length EL of approximately 0.675". The anvil body 12302 may also be formed with downwardly extending tissue stop members 12305 that are configured to prevent the clamped tissue from extending proximally beyond the proximal-most staples or fasteners in a staple cartridge 12700 that is seated in the elongate channel 12210. In the illustrated example, the tissue stops 12305 may have a stop length SL of approximately 0.400" and the distance PSD from a distal end of each tissue stop 12305 to the centerline of the passage 12360 is approximately 0.500". This distance may correspond to the distance from the proximal-most staples or fasteners to the pivot axis PA about which the anvil 12300 pivots relative to the endcap 12400.

Figure 58:
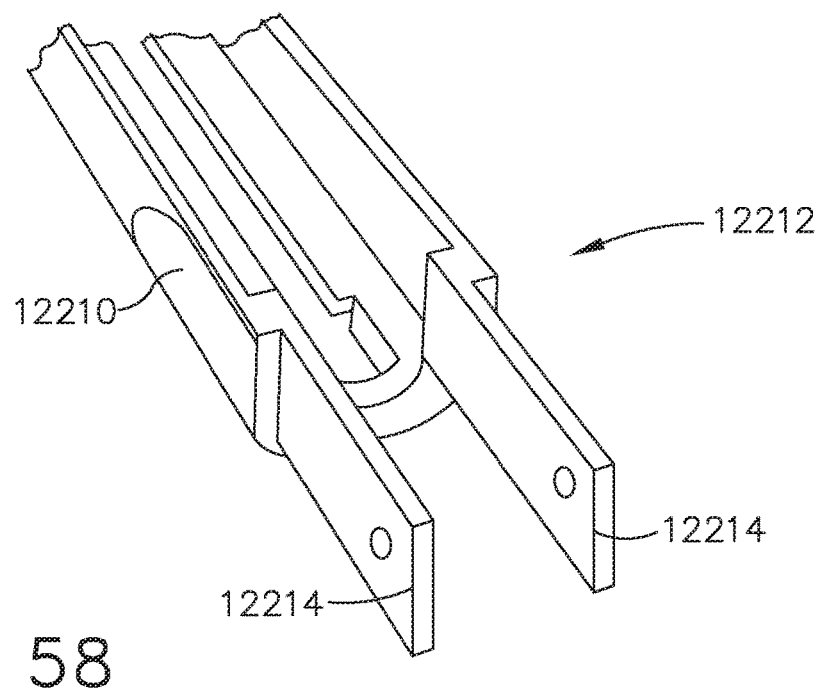
FIG. 58 is a perspective proximal end view of a portion of an elongate channel of the surgical end effector of FIG. 57.

As can be seen in FIG. 58, a pair of channel attachment tabs 12214 protrude from a proximal end 12212 of the elongate channel 12210. The channel attachment tabs 12214 are configured to be seated in corresponding grooves 12408 in the endcap 12400. See FIG. 60. The tabs 12214 may be welded, glued, pinned etc. to the end cap 12400.

Turning now to FIGS. 55 and 59-61, the rotary driven closure system 12500 also comprises an axially movable closure shuttle 12520 that is in threaded engagement with a threaded portion 12512 of the closure drive shaft 12510. In the illustrated arrangement, the closure shuttle 12520 comprises a shuttle base portion 12522 that extends through a proximal cap slot 12410 formed in the bottom of the end cap 12400. A lateral flange 12524 extends laterally from each side of the shuttle base portion 12522 to slidably engage the bottom of the end cap 12400. See FIG. 55. As can be further seen in FIG. 55, the closure drive shaft 12510 is hollow to permit the firing drive shaft 12610 to concentrically extend therethrough. Thus, rotation of the closure drive shaft 12510 in a first rotary direction will cause the closure shuttle 12520 to move distally and rotation of the closure drive shaft 12510 in an opposite rotary direction will cause the closure shuttle 12520 to move in a proximal direction.

Figure 59:
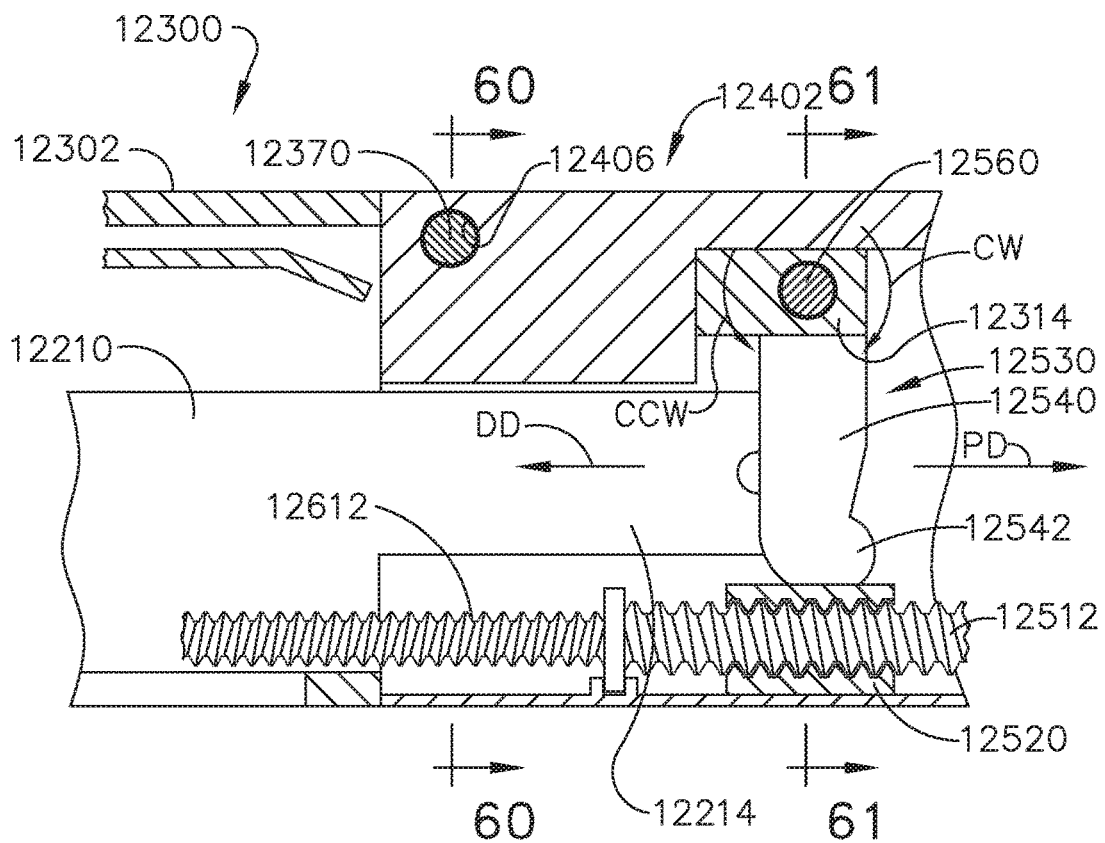
FIG. 59 is a partial side elevational view of a portion of the surgical end effector of FIG. 57, with some components shown in cross-section and with the anvil thereof in a closed position.
Figures 60, 61:
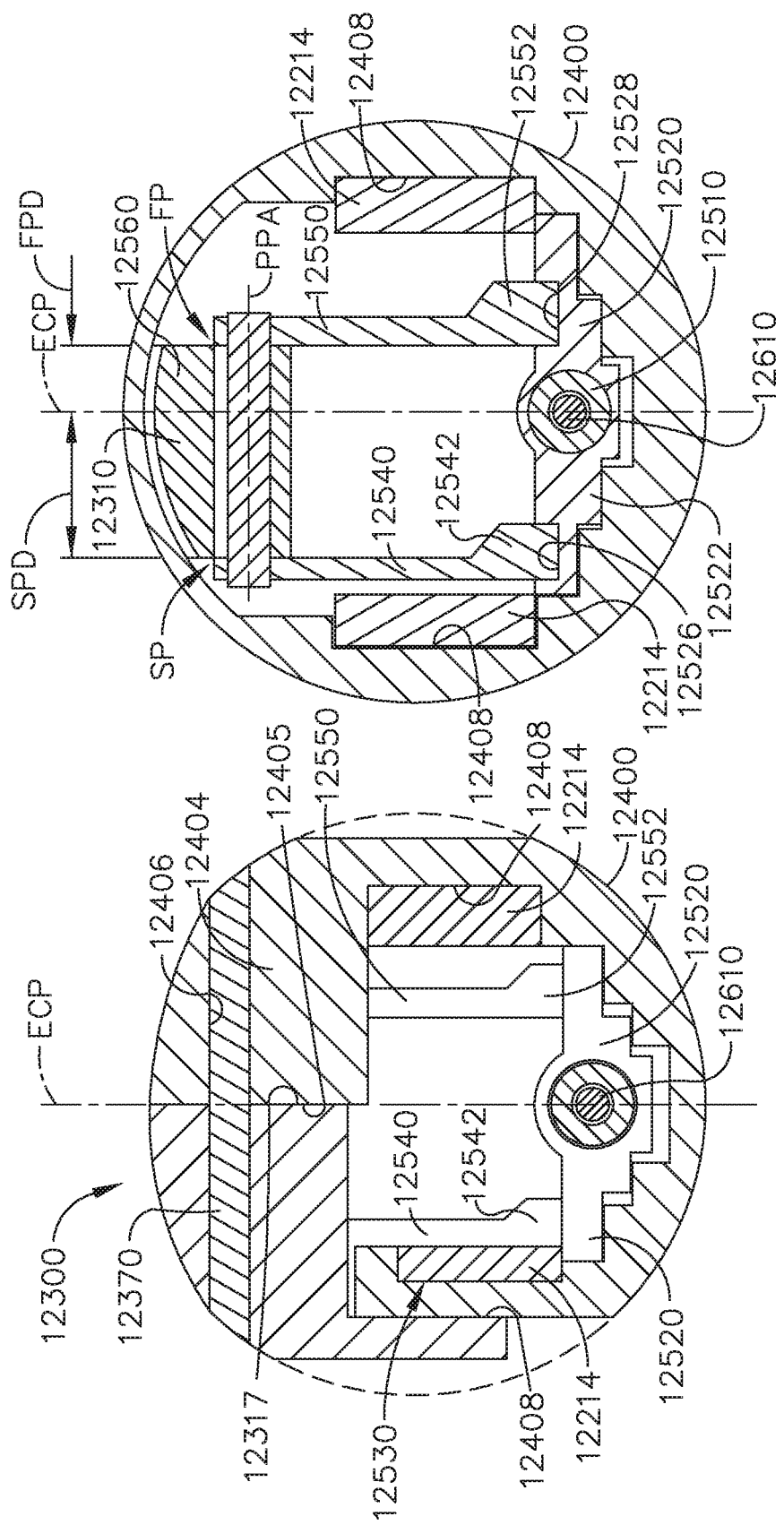
FIG. 60 is a cross-sectional end view of the surgical end effector of FIG. 59 taken along line 60-60 in FIG. 59.
FIG. 61 is a cross-sectional end view of the surgical end effector of FIG. 59 taken along line 61-61 in FIG. 59.

In the illustrated example, the axial movement of the closure shuttle 12520 is transferred to the anvil 12300 by a pivoting closure linkage assembly 12530. In one arrangement, the closure linkage assembly 12530 includes a first pivot arm 12540 and a second pivot arm 12550 that are each pivotally attached to the proximal end portion 12314 of the anvil mounting tab 12310 and suspended therefrom. As can be seen in FIG. 61, for example, the first pivot arm 12540 and the second pivot arm 12550 may be pivotally coupled to the proximal end portion 12314 of the anvil mounting tab 12310 by a pivot pin 12560 that defines a common proximal pivot axis PPA about which the pivot arms 12540 and 12550 can pivot. The first pivot arm 12540 comprises a first free end 12542 that is wider than the remaining portion of the first pivot arm 12540 and is configured to be movably and drivably engaged in a first drive groove 12526 in the closure shuttle base portion 12522. See FIG. 61. The first pivot arm 12540 is coupled to the anvil mounting tab 12310 at a first point FP that is located a first pivot arm distance FPD from the end effector center plane ECP. Likewise, the second pivot arm 12550 comprises a second free end 12552 that is wider than the remaining portion of the second pivot arm 12550 and is configured to be movably and drivably engaged in a second drive groove 12528 in the closure shuttle base portion 12522. The second pivot arm 12550 is coupled to the anvil mounting tab 12310 at a second point SP that is located a second pivot arm distance SPD from the end effector center plane ECP. In the illustrated arrangement the closure system is asymmetrically coupled to the anvil 12300. For example, as can be seen in FIG. 61, SPD>FPD. When the closure shuttle 12520 is driven in the distal direction DD, the pivot arms 12540 and 12550 by virtue of their engagement with the closure shuttle 12520 are caused to pivot in a first direction (clockwise CW in FIG. 59) which causes a pivotal opening motion to be applied to the anvil mounting tab 12310 to pivot the anvil 12300 about the pivot axis PA relative to the end cap 12400 to an open position. When the closure shuttle 12520 is axially moved in a proximal direction PD, the pivot arms 12540, 12550 pivot in a second direction (counterclockwise CCW in FIG. 59) which causes a closure motion to be applied to the anvil mounting tab 12310 to pivot the anvil 12300 about the pivot axis PA relative to the end cap 12400 to a closed position (FIG. 59). The larger free end portions 12542, 12552 of the pivot arms 12540, 12550, respectively are more robust than the remaining portions of the pivot arms to better distribute the closure forces through the pivot arms.

Figure 63:
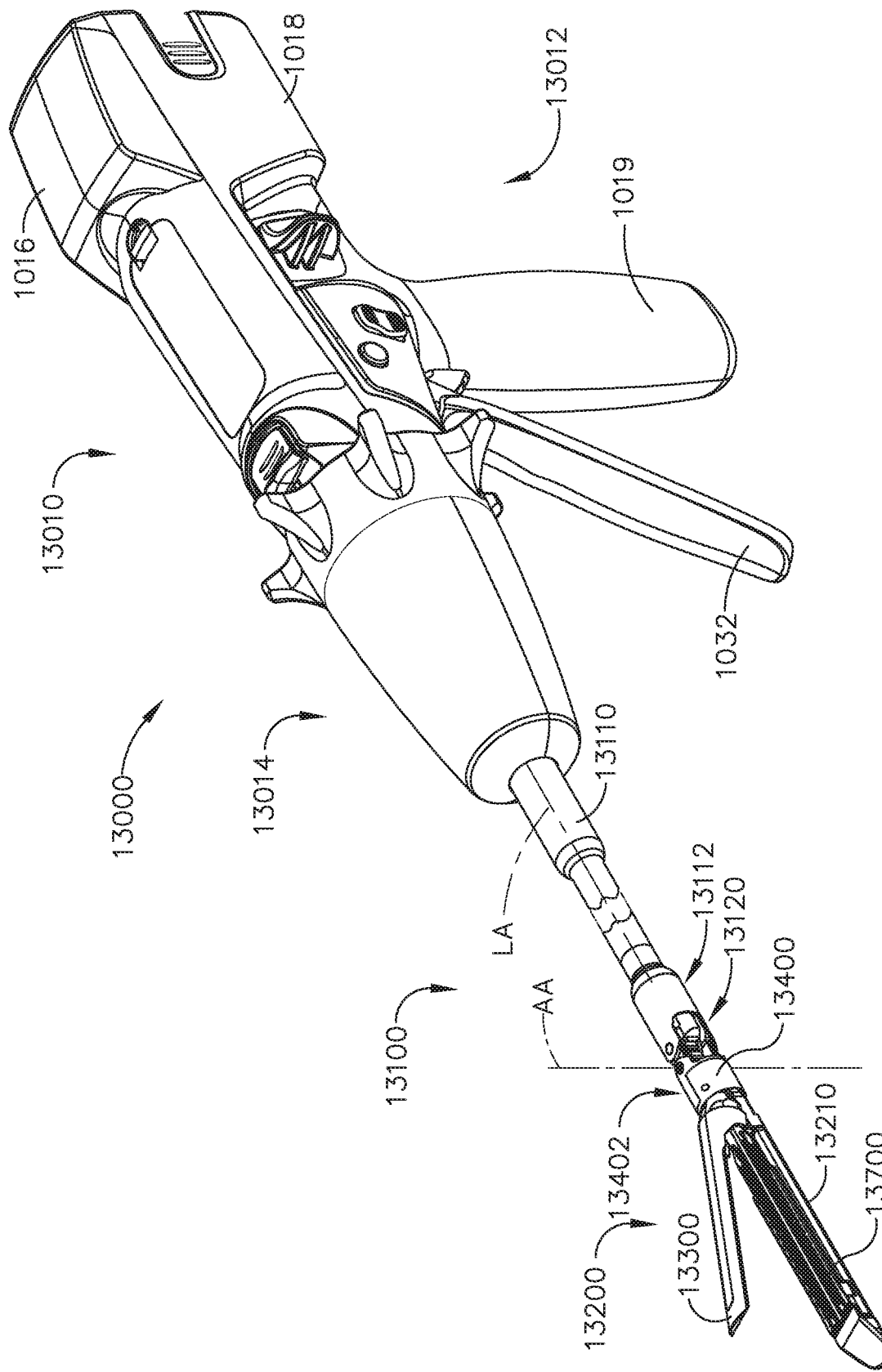
FIG. 63 is a perspective view of another powered surgical instrument.

FIG. 63 depicts a surgical instrument 13000 that may be used to cut and staple tissue. The instrument includes a housing 13010 that comprises a handle 13012 that is configured to be grasped, manipulated and actuated by the clinician. As can be seen in FIG. 63, for example, the instrument 13000 includes a shaft assembly 13100 that has a surgical end effector 13200 operably coupled thereto that is configured to cut and staple tissue. As will be discussed in further detail below, for example, the surgical end effector 13200 comprises an elongated channel 13210 that is configured to operably support a replaceable surgical staple cartridge 13700 therein and an anvil 13300 that is movably supported relative thereto for movement between open and closed positions. The shaft assembly 13100 comprises an interchangeable shaft assembly that is intended to be removably couplable to the handle assembly 13012 in the various manners disclosed herein. However, in other arrangements, the shaft assembly 13100 may comprise a dedicated shaft assembly that is not intended to be removed from the handle 13012. In still other arrangements, the shaft assembly 13100 may be operably coupled to or operably interface with a robotic system that is capable of generating the rotary operating motions necessary to operate the surgical end effector in the various manners disclosed herein. Only those specific components necessary to understand the functions and operation of the shaft assembly 13100 will be discussed in further detail below.

In the illustrated example, the shaft assembly 13100 includes an articulation joint 13120 that facilitates articulation of the surgical end effector 13200 about an articulation axis AA that is transverse to a longitudinal shaft axis LA. Other shaft assemblies, however, may not be capable of articulation. In accordance with one aspect, the shaft assembly 13100 comprises a proximal outer shaft tube or member 13110 that extends distally from a nozzle assembly 13014 as will be discussed in further detail below, the surgical end effector 13200 is operably attached to an end cap attachment feature 13400. In one arrangement, the end cap attachment feature 13400 comprises a tubular shape body 13402 that is similar in size to the proximal outer shaft tube 13110 and is coupled to a distal end 13112 of the proximal outer shaft tube 13110 to form the articulation joint 13120. The end cap 13400 may also comprise a proximal portion of the elongate channel 13210. The shaft assembly 13100 may also include an internal spine member (not shown) that is pivotally coupled to the end cap 13400. A proximal end of the internal spine member may be rotatably coupled to a chassis (not shown) within the nozzle assembly 13014 in the various manners disclosed herein, for example.

Figure 64:
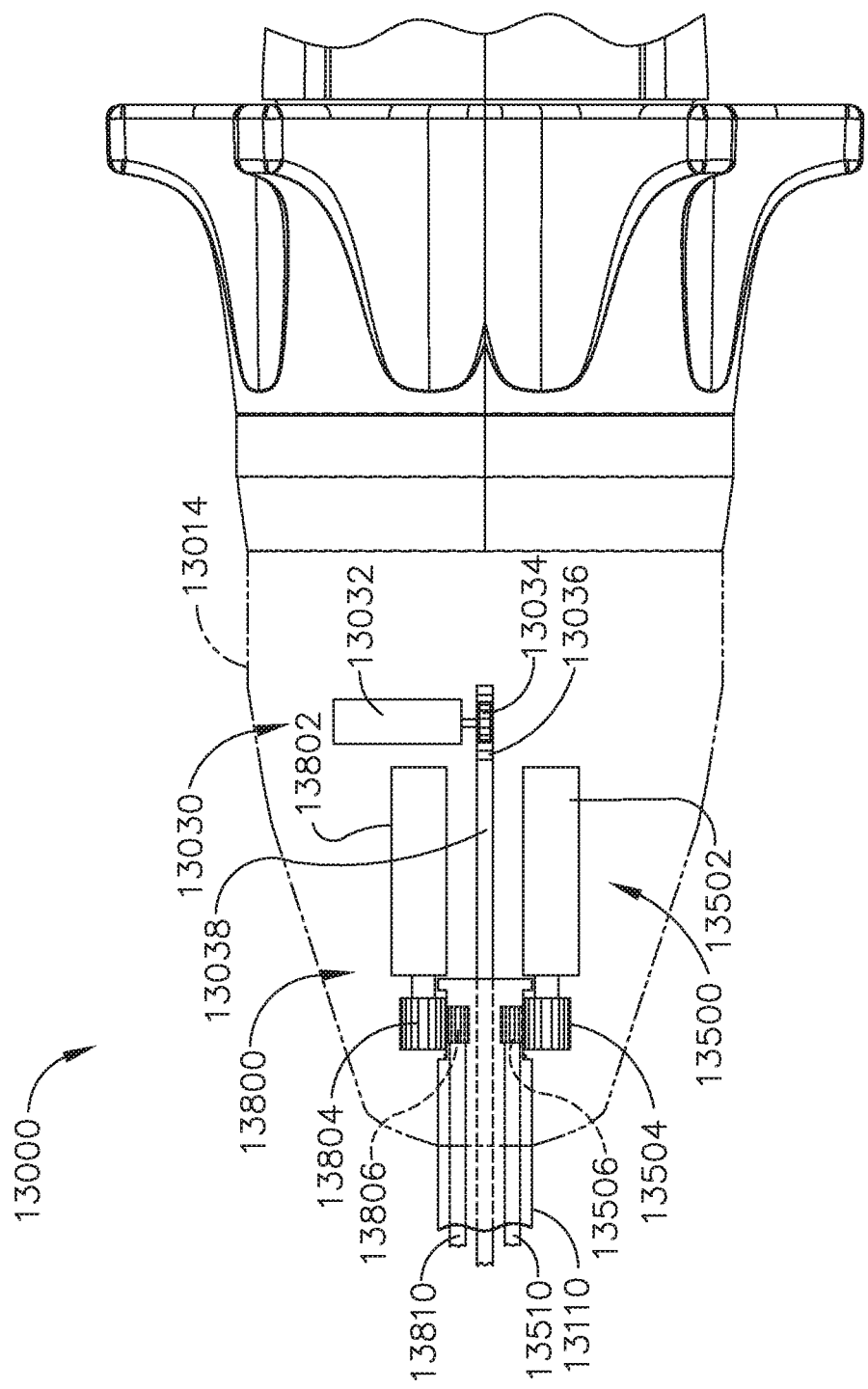
FIG. 64 is a top view of the powered surgical instrument of FIG. 63.

In the illustrated example, the surgical end effector 13200 is selectively articulatable about the articulation axis AA by an articulation system 13030. In one form, the articulation system 13030 includes an articulation motor 13032 that is operably supported in the nozzle assembly 13014, for example. See FIG. 64. In other examples, the articulation motor may be operably supported in the housing or handle or other portion of a robotic system. Referring to FIG. 64, the articulation motor 13032 is coupled to an articulation drive gear 13034 that is in meshing engagement with a drive gear rack 13036 that is attached to or otherwise formed in a proximal articulation driver 13038. A distal end of the proximal articulation driver 13038 is pivotally coupled to a distal articulation link (not shown) that spans the articulation joint and is coupled to the end cap 13400. Operation of the articulation motor 13032 will cause axial movement of the proximal articulation driver 13038. Axial movement of proximal articulation driver 13038 will apply articulation motions to the end cap 13400 and the elongate channel 13210 attached thereto to thereby cause the surgical end effector 13200 to articulate about the articulation axis AA relative to the shaft assembly 13100. Other articulation systems and arrangements may be employed in the various manners disclosed herein. In other embodiments, the surgical end effector may not be articulatable.

As indicated above, the surgical end effector 13200 includes an anvil 13300 that is selectively movable relative to the elongate channel 13210 between open and closed configurations by a rotary driven closure system 13500. As can be seen in FIG. 64, in one arrangement, the rotary driven closure system 13500 comprises a closure motor 13502 that is operably supported in the nozzle assembly 13014, for example. In other examples, the closure motor 13502 may be operably supported in the housing or handle or other portion of a robotic system. The closure motor 13502 is coupled to a closure drive gear 13504 that is in meshing engagement with a driven gear 13506 that is attached to or otherwise formed in rotary closure drive shaft 13510. The closure drive shaft 13510 may be flexible to permit articulation of the surgical end effector 13200 in the manner described above.

Figure 65:
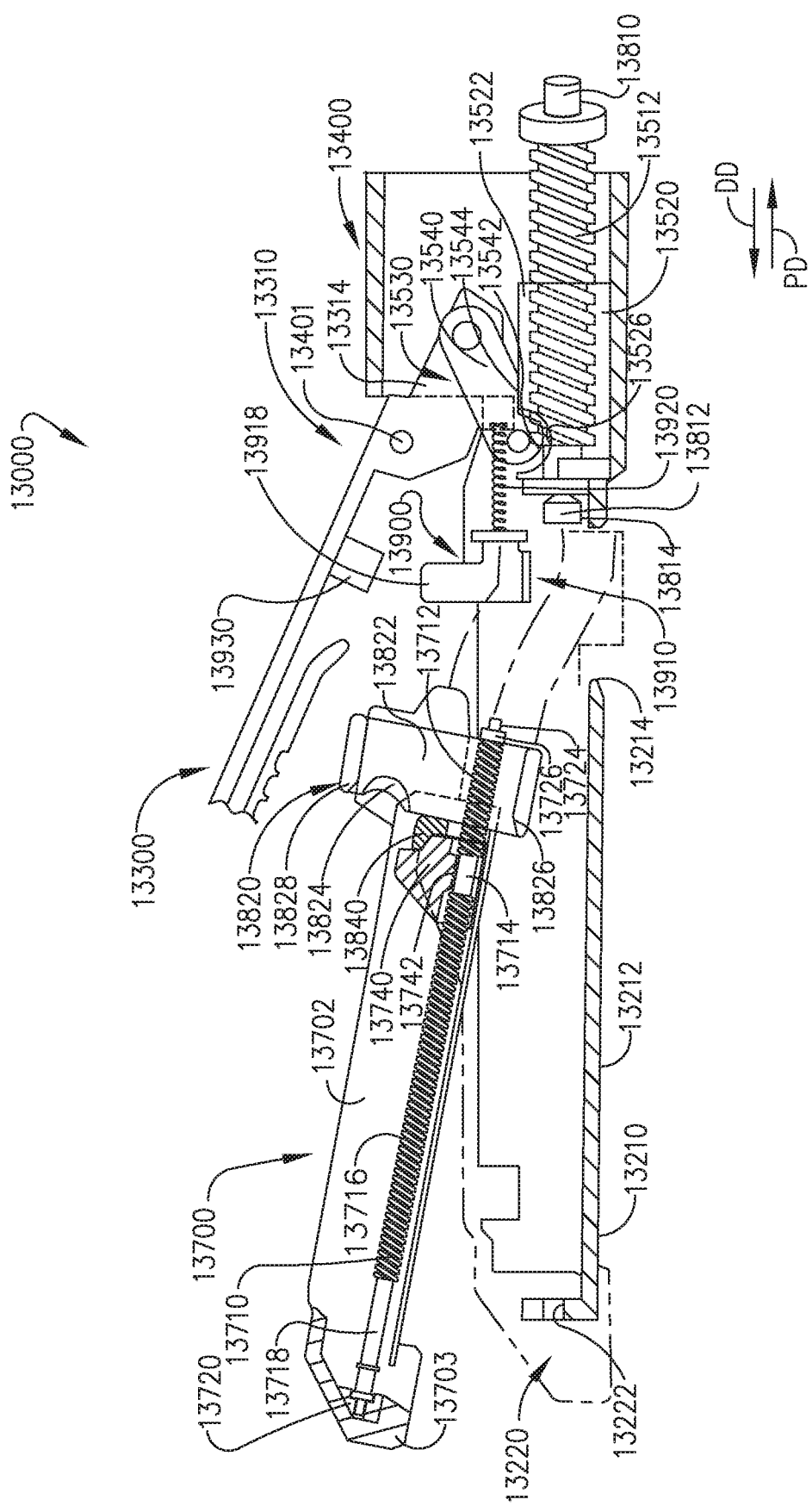
FIG. 65 is a partial cross-sectional side view of a surgical end effector of the powered surgical instrument of FIG. 63, with a surgical staple cartridge being operably installed therein.

As can be seen in FIG. 65, the anvil 13300 includes a proximally protruding anvil mounting tab 13310 that is configured to be pivotally coupled to a corresponding portion of the end cap 13400 by, for example, a rivet 13401 or other pivot arrangements disclosed herein. In the illustrated arrangement, the rotary driven closure system 13500 also comprises an axially movable closure shuttle 13520 that is in threaded engagement with a threaded distal closure shaft segment 13512 that is configured to be drivingly coupled the closure drive shaft 13510. In the illustrated arrangement, the closure shuttle 13520 comprises a shuttle base portion 13522 that extends through a proximal cap slot (not shown) that is formed in the bottom of the endcap 13400. A lateral flange (not shown) extends laterally from each side of the shuttle base portion 13522 to slidably engage the bottom of the endcap 13400 in the various manners disclosed herein. In one arrangement, for example, the anvil 13300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein.

In the illustrated example, the axial movement of the closure shuttle 13520 is transferred to the anvil 13300 by a pivoting closure link assembly 13530. In one arrangement, the closure link assembly 13530 includes a pair of pivot arms 13540 (only one can be seen in FIG. 65) that are each pivotally attached to a proximal end portion 13314 of the anvil mounting tab 13310 and suspended therefrom. Each pivot arm 13540 comprises a free end 13542 that includes a notch 13544 that is configured to drivingly engage a corresponding drive groove 13526 in the closure shuttle base portion 13522. When the closure shuttle 13520 is driven in the distal direction DD, the pivot arms 13540, by virtue of their engagement with the closure shuttle 13520, pivot in a first direction to apply pivotal opening motion to the anvil mounting tab 13310. This opening motion causes the anvil 13300 to pivot to an open position. When the closure shuttle 13520 is axially moved in a proximal direction PD, the pivot arms 13540 pivot in a second direction which causes a pivot closure motion to be applied to the anvil mounting tab 13310 and pivot the anvil 13300 to a closed position.

Figure 66:
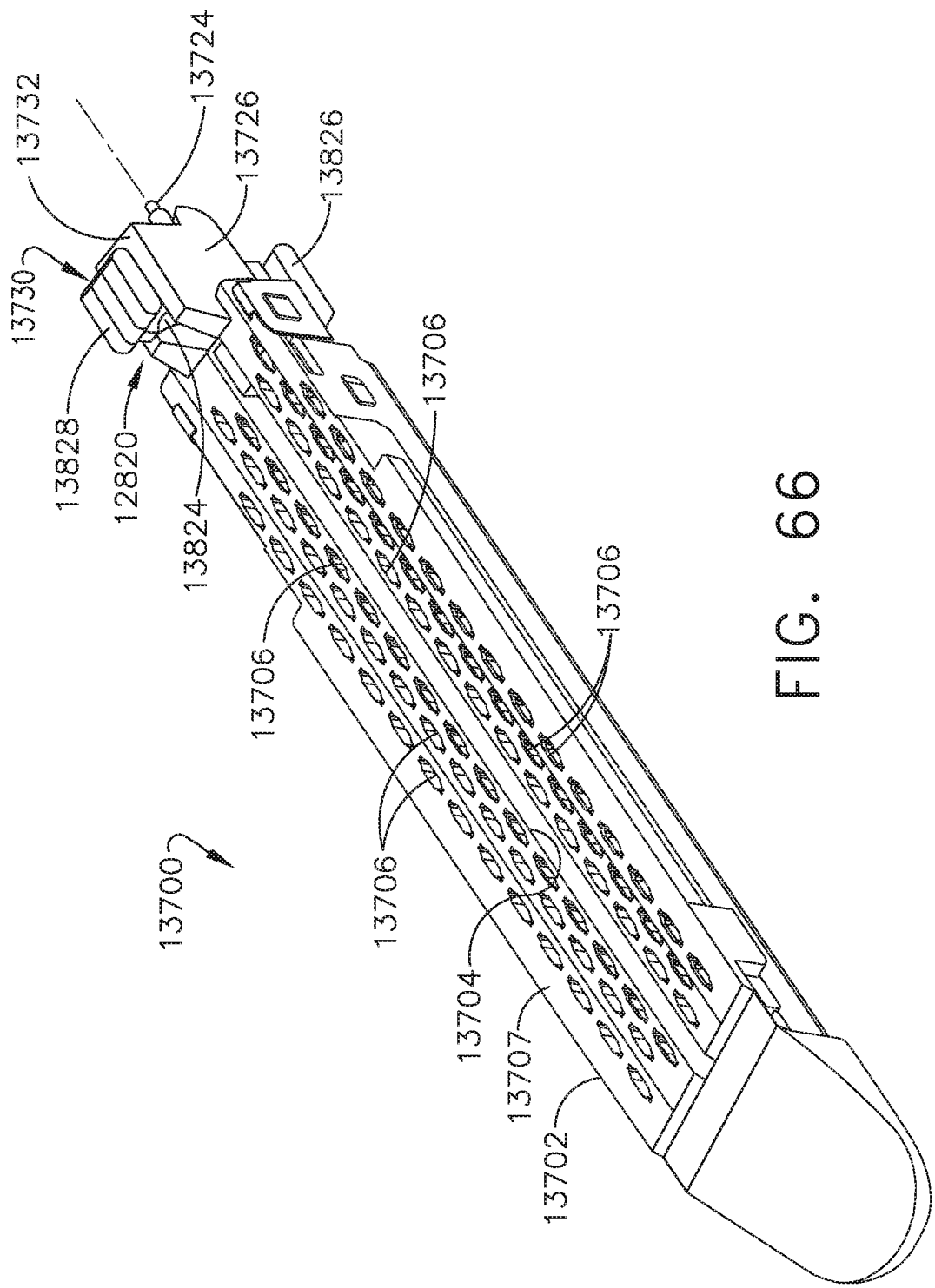
FIG. 66 is a perspective view of the surgical staple cartridge of FIG. 65.

As also indicated above, the surgical end effector 13200 is configured to operably support a replaceable surgical staple cartridge 13700 therein. The staple cartridge 13700 includes an onboard firing member 13820 that is configured to be rotatably driven between a starting and ending position within the staple cartridge 13700. The firing member 13820 comprises a vertically extending firing member body 13822 that has a tissue cutting surface 13824 formed thereon or attached thereto. A pair of channel engagement tabs 13826 extend laterally from the bottom of the firing member body 13822 and a pair of anvil engagement tabs 13828 extend from the top portion of the firing member body 13822 such that the firing member 13820 resembles an I-beam configuration when viewed from an end thereof. As can be seen in FIG. 66, in the illustrated example, the surgical staple cartridge 13700 comprises an elongate cartridge body 13702 that includes a deck surface 13707. The cartridge body 13702 further comprises a centrally disposed elongate cartridge slot 13704 that is configured to accommodate the axial travel of the firing member 13820 therein. Also in the illustrated example, three lines of surgical staple pockets 13706 are formed on each side of the elongate slot 13704 and open through the deck surface 13707. Each staple pocket 13706 may have a staple driver (not shown) associated therewith that supports a surgical staple or fastener (not shown) thereon.

As can be seen in FIG. 65, the cartridge body 13702 operably supports an onboard rotary firing drive shaft 13710. The firing drive shaft 13710 includes a proximal thread segment 13712, an unthreaded segment 13714 and a distal thread segment 13716 that extends from the unthreaded segment 13714 to an unthreaded distal end 13718. The unthreaded distal end 13718 of the firing drive shaft 13710 is rotatably supported in a distal bearing 13720 that is supported in a distal end 13703 of the cartridge body 13702. In the illustrated example, the firing member body 13822 is threaded onto the proximal thread segment 13712 when in a proximal-most, "loading position". As can be seen in FIG. 66, a safety garage 13732 is formed on a proximal end 13730 of the cartridge body 13702 such that the tissue cutting surface 13824 is protected thereby (unexposed) when the firing member 13820 is in the loading position. When the firing member 13820 is in the loading position, the bottom of the firing member body 13822 is configured to extend through a loading opening 13214 in the bottom 13212 of the elongate channel 13210 during installation of the cartridge 13700 into the elongate channel 13210. As can be seen in FIG. 67, a channel slot 13216 is provided in the bottom 13212 of the elongate channel 13210 and extends distally from the loading opening 13214. When the staple cartridge 13700 is operably seated in the elongate channel 13210, the bottom portion of the firing member 13820 protrudes through the loading opening 13214 such that when the firing member 13820 is advanced distally, the firing member body 13822 is aligned with the channel slot 13216 and the channel engagement tabs 13826 are positioned to slidably engage the bottom 13212 of the elongate channel 13210 on each side of the channel slot 13216.

In one example, at least one C-shaped clip 13890 may be journaled within the cartridge body 13702 such that a center portion 13892 of the clip 13890 extends through the elongate cartridge slot 13704 in the cartridge body 13702 such that an upper leg 13894 of the clip 13890 rides on an inside surface or ledge 13708 in the cartridge body 13702 adjacent the cartridge slot 13704. A lower leg 13896 of the clip 13890 rides on a bottom surface 13213 of the channel bottom 13212 as shown in FIG. 68. When the cartridge 13700 is initially installed, the C-shaped clip(s) 13890 may be positioned proximally of the elongate channel slot 13216 such that the cartridge 13700 may be properly seated therein. When the firing member 13820 is distally advanced, the C-shaped clip(s) 13890 is advanced distally down the aligned cartridge slot 13704 and channel slot 13216 to provide additional stabilization of the cartridge 13700 during the firing operation.

As can also be seen in FIG. 67, in at least one arrangement, at least one cartridge locator member 13722 is formed on or otherwise attached to the cartridge body 13702 and is located and sized to be seated in a corresponding notch 13218 or other mating feature formed in the elongate channel 13210 to ensure that the cartridge 13700 is properly seated in the elongate channel 13210 during installation. In one example, locator members 13722 are formed on each lateral side of the cartridge body 13702. Also in the illustrated example, a drive shaft support cradle 13222 is formed on a distal end 13220 of the channel 13210 and is configured to rotatably cradle the unthreaded distal end 13718 of the firing drive shaft 13710 (proximal to the support bearing 13720). See FIG. 65.

Returning to FIG. 64, the surgical instrument 13000 also employs a rotary driven firing system 13800 that is configured to apply rotary drive motions to the firing member 13820 to drive the firing member 13820 between the starting and ending positions within the staple cartridge 13700. In the example depicted in FIG. 64, the rotary driven firing system 13800 includes a firing motor 13802 that is operably supported in the nozzle assembly 13014. In other examples, the firing motor 13802 may be operably supported in the housing or handle or other portion of a robotic system. The firing motor 13802 is coupled to a firing drive gear 13804 that is in meshing engagement with a driven gear 13806 that is attached to or otherwise formed in rotary firing drive shaft 13810. The firing drive shaft 13810 may be flexible to permit articulation of the surgical end effector 13200 in the manner described above. As can be seen in FIGS. 65 and 67, the firing drive shaft 13810 extends through the hollow distal closure shaft segment 13512 that is configured to be drivingly coupled to the closure drive shaft 13510 and has a drive coupler 13812 attached thereto. In one arrangement, the drive coupler 13812 comprises a female drive socket 13814 that is configured to drivably receive a corresponding male coupler 13724 on the firing drive shaft 13710. When the male coupler 13724 is brought into driving engagement with the female drive socket 13814, rotation of the firing drive shaft 13810 will result in rotation of the firing drive shaft 13710 in the surgical staple cartridge 13700.

FIG. 65 illustrates the firing member 13820 in the loading position. When in that position, the firing member 13820 may abut a collar portion 13726 of the male coupler 13724. As can also be seen in FIG. 65, the staple cartridge 13700 also includes a sled or camming assembly 13740 that is movably supported in the staple cartridge 13700. The camming assembly 13740 is threadably journaled on the firing drive shaft 13710 by a series of internal threads 13742. As can be seen in FIG. 65, when the firing member 13820 is in the loading position, the internal threads 13742 in the camming assembly 13740 are located on the unthreaded segment 13714 of the firing drive shaft 13710.

Figure 70:
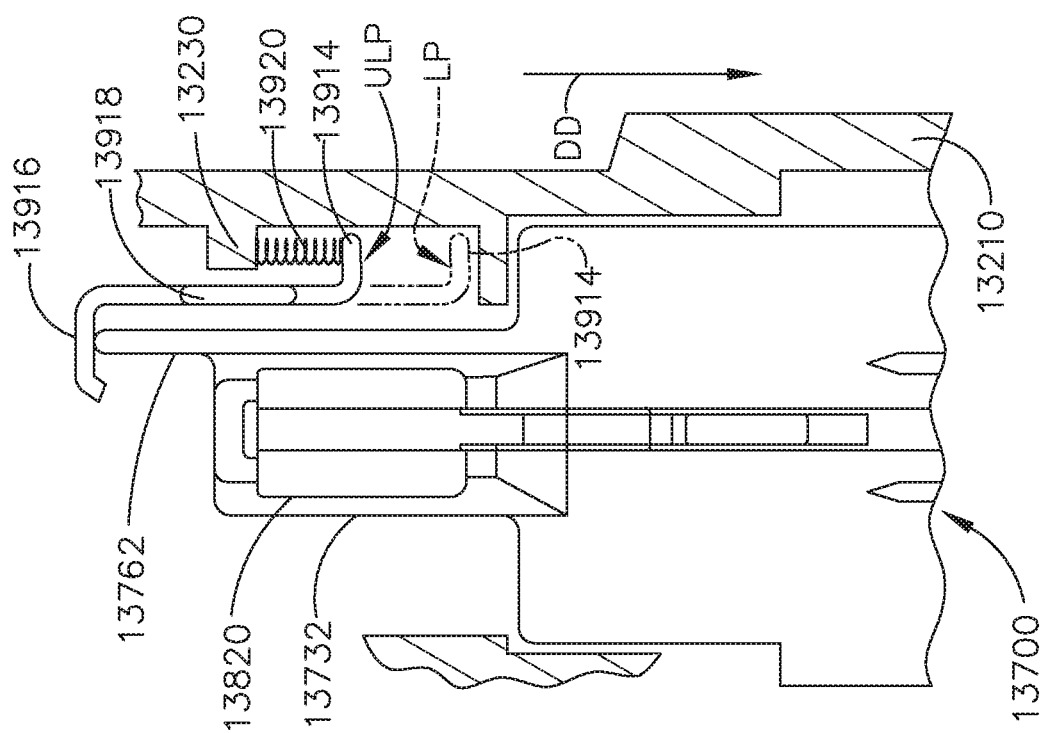
FIG. 70 is a top cross-sectional view of the firing lockout assembly of FIG. 69 in engagement with a portion of the surgical staple cartridge of FIG. 66.
Figure 69:
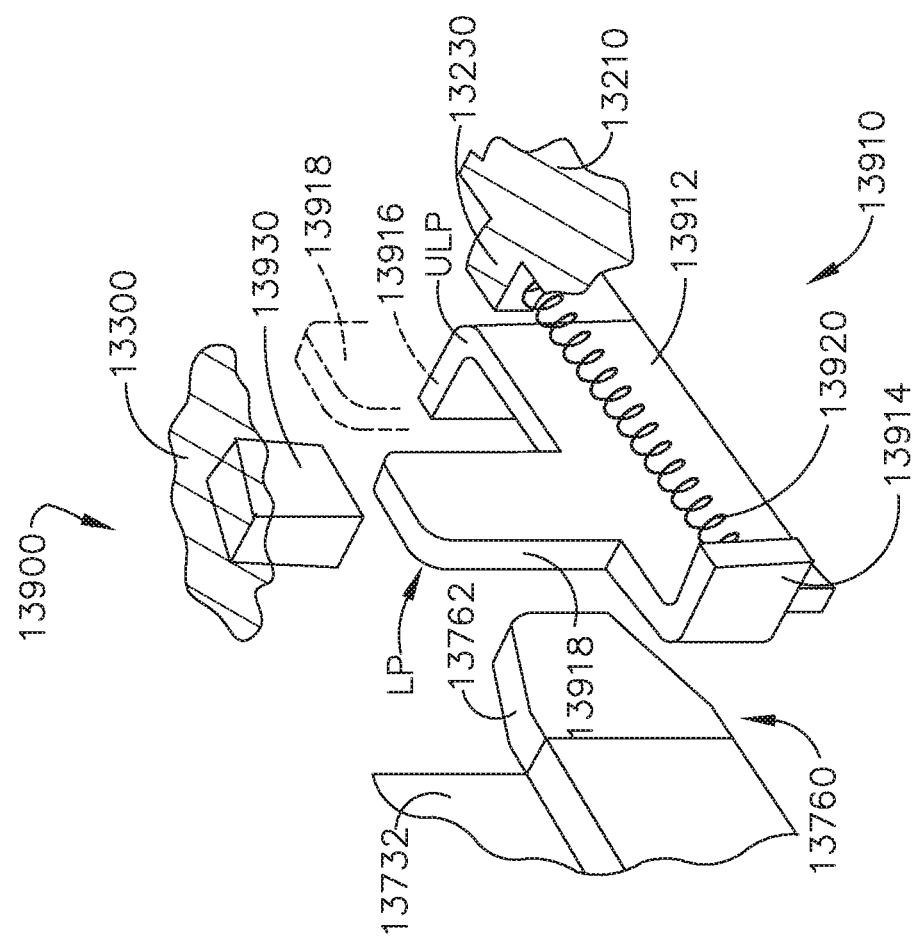
FIG. 69 is a partial exploded assembly view of a firing lockout assembly of the surgical end effector of FIG. 65.

The illustrated example also employs an anvil lockout assembly 13900 that is configured to prevent the closure of the anvil 13300 until the cartridge 13700 has been properly seated in the elongate channel 13210. In one arrangement, the anvil lockout assembly 13900 comprises an anvil lockout member 13910 that is movably supported in the elongate channel 13210. Turning to FIGS. 69 and 70, in one arrangement, the anvil lockout member 13910 comprises a clip body 13912 that has a distal spring tab 13914 protruding laterally from a distal end thereof and a proximal key tab 13916 protruding laterally from an opposite lateral side of the clip body 13912. The clip body 13912 further includes a vertically extending lock tab 13918 that protrudes upward from the clip body 13912. As can be seen in FIGS. 69 and 70, the lockout member 13910 is axially movable between a distal locking position LP and a proximal unlocked position ULP. A lock spring 13920 is provided between a channel lug 13230 and the distal spring tab 13914 to bias the lockout member 13910 distally into the locked position LP. FIGS. 65 and 69 illustrate the anvil lockout assembly 13900 in the locked position LP. As can be seen in FIGS. 65 and 69, the vertically extending lock tab 13918 is vertically aligned with an anvil lockout protrusion 13930 formed on the anvil 13300. Thus, when the anvil lockout assembly 13900 is in the locked position, the user cannot move the anvil 13300 to the closed position.

In the illustrated arrangement, the cartridge body 13702 includes a key member 13760 that is configured to move the lockout member 13910 from the locked position LP to the unlocked position ULP when the cartridge 13700 has been properly seated within the elongate channel 13210. In one example, the key member 13760 comprises a proximally extending fin 13762 that is configured to contact the proximal key tab 13916 on the clip body 13912. When the cartridge 13700 has been operably seated in the elongate channel 13210, the fin 13762 moves the lockout member 13910 proximally from the locked position LP to the unlocked position ULP.

Figure 71:
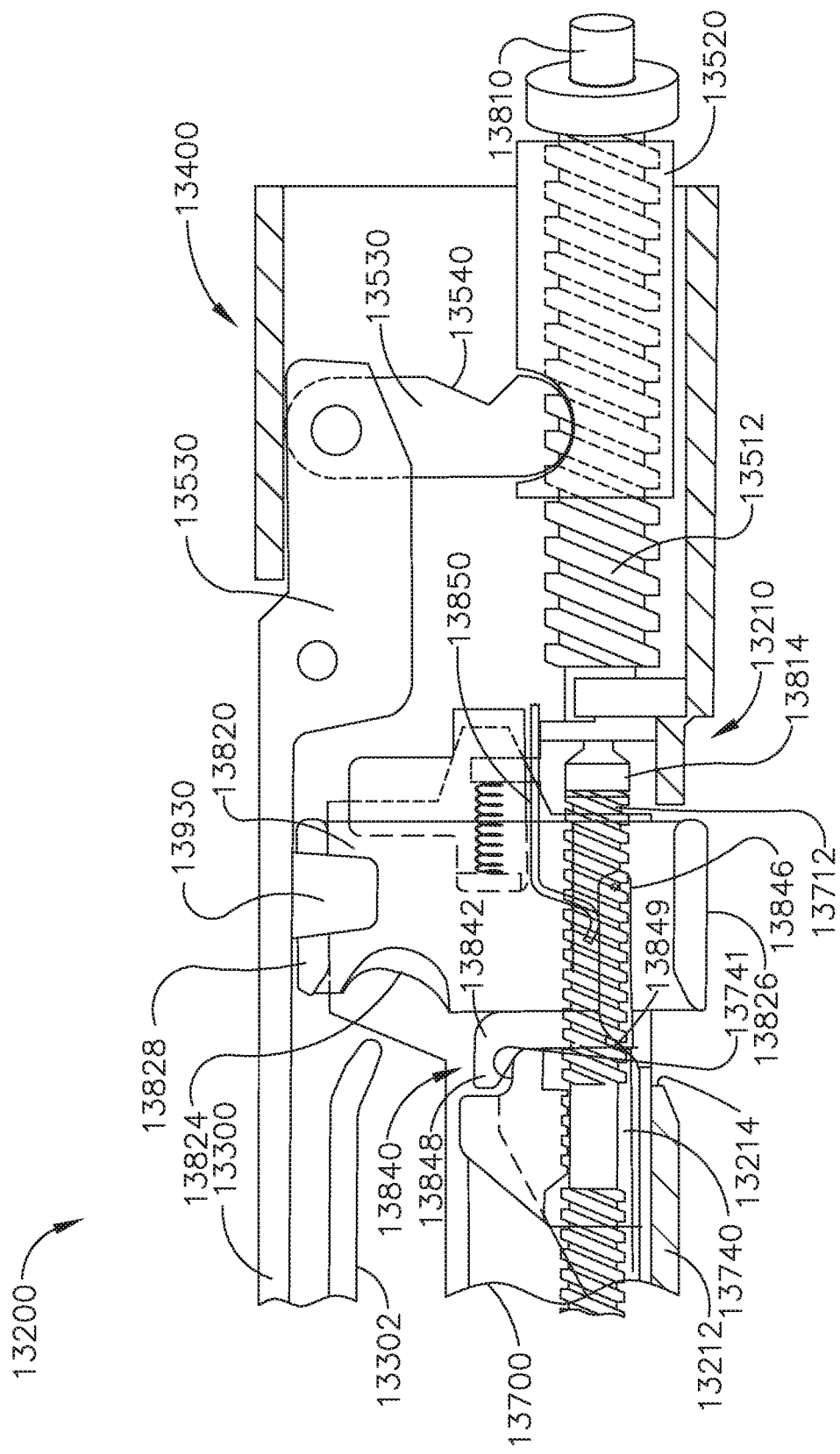
FIG. 71 is a side cross-sectional view of the surgical end effector of FIG. 65 with a surgical staple cartridge operably installed therein and the firing lockout assembly in an unlocked position.

As can be seen in FIG. 71, the firing member 13820 may also be equipped with an onboard firing member lockout assembly 13840 that comprises a lockout member 13842 that is pivotally coupled to the firing member body 13822 by pivot pins 13846. The lockout member 13842 includes a sled latch 13848 that is configured to be engaged by the camming assembly 13740 when the camming assembly 13740 is in an unfired position. As can be seen in FIG. 71, the camming assembly 13740 includes a firing member ledge 13741 that is configured to engage the sled latch 13848 on the lockout member 13482. A lockout spring 13850 is mounted in the elongate channel 13210 and is configured to bias the lockout member 13842 downward such that if the camming assembly 13740 is not in its unfired position, a distal edge 13849 of the lockout member 13842 engages a distal edge of the loading opening 13214. When in that position, should the user inadvertently attempt to distally advance the firing member 13820, the lockout member 13842 contacts the distal edge of the loading opening 13214 to prevent the distal advancement of the firing member 13820.

Figure 72:
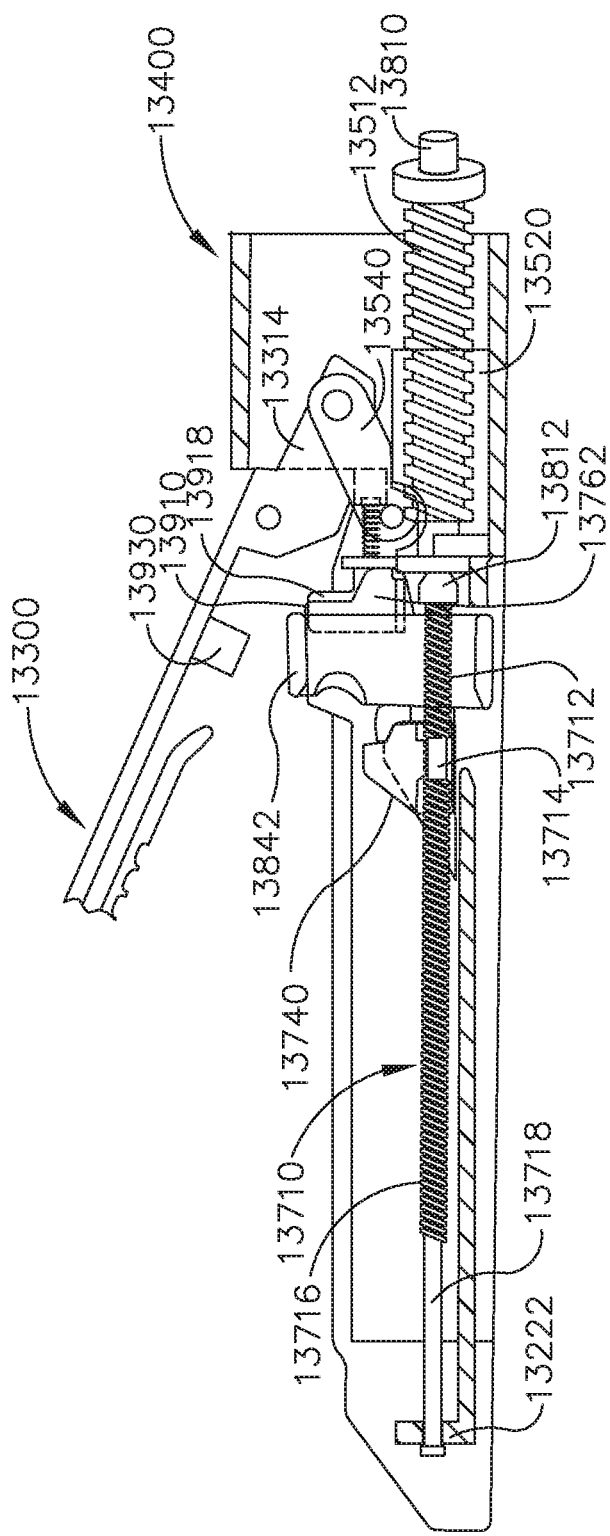
FIG. 72 is another side cross-sectional view of the surgical end effector of FIG. 65 with a surgical staple cartridge operably installed therein and the anvil thereof in an open position.

FIGS. 65 and 67 illustrate insertion of a fresh, unfired staple cartridge 13700 into the end effector 13200. As the user inserts the cartridge 13700 into the channel 13210, the male coupler 13724 is inserted into the female coupler 13812 and the cartridge body 13702 is seated in the channel 13210 as shown in FIG. 72. When in that position, the fin 13762 biases the lockout member 13910 into an unlocked position. The user may then move the anvil 13300 to a closed position by activating the closure drive system 13500 (FIG. 64) to rotate the closure drive shaft 13510 in a first rotary direction to drive the closure shuttle 13520 in a proximal direction PD. Once the closure shuttle 13520 has moved the anvil 13300 to the closed position, the user may then activate the firing system 13800. As can also be seen in FIG. 72, the camming assembly 13740 has pivoted the firing member lockout member 13842 into an unlocked position. As the firing drive shaft 13810 is rotated in a first rotary direction, the proximal threaded segment 13712 of the cartridge firing drive shaft 13710 drives the firing member 13820 distally (distal direction DD). As the firing member 13820 moves distally, the camming assembly 13740 is urged into threaded engagement with the distal thread segment 13716 of the cartridge firing drive shaft 13710. Continued rotation of the cartridge firing drive shaft 13710 causes the firing member 13820 and the camming assembly 13740 to move distally to their respective ending positions. As the camming assembly 13740 is driven distally, the camming portions thereon drive the drivers that are supported in the staple cartridge 13700 toward the closed anvil 13300 such that the staples or fasteners supported thereon are forced through the tissue that is clamped between the anvil 13300 and the cartridge 13700 and into forming contact with the underside of the anvil 13300. The firing member 13820 is proximal to the camming assembly 13740 so that the tissue cutting surface thereon 13824 cuts the clamped tissue after it has been stapled. In various aspects, as the firing member 13820 is distally driven through the surgical staple cartridge 13700, the firing member 13820, through the engagement of the anvil engagement tabs 13828 with the anvil 13300 and the engagement of the channel engagement tabs 13826 with the channel 13210, may serve to maintain a desired amount of tissue gap between the deck surface 13707 on the staple cartridge 13700 and a staple forming undersurface 13302 on the anvil 13300. Once the camming assembly 13740 and firing member 13820 have reached their ending positions, the firing drive shaft 13810 may be rotated in a reverse rotary direction to drive the firing member 13820 and camming assembly 13740 back to their respective starting positions. Once the firing member 13820 has returned to the starting position, the closure drive shaft 13510 may be rotated in a second rotary direction to drive the closure shuttle 13520 in a distal direction DD to pivot the anvil 13300 to the open position (FIG. 72) to enable to the stapled tissue to be unclamped from the end effector 13200. In the example that includes the C-shaped clip(s) 13890, the clips are also driven distally by the camming assembly 13740 and/or firing member 13820 until the clip(s) 13890 reach an ending position wherein the lower leg(s) 13896 thereof are located in an opening (not shown) in the channel bottom 13212 to enable the spent cartridge 13700 to be removed from the elongate channel 13210.

FIGS. 73-80 depict another surgical end effector 14200 that is employed with a surgical instrument 14000 that is very similar to instrument 13000 described above. The surgical end effector 14200 is somewhat similar to end effector 13200 described above, except for the differences discussed below. At lest some of the components of surgical instrument 14000 that are identical to the components of surgical instrument 13000 are set forth herein with like element numbers. The surgical end effector 14200 comprises an elongate channel 14210 that is configured to operably support a replaceable surgical staple cartridge 14700 therein. The surgical end effector 14200 further includes an anvil 14300 that is selectively pivotable relative to the elongate channel 14210 between open and closed configurations by the rotary driven closure system 13500 (FIG. 64). As can be seen in FIGS. 73 and 74, the anvil 14300 includes a proximally protruding anvil mounting tab 14310 that is configured to be pivotally coupled to a corresponding portion of an end cap 14400 that is either attached to or comprises a portion of the elongate channel 14210. The anvil mounting tab 14310 is attached to the end cap 14400 by, for example, a rivet 14401 or other pivot arrangements disclosed herein. The end effector 14200 also employs the rotary driven closure system 13500 described above. In one arrangement, for example, the anvil 14300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein.

As was discussed above, the rotary driven closure system 13500 comprises an axially movable closure shuttle 13520 that is threaded onto a threaded distal closure shaft segment 13512 that is configured to be drivingly coupled the closure drive shaft 13510 (FIG. 64). In the illustrated arrangement, the closure shuttle 13520 comprises a shuttle base portion 13522 that extends through a proximal cap slot (not shown) that is formed in the bottom of the end cap 14400. A lateral flange (not shown) extends laterally from each side of the shuttle base portion 13522 to slidably engage the bottom of the end cap 14400 in the various manners disclosed herein.

In the illustrated example, the axial movement of the closure shuttle 13520 is transferred to the anvil 14300 by a pivoting closure link assembly 13530. In one arrangement, the closure link assembly 13530 includes a pair of pivot arms 13540 (only one can be seen in FIGS. 73 and 74) that are each pivotally attached to a proximal end portion 14314 of the anvil mounting tab 14310 and suspended therefrom. Each pivot arm 13540 comprises a free end 13542 that includes a notch 13544 that is configured to drivingly engage a corresponding drive groove 13526 in the closure shuttle base portion 13522. When the closure shuttle 13520 is driven in the distal direction DD, the pivot arms 13540, by virtue of their engagement with the closure shuttle 13520, apply a pivotal opening motion to the anvil mounting tab 14310 to pivot the anvil 14300 to an open position (FIG. 73). When the closure shuttle 13520 is axially moved in a proximal direction PD, the pivot arms 13540 pivot in a second direction which causes a pivot closure motion to be applied to the anvil mounting tab 13310 to pivot the anvil 13300 to a closed position (FIG. 80).

Unlike the surgical end effector 13200 wherein the firing member 13820 is contained within the replaceable surgical staple cartridge 13700, the surgical end effector 14200 employs a dedicated firing member 14820 that is permanently journaled on the rotary firing drive shaft 13810. In the illustrated example, the rotary firing drive shaft 13810 and the threaded distal closure shaft segment 13512 are rotatably supported in the elongate channel 14210. As will be discussed in further detail below, a portion of the rotary firing drive shaft 13810 that is distal to the threaded distal closure shaft segment 13512 includes a proximal threaded segment 13811, an unthreaded segment 13815, and a distal threaded segment 13817.

Figure 75:
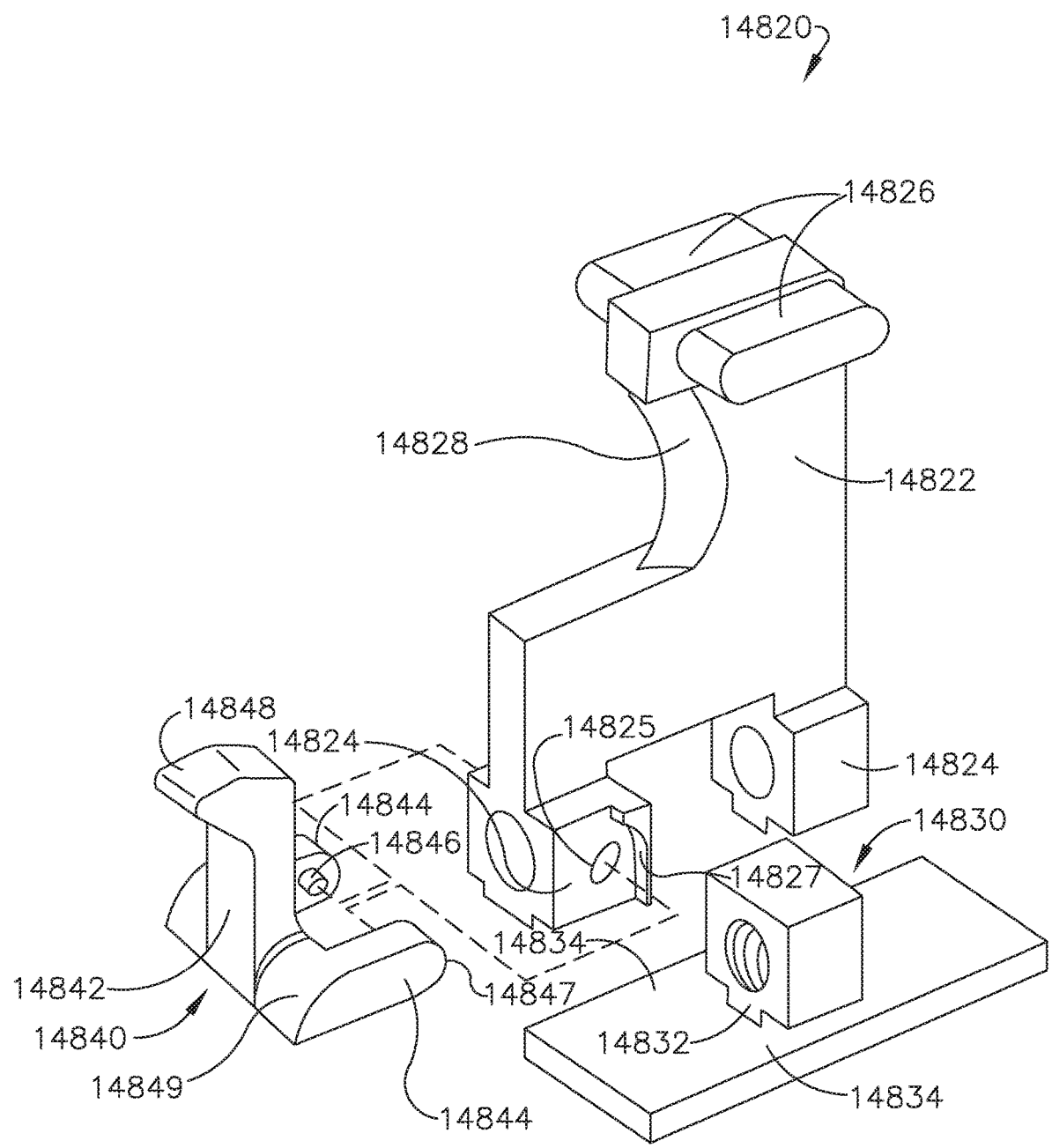
FIG. 75 is an exploded assembly view of a firing member and firing member lockout feature of the surgical end effector of FIG. 73.

FIG. 75 illustrates one form of a firing member 14820 that may be employed with the end effector 14200. As can be seen in FIG. 75, the firing member 14820 comprises a body portion 14822 that includes two downwardly extending hollow mounting portions 14824 that are unthreaded and spaced from each other to receive a threaded drive nut 14830 therebetween. The threaded drive nut 14830 is configured to threadably engage the threaded segments 13811, 13817 of the rotary firing drive shaft 13810. The drive nut 14830 includes a vertical tab portion 14832 that is sized to extend through an axial slot 14216 in the bottom of the elongate channel 14210. Two laterally extending retention flanges 14834 are formed on the threaded drive nut 14830 and are configured to engage the bottom of the elongate channel 14210. In addition, two laterally extending anvil engagement tabs 14826 are formed on the top of the firing member body 14822 and are configured to engage the anvil 14300 as the firing member 14820 is axially moved within the end effector 14200. A tissue cutting surface 14828 is formed or attached to the firing member body 14822.

In this arrangement, the firing member 14820 includes a firing member lockout feature 14840 that is configured to prevent the distal advancement of the firing member 14820 from its starting position unless a fresh unfired staple cartridge has been properly seated in the elongate channel 14210. As can be seen in FIG. 75, in one example, the firing member lockout feature 14840 comprises a lockout body 14842 that has two spaced attachment legs 14844 protruding therefrom that extend around the mounting portions 14824 of the firing member body 14822. Each attachment leg 14844 includes an inwardly extending pivot pin 14846 that is adapted to be pivotally received in a corresponding slotted opening 14825 provided in the mounting portions 14824. The lockout feature 14840 further includes a sled latch 14848 that is configured for contact with a camming sled or assembly 14740 (FIG. 77) operably supported in a staple cartridge 14700.

Figure 77:
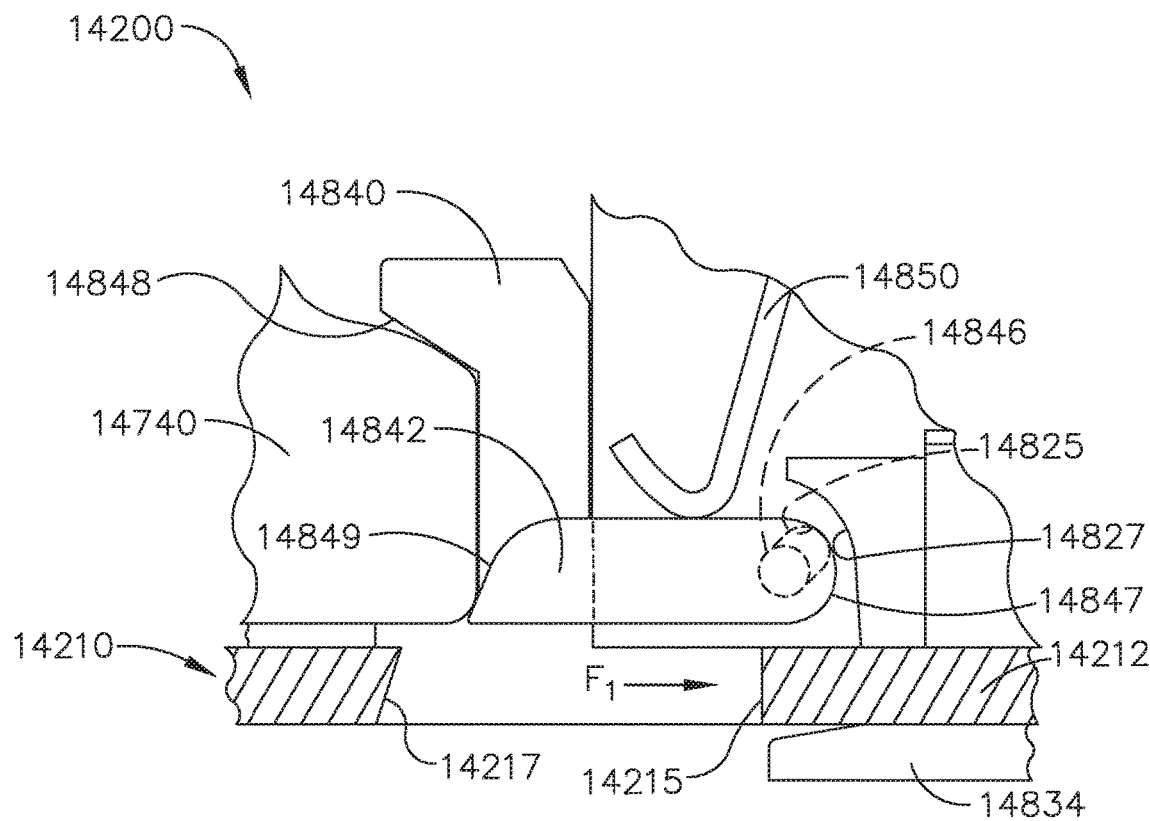
FIG. 77 is another enlarged view of a portion of the firing member lockout feature of FIG. 76 in a locked position prior to installation of a surgical staple cartridge into the elongate channel of the surgical end effector of FIG. 73.
Figure 76:
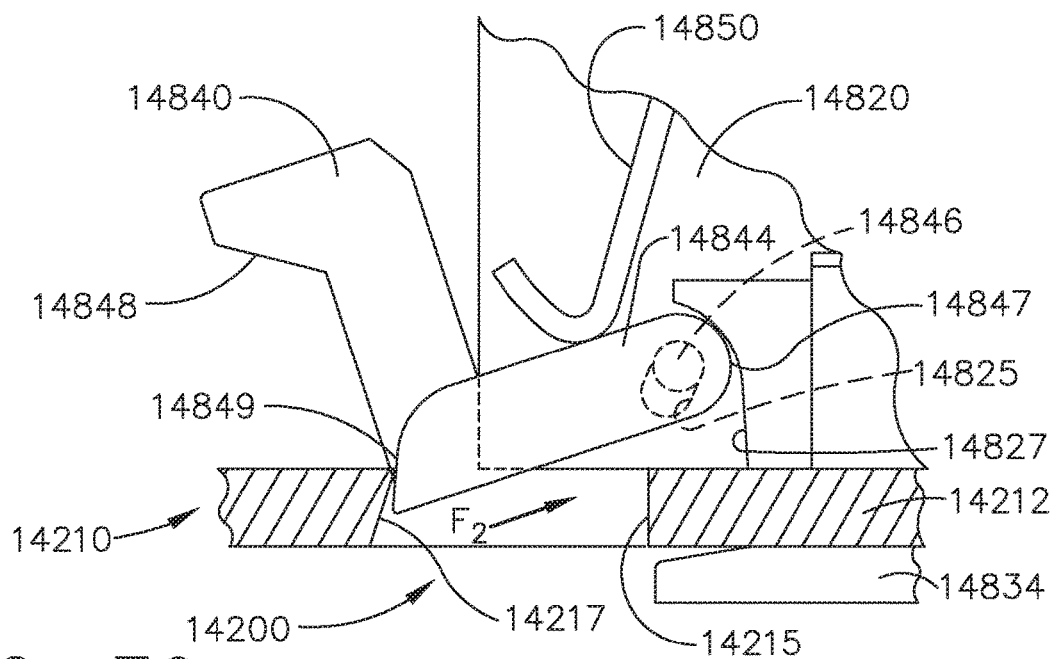
FIG. 76 is an enlarged view of a portion of the firing member lockout feature of FIG. 75 in engagement with a portion of a surgical staple cartridge installed in an elongate channel of the surgical end effector of FIG. 73.

FIGS. 76 and 77 illustrate the firing member 14820 in a proximal-most starting position. As can be seen in FIGS. 76 and 77, a firing lockout hole 14215 is provided through the bottom of the elongate channel 14210. A lockout spring 14850 is mounted in the elongate channel 14210 and is configured to bias the lockout feature 14840 downward such that, if a fresh unfired staple cartridge has not been properly loaded into the elongate channel 14210, a distal edge 14849 of the lockout body 14842 engages the angled distal edge 14217 of the firing lockout hole 14215. When in that position, should the user inadvertently attempt to distally advance the firing member 14820, the lockout feature 14840 prevents the distal advancement of the firing member 14820. As noted in FIG. 76, under high force "$F_2$" the pins 14846 slide up their respective slot 14825. As the pins 14846 slide up their respective slots 14825, the proximal ends 14847 of the attachment legs 14844 engage a corresponding backstop wall 14827 that is formed on the mounting portions 14824 of the firing member body 14822 to reduce stress placed on the pivot pins 14846. See FIG. 76.

Figure 78:
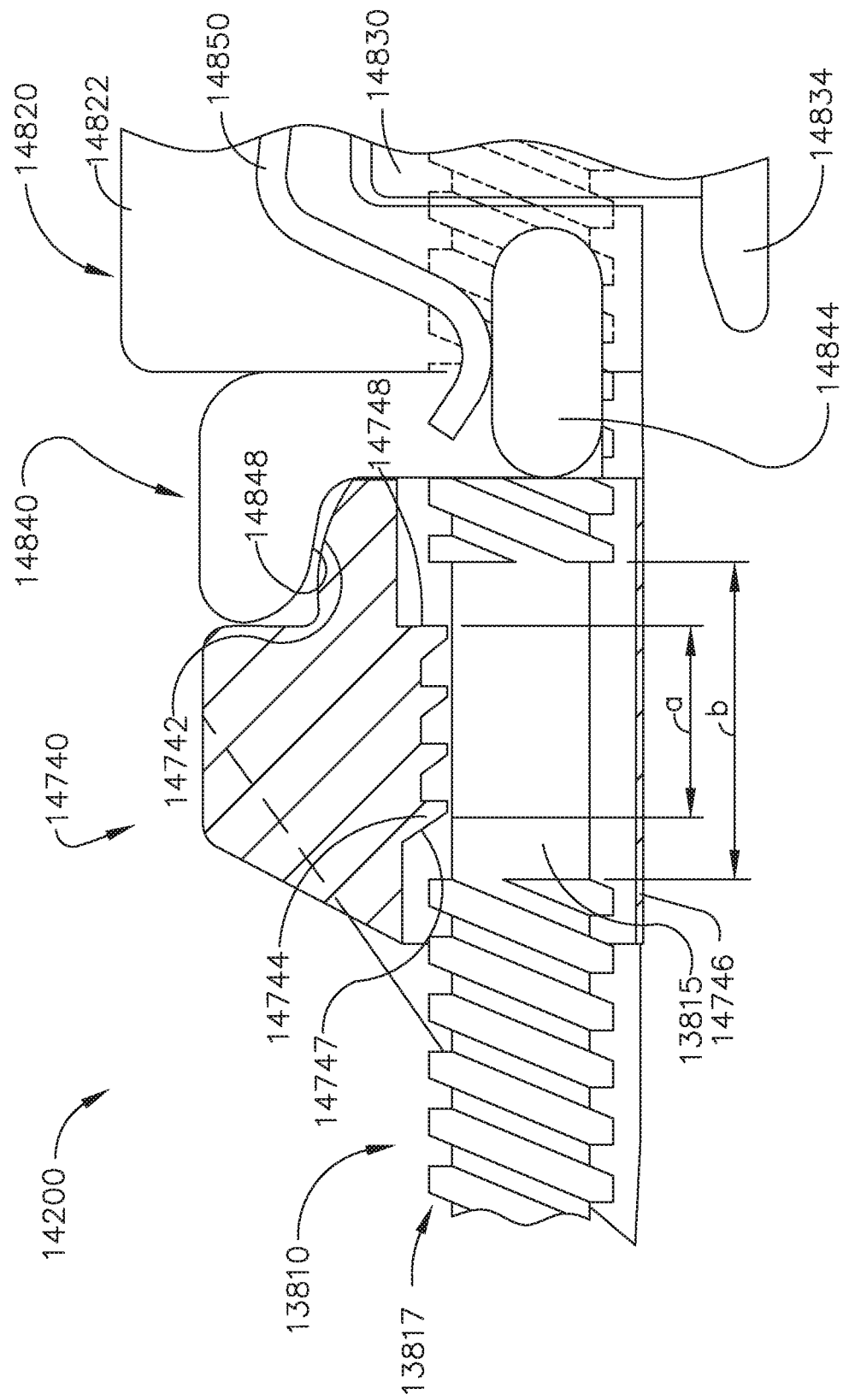
FIG. 78 is a cross-sectional view of a portion of the surgical end effector of FIG. 73 and a camming assembly of a surgical staple cartridge installed in the end effector.

A fresh, unfired surgical staple cartridge 14700 contains a camming assembly 14740 that is located in a starting position that is proximal to the lines of staple drivers that are supported in the cartridge body. As used herein, the terms "fresh, unfired" means that the staple cartridge has all of its intended staples or fasteners in their respective unfired positions and the camming assembly is in a proximal unfired starting position. When a fresh, unfired surgical staple cartridge 14700 has been properly seated within the elongate channel 14210, a proximally extending unlocking portion 14742 on the camming assembly 14740 engages the sled latch 14848 on the lockout feature 14840 to pivot the lockout feature 14840 into an unlocked position wherein the lockout feature 14840 does not extend into the firing lockout hole 14215 in the elongate channel. FIG. 78 illustrates a camming assembly 14740 in the starting position. The remaining portions of the surgical staple cartridge 14700 have been omitted for clarity. As can be seen in FIG. 78, the camming assembly 14740 includes a segment of internal threads 14744 that has a length "a" that is less than the axial length "b" of the unthreaded portion 13815 on the rotary firing drive shaft 13810. The bottom 14746 of the camming assembly 14740 is open to enable the camming assembly 14740 to snap over the rotary firing drive shaft 13810 when the cartridge 14700 is seated in the elongate channel 14210.

In one example, the internal threads 14744 in the camming assembly 14740 are configured to only drive the camming assembly 14740 in the distal direction. For example, the internal threads 14744 may have a leading portion 14747 that is configured to facilitate threaded engagement with the threaded segment 13817 on the firing drive shaft 13810. However, the internal threads 14744 may have a trailing portion 14748 that is configured to prevent threaded engagement with the threads 13817 when the camming assembly 14740 has been driven to its ending position and the firing drive shaft 13810 is rotated in an opposite direction to drive the firing member 14820 back to the starting position. In FIGS. 79 and 80, the ending position of the camming assembly 14740 is illustrated in phantom lines. As can be seen in FIGS. 79 and 80, a distal portion 13819 of the firing drive shaft 13810 is devoid of threads. When the camming assembly 14740 has been distally driven into its ending position, the internal threads 14744 disengage the threaded segment 13817 of the firing drive shaft 13810. When the firing drive shaft 13810 is rotated in the opposite direction, the internal threads 14744 are designed to slip and not re-engage the threaded segment 13817 such that the camming assembly 14740 remains in the ending position within the staple cartridge 14700 as the firing member 14820 is retracted back to the starting position. Thus, once a staple cartridge 14700 has been spent (e.g., completely fired) the camming assembly 14740 is not returned to its starting position. Thus, if the spent cartridge were to be inadvertently re-installed in the end effector 14200, the camming assembly 14740 is not in position to unlock the lockout feature 14840. This condition may be assisted by interference with fallen staple drivers located within the cartridge body after the cartridge was fired. In addition, the internal threads 14744 may have a pitch diameter that is larger than a pitch diameter of the threads 13817 on the firing drive shaft 13810 to facilitate some "play" therebetween which may permit the firing member 14820 to make contact with the camming assembly 14740 as they are driven distally. Such arrangement may facilitate some movement of the camming assembly 14740 when the cartridge body 14702 is installed in the elongate channel 14210 while still establishing threaded driving contact with the threaded segment 13817 of the firing drive shaft 13810.

The end effector 14200 as depicted also includes an anvil lockout assembly 13900 that is configured to prevent the closure of the anvil 14300 unless a staple cartridge 14700 has been properly seated therein. Operation of the anvil lockout member 13910 was described above and will not be repeated for the sake of brevity.

FIG. 73 illustrates the surgical end effector 14200 without a surgical staple cartridge installed therein and with the anvil 14300 in a fully open position. As can be seen in FIG. 73, the closure shuttle 13520 is in its distal-most position. As can be further seen in FIG. 73, the vertically extending lock tab 13918 of the anvil lockout member 13910 is aligned with the anvil lockout protrusion 14930 that is formed on the anvil 14300. FIG. 74 illustrates that the anvil 14300 cannot be closed during the inadvertent actuation of the closure drive system. In FIG. 73, the closure shuttle 13520 has moved proximally from its starting position, but the anvil 14300 is prevented from closing due to the contact between the lock tab 13918 and the lockout protrusion 14930. As can also be seen in FIGS. 73 and 74, the firing member lockout feature 14840 is biased into the locked position wherein the lockout feature 14840 is aligned to contact the elongate channel bottom 14212. In the event that the user inadvertently actuates the firing drive system, the lockout feature 14840 will contact the bottom 14212 of the elongate channel 14210 to prevent the distal advancement of the firing member 14820.

FIG. 79 illustrates the end effector 14200 after a fresh, unfired surgical staple cartridge 14700 has been installed therein. As can be seen in that Figure, the camming assembly 14740 within the cartridge body 14702 is in a proximal-most, starting position wherein the unlocking portion 14742 on the camming assembly 14740 is in engagement with the sled latch 14848 on the lockout feature 14840. This contact between the unlocking portion 14742 and the sled latch 14848 moves the lockout feature 14840 into the unlocked position. As can also be seen in FIG. 79, a proximally extending fin 14762 on the cartridge body 14702 has biased the lockout member 13910 proximally from the locked position to the unlocked position to thereby permit the anvil 14300 to be closed. As was discussed above, the length a of the internal thread segment 14744 in the camming assembly 14740 is less than the length b of the unthreaded segment 13815 on the firing drive shaft 13810. In addition, a length "c" of the threads within the threaded firing nut 14830 is greater than the length b of the unthreaded segment 13815 on the firing drive shaft 13810. Thus: a<b<c.

FIG. 80 illustrates the surgical end effector 14200 of FIG. 79 with the anvil 14300 in the fully closed position. As can be seen in FIG. 80, the distal closure shaft segment 13512 has been rotated in the first rotary direction to cause the closure shuttle 13520 to move axially to its proximal-most position to thereby cause the closure link assembly 13530 to pivot the anvil 14300 to its fully closed position. As can be seen in FIG. 80, when the anvil 14300 is in the fully closed position, the pivot arms 13540 are nearly vertical relative to the drive shaft axis DSA. Such configuration results in the application of a maximum closure moment to the anvil (e.g., moment arm angle MA is approximately 90°). As can be further seen in FIG. 80, the anvil engagement features 14826 are aligned with corresponding elongate passages 14301 that are formed on each lateral side of the anvil slot to permit axial travel therein as the firing member 14820 is distally advanced from its starting position to ending position. To distally advance the firing member 14820, the user activates the firing drive system 13800 (FIG. 64) to rotate the firing drive shaft 13810 in a first rotary direction. As the firing member 14820 is driven distally, the firing member 14820 advances the camming assembly 14740 on the unthreaded segment 13815 until the segment of internal threads 14744 threadably engage the threaded segment 13817. Once threads 14744 are in threaded engagement with the threaded segment 13817, rotation of the drive shaft 13810 causes the camming assembly 14740 to continue to move distally. As the camming assembly 14740 moves distally, the camming surfaces thereon drive the staple drivers that are stored in the cartridge 14700 upward. The upward movement of the staple drivers causes the staples or fasteners supported thereon to pierce through the tissue that is clamped between the anvil 14300 and the cartridge 14700 and into forming contact with the staple forming underside 14303 of the anvil 14300. As the firing member 14820 is driven distally, the tissue cutting surface 14828 cuts through the clamped tissue after the fasteners have been formed in the tissue. The firing drive shaft 13810 continues to be rotated until the firing member 14820 has reached its ending position at which time, a sensor or sensors may stop the firing motor 13802 from rotating in the first direction. An instrument controller may then cause the firing motor 13802 to rotate in an opposite direction to retract the firing member 14820 back to its starting position or the controller may require the user to initiate a retraction rotation. In either event, the camming assembly 14740 remains in the distal end of the cartridge 14700. The user may then remove the spent cartridge from the end effector and discard it. Because the camming assembly 14740 remains in the distal end of the spent cartridge, should the spent cartridge be inadvertently mistaken for a fresh unfired cartridge and reloaded into the end effector, the lockout feature 14840 will remain in the locked position to prevent inadvertent firing of the firing member. As can be seen in FIG. 80, the axial length "e" of laterally extending retention flanges 14834 of the firing member 14820 is longer than the axial length "d" of the firing lockout hole 14215 in the bottom 14212 of the channel 14210. In addition, an installation hole 14213 is provided through a distal portion of the cartridge bottom 4212 to facilitate installation of the firing member 14820 therethrough. Thus, the axial length "f" of the installation hole 14213 is greater than the axial length "e" of laterally extending retention flanges 14834 of the firing member 14820. Thus: d<e<f.

Figure 81:
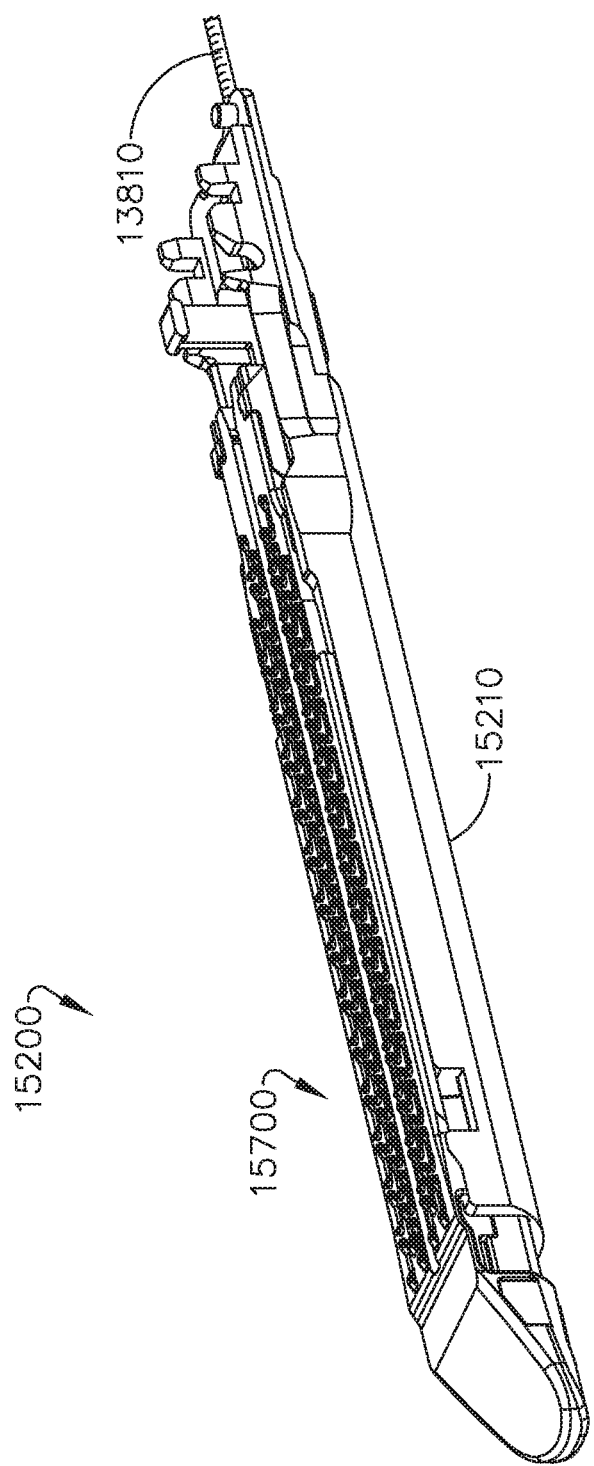
FIG. 81 is a perspective view of a portion of another surgical end effector with a surgical staple cartridge installed therein.

FIG. 81 illustrates a portion of another surgical end effector 15200 with the anvil thereof omitted for clarity. The surgical end effector 15200 includes a two piece firing member 15820 that is axially driven between a starting position and an ending position within the end effector 15200. The end effector 15200 may employ a rotary closure shuttle 13520 that is axially driven by a closure drive shaft 13510 for applying opening and closing motions to the anvil. As was described above, the closure shuttle 13520 is supported for axial travel within the end cap 14400 as shown in FIGS. 82 and 83. See e.g., FIGS. 64 and 65 for further details concerning the opening and closing of the anvil. In addition, the two piece firing member 15820 is axially driven by a rotary firing drive shaft 13810 that extends through a distal closure drive shaft segment in the various manners disclosed herein.

As can be seen in FIG. 82, the firing member 15820 comprises a body portion 15822 that includes two downwardly extending hollow mounting portions 15824 that are unthreaded and spaced from each other to receive a threaded drive nut 15830 therebetween. The threaded drive nut 15830 is configured to threadably engage the threaded rotary firing drive shaft 13810. The drive nut 15830 includes a vertical tab portion (not shown) that is sized to extend through an axial slot (not shown) in the bottom of an elongate channel 15210 of the surgical end effector 15200. Two laterally extending retention flanges 15834 are formed on the threaded drive nut 15830 and are configured to engage the bottom of the elongate channel 15210. In addition, two laterally extending anvil engagement tabs 15826 are formed on the top of the firing member body 15822 and are configured to engage the anvil as the firing member 15820 is axially moved within the end effector 15200. In the illustrated example, the firing member 15820 is configured to operably interface with a camming assembly 15740 that has an onboard tissue cutting knife 15743 thereon. See FIGS. 87 and 89. In alternative arrangements, a tissue cutting surface is formed or attached to the body member 15822.

Figure 87:
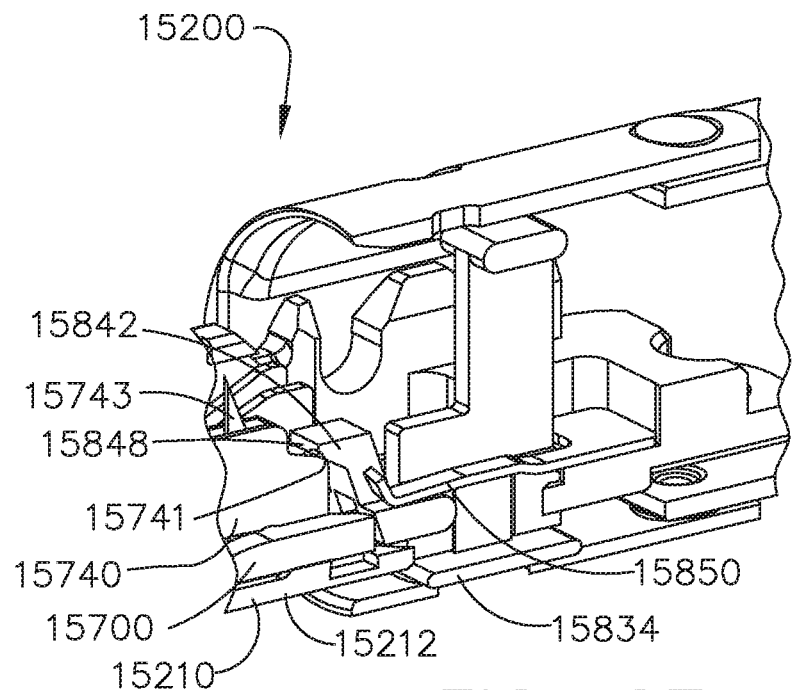
FIG. 87 is another partial perspective view of the surgical end effector of FIG. 86 with a portion of the cartridge removed to enable the firing lockout member to be viewed in engagement with the camming assembly of the cartridge.
Figure 89:
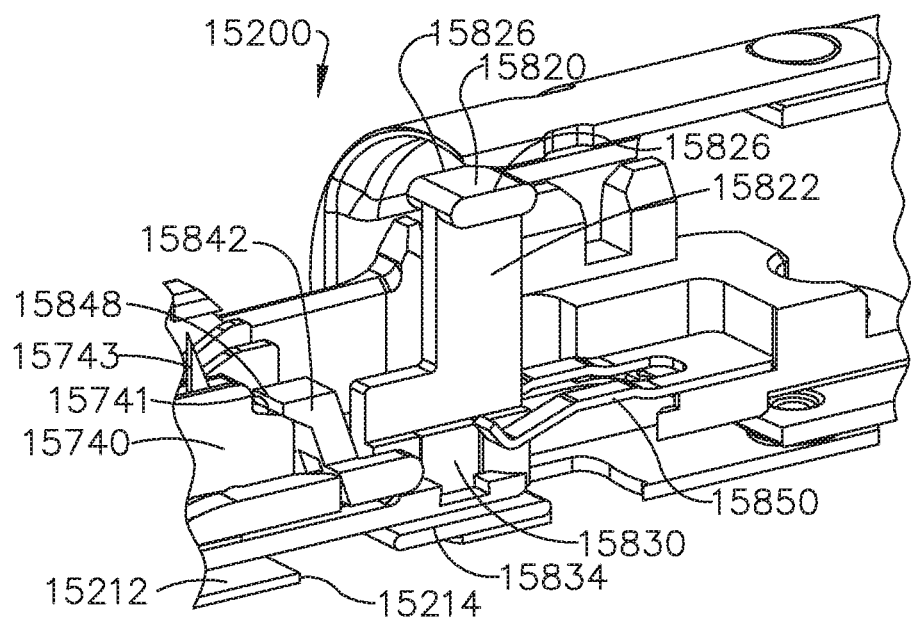
FIG. 89 is another partial perspective view of the surgical end effector of FIG. 86 with a portion of the cartridge omitted to enable the firing lockout member to be viewed in engagement with the camming assembly of the cartridge.

As can also be seen in FIG. 82, the firing member 15820 may also be equipped with an onboard firing member lockout assembly 15840 that comprises a lockout member 15842 that is pivotally coupled to the firing member body 15822. The lockout member 15842 includes a sled latch 15848 that is configured to be engaged by the camming assembly 15740 when the camming assembly 15740 is in an unfired position. As can be seen in FIGS. 87 and 89, the camming assembly 15740 includes a firing member ledge 15741 configured to engage the sled latch 15848 on the lockout member 15482. A lockout spring 15850 is mounted in the elongate channel 15210 and is configured to bias the lockout member 15842 downward such that if the camming assembly 15740 is not in its unfired position, a distal edge 15849 engages a distal edge of a lockout cavity 15214 in a bottom 15212 of the channel 15210. When in that position, should the user inadvertently attempt to distally advance the firing member 15820, the lockout member 15842 contacts the distal edge of the lockout cavity 15214 to prevent the distal advancement of the firing member 15820.

Figure 84:
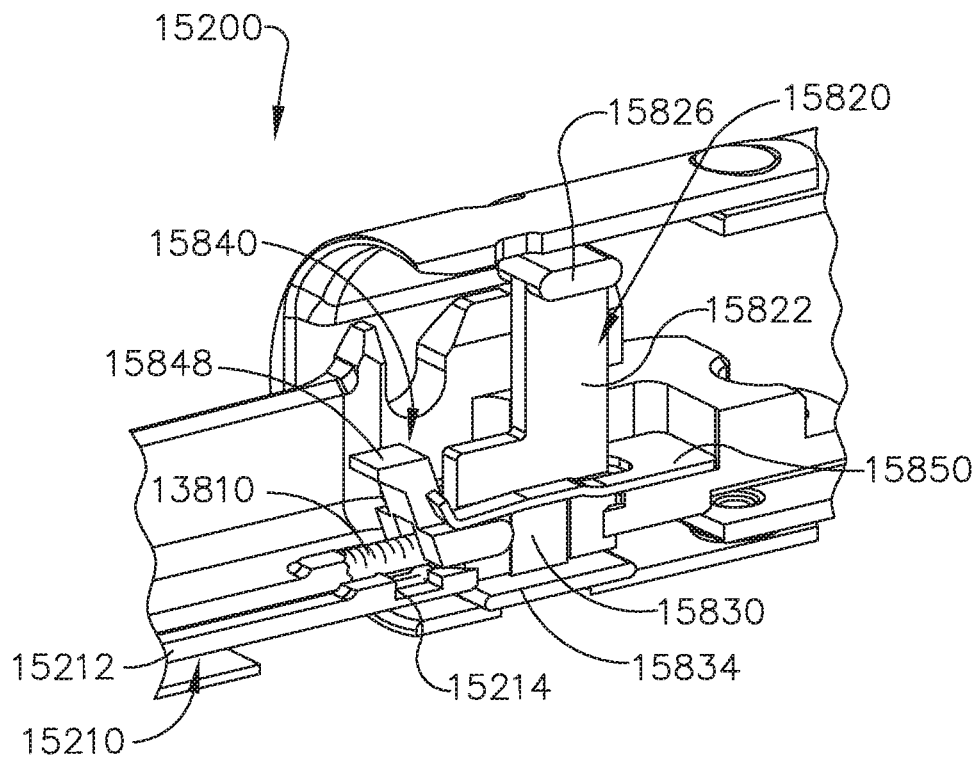
FIG. 84 is a partial perspective view of the surgical end effector of FIG. 81 prior to installing a staple cartridge therein.
Figure 85:
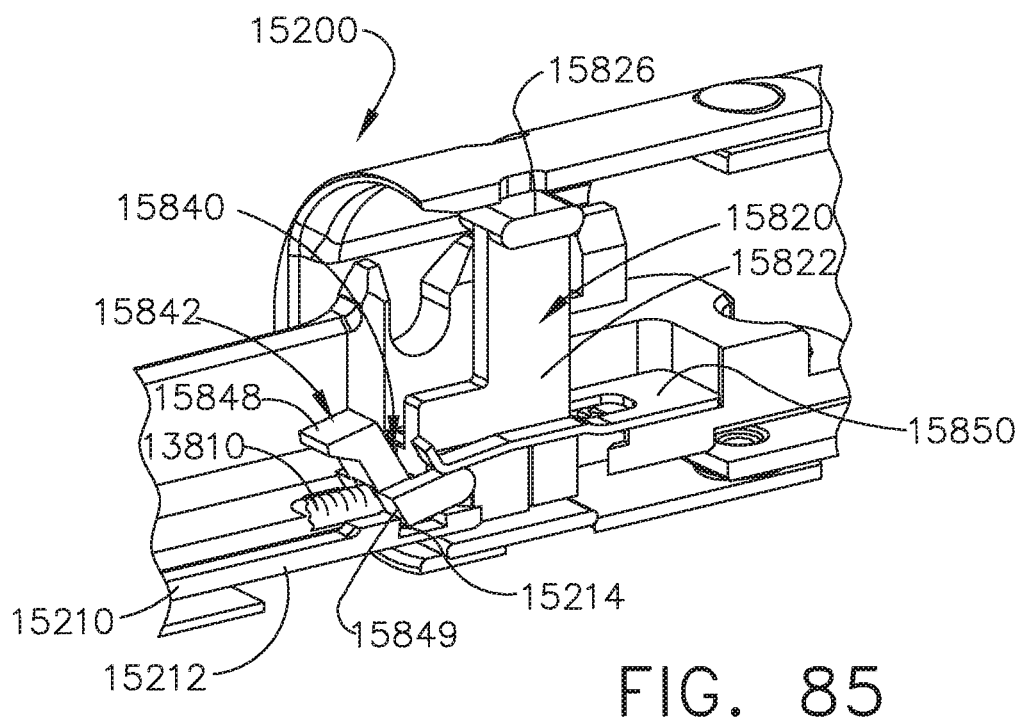
FIG. 85 is another partial perspective view of the surgical end effector of FIG. 84 with a firing lockout member thereof in a locked position because no cartridge has been installed in the end effector.
Figure 86:
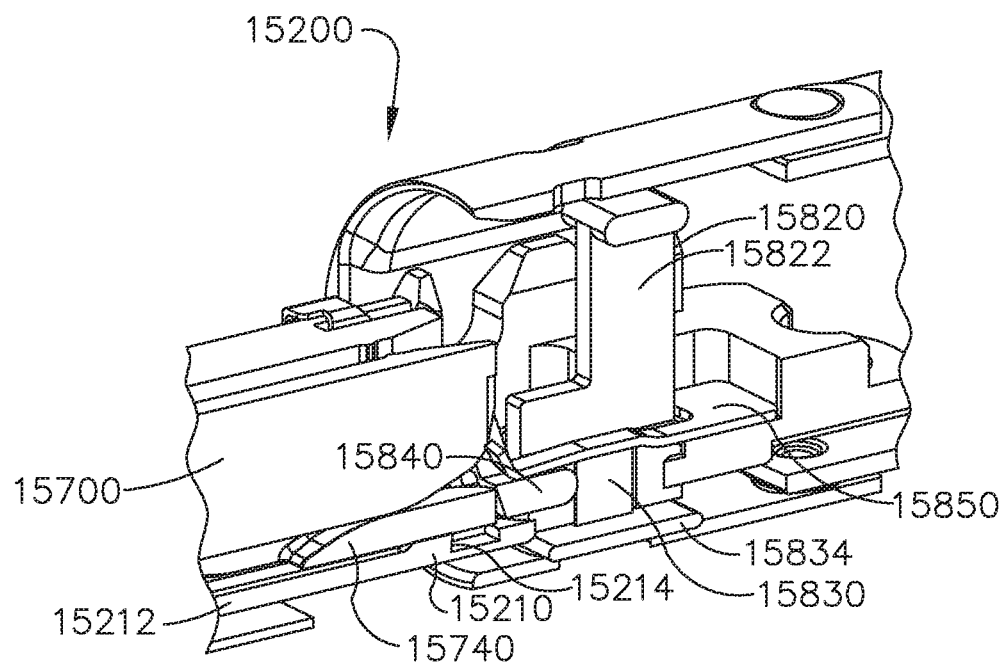
FIG. 86 is another partial perspective view of the surgical end effector of FIG. 84 with a cartridge installed therein.
Figure 88:
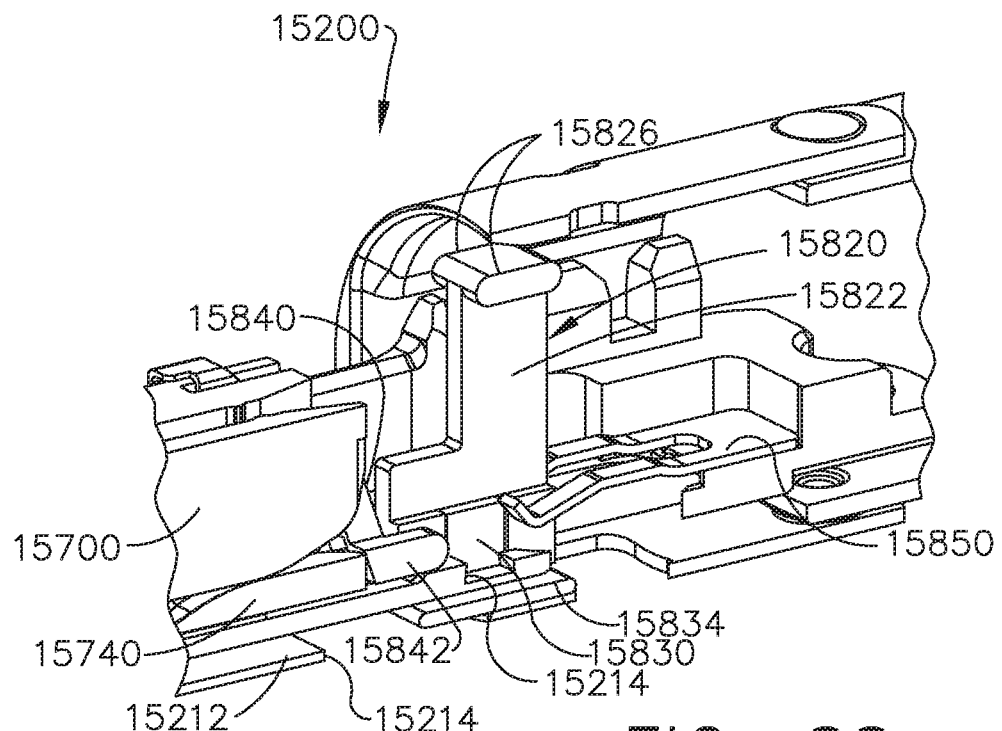
FIG. 88 is another partial perspective view of the surgical end effector of FIG. 86 with a cartridge installed therein and a firing member of the surgical end effector moved distally forward.

FIG. 84 illustrates the end effector 15200 prior to installation of a surgical staple cartridge 15700 (FIG. 81) therein. As can be seen in FIG. 84, the firing member 15820 is in its proximal-most starting position. FIG. 85 illustrates what happens if the firing member 15820 is inadvertently distally advanced when no cartridge is present. As can be seen in FIG. 85, the lockout member 15842 has been biased downward by spring 15850 such that the distal end surface 15849 of the lockout member 15842 has contacted the distal edge of the lockout cavity 15214 in the channel 15210 to prevent further distal advancement of the firing member 15820. FIGS. 86 and 87 illustrate the end effector 15200 with an unfired surgical staple cartridge 15700 operably loaded in the elongate channel 15210. As can be seen in FIG. 89, the firing member ledge 15741 on the camming assembly 15740 is in unlocking engagement with the sled latch 15848 on the lockout member 15482 which lifts the firing member 15820 out of locking engagement with the lockout cavity 15214. FIGS. 88 and 89 illustrate the position of the firing member 15820 after the firing process has been commenced and the firing member 15820 has started to move in the distal direction.

Figure 90:
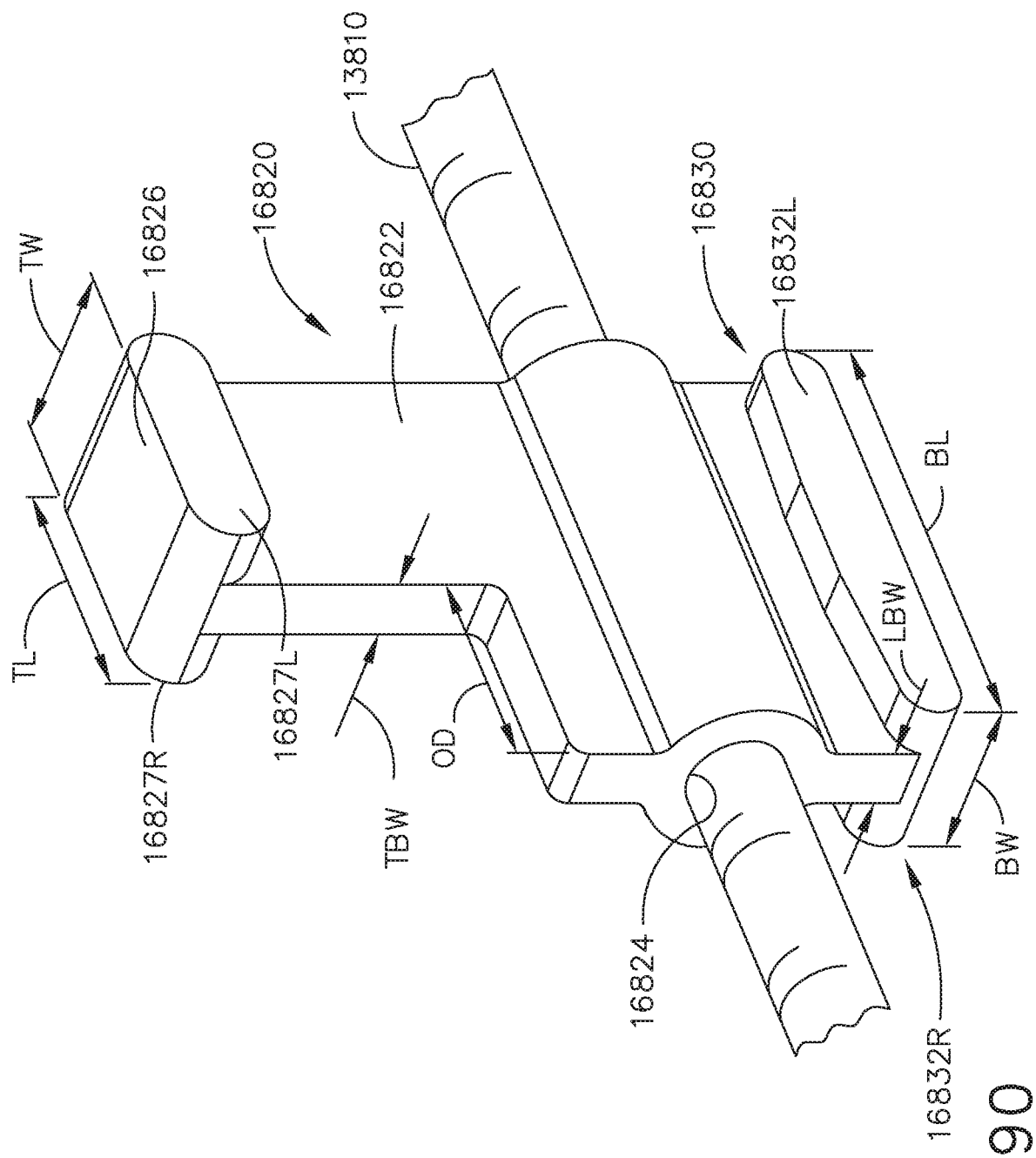
FIG. 90 is a perspective view of another firing member threadably engaged with a rotary firing drive shaft of a surgical end effector.

FIG. 90 illustrates an alternative firing member 16820 that may be used in connection with the end effector 15200 described above, as well as with various other end effector arrangements disclosed herein. As can be seen in FIG. 90, the firing member 16820 comprises a body portion 16822 that includes an axially extending threaded passage 16824 that is adapted to be threadably engaged by the firing drive shaft 13810 in the various manners disclosed herein for example. During the firing process, the firing member body 16822 is configured to extend through an axial slot in a surgical staple cartridge that has been installed in the elongate channel of the end effector. The axial slot in the staple cartridge is vertically aligned with an axial slot in the bottom of the elongate channel 15210 to enable a bottom portion of the firing member body 16822 to extend therethrough during the firing process. A bottom channel engagement member or base 16830 is attached to or formed on the firing member body 18622 as shown in FIG. 90. The base 16830 is configured to slidably engage the bottom of the channel during firing. In addition, a top anvil engagement member 16826 is formed on or attached to the top portion of the firing member body 16822.

Still referring to FIG. 90, in one aspect, the base 16830 comprises a left flange assembly 16832L that protrudes laterally from a left side of the firing member body 16822 and a right flange assembly 16832R that protrudes laterally from a right side of the firing member body 16822. The base 16830 has a base width BW that is greater than the width LBW of the lower portion of the firing member body 16822. In one aspect, the lower body width LBW is less that the widths of the axial slots in the surgical staple cartridge and elongate channel and the base width BW is greater than the widths of the axial slots in the surgical staple cartridge and the elongate channel. The top anvil engagement member 16826 comprises a left top flange assembly 16827L that protrudes laterally from a left side of the firing member body 16822 and a right top flange assembly 16827R that protrudes laterally from a right side of the firing member body 16822. The top anvil engagement member 16826 has a width TW that is greater than the width TBW of the upper portion of the firing member body 16822. In one aspect, the top body width TBW is less that the width of an axial slot in the anvil to enable the top portion of the firing member body 16822 to slidably pass therethrough, while the width TW of the top anvil engagement member 16826 is greater than the width of the anvil slot.

Figure 91:
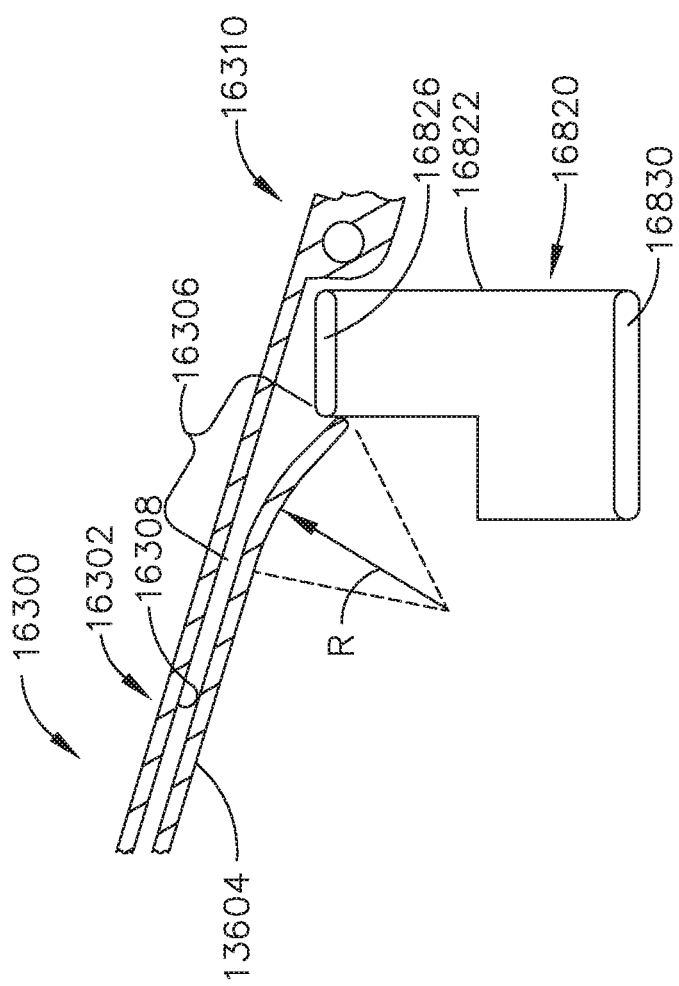
FIG. 91 is a side elevational view of the firing member of FIG. 90 in relation to an anvil of a surgical end effector with the anvil in an open position and shown in cross-section.

FIG. 91 illustrates the firing member 16820 and an anvil 16300 which may be identical to many of the anvil configurations disclosed herein except for the differences noted below. As can be seen in FIG. 91, the anvil 16300 comprises an elongate anvil body 16302 and an anvil mounting portion 16310. The elongate anvil body portion 16302 comprises an elongate anvil slot (not shown) that is configured to accommodate the axial passage of the top anvil engagement member 16826 of the firing member body 16822 therethrough. The anvil body 16302 further includes an axially extending ledge 16304 that defines an axial flange passage 16308 on each side of the anvil slot for accommodating the corresponding right top flange 16827R and left top flange 16827L therein. In the example illustrated in FIG. 91, a proximal portion 16306 of the ledge 16304 is formed with a radial or gradual slope as shown. FIG. 91 also illustrates the firing member 16820 in a position wherein the top anvil engagement member 16826 is ready to ride on the proximal portion 16306 of the ledge 16304 and commence the application of a closing motion to the anvil 16300. In this example, the proximal portion 16306 of the ledge 16304 is arcuate or gradually sloped to facilitate easy transition of the top anvil engagement member 16826 onto the ledge 16304. In one example, the slope may be from approximately 0°-8°. This may reduce the amount of friction and binding forces that may occur between the firing member 16820 and the anvil 16300 during initial closure of the anvil 16300. As the firing member 16820 enters the flange passage 16308 in the anvil body 16302, the firing member body 16820 may tip slightly (tip angle TA—See FIG. 92) relative to a reference axis RA that is perpendicular to the channel bottom 15212. The distal ends of the bottom flanges 16832R, 16832L are radiused to assist in such transition. In addition, by having the top anvil engagement member 16826 proximally axially offset by an offset distance OD and/or by making the axial length TL of the top anvil engagement member 16826 less than the axial base length BL, the amount of binding between the top anvil engagement member 16826 and the proximal portion 16306 of the ledge 16304 may be reduced. Of course, all of the friction and binding forces that are created during this process generally add to the amount of the closure forces that must be applied to the firing member 16820 to close the anvil 16300.

Figure 93:
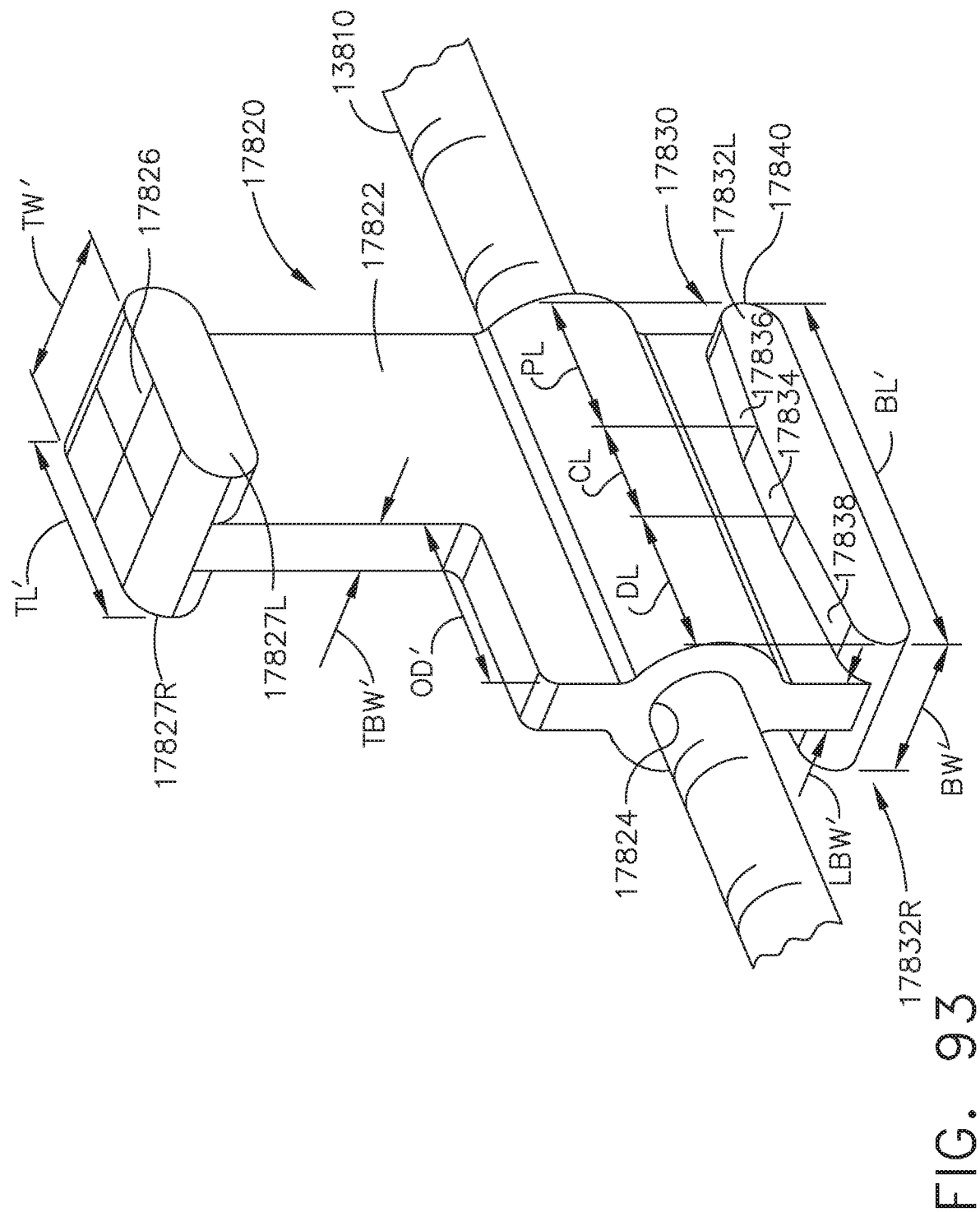
FIG. 93 is a perspective view of another firing member in threaded engagement with a rotary firing drive shaft of a surgical end effector.

FIG. 93 illustrates an alternative firing member 17820 that may be used in connection with the end effector 15200 described above, as well as with various other end effector arrangements disclosed herein. As can be seen in FIG. 93, the firing member 17820 comprises a body portion 17822 that includes an axially extending threaded passage 17824 that is adapted to be threadably engaged by the firing drive shaft 13810 in the various manners disclosed herein for example. As was discussed above, during the firing process, the firing member body 17822 is configured to extend through an axial slot in a surgical staple cartridge that has been installed in the elongate channel of the end effector. The axial slot in the staple cartridge is vertically aligned with an axial slot in the bottom of the elongate channel to enable a bottom portion of the firing member body 17822 to extend therethrough during the firing process. A bottom channel engagement member or base 17830 is attached to or formed on the firing member body 17822 as shown in FIG. 93. The base 17830 is configured to slidably engage the bottom of the channel during firing. In addition, a top anvil engagement member 17826 is formed on or attached to the top portion of the firing member body 17822.

Still referring to FIG. 93, in one aspect, the base 17830 comprises a left flange assembly 17832L that protrudes laterally from a left side of the firing member body 17822 and a right flange assembly 17832R that protrudes laterally from a right side of the firing member body 17822. The base 17830 has a base width BW' that is greater than the width LBW' of the lower portion of the firing member body 17822. In one aspect, the lower body width LBW' is less that the widths of the axial slots in the surgical staple cartridge and elongate channel. The base with BW' is greater than the widths of the axial slots in the surgical staple cartridge and the elongate channel. The top anvil engagement member 17826 comprises a left top flange assembly 17827L that protrudes laterally from a left side of the firing member body 17822 and a right top flange assembly 17827R that protrudes laterally from a right side of the firing member body 17822. The top anvil engagement member 17826 has a width TW' that is greater than the width TBW' of the upper portion of the firing member body 17822. In one aspect, the top body width TBW' is less that the width of an axial slot in the anvil to enable the top portion of the body 17822 to slidably pass therethrough, while the width TW' of the top anvil engagement member 17826 is greater than the width of the anvil slot.

In on aspect, each of the left and right flange assemblies 17832L, 17832R comprises a central segment 17834 having an axial length CL, a proximal segment 17836 having an axial proximal length PL and a distal segment 17838 having an axial distal length DL. See FIG. 93. The base 16830 has an overall axial length BL'. Thus: BL'=PL+CL+DL. In one example, PL and DL are each >CL. In one arrangement PL=DL>CL. For each flange assembly 17832L and 17832R, a proximal end 17840 of the proximal segment 17836 is radiused to reduce frictional engagement with the elongate channel during retraction of the firing member 17820 back to a starting position. In addition, the proximal segment 17836 may have a proximal tapered upper surface 17842 that tapers proximally from the central segment 17834 to the radiused proximal end 17840. For example, the thickness HC of the central segment 17834 is greater than the thickness HD of the proximal end 17840 as shown. In one arrangement, for example, the proximal tapered upper surface 17842 may angle downward from a horizontal upper surface 17837 of the central segment 17834 at a proximal flange angle PFA of approximately less than 8 degrees and preferably below four degrees and greater than zero degrees. Thus, in at least one example, 8°>PFA<4°. Likewise, a distal end 17844 of the distal segment 17838 is radiused to reduce frictional engagement with the elongate channel during the firing process. In addition, the distal segment 17838 may have a distal tapered upper surface 17846 that tapers proximally from the central segment 17834 to the radiused distal end 17844. See FIG. 95. For example, the thickness HC of the central segment 17834 is greater than the thickness HD of the distal end 17844 as shown. In one arrangement, for example, the distal tapered upper surface 17846 may angle downward from the horizontal upper surface 17837 of the central segment 17834 at a distal flange angle DFA of approximately less than 8 degrees and preferably below four degrees and greater than zero degrees. Thus, in at least one example, 8°>DFA<4°.

FIG. 96 illustrates the firing member 17820 and an anvil 17300 which may be identical to many of the anvil configurations disclosed herein except for the differences noted below. As can be seen in FIG. 96, the anvil 17300 comprises an elongate anvil body 17302 and an anvil mounting portion 17310. The elongate anvil body portion 17302 comprises an elongate anvil slot (not shown) configured to accommodate the axial passage of the upper portion of the firing member body 17822 therethrough. The anvil body 17302 further includes an axially extending ledge 17304 that defines an axial flange passage 17308 on each side of the anvil slot for accommodating the corresponding right top flange 17827R and left top flange 17827L therein. In the example illustrated in FIG. 96, the ledge 17304 includes a distal portion 17305, a transition portion 17306 and a proximal portion 17307. The distal portion 17305 is formed with no axial slope, i.e., horizontal. The transition portion 17306 is formed at a transition angle TLA relative to the distal portion 17305. The proximal portion 17307 is formed at a proximal angle PLA relative to the distal portion 17305 that is greater than the transition angle TLA. This arrangement serves to reduce the amount of friction and binding forces established between the firing member 17820 and the anvil 17300 during the closure process. In addition, by having the top anvil engagement member 17826 proximally axially offset by an offset distance OD' and/or by making the axial length TL' of the top anvil engagement member 17826 less than the axial base length BL', the amount of binding between the top anvil engagement member 17826 and the proximal portion 17307 of the ledge 17304 may be reduced. Of course, all of the friction and binding forces that are created during this process generally add to the amount of the closure forces that must be applied to the firing member 17820 to close the anvil 17300. Such configuration may also serve to improve the guidance of the firing member 17820 as well as to reduce twist or bending loads applied to the rotary firing drive shaft 13810 during the firing process.

Figure 97:
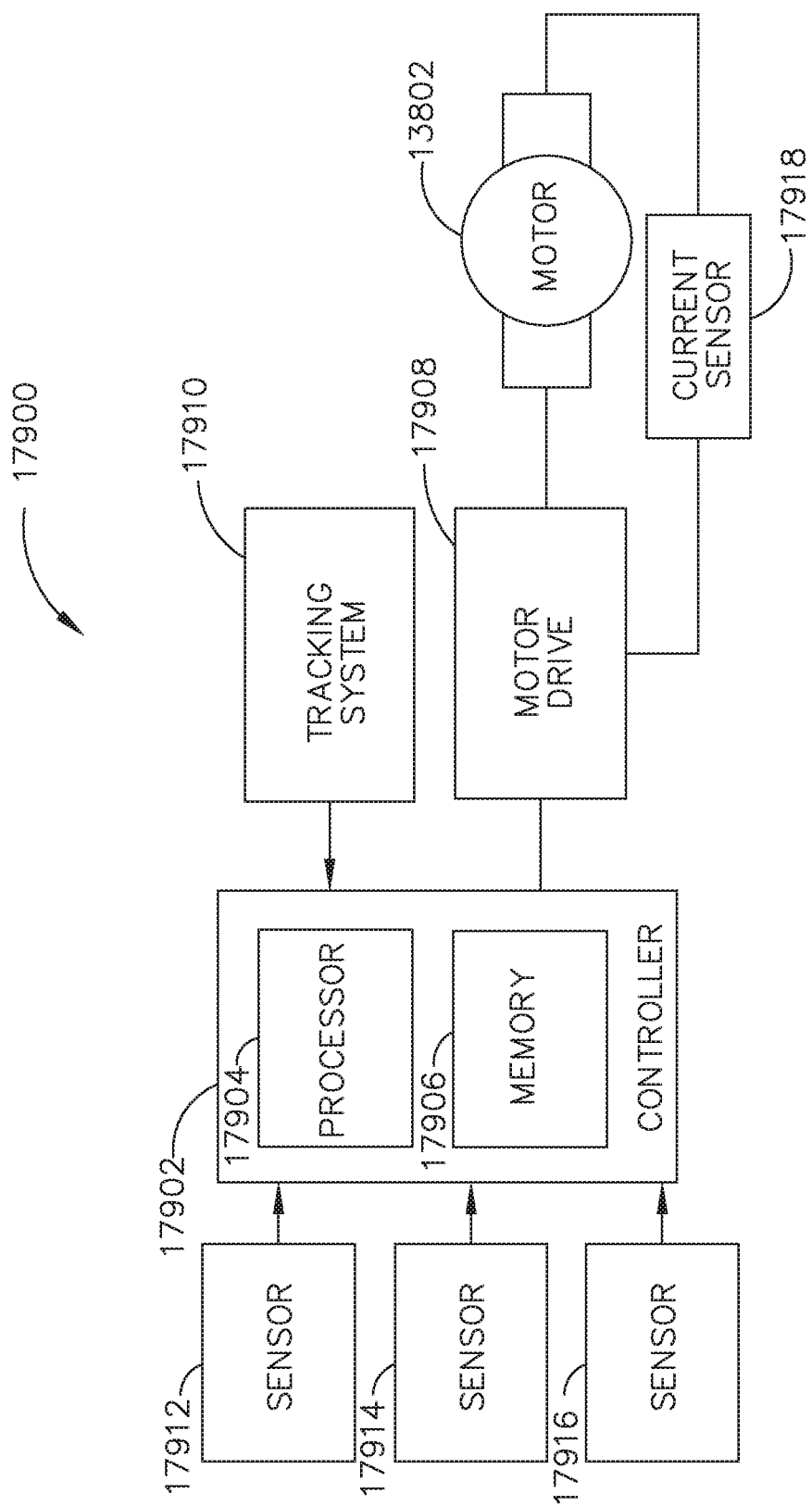
FIG. 97 is a logic diagram of a feedback system example of a powered surgical instrument.

FIG. 97 illustrates an example of a logic diagram of a feedback system 17900 that may be employed by many of the motor driven surgical instruments disclosed herein in connection with the firing systems thereof. For example, the feedback system 17900 may be employed by the firing system 13800 of the surgical instrument 13000. The feedback system 17900 comprises a circuit. The circuit includes a controller 17902 comprising a processor 17904 and a memory 17906. The firing motor 13802 is driven by a motor driver 17908 to rotate the firing drive shaft 13810 to axially drive the firing member 13820. A tracking system 17910 is configured to determine the position of the firing member 13820. The position information is provided to the processor 17904, which can be programmed or configured to determine the position of the firing member 13820 as well as the position of the camming assembly 13740, and the firing drive shaft 13810, etc.

In the aspect illustrated in FIG. 97, a sensor 17912, such as, for example, a strain gauge or a micro-strain gauge, is configured to measure one or more parameters of the end effector 13200, such as, for example, the amplitude of the strain exerted on the anvil 13300 during a clamping operation, which can be indicative of the closure forces applied to the anvil 13300. The measured strain is converted to a digital signal and provided to the processor 17904. Alternatively, or in addition to the sensor 17912, a sensor 17914, such as, for example, a load sensor, can measure the closure force applied by the closure drive system 13500 to the anvil 13300. The sensor 17916, such as, for example, a load sensor, can measure the firing force applied to an I-beam in a firing stroke of the surgical instrument 13000. Alternatively, a current sensor 17918 can be employed to measure the current drawn by the firing motor 13802. The force required to advance the firing member 13820 can correspond to the current drawn by the firing motor 13802, for example. The measured force is converted to a digital signal and provided to the processor 17904.

Figure 98:
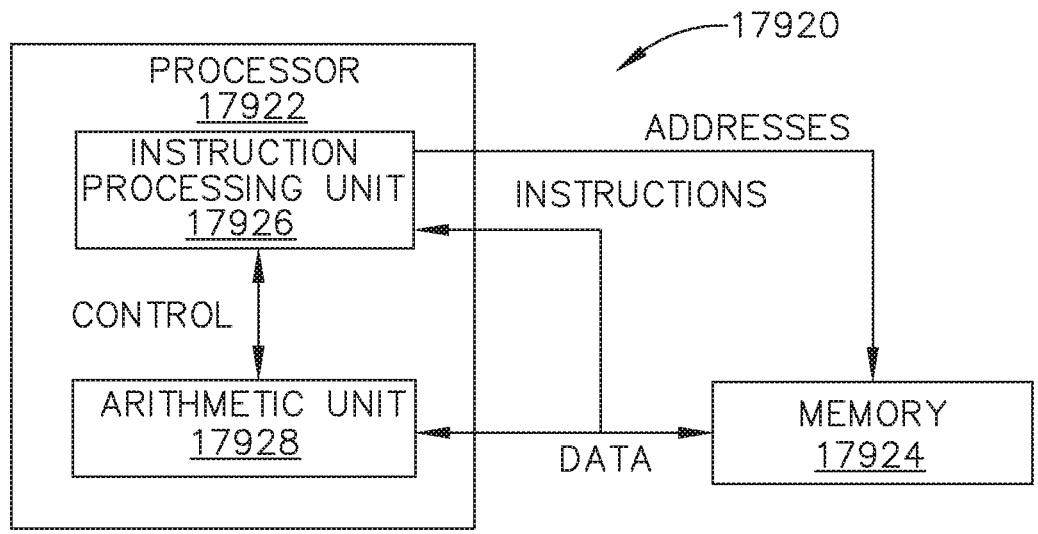
FIG. 98 is a diagram of a control circuit example for a powered surgical instrument.

FIG. 98 illustrates a control circuit configured to control aspects of the surgical instrument 13000 or other surgical instruments/systems disclosed herein. FIG. 98 illustrates a control circuit 17920 that is configured to control aspects of the surgical instrument 13000 according to one aspect of this disclosure. The control circuit 17920 can be configured to implement various processes described herein. The control circuit 17920 may comprise a controller comprising one or more processors 17922 (e.g., microprocessor, microcontroller) coupled to at least one memory circuit 17924. The memory circuit 17924 stores machine executable instructions that when executed by the processor 17922, cause the processor 17922 to execute machine instructions to implement various processes described herein. The processor 17922 may be any one of a number of single or multi-core processors known in the art. The memory circuit 17924 may comprise volatile and non-volatile storage media. The processor 17922 may include an instruction processing unit 17926 and an arithmetic unit 17928. The instruction processing unit may be configured to receive instructions from the memory circuit 17924 of this disclosure.

Figure 99:
FIG. 99 is a diagram of combinational logic circuit example for a powered surgical instrument.

FIG. 99 illustrates a combinational logic circuit 17930 that is configured to control aspects of the surgical instrument 13000 or other surgical instruments/systems disclosed herein. The combinational logic circuit 17930 can be configured to implement various processes described herein. The circuit 17930 may comprise a finite state machine comprising a combinational logic circuit 17932 that is configured to receive data associated with the surgical instrument 13000 at an input 17934, process the data by the combinational logic 17932, and provide an output 17936.

Figure 100:
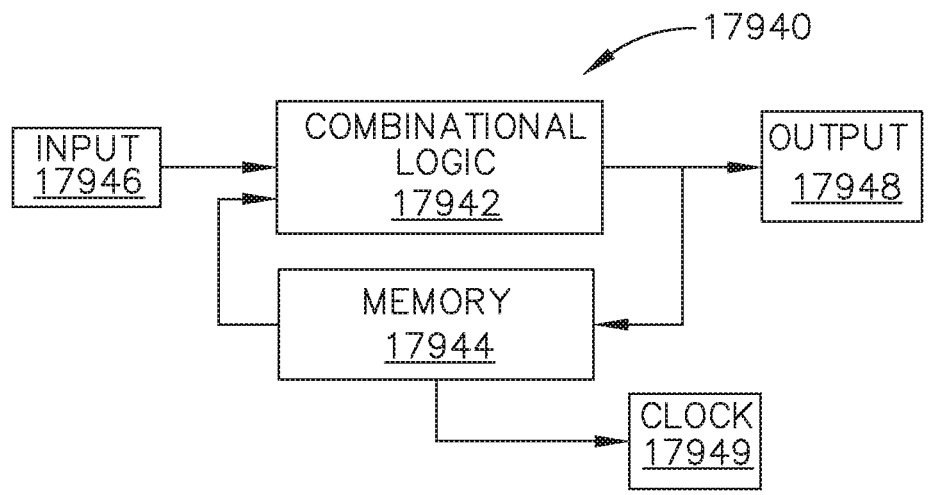
FIG. 100 is a diagram of a sequential logic circuit example for a powered surgical instrument.

FIG. 100 illustrates a sequential logic circuit 17940 configured to control aspects of the surgical instrument 13000 or other surgical instruments/systems disclosed herein. The sequential logic circuit 17940 can be configured to implement various processes described herein. The circuit 17940 may comprise a finite state machine comprising a combinational logic circuit 17942. The sequential logic circuit 17940 may comprise the combinational logic circuit 17942, at least one memory circuit 17944, and a clock 17949, for example. The at least one memory circuit 17944 can store a current state of the finite state machine. In certain instances, the sequential logic circuit 17940 may be synchronous or asynchronous. The combinational logic circuit 17942 is configured to receive data associated with the surgical instrument 13000 or other surgical instruments/systems disclosed herein at an input 17946, process the data by the combinational logic circuit 17942, and provide an output 17948. In other aspects, the circuit may comprise a combination of the processor 17922 and the finite state machine to implement various processes herein. In other aspects, the finite state machine may comprise a combination of the combinational logic circuit 17930 and the sequential logic circuit 17940.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor. Each of the motors disclosed herein may comprise a torque sensor to measure the output torque on the shaft of the motor. The force on an end effector may be sensed in any conventional manner such as by force sensors on the outer sides of the jaws or by a torque sensor for the motor actuating the jaws.

When clamping on thick tissue, as can happen when using longer end effectors such as, for example, 60 mm end effectors, the anvil can be considerably stressed. For example, the anvil may actually bend which can cause the staple-forming undersurface thereof to bend upward away from the deck of the surgical staple cartridge. Such condition is generally undesirable not only from a component reliability stand point, but the condition can also lead to malformed staples. In extreme conditions, in its initial closing position, the anvil position may be at an angle relative to the surgical staple cartridge.

Figure 101:
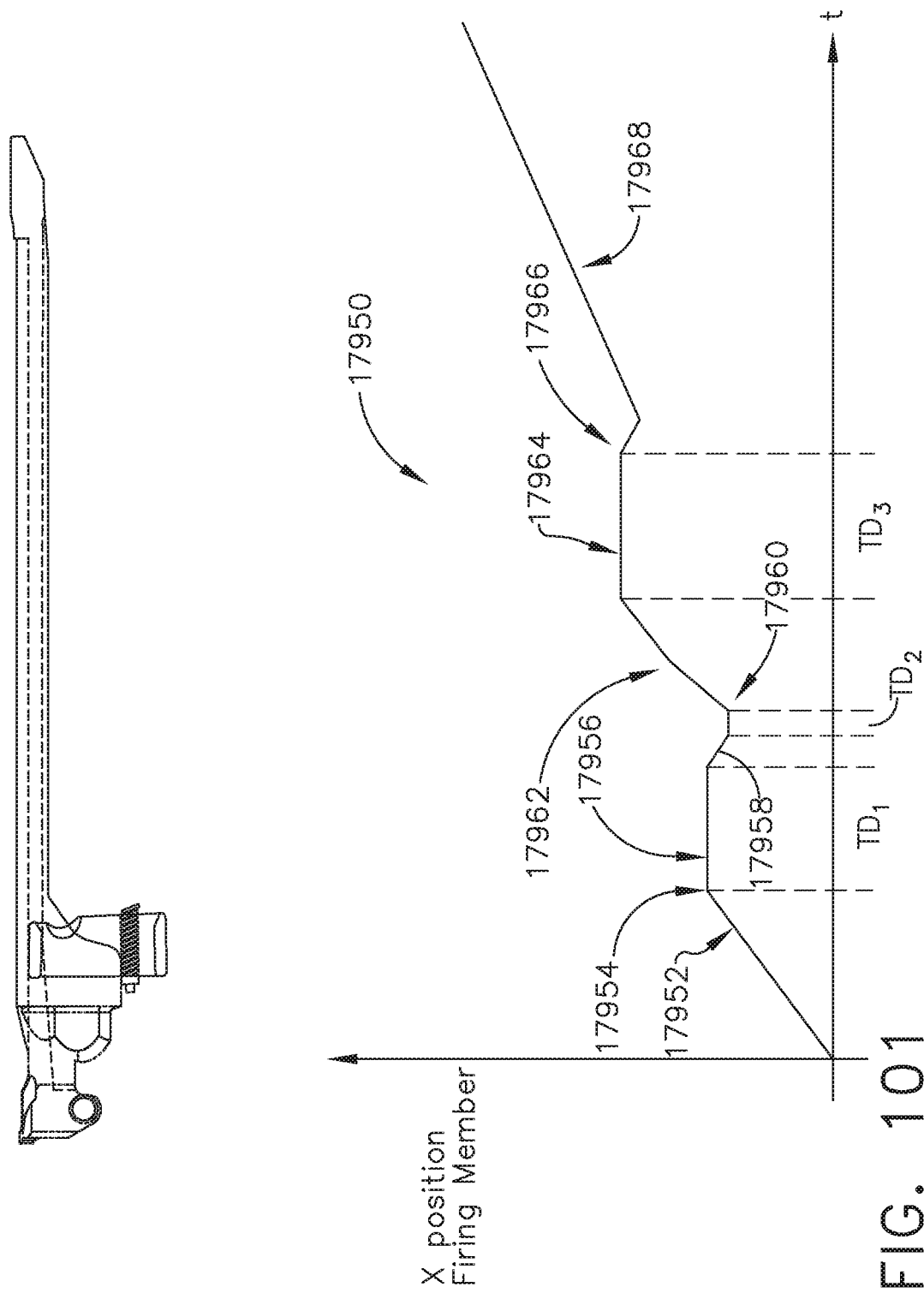
FIG. 101 is a graphical depiction of a firing process control system example for a powered surgical instrument.
Figure 102:
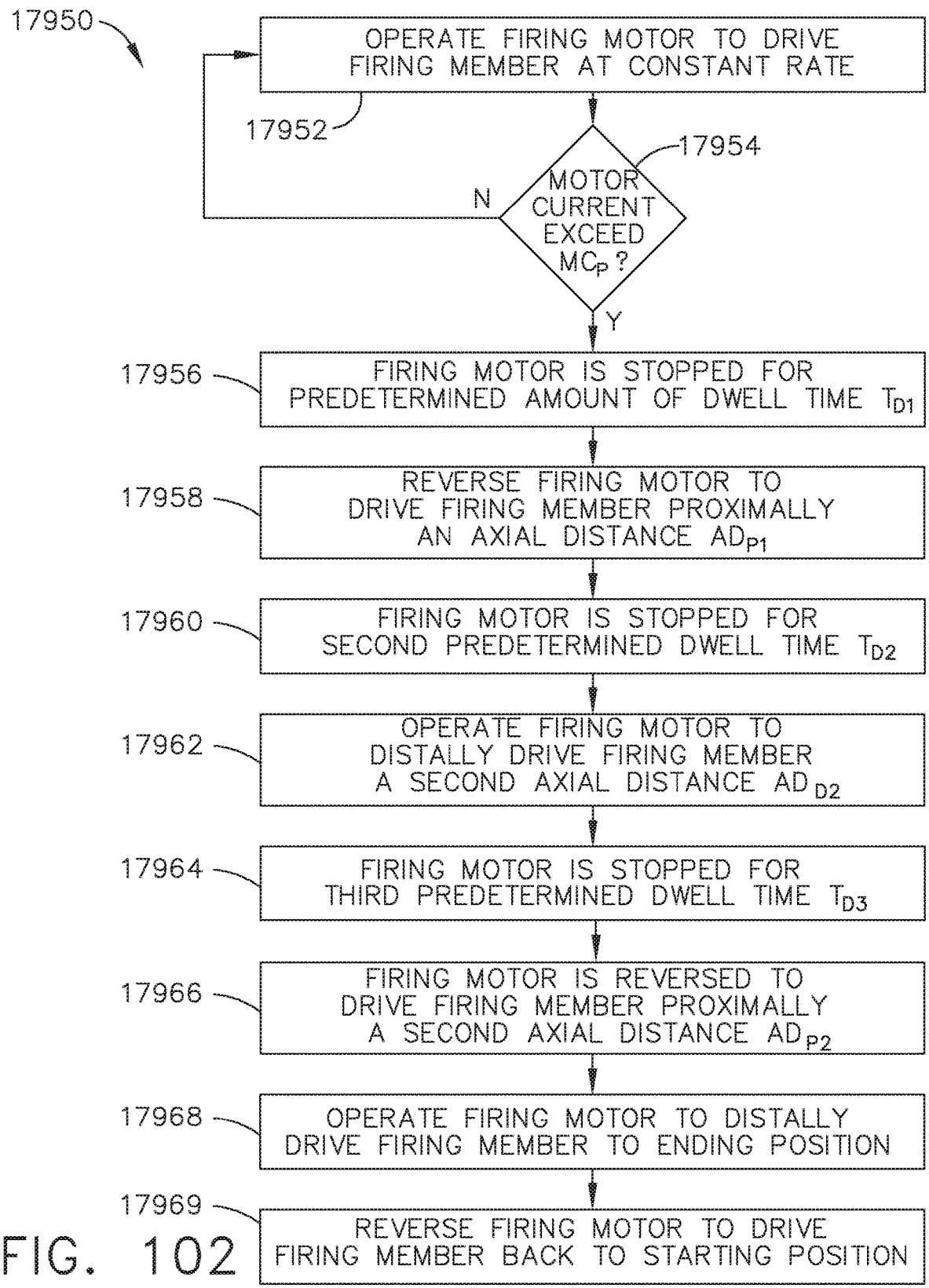
FIG. 102 is a sequential logic circuit example for operating a firing control system of a powered surgical instrument.

FIGS. 101 and 102 illustrate a process 17950 that may be used to operate various firing control systems disclosed herein. FIG. 101 illustrates one form of process 17950 in graphical form relating the x position of the firing member 14820 (or firing member 13820, for example) to an amount of time that has elapsed during the firing process. The firing process is commenced 17952 by operating the firing motor 13802 to drive the firing member 14820 at a constant rate. As the firing motor 13802 is operated to drive the firing member 14820 at a constant rate forward (17952), the control circuit monitors the firing motor 13802 current at 17954 until the motor current exceeds a predefined motor current threshold $MC_P$ associated with the final closed position of the anvil. The predetermined motor current threshold $MC_P$ may be selected based on an axial distance that the firing member 14820 must travel until the anvil 13300 reaches a final closed position. In one arrangement, for example, the firing member 14820 may initially travel about (0.250") distally from its starting position. At this stage, the firing motor 13802 is stopped 17956 for a predetermined first amount of dwell time $T_{D1}$ which allows fluid in the clamped tissue to begin to flow or migrate out of the clamped tissue (tissue creep). Further, after the waiting period, the firing member 14820 may encounter a lower amount of vertical load or resistance improving the likelihood of traversing through that location. In one arrangement, $T_{D1}$ may be 1-5 seconds, for example. After the expiration of the first amount of dwell time $T_{D1}$, the firing motor 13802 may be driven in a reversed rotary direction 17958 to retract (axially move in a proximal direction) the firing member 14820 a predetermined axial distance $AD_{P1}$. In one example, $AD_{P1}$ may be approximately 0.1"-0.15", for example. Such action allows the tissue to continue to creep (fluid to exit the clamped tissue). Once the firing member 14820 has been retracted the predetermined axial distance $AD_{P1}$, the firing motor 13802 is stopped 17960 for a second predetermined amount of dwell time $TD_2$. In one example, $TD_2$ may be approximately 0.5-1.0 seconds, for example. After the expiration of $TD_2$, the firing motor 13802 is operated 17962 to distally drive the firing member 14820 a second axial distance $AD_{D2}$. In one example, the second axial distance $AD_{D2}$ may be approximately 0.0125"-0.250", for example. At this stage 17964, the firing motor 13802 is stopped for a third predetermined amount of dwell time $TD_3$ to facilitate additional tissue creep. In one arrangement, $T_{D3}$ may be 1-5 seconds, for example. After the expiration of the third amount of dwell time $T_{D3}$, the firing motor 13802 is driven in a reversed rotary direction 17966 to retract (axially move in a proximal direction) the firing member 14820 a second predetermined axial distance $AD_{P2}$. In one example, $AD_{P2}$ may be approximately 0.1"-0.15", for example. At this point, the firing motor 13802 may be operated 17968 to drive the firing member 14820 distally until it reaches its ending position. In the alternative, after the firing member 14820 has been proximally driven the axial distance $AD_2$, the firing motor 13802 may be stopped for another dwell time $TD_4$ before being operated to drive the firing member distally. In one example, $TD_4$ may be approximately 0.5-1.0 seconds, for example. In a preferred arrangement, the firing member 14820 has entered the portion of the anvil track that is parallel to the elongate channel at 17968. Once the firing member 14820 has reached its ending position (as may be detected by a sensor), the firing motor 13802 may be reversed 17969 to retract the firing member 14820 back to the starting position. Such process may serve to reduce an amount of bending and other stresses encountered by the anvil during clamping and stapling of robust tissue.

Figure 103:
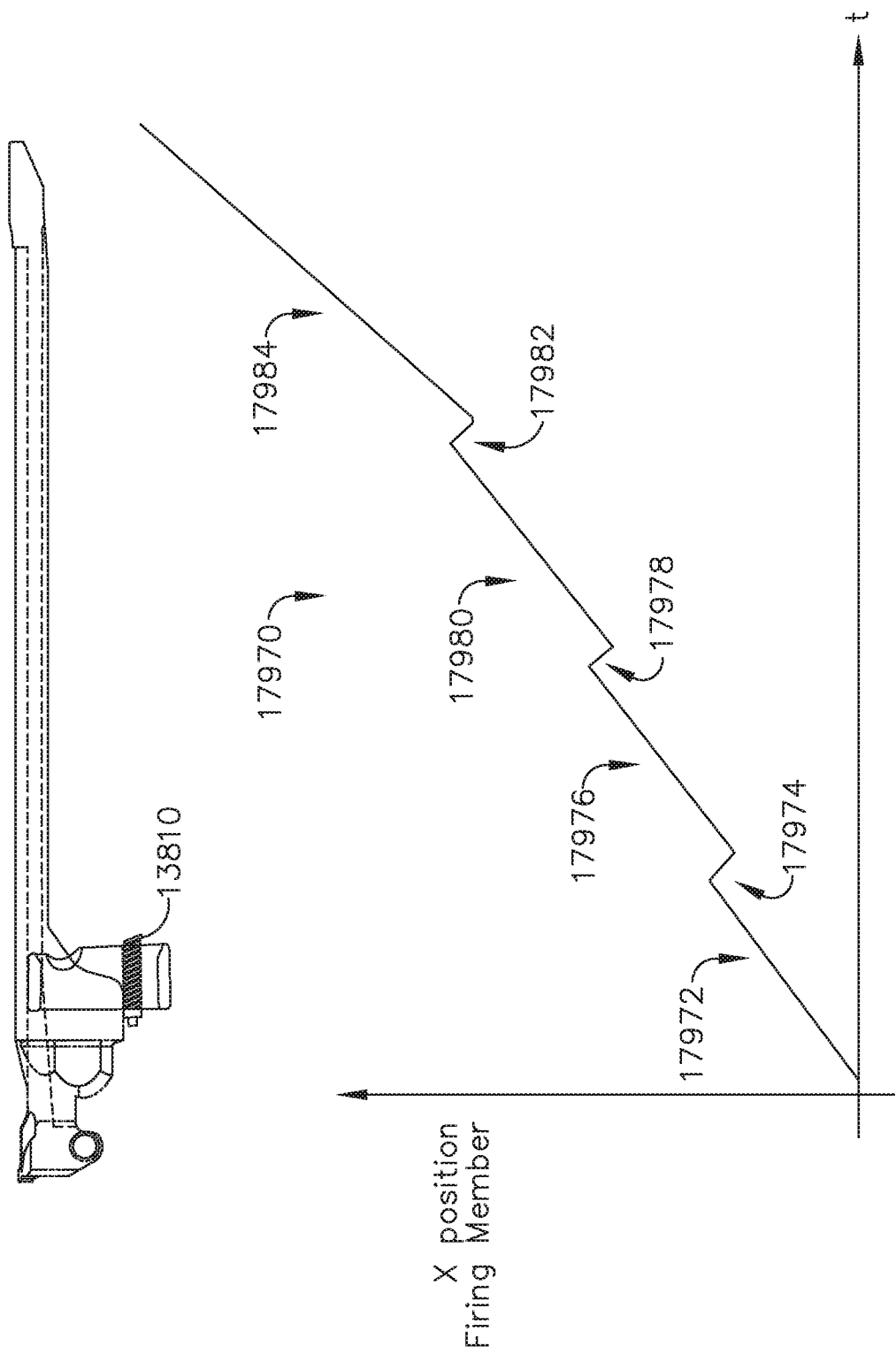
FIG. 103 is a graphical depiction of another firing process control system example for a powered surgical instrument.
Figure 104:
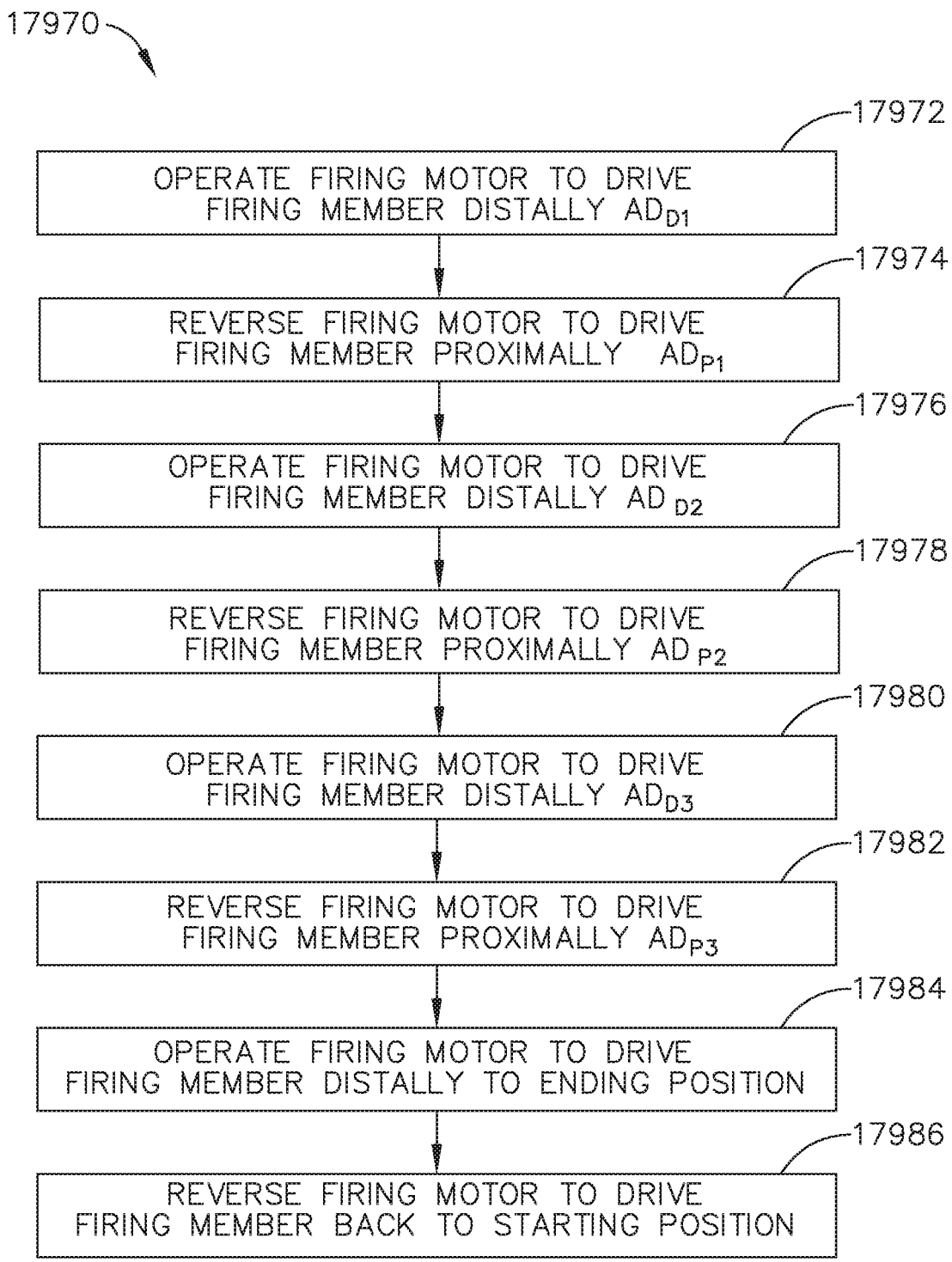
FIG. 104 is a sequential logic circuit example for operating a firing control system of another powered surgical instrument.
Figure 105:
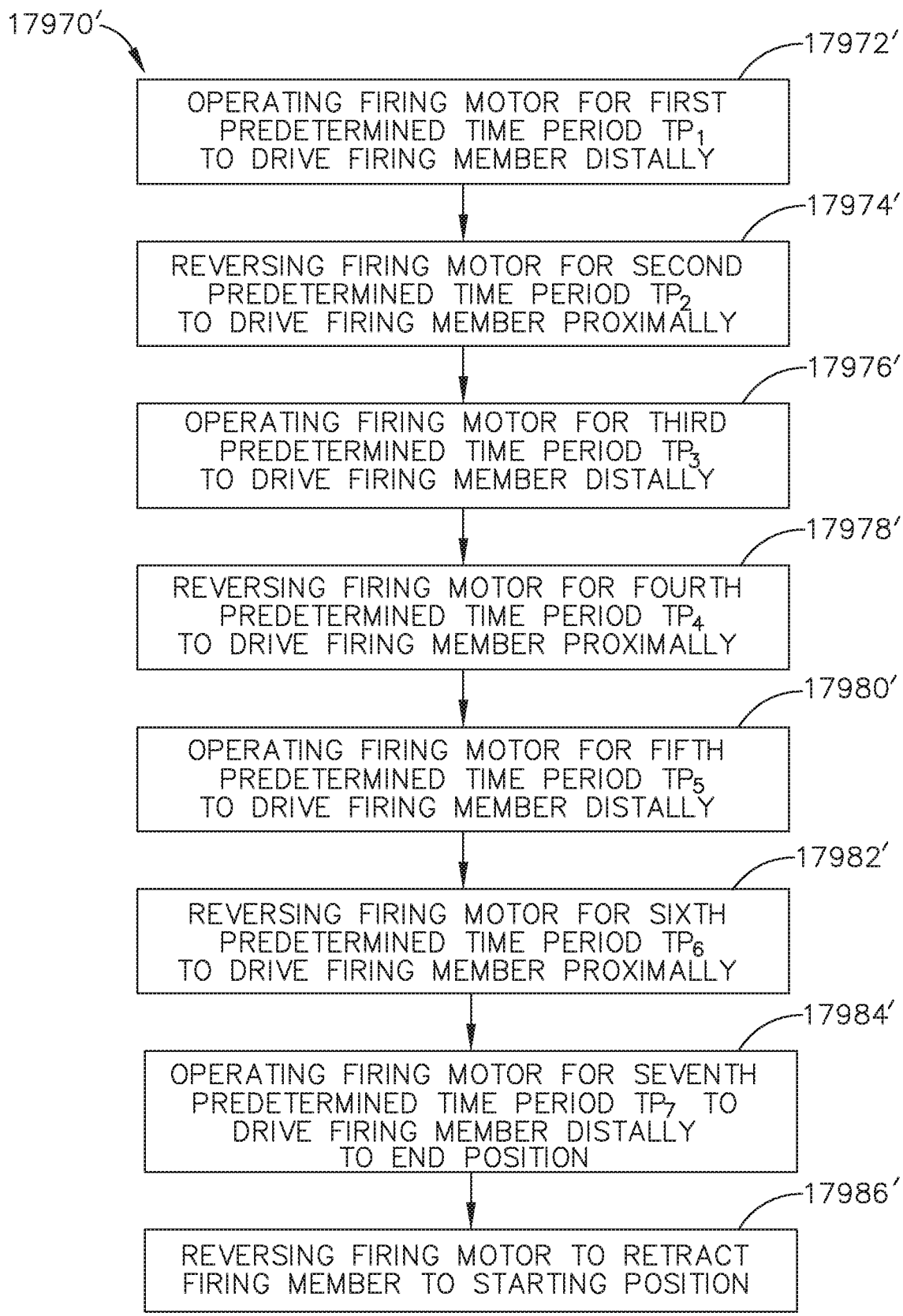
FIG. 105 is a sequential logic circuit example for operating a firing control system of another powered surgical instrument.

FIGS. 103 and 104 illustrate another process 17970 of operating the various firing control systems disclosed herein. FIG. 103 illustrates one process 17970 in graphical form relating the x position of the firing member 14820 (or 13820, for example) to the amount of time elapsed during the firing process. The firing process is commenced 17972 by operating the firing motor 13802 to drive the firing member 14820 a first axial distal distance $AD_{D1}$. The position of the firing member 14820 may be detected by sensors (Hall effect, etc.) positioned in the anvil 14300 and conveyed to the control circuit 17920. In an alternative process 17970', the firing motor 13802 may be operated for a first predetermined time period $TP_1$ (17972') to drive the firing member 14820 the first axial distal distance $AD_{D1}$. See FIG. 105. Thereafter, the firing motor 13802 is driven in a reversed rotary direction 17974 to retract (axially move in a proximal direction) the firing member 14820 a predetermined axial proximal distance $AD_{P1}$. In one example, $AD_{P1}$ may be approximately 0.1"-0.15", for example. Such action allows the tissue to continue to creep (fluid to migrate out of or exit the clamped tissue). In process 17970', the firing motor 13802 may be operated for a second predetermined time period $TP_2$ (17974') to drive the firing member 13820 the first axial proximal distance $AD_{P1}$. Once the firing member 14820 has been retracted the predetermined axial proximal distance $AD_{P1}$, the firing motor 13802 is driven at 17976 to distally drive the firing member 14820 a second axial distal distance $AD_{D2}$. In the alternative process 17970', the firing motor 13802 may be operated for a third predetermined time period $TP_3$ (17976') to drive the firing member 14820 the second axial distal distance $AD_{D2}$. Thereafter, the firing motor 13802 is driven in a reversed rotary direction 17978 to retract the firing member 14820 a second predetermined axial proximal distance $AD_2$. In one example, $AD_2$ may be approximately 0.1"-0.15", for example. In the alternative process 17970', the firing motor 13802 may be operated for a fourth predetermined time period $TP_4$ (17978') to drive the firing member 14820 the second axial proximal distance $AD_2$. Thereafter, the firing motor 13802 is driven at 17980 to distally drive the firing member 14820 a third axial distal distance $AD_{D3}$. In the alternative process 17970', the firing motor 13802 may be operated for a fifth predetermined time period $TP_5$ (17980') to drive the firing member 14820 the third axial distal distance $AD_{D3}$. Thereafter, the firing motor 13802 is driven in a reversed rotary direction 17982 to retract the firing member 14820 a third predetermined axial proximal distance $AD_{P3}$. In one example, $AD_{P3}$ may be approximately 0.1"-0.15", for example. In the alternative process 17970', the firing motor 13802 may be operated for a sixth predetermined time period $TP_6$ (17982') to drive the firing member 14820 the third axial proximal distance $AD_{P3}$. Thereafter, the firing motor 13802 is driven at 17984 to distally drive the firing member 14820 to its ending position. In the alternative process 17970', the firing motor 13802 may be operated for a seventh predetermined time period $TP_7$ (17984') to drive the firing member 14820 to the ending position. Once the firing member 14820 has reached its ending position (as detected by a sensor, for example), the firing motor 13802 may be reversed 17986, 17986' to retract the firing member 14820 back to the starting position.

In a preferred arrangement, the firing member 14820 has entered the portion of the anvil track that is parallel to the elongate channel at 17984 Such process may serve to reduce the bending and stressing of the anvil during clamping and stapling of robust tissue. The various axial distal distances and the time periods may be altered in other arrangements. In one arrangement, the axial distal distanced $AD_{D1}$, $AD_{D2}$, $AD_{DS}$ may be equal or they may be different. Likewise the time periods $TP_1$, $TP_3$, $TP_5$ may be equal or they may be different.

The processes 17950, 17970, 17970' may be particularly useful when clamping and firing through relatively thick tissue. Some rotary driven end effector arrangements may be constructed with a relatively short anvil mounting joint which may necessarily include relatively steep anvil starting ramps adjacent the anvil mounting portion of the anvil. Such steep starting ramps can be particularly difficult to traverse when using conventional closure and firing system processes. Various processes and procedures disclosed herein allow/facilitate the complete closure of the anvil while reducing/minimizing the amount of binding stresses normally encountered by the firing member when otherwise using convention firing and closing processes.

Figure 106:
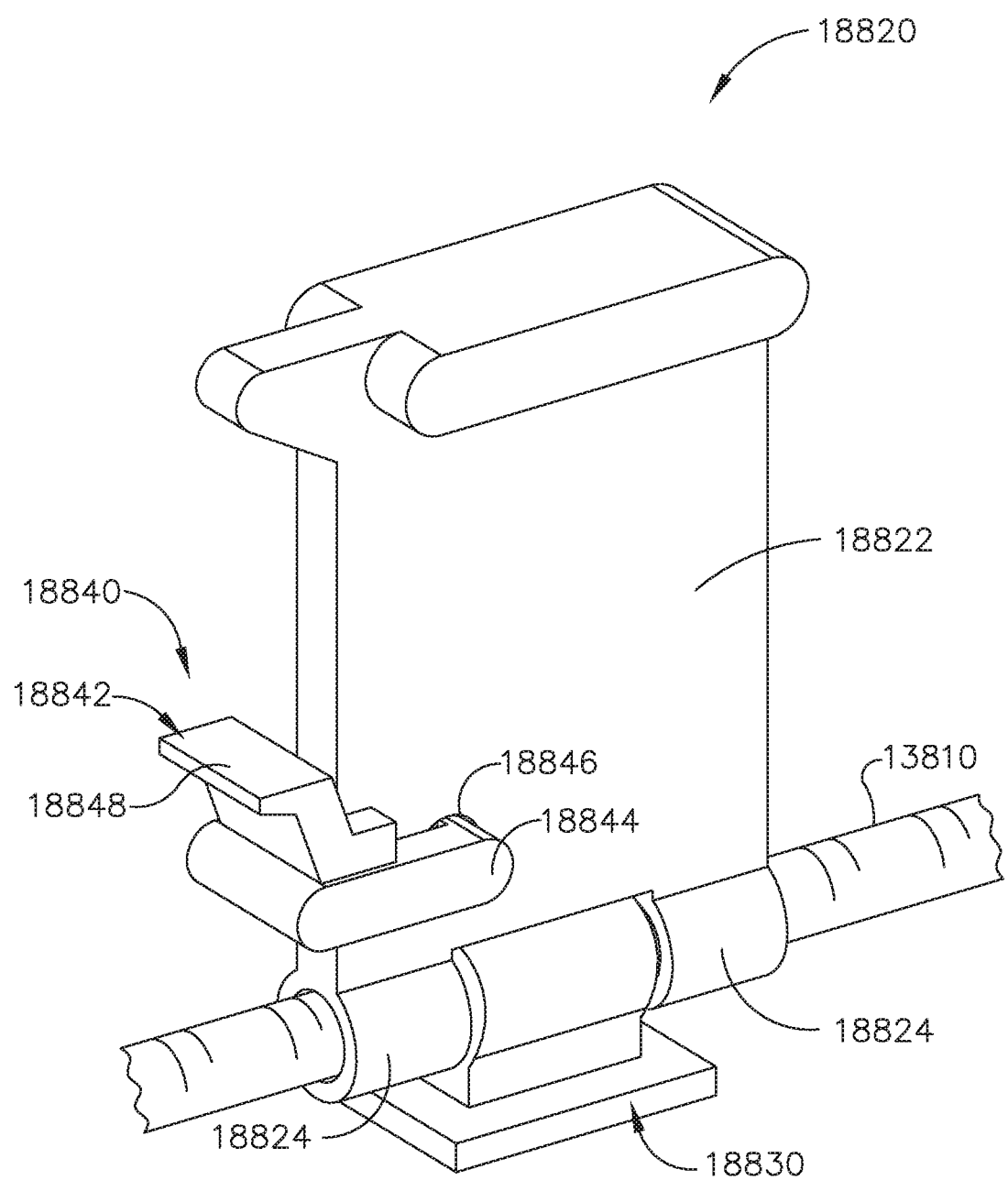
FIG. 106 is a perspective view of another firing member of a surgical end effector in installed on a rotary firing drive shaft thereof.
Figure 107:
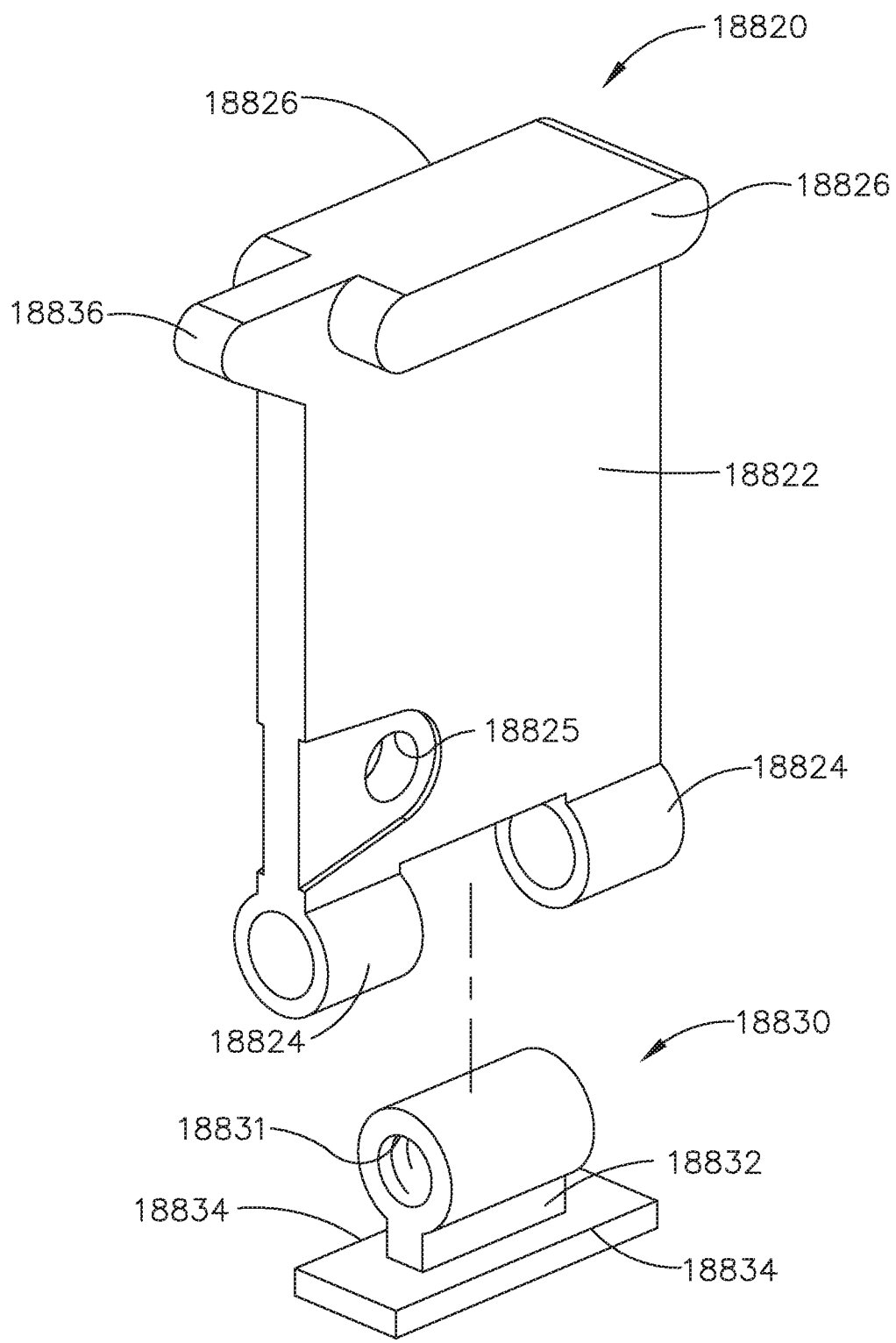
FIG. 107 is an exploded assembly view of portions of the firing member of FIG. 106.
Figure 108:
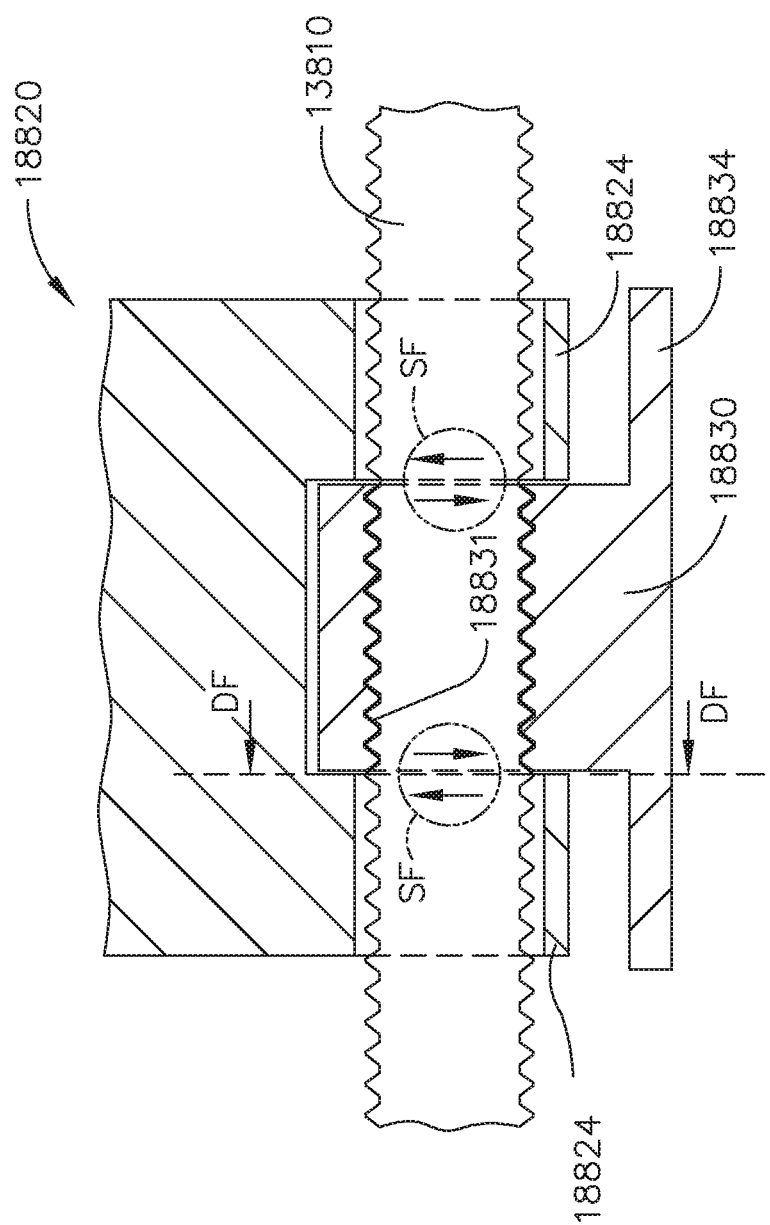
FIG. 108 is a partial cross-sectional view of the firing member and a drive nut arrangement installed on the rotary firing drive shaft of FIG. 106.

FIGS. 106 and 107 illustrates another form of firing member 18820 that may be similar in many aspects to firing member 14820. As can be seen in FIGS. 106 and 107, the firing member 18820 comprises a body portion 18822 that includes two downwardly extending hollow mounting portions 18824 that are unthreaded and spaced from each other to receive a threaded drive nut 18830 therebetween. As can be seen in FIGS. 107 and 108, the drive nut 18830 includes a threaded passage 18831 that is configured to threadably engage the firing drive shaft 13810. The drive nut 18830 includes a vertical tab portion 18832 that is sized to extend through an axial slot in the bottom of the elongate channel as was described above. Two laterally extending channel engagement flanges 18834 are formed on the threaded drive nut 18830 and are configured to engage the bottom of the elongate channel. Rotation of the firing drive shaft 13810 causes the drive nut 18830 to move axially. As the drive nut 18830 moves axially, the drive nut 18830 applies axial drive forces DF to the firing member body 18822 as shown in FIG. 108 to drive the firing member 18820 axially. Such configuration causes shear forces SF to be applied to the firing drive shaft 13810 as shown. This loading arrangement puts the firing drive shaft 13810 into a shear failure mode, which may be preferred to bending. See FIG. 108. The system is assembled by passing the firing drive shaft 13810 through one of the hollow mounting portions 18824 and threading it into the threaded passage 18831 in the drive nut 18830 until the firing drive shaft 13810 passes through the second hollow mounting portion 18824 and the assembled firing member 18820 is in the desired position on the firing drive shaft 13810. In addition, two laterally extending anvil engagement tabs 18826 are formed on the top of the firing member body 18822 and are configured to engage an anvil as the firing member 18820 is axially moved within an end effector. The top portion of the firing member body 18822 further comprises a distally extending anvil nose portion 18836.

In this arrangement, the firing member 18820 includes a firing member lockout feature 18840 that is configured to prevent the distal advancement of the firing member 18820 from its starting position unless a fresh unfired staple cartridge has been properly seated in the elongate channel. In one example, the firing member lockout feature 18840 comprises a lockout body 18842 that has two spaced attachment legs 18844 protruding therefrom that extend around the firing member body 18822. Each attachment leg 18844 includes an inwardly extending pivot pin 18846 that is adapted to be pivotally received in an opening 18825 in the mounting portions 18824. The lockout feature 18840 further includes a sled latch 18848 that is configured for contact with a camming assembly 18740 in a staple cartridge.

Figure 109:
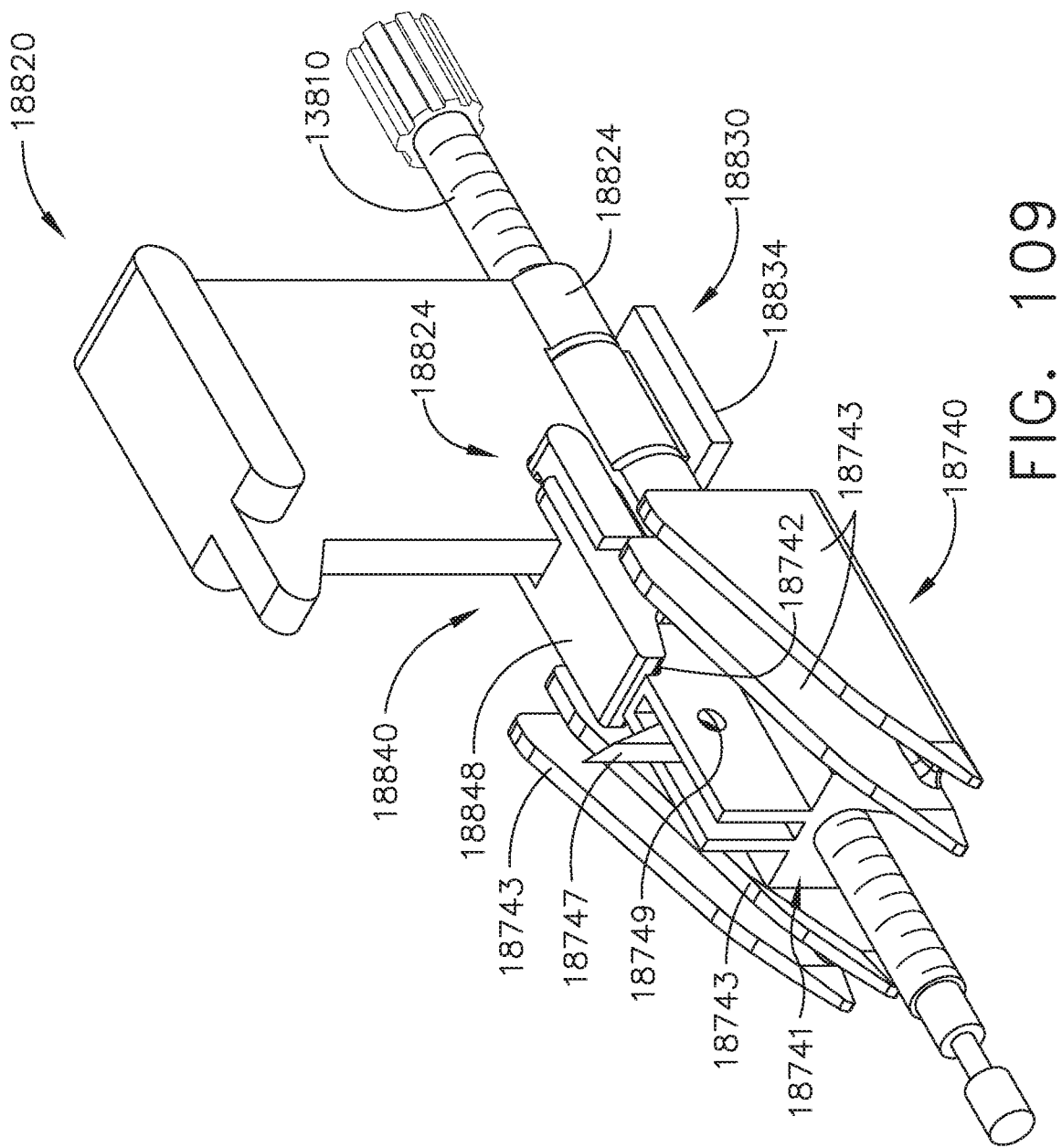
FIG. 109 is a partial perspective view of another firing member of a surgical end effector installed on a rotary firing drive shaft thereof an in unlocking engagement with a camming assembly of a surgical staple cartridge with a tissue cutting member thereof in a deployed position.
Figure 110:
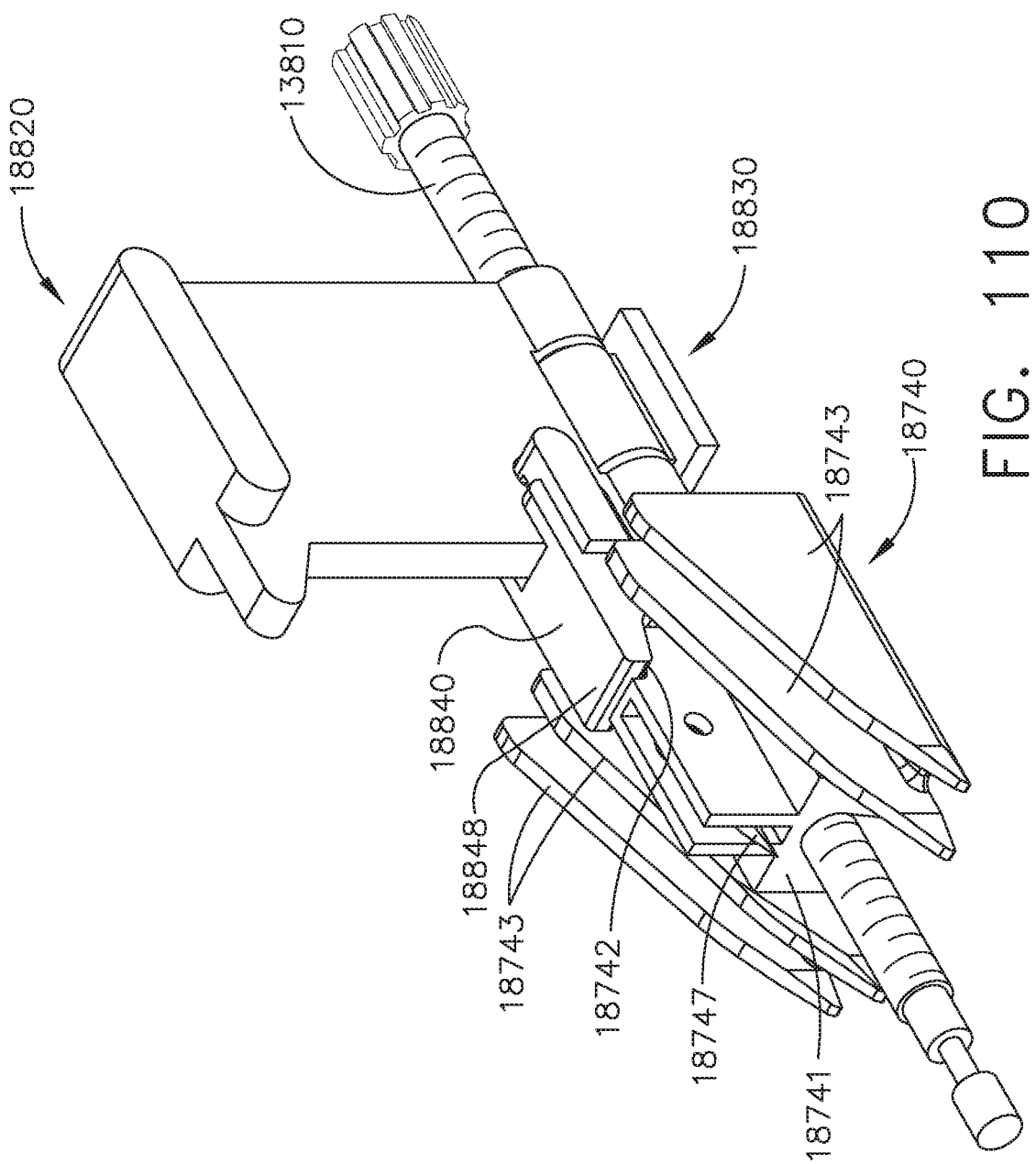
FIG. 110 is another partial perspective view of the firing member and camming assembly of FIG. 109 with the tissue cutting member in a stored position.

Turning to FIGS. 109 and 110, the firing member 18820 is configured to operably interface with camming assembly 18740 that is similar in many aspects to camming assembly 14740 described above. For example, in one aspect, the camming assembly 18740 is operably supported in the staple cartridge and is configured to be snapped over or otherwise operably interface with the firing drive shaft 13810 in any of the various manners described herein. For example, the camming assembly 18740 comprises a camming assembly body 18741 that may have a series of internal thread segments (not shown) that are configured to threadably engage threads or thread segments on the firing drive shaft 13810 in the manners described above. In other arrangements, the camming assembly 18740 may not have threads. In such configurations the firing member body 18822 is configured to extend around the firing drive shaft 13810 (without threaded engagement), for example. In such configuration, the camming assembly 18740 is driven distally through the staple cartridge by the firing member 18820. Once the firing member 18820 and the camming assembly 18740 have been driven into their distal-most ending positions, the firing member 18820 may be retracted back to its starting position by rotating the firing drive shaft 13810 in a reverse rotary direction while the camming assembly 18740 remains in its ending position.

As can further be seen in FIGS. 109 and 110, the camming assembly body 18741 comprises a proximally extending unlocking portion 18742 that is configured to engage the sled latch 18848 on the lockout feature 18840. Thus, as was described above, when a fresh, unfired surgical staple cartridge that contains a camming assembly 18740 has been properly seated within the elongate channel of the end effector, the unlocking portion 18742 on the camming assembly 18740 engages the sled latch 18848 on the lockout feature 18840 to pivot the lockout feature 18840 into an unlocked position wherein the lockout feature 18840 does not extend into a lockout hole in the elongate channel. As can also be seen in FIGS. 109 and 110, the camming assembly body 18741 includes a series of cam members 18743 that are aligned with corresponding staple drivers supported in lines within the staple cartridge.

Once a fresh staple cartridge containing the camming assembly 18740 therein in its unfired starting position has been properly loaded into the elongate channel of the end effector and the anvil thereof has been moved to a closed position through activation of the closure system, the firing system can then be activated to drive the firing member 18820 distally. Continued distal movement of the firing member 18820 causes the internal threads (if present) in the camming assembly 18740 to engage the corresponding threads on the firing drive shaft 13810. Continued rotation of the firing drive shaft 13810 causes the camming assembly 18740 and firing member 18820 to move distally through the staple cartridge in the manners described herein. As the cam members 18743 contact the corresponding staple drivers in the cartridge body, the cam members 18743 drive the drivers upward in their respective pockets. As the drivers are driven upwardly, the staples or fasteners supported thereon are forced through the tissue that is clamped between the cartridge and the anvil and into forming contact with the staple-forming undersurface of the anvil.

Unlike camming assembly 14740, the camming assembly 18740 contains a tissue cutting member or blade 18747. In one aspect, the tissue cutting member 18747 is movably supported on the camming assembly body 18741 such that it is movable from a deployed position (FIG. 109) to a recessed or stored position (FIG. 110). In one aspect, the cam members 18743 extend distally beyond the tissue cutting member 18747 such that the staples or fasteners are deployed through the tissue before the tissue cutting member 18747 cuts through the tissue. Thus, the clamped tissue is stapled and thereafter cut as the firing member 18820 and camming assembly 18740 are driven distally. In one aspect, the tissue cutting member 18747 is pivotally supported on a pivot pin 18749 such that it is pivotable between the deployed position and the stored position. The tissue cutting member 18747 is mounted in a blade mounting portion 18746 defined in the camming assembly body 18741. In one example, the tissue cutting member 18747 may be releasably retained in the deployed position by a detent (not shown) in the tissue cutting member 18747 that is configured to releasably engage a corresponding recess in the camming assembly body 18741. Other releasable tissue cutting retainer arrangements are contemplated. In at least one arrangement, once the camming assembly 18740 has been driven to a distal-most ending position within the staple cartridge, the tissue cutting member 18747 is configured to be pivoted to the stored position through contact with a corresponding actuation feature provided in a distal end of the cartridge body. At the completion of the firing stroke, the firing drive shaft 13810 is rotated in an opposite direction to cause the firing member 18820 to be proximally driven back to the starting position within the end effector. The camming assembly 18740 disengages from the firing drive shaft 13810 and remains in the ending position. After the firing member 18820 has returned to the starting position, the closure system may be activated to move the anvil to the open position to thereby release the stapled tissue from the end effector. Thereafter, the "spent" staple cartridge may be removed from the elongate channel of the end effector. Should the user attempt to reuse the spent cartridge, because the camming assembly 18740 is not in the starting position, the lockout feature 18840 will prevent the inadvertent actuation of the firing member 18820.

Figure 111:
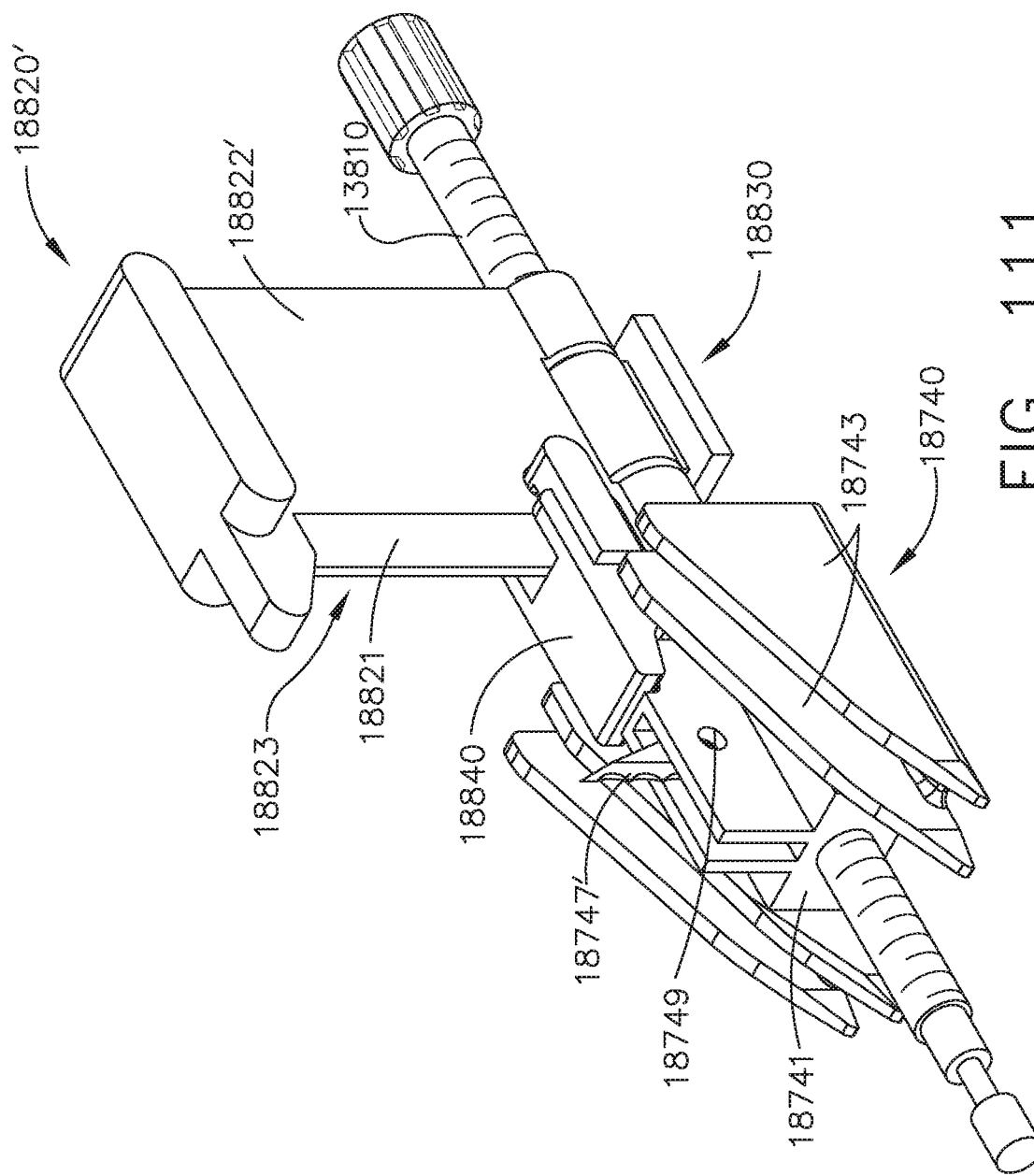
FIG. 111 is a partial perspective view of another firing member of a surgical end effector installed on a rotary firing drive shaft thereof and in unlocking engagement with a camming assembly of a surgical staple cartridge with a tissue cutting member thereof in a deployed position.

FIG. 111 illustrates an alternative firing member arrangement 18820' that is identical to firing member 18820 described above, except that a tissue separating feature 18821 is formed on a distal edge 18823 of the firing member body 18822'. Stated another way, the distal edge 18823 of the firing member body 18822' tapers to a thinner cross-section without forming a tissue cutting edge thereon. This tissue separating feature may be formed using various metal injection molding techniques, for example. Such feature helps to spread the tissue (without additionally cutting) after it has been cut by the tissue cutting member 17847' on the camming assembly 18740.

Such camming assembly arrangements provide a fresh cutting surface with each new cartridge. In addition, tissue cutting members across different cartridges may have different profiles, thicknesses and aggressiveness depending upon the particular application. For example, a cartridge that is configured for use with a buttress material may have a more robust tissue cutting member (e.g., the tissue cutting member may be sharper, thicker have a lesser hone angle, be serrated, etc.). FIG. 111 illustrates a serrated tissue cutting member 18747', for example. Thus, the particular configuration of the tissue cutting member may be tailored to the particular type and thickness of tissue to be cut and stapled.

Figure 112:
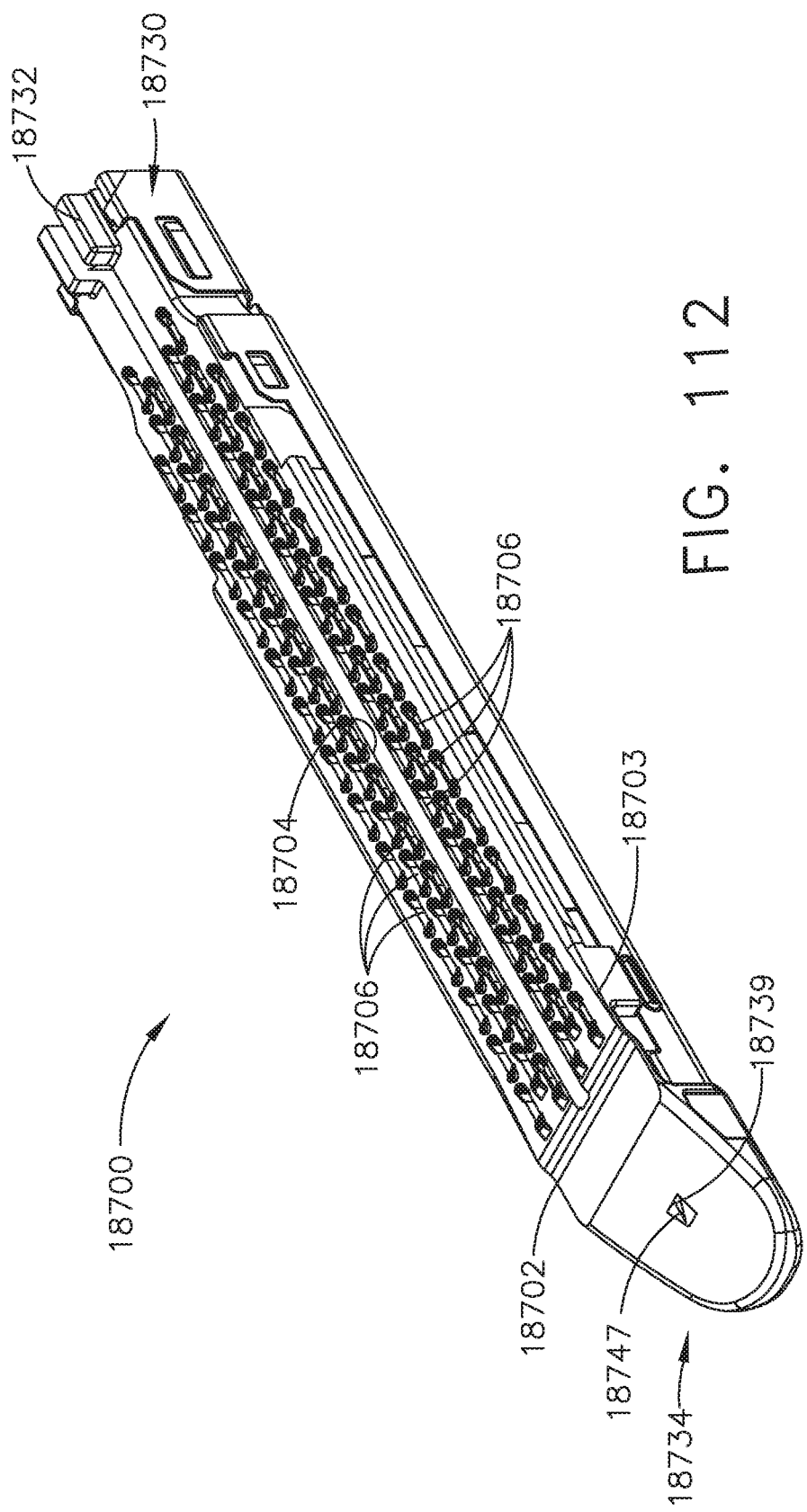
FIG. 112 is a perspective view of another surgical staple cartridge.
Figure 113:
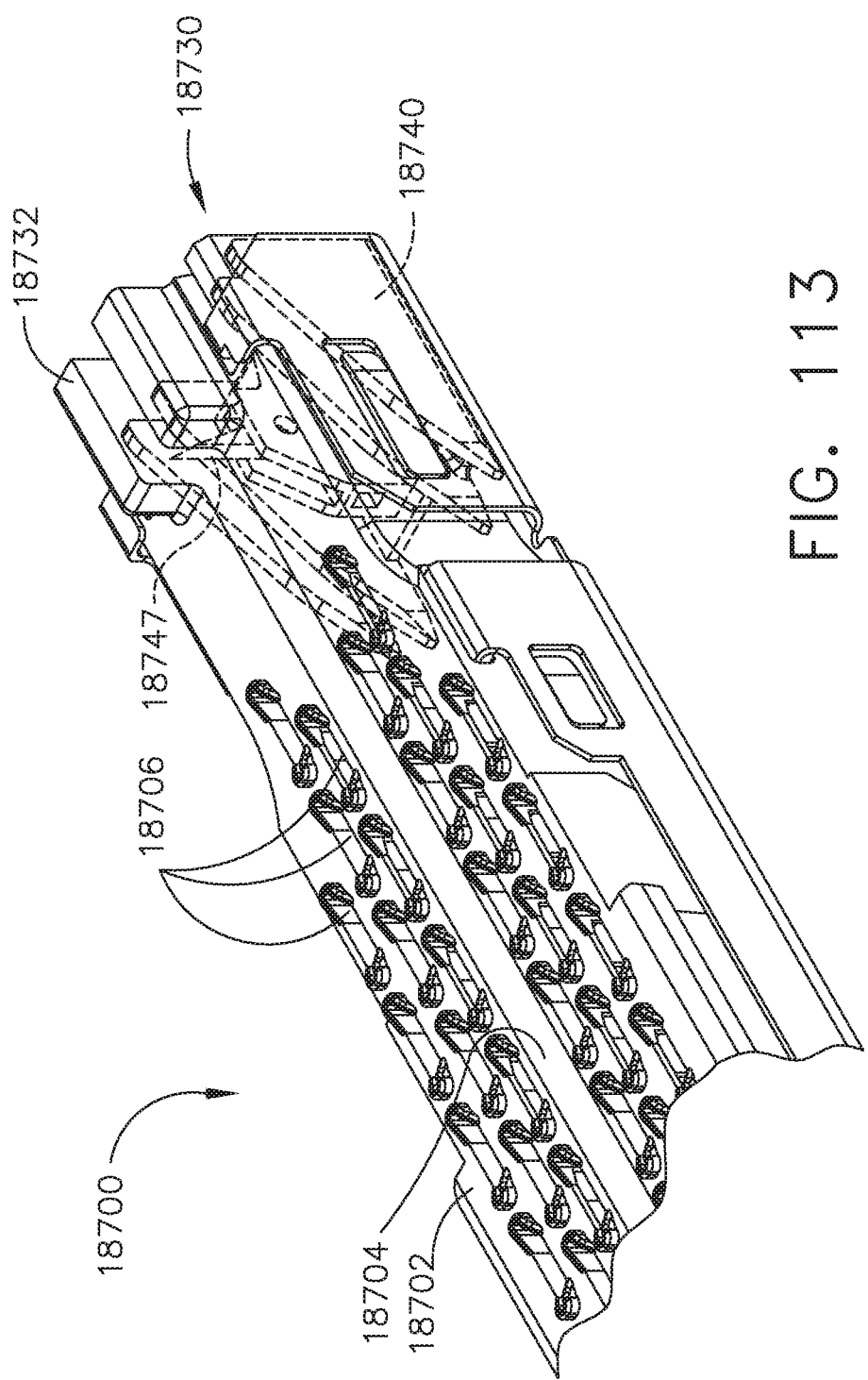
FIG. 113 is an enlarged perspective view of a proximal end of the surgical staple cartridge of FIG. 112 with a camming assembly thereof shown in broken lines.

FIGS. 112 and 113 depict a surgical staple cartridge 18700 that includes a camming assembly 18740' that may be identical to the camming assembly 18740 except for the differences noted below, for example. The cartridge 18700 comprises an elongate cartridge body 18702 that has a centrally disposed elongate cartridge slot 18704 that is configured to accommodate the axial travel of the firing member 18820 therein. Also in the illustrated example, three lines of surgical staple pockets 18706 are formed on each side of the elongate slot 18704. Each staple pocket 18706 defines an opening in a cartridge deck surface 18703 of the cartridge body 18702. Each staple pocket 18706 may have a staple driver (not shown) associated therewith that supports one or more surgical staples or fasteners (not shown) thereon. As can seen in FIG. 113, a safety garage 18732 is formed on a proximal end 18730 of the cartridge body 13702 such that the tissue cutting member 18747 (in its deployed position) is protected thereby (unexposed) when the camming assembly 18740 is in its starting position.

Figure 114:
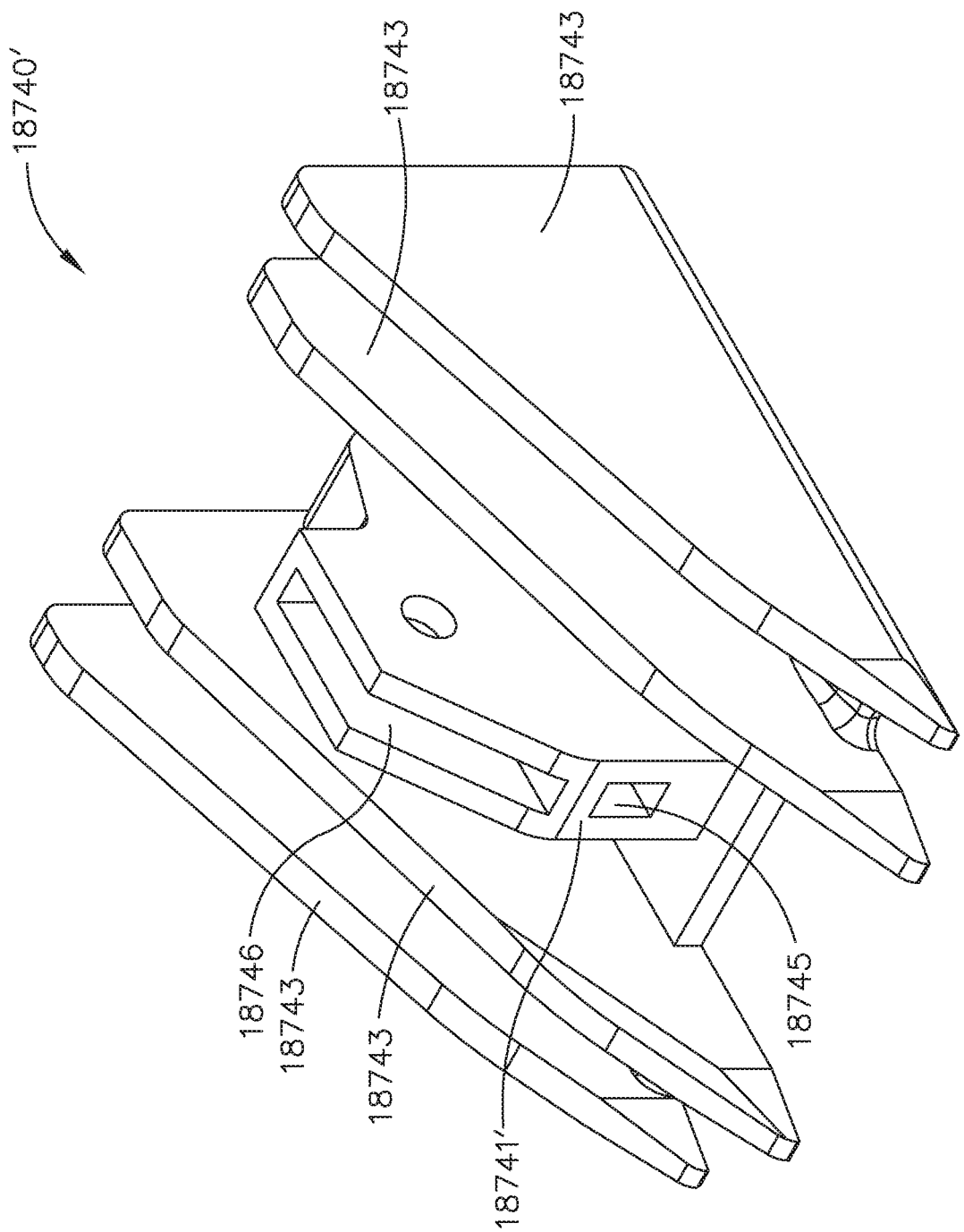
FIG. 114 is a perspective view of the camming assembly of the surgical staple cartridge of FIG. 112 with a tissue cutting member thereof omitted.
Figure 115:
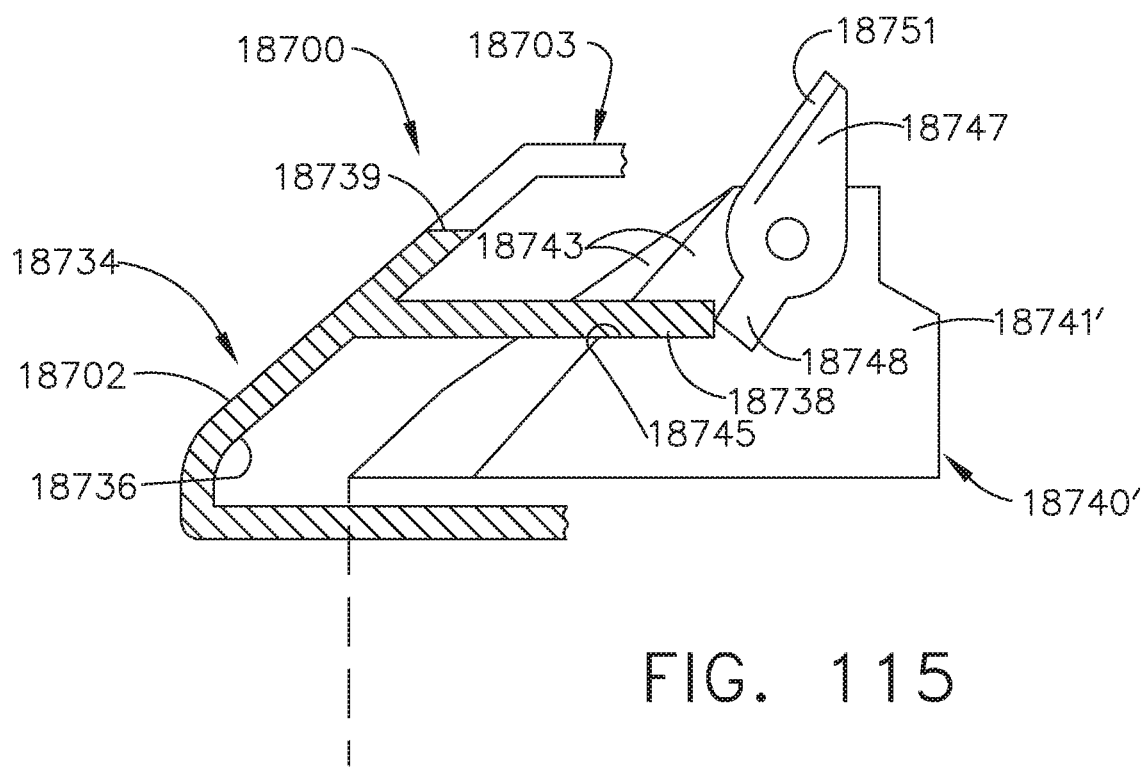
FIG. 115 is a cross-sectional view of a distal end of the surgical staple cartridge of FIG. 112, with the camming assembly thereof approaching a distalmost, ending position therein.
Figure 116:
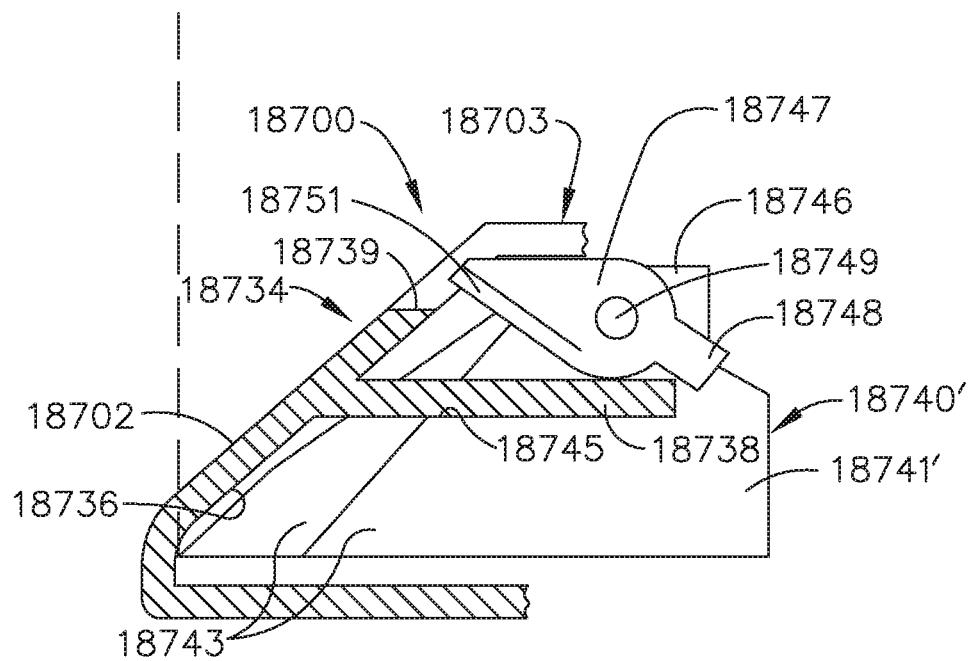
FIG. 116 is another cross-sectional view of the distal end of the surgical staple cartridge of FIG. 112, after the camming assembly has reached the ending position and the tissue cutting member thereof has been moved to a stored position.

FIG. 114 illustrates one form of the camming assembly 18740' with the tissue cutting member omitted for clarity. The camming assembly 18740' is substantially identical to the camming assembly 18740, except that the camming assembly body 18741' additional includes a retraction passage 18745 that extends into the blade mounting portion 18746. Turning to FIGS. 115 and 116, in one aspect, the tissue cutting member 18747 includes an actuation tail 18748 that, when contacted by retraction member 18738 that is formed on a distal end 18734 of the cartridge body 18702, can pivot the tissue cutting member 18747 from its deployed position (FIG. 115) to its recessed or stored position (FIG. 116). As can be seen in FIG. 115, as the camming assembly 18740' approaches the ending position, the retraction member 18738 extends through the retraction passage 18745 in the camming assembly body 18741' to contact the actuation tail 18748 on the tissue cutting member 18747. The retraction member 18738 pivots the tissue cutting member 18747 to the recessed or stored position (FIG. 116) when the camming assembly 18740' reaches the final distal-most position in distal end 18734 of the cartridge body 18702. As can be seen in FIG. 116, in one example, the cam members 18743 contact an end wall 18736 in the distal end 18734 of the cartridge body 18702. A clearance opening 18739 is provided in the distal end of the cartridge body 18702 to provide sufficient clearance for the tissue cutting member 18747 to pivot to the recessed or stored position. As can be further seen in FIG. 116, when the tissue cutting member 18747 is in the recessed or stored position, the cutting surface 18751 thereon is stored below the cartridge deck surface 18703 of the cartridge body 18702 to prevent access thereto.

Figure 117:
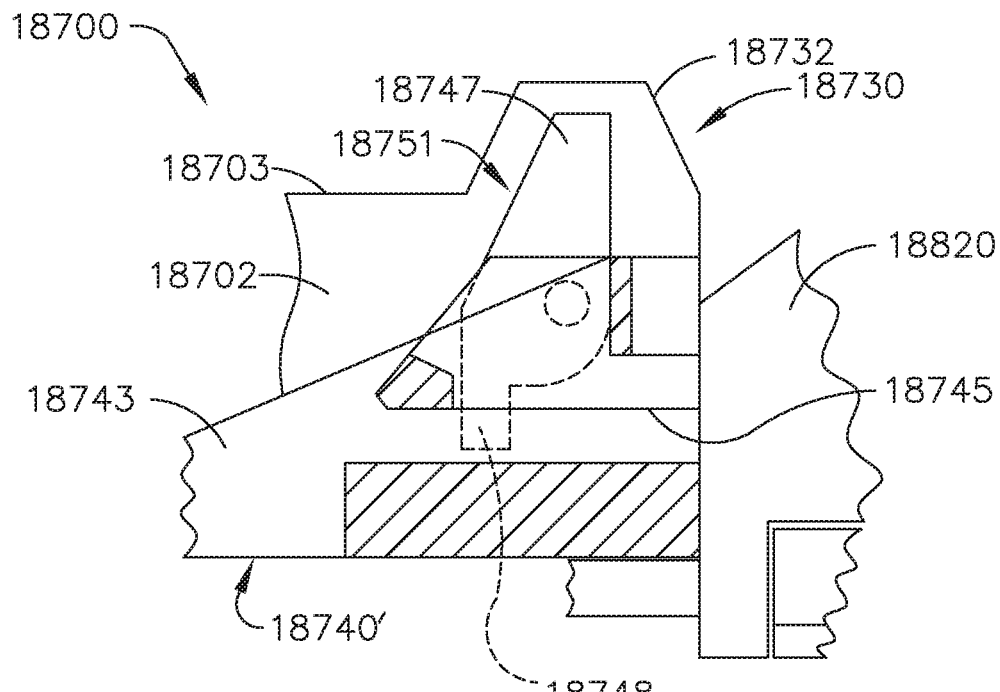
FIG. 117 is a partial cross-sectional side view of a proximal end of the surgical staple cartridge of FIG. 112 with the tissue cutting member thereof in a deployed position.
Figure 118:
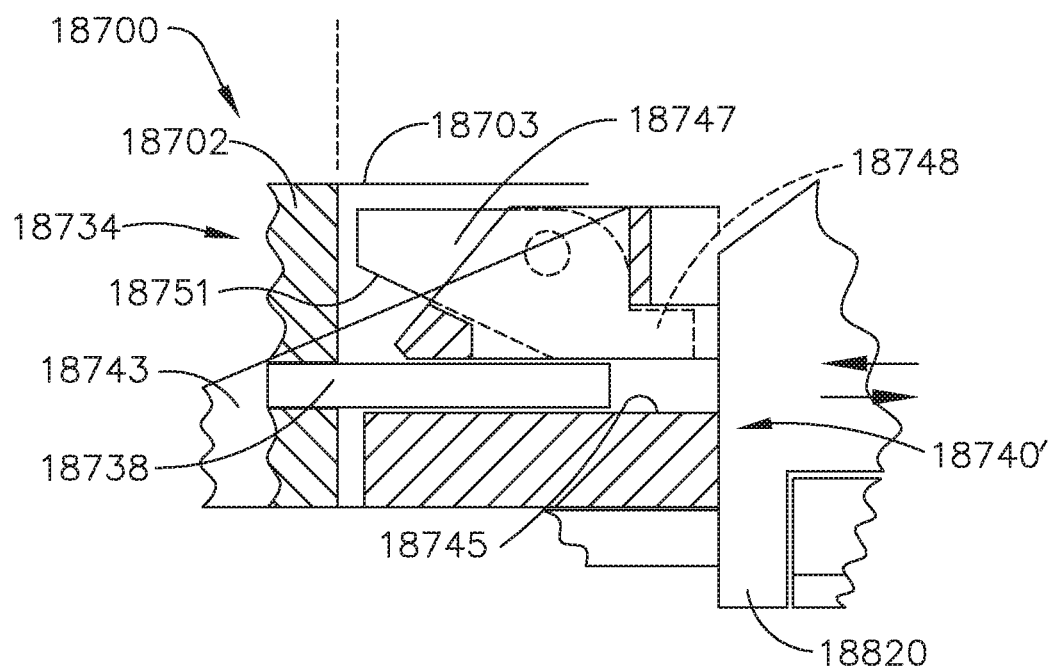
FIG. 118 is another partial cross-sectional side view of a distal end of the surgical staple cartridge of FIG. 112 with the tissue cutting member thereof in a stored position.
Figure 119:
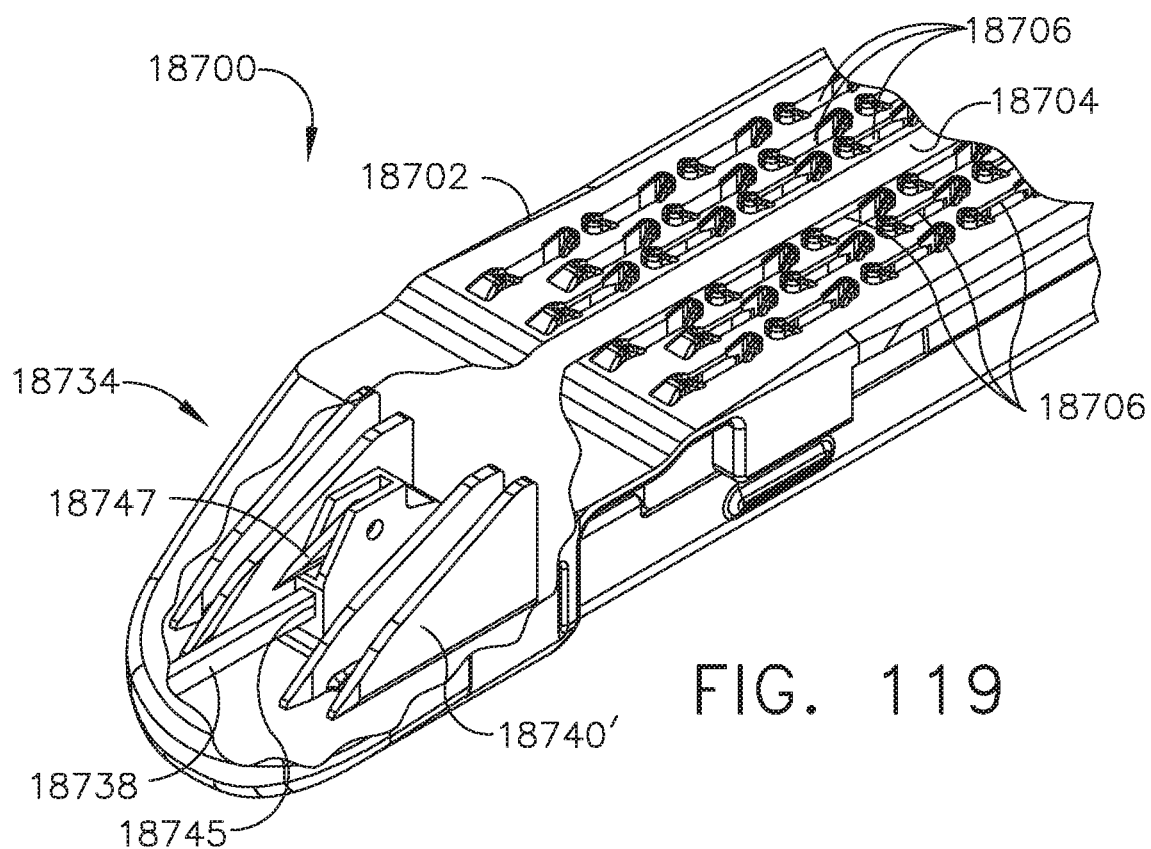
Figure 120:
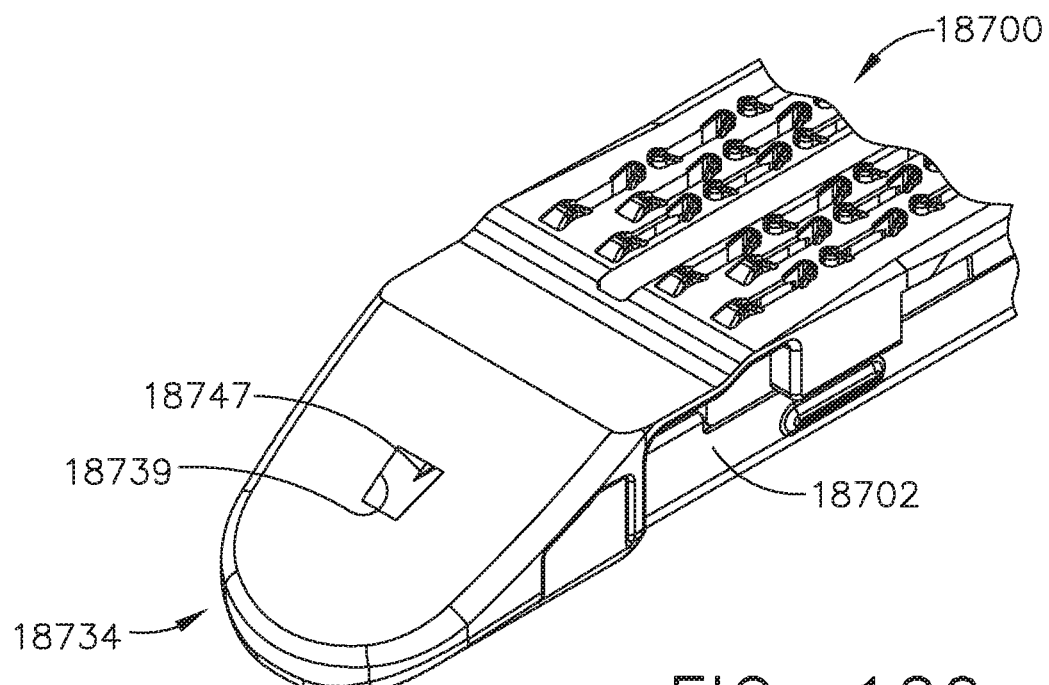

FIG. 117 illustrates the camming assembly 18740' in the starting position with the tissue cutting member 18747 in the deployed state. As can be seen in FIG. 117, the tissue cutting member 18747 is positioned within the garage portion 18732 on the proximal end 18730 of the cartridge body 18702 such that the tissue cutting surface 18751 thereon is completely received therein and not exposed to prevent the user from being injured while handling the cartridge 18700. FIG. 118 illustrates the tissue cutting member 18747 after being moved into to the recessed or stored position at the distal end of the cartridge. As can be seen in FIG. 118, the tissue cutting surface 18751 is safely located below the cartridge deck surface 18703 to prevent inadvertent injury during removal and disposal of the spent cartridge after firing. See also FIGS. 119 and 120.

Figure 121:
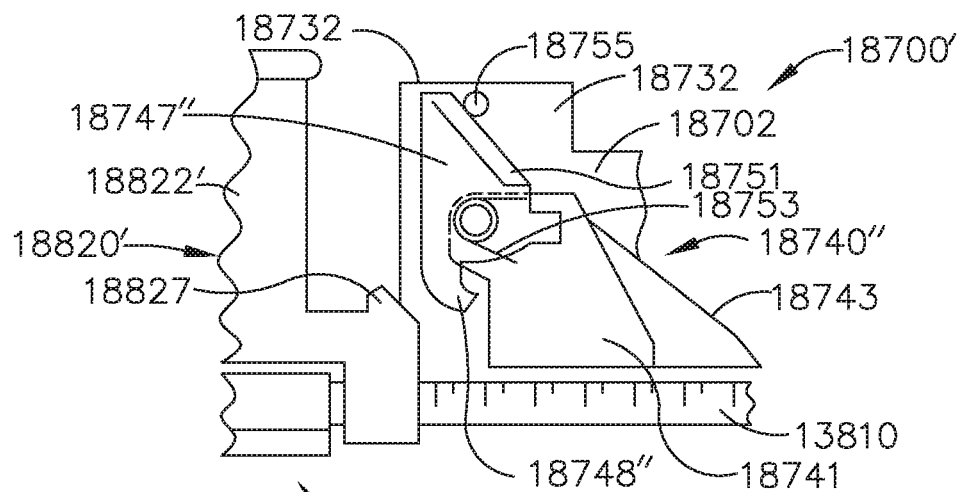
Figure 122:
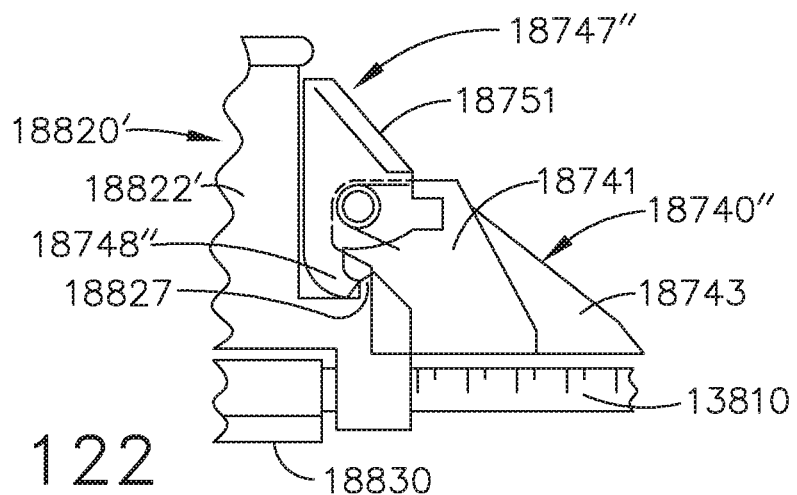
Figure 123:
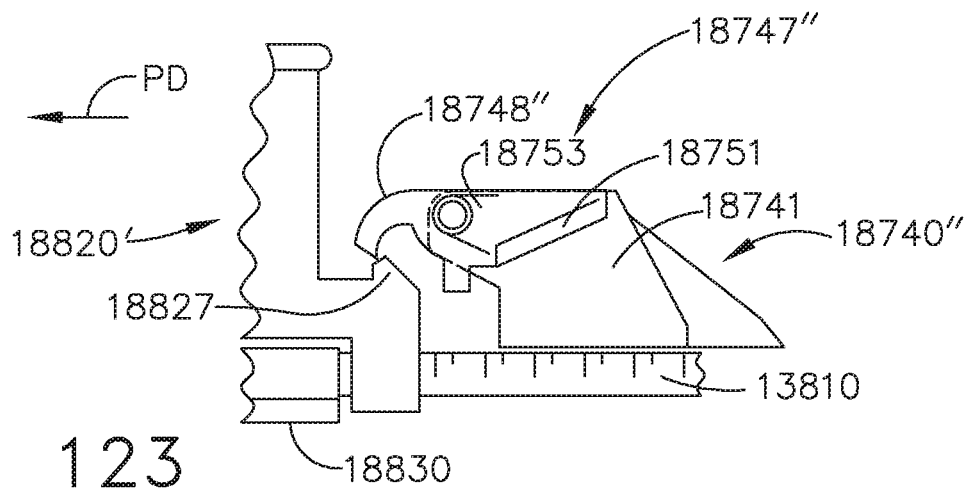

FIGS. 121-123 illustrate an alternative tissue cutting member 18747" that is configured to interact with a cutting member retainer that is provided on the firing member. FIG. 121 illustrates a firing member 18820' which is otherwise identical to firing member 18820 described above. However, firing member 18820' also includes a cutting member retainer 18827. As can be seen in FIG. 121, the camming assembly 18740" is in its starting position within the staple cartridge 18700'. The tissue cutting member 18747" is in its deployed position and is received within the garage portion 18732 of the cartridge body 18702. A torsion spring 18753 is mounted on the camming assembly body 18741 and is configured to apply a biasing motion to the tissue cutting member 18747" that would cause the tissue cutting member 18747" to pivot to the storage position. To retain the tissue cutting member 18747" in the deployed position against the biasing motion applied by the spring 18753 prior to firing, a frangible blade retainer 18755 is supported in the garage 18732 to retain the tissue cutting member 18747" in the deployed position. The blade retainer 18755 may be fabricated from a soft material such as rubber, etc., that may be severed by the tissue cutting surface 18751 on the tissue cutting member 18747" when the camming assembly 18740" is distally advanced through the cartridge 18700" during the firing process.

FIG. 121 illustrates the position of the staple cartridge 18700' and the firing member 18820' after the cartridge 18700' has been properly loaded into the end effector and prior to firing. As can be seen in FIG. 121, the firing member 18820' is in the starting position and has not been distally advanced into engagement with the camming assembly 18740". In FIG. 122, the firing member 18820' has been initially distally advanced to contact the camming assembly 18740" to a point wherein the cutting member retainer 18827 on the firing member 18820' has engaged an actuation tail 18748" on the tissue cutting member 18747" to retain the tissue cutting member 18747" in the deployed position during the firing process. Distal advancement of the firing member 18820' and the camming assembly 18740" will cause the tissue cutting member 18747" to cut through the frangible blade retainer 18755 in the cartridge body garage 18732 as the firing process proceeds. FIG. 123 illustrates the camming assembly 18740" in its ending position and after the firing member 18820' has initially began the retraction movement in a proximal direction PD. As can be seen in FIG. 122, the cutting member retainer 18827 has disengaged from the actuation tail 18748" on the tissue cutting member 18747" to permit the torsion spring 18753 to bias the tissue cutting member 18747" into the storage position. The firing member 18820' is retracted back into the starting position to enable the spent cartridge to be removed form the end effector. If, at any time during the firing process (i.e., during the distal advancement of the firing member 18820' and the camming assembly 18740") the firing process is stopped and it becomes necessary to retract the firing member 18820', proximal movement of the firing member 18820" will result in the disengagement of the actuation tail 18748" from the cutting member retainer 18827 at which point the torsion spring 18753 will bias the tissue cutting member 18747" into the storage position. Thus, the camming assembly 18470" does not have to be in the ending position to have the tissue cutting member 18747" be biased into the storage position.

Figure 124:
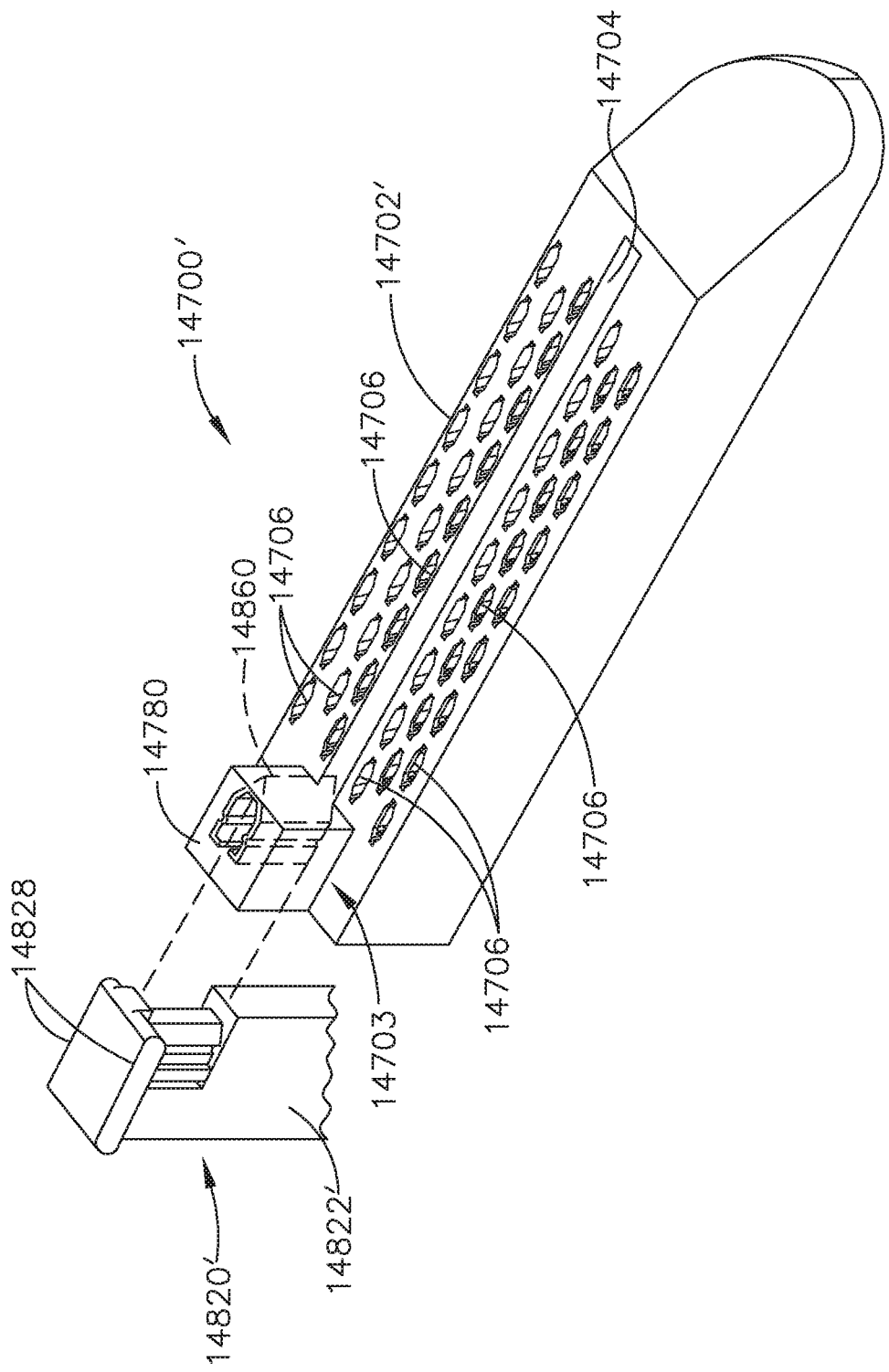

FIG. 124 illustrates one form of a replaceable staple cartridge 14700' that is substantially identical to the staple cartridge 14700 described in detail above except for the differences discussed below. The staple cartridge 14700' may be used in connection with the surgical instrument 14000 described above, for example. In one aspect, the surgical instrument 14000 includes a firing member 14820' that is very similar to firing member 14820 described above, except for the differences discussed below. The firing member 14820' comprises a body portion 14822' that includes two downwardly extending hollow mounting portions that are unthreaded and spaced from each other to receive a threaded drive nut therebetween. The threaded drive nut is configured to threadably engage the threaded segments of the rotary firing drive shaft in the manner described above. The firing member 14820' has a pair of channel engagement tabs that extend laterally from the bottom of the firing member body 14822' and a pair of anvil engaging tabs 14828 extend from the top portion of the firing member body 14822' such that the firing member 14820' resembles an I-beam configuration when viewed from an end thereof.

Still referring to FIG. 124, the surgical staple cartridge 14700' comprises an elongate cartridge body 14702' that has a centrally disposed elongate cartridge slot 14704 that is configured to accommodate the axial travel of the firing member 14820' therein. Also in the illustrated example, three lines of surgical staple pockets 14706 are formed on each side of the elongate slot 14704. Each staple pocket 14706 may have a staple driver (not shown) associated therewith that supports a surgical fastener (not shown) thereon. In one aspect, the replaceable staple cartridge 14700' includes a replaceable blade structure 14860 that may be specifically tailored to the type and composition of tissue that the cartridge 14700' is intended to cut and staple. More specifically, the cartridge body 14702' includes a blade storage garage 14780 that is formed on a proximal end 14703 of the cartridge body 14702'.

Figure 125:
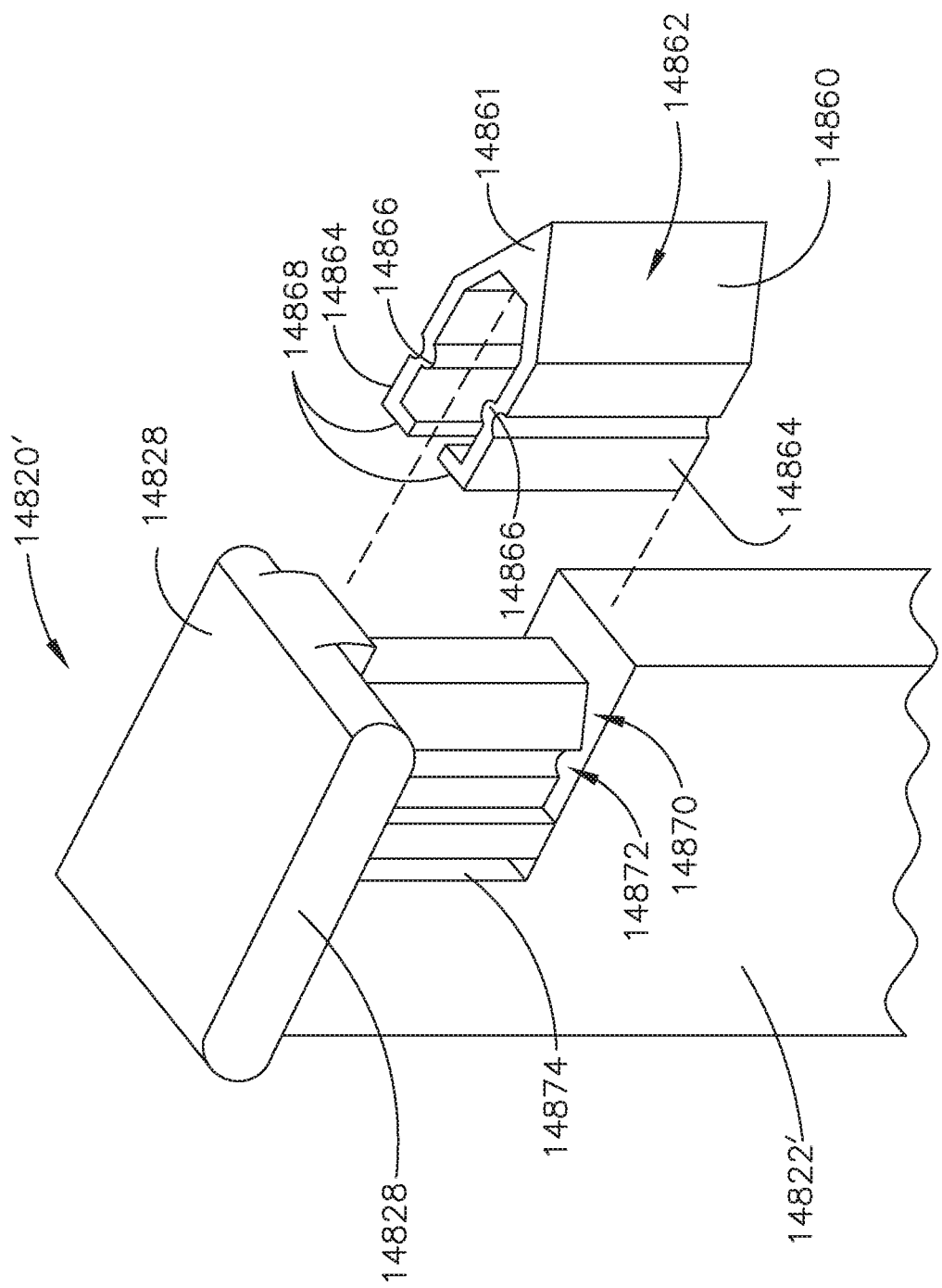
Figure 126:
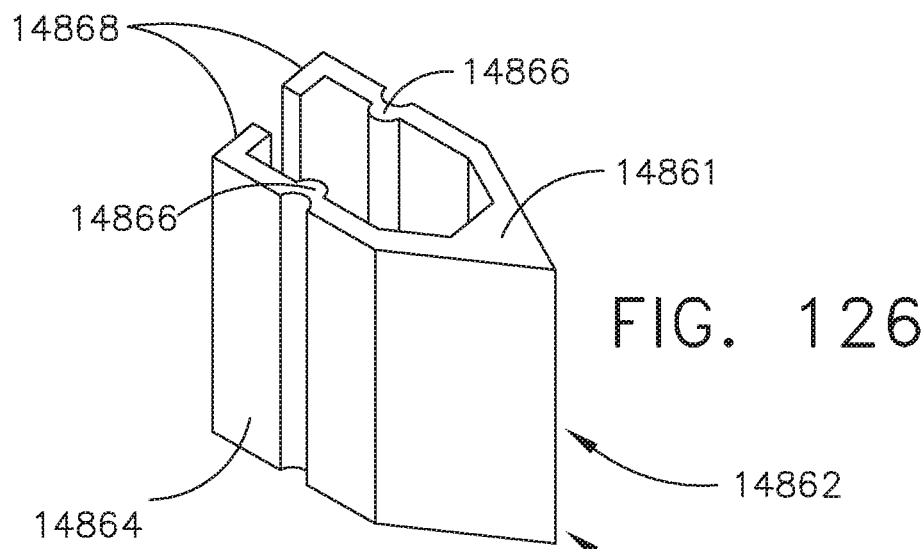

In the illustrated example, the firing member 14820' is configured to removably support a removable blade structure 14860 that is stored in the blade storage garage 14780 in the cartridge 14700'. In one aspect, the removable blade structure 14860 comprises a blade body 14861 that terminates in a tissue cutting edge 14862. See FIGS. 125 and 126. The blade body 14861 additionally comprises two flexible attachment legs 14864 that each has a locating detent 14866 and a retainer tab 14868 thereon. As can be seen in FIG. 125, the upper portion of the firing member body 14822' is formed with a blade mounting feature 14870 that is configured to snappingly receive the blade structure 14860 thereon. The blade mounting feature 14870 includes locating grooves 14872 corresponding to the locating detents 14866 on the blade body 14861 and two latch cavities 14874 that correspond to the retainer tabs 14868 on the blade body 14861.

Turning to FIG. 127, the blade structure 14860 is stored in a cavity 14782 in the blade storage garage 14780. The firing member body 14822' is sized to pass through an opening 14784 that is defined between two inwardly extending ejection tabs 14786 that are formed in a proximal end 14781 of the blade storage garage 14780. When the surgical staple cartridge 14700' is initially installed in the elongate channel of the surgical end effector, the firing member 14820' is in a starting position which is proximal to the proximal end 14781 of the blade storage garage 14780. Initial actuation of the firing member 14820' in the distal direction DD will cause the blade mounting feature 14870 to enter through the opening 14784 in the blade storage garage 14780 into engagement with the blade structure 14860 therein. See FIG. 127. Continued distal advancement of the firing member 14820' will cause the blade structure 14860 to snap into engagement with the blade mounting feature 14870 such that the blade structure 14860 travels with the firing member 14820' axially down the slot 14704 to cut tissue that is clamped between the anvil and the surgical staple cartridge 14700'. See FIG. 128. As can be seen in FIG. 128, the retainer tabs 14868 are seated in the corresponding latch cavities 14874 in the blade mounting feature 14870. The blade structure 14860 is sized relative to the axial slot 14704 in the cartridge body 14702' such that the retainer tabs 14868 are tightly retained in their respective latch cavities 14874 during firing and retraction back into the blade storage garage 14780. FIG. 129 depicts the retraction of the firing member 14820' in the proximal direction PD. As can be seen in FIG. 128, when the retainer tabs 14868 contact the rejection tabs 14786, the retainer tabs 14868 are prevented from moving proximally to enable the blade mounting feature 14870 to disengage the blade structure 14860. In one aspect, the cavity 14782 in the blade storage garage 14780 is wider than the slot 14704 in the cartridge body 14702' to thereby enable the flexible attachment legs 14864 of the blade structure 14860 to splay laterally outward and disengage the blade mounting feature 14870. Thus, the blade structure 14860 remains in the blade storage garage 14780 to be discarded with the spent staple cartridge 14700'.

Figure 130:
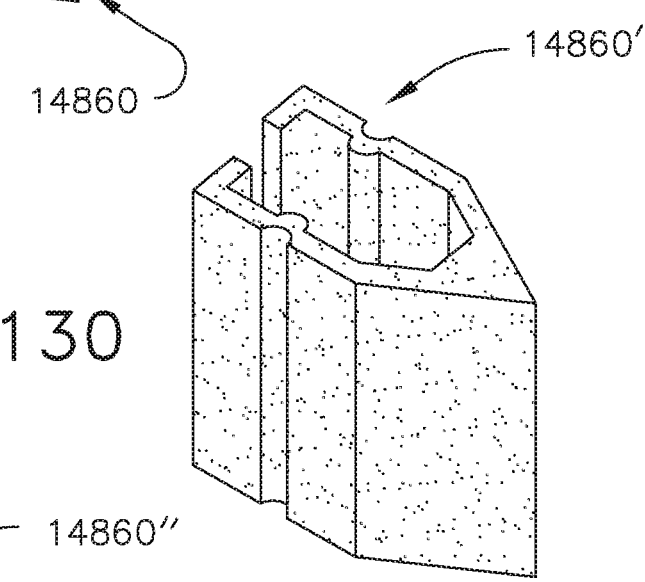

The replaceable staple cartridges 14700' may contain a particular blade structure that is specifically tailored to the type and composition of the tissue to be cut. For example, a blade structure 14860' that is fabricated from hardened metal may be used in applications wherein the blade structure may have to transect staple lines. See FIG. 130. In applications wherein the blade may have to cut through a buttress material, a blade structure 14860" that has a serrated cutting edge 14862" may be advantageously employed. See FIG. 131. Such arrangement provides the user with a fresh blade with each new staple cartridge.

FIG. 132 illustrates another form of a replaceable staple cartridge 13700' that is substantially identical to the staple cartridge 13700 described above except for the differences discussed below. The staple cartridge 13700' may be used in connection with the surgical instrument 13000 described above, for example. In one aspect, the staple cartridge 13700' includes an onboard firing member 13820' that is identical to firing member 13820 described above, except for the differences discussed below. In the manner discussed above, for example, the firing member 13820' comprises a vertically extending firing member body 13822' that is configured to be axially driven within the surgical staple cartridge 13700' by an onboard rotary firing drive shaft 13710 as described herein. The firing member 13820' has a pair of channel engagement tabs that extend laterally from the bottom of the firing member body 13822' and a pair of anvil engagement tabs 13828 extend from the top portion of the firing member body 13822 such that the firing member 13820' resembles an I-beam configuration when viewed from an end thereof.

Still referring to FIG. 132, the surgical staple cartridge 13700' comprises an elongate cartridge body 13702' that has a centrally disposed elongate cartridge slot 13704 that is configured to accommodate the axial travel of the firing member 13820' therein. Also in the illustrated example, three lines of surgical staple pockets 13706 are formed on each side of the elongate slot 13704. Each staple pocket 13706 may have a staple driver (not shown) associated therewith that supports a surgical fastener (not shown) thereon. In one aspect, the firing member 13820' is configured to removably support a removable blade structure 14860 in the manner described above. The blade structure 14860 is stored in a blade storage garage 13780 that is formed in the proximal end 13701 of the cartridge body 13702' as was discussed in detail above. In this case however, the blade structure 14860 remains on the onboard firing member 13820' and may be discarded with the cartridge and onboard firing member 13820'.

Various aspects of the subject matter described herein are set out in the following examples.

Example 1

A surgical staple cartridge configured for use with a surgical stapler including a channel and anvil movably supported relative thereto and a firing member that is configured to progressively axially engage the anvil and channel. The surgical staple cartridge comprises a cartridge body, a plurality of surgical staples removably stored in the cartridge body, a cam assembly, and a cutting member supported on the cam assembly for travel therewith. The cartridge body comprises a cartridge deck surface. The cam assembly is movably supported in the cartridge body and configured to operably interface with the firing member such that axial movement of the firing member in a distal direction drives the cam assembly from a starting position in the cartridge body to an ending position.

Example 2

The surgical staple cartridge of Example 1, wherein the cutting member is movably supported by the cam assembly and is movable between a deployed position wherein at least a portion of the cutting member extends above the cartridge deck surface of the cartridge body and a recessed position wherein the portion of the cutting member is below the cartridge deck surface.

Example 3

The surgical staple cartridge of Example 2, wherein the cutting member is retained in the deployed position when the cam assembly is in the starting position.

Example 4

The surgical staple cartridge of Examples 2 or 3, wherein the cartridge body comprises a garage portion configured to enclose the portion of the cutting member when the cam assembly is in the starting position and the cutting member is in the deployed position.

Example 5

The surgical staple cartridge of Example 4, wherein the cutting member is retained in the deployed position by a severable retainer in the garage portion.

Example 6

The surgical staple cartridge of Example 2, wherein the cutting member is retained in the deployed position by a latch feature on the firing member when the cartridge body is operably seated in the channel.

Example 7

The surgical staple cartridge of Example 6, wherein the cutting member is retained in the deployed position by the latch feature on the firing member when the firing member drives the cam assembly in the distal direction from the starting position to the ending position.

Example 8

The surgical staple cartridge of Example 2, wherein the cartridge body further comprises a release feature configured to move the cutting member to the recessed position when the cam assembly is moved to the ending position.

Example 9

The surgical staple cartridge of Examples 6 or 7, wherein the latch feature on the firing member is configured to disengage the cutting member when the firing member is retracted in a proximal direction.

Example 10

The surgical staple cartridge of Examples 6 or 7, further comprising a biaser for biasing the cutting member into the recessed position when the latch feature is disengaged from the cam assembly.

Example 11

The surgical staple cartridge of Examples 1, 2, 3, 4, 5, 6, 7, 8, 9, or 10, wherein the firing member is motor driven.

Example 12

A surgical staple cartridge configured for use with a surgical stapler including a channel and anvil movably supported relative thereto and a firing member that is configured to progressively axially engage the anvil and channel. The surgical staple cartridge comprises a cartridge body, a plurality of surgical staples removably stored in the cartridge body, a cam assembly, and a cutting member. The cartridge body comprises a cartridge deck surface. The cam assembly is movably supported in the cartridge body and configured to operably interface with the firing member such that axial movement of the firing member in a distal direction drives the cam assembly from a starting position in the cartridge body to an ending position. The cutting member is configured for removable attachment to the firing member when the firing member is driven distally into contact therewith. The cutting member is stored in a ready position in a proximal portion of the cartridge body.

Example 13

The surgical staple cartridge of Example 12, wherein the cutting member is configured to be clipped onto the firing member when the firing member is driven distally into contact therewith.

Example 14

The surgical staple cartridge of Examples 12 or 13, wherein the cutting member comprises a body member that defines a knife blade and a pair of spaced spring arms that define a retention space therebetween that is configured to retainingly receive a portion of the firing member therebetween.

Example 15

The surgical staple cartridge of Examples 12, 13, or 14, wherein the cutting member is removably attached to the firing member as the firing member is driven distally from an initial position and wherein, when the firing member is retracted back to the initial position, the cutting member is removed therefrom to be retained within a blade storage garage on the proximal portion of the cartridge body.

Example 16

The surgical staple cartridge of Examples 12, 13, or 14, wherein the cutting member is retained within a blade storage garage on a proximal end of the cartridge body prior to attachment to the firing member.

Example 17

The surgical staple cartridge of Examples 12, 13, 14, 15, or 16, wherein the firing member is threaded onto a rotary drive shaft, and wherein the cam assembly is slidably journaled on the rotary drive shaft.

Example 18

A surgical instrument comprising a cartridge support, an anvil, an I-beam firing member, and a surgical staple cartridge. One of the anvil and the cartridge support is movable relative to the other of the anvil and the cartridge support between open and closed positions. The I-beam firing member is configured to progressively axially engage the anvil and the cartridge support. The surgical staple cartridge comprises a cartridge body, a plurality of surgical staples removably stored in the cartridge body, a cam assembly, and a cutting member. The cartridge body is configured to be removably supported in the cartridge support and comprises a cartridge deck surface. The cam assembly is movably supported in the cartridge body and configured to operably interface with the I-beam firing member such that axial movement of the I-beam firing member in a distal direction drives the cam assembly from a starting position in the cartridge body to an ending position. The cutting member is movably supported by the cam assembly between a deployed position wherein at least a portion of the cutting member extends above the cartridge deck surface of the cartridge body and a recessed position wherein the portion of the cutting member is below the cartridge deck surface.

Example 19

The surgical instrument of Example 18, further comprising an elongate shaft assembly operably coupled to the cartridge support, a housing operably attached to the elongate shaft assembly, and a motor operably supported by the housing and interfacing with the I-beam firing member to axially drive the I-beam firing member.

Example 20

The surgical instrument of Examples 18 or 19, wherein the cutting member is retained in the deployed position by a latch feature on the I-beam firing member when the cartridge body is operably seated in the cartridge support.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical staple cartridge configured for use with a surgical stapler including a channel and an anvil movably supported relative thereto and a firing member that is configured to progressively axially engage the anvil and the channel, wherein said surgical staple cartridge comprises:
   a cartridge body comprising a cartridge deck surface;
   a plurality of surgical staples removably stored in said cartridge body;
   a cam assembly movably supported in said cartridge body and configured to operably interface with the firing member such that axial movement of the firing member in a distal direction drives said cam assembly from a starting position in said cartridge body to an ending position; and
   a cutting member movably supported by said cam assembly, wherein said cutting member is movable between a deployed position wherein at least a portion of said cutting member extends above said cartridge deck surface of said cartridge body and a recessed position wherein said at least a portion of said cutting member is below said cartridge deck surface, wherein said cutting member is retained in said deployed position when said cam assembly is in said starting position, wherein said cartridge body further comprises a garage portion configured to enclose said at least a portion of said cutting member when said cam assembly is in said starting position and said cutting member is in said deployed position, and wherein said cutting member is retained in said deployed position by a severable retainer in said garage portion.

2. The surgical staple cartridge of claim 1, wherein said cartridge body further comprises a release feature configured to move said cutting member to said recessed position when said cam assembly is moved to said ending position.

3. The surgical staple cartridge of claim 1, wherein the firing member is motor driven.

4. A surgical staple cartridge configured for use with a surgical stapler including a channel and an anvil movably supported relative thereto and a firing member that is configured to progressively axially engage the anvil and the channel, wherein said surgical staple cartridge comprises:
   a cartridge body comprising a cartridge deck surface;
   a plurality of surgical staples removably stored in said cartridge body;
   a cam assembly movably supported in said cartridge body and configured to operably interface with the firing member such that axial movement of the firing member in a distal direction drives said cam assembly from a starting position in said cartridge body to an ending position; and
   a cutting member movably supported by said cam assembly, wherein said cutting member is movable between a deployed position wherein at least a portion of said cutting member extends above said cartridge deck surface of said cartridge body and a recessed position wherein said at least a portion of said cutting member is below said cartridge deck surface, and wherein said cutting member is retained in said deployed position by a latch feature on the firing member when said cartridge body is operably seated in the channel.

5. The surgical staple cartridge of claim 4, wherein said cutting member is retained in said deployed position by said latch feature on the firing member when the firing member drives said cam assembly in said distal direction from said starting position to said ending position.

6. The surgical staple cartridge of claim 5, wherein said latch feature on the firing member is configured to disengage said cutting member when the firing member is retracted in a proximal direction.

7. The surgical staple cartridge of claim 4, further comprising a biaser for biasing said cutting member into said recessed position when said latch feature is disengaged from said cam assembly.

8. The surgical staple cartridge of claim 4, wherein said cartridge body further comprises a release feature configured to move said cutting member to said recessed position when said cam assembly is moved to said ending position.

9. The surgical staple cartridge of claim 4, wherein the firing member is motor driven.

10. A surgical staple cartridge configured for use with a surgical stapler including a channel and an anvil movably supported relative thereto and a firing member that is configured to progressively axially engage the anvil and the channel, said surgical staple cartridge, comprising:
   a cartridge body comprising a cartridge deck surface;
   a plurality of surgical staples removably stored in said cartridge body;
   a cam assembly movably supported in said cartridge body and configured to operably interface with the firing member such that axial movement of the firing member in a distal direction drives said cam assembly from a starting position in said cartridge body to an ending position; and
   a cutting member stored in a ready position in a proximal portion of said cartridge body, wherein said cutting member comprises a body member that defines a knife blade and a pair of spaced spring arms that define a retention space therebetween that is configured to retainingly receive a portion of the firing member therebetween to removably attach said cutting member to the firing member when the firing member is driven distally into contact with said cutting member, when said cutting member is in said ready position.

11. The surgical staple cartridge of claim 10, wherein said cutting member is removably attached to the firing member as the firing member is driven distally from an initial position, and wherein, when the firing member is retracted back to the initial position, the cutting member is removed therefrom to be retained within a blade storage garage on said proximal portion of said cartridge body.

12. The surgical staple cartridge of claim 10, wherein said cartridge body further comprises a release feature configured to move said cutting member to a recessed position when said cam assembly is moved to said ending position.

13. The surgical staple cartridge of claim 10, wherein the firing member is motor driven.

14. A surgical staple cartridge configured for use with a surgical stapler including a channel and an anvil movably supported relative thereto and a firing member that is configured to progressively axially engage the anvil and the channel, said surgical staple cartridge, comprising:
  a cartridge body comprising a cartridge deck surface;
  a plurality of surgical staples removably stored in said cartridge body;
  a cam assembly movably supported in said cartridge body and configured to operably interface with the firing member such that axial movement of the firing member in a distal direction drives said cam assembly from a starting position in said cartridge body to an ending position; and
  a cutting member configured for removable attachment to the firing member when the firing member is driven distally into contact therewith, wherein said cutting member is retained within a blade storage garage on a proximal end of said cartridge body prior to attachment to the firing member.

15. The surgical staple cartridge of claim 14, wherein the firing member is threaded onto a rotary drive shaft, and wherein said cam assembly is slidably journaled on the rotary drive shaft.

16. The surgical staple cartridge of claim 14, wherein said cartridge body further comprises a release feature configured to move said cutting member to a recessed position when said cam assembly is moved to said ending position.

17. The surgical staple cartridge of claim 14, wherein the firing member is motor driven.

18. A surgical instrument, comprising:
  a cartridge support;
  an anvil wherein one of said anvil and said cartridge support is movable relative to the other of said anvil and said cartridge support between open and closed positions;
  an I-beam firing member configured to progressively axially engage said anvil and said cartridge support; and
  a surgical staple cartridge, comprising
    a cartridge body configured to be removably supported in said cartridge support and comprising a cartridge deck surface;
    a plurality of surgical staples removably stored in said cartridge body;
    a cam assembly movably supported in said cartridge body and configured to
  operably interface with said I-beam firing member such that axial movement of said I-beam firing member in a distal direction drives said cam assembly from a starting position in said cartridge body to an ending position; and
    a cutting member movably supported by said cam assembly between a
  deployed position wherein at least a portion of said cutting member extends above said cartridge deck surface of said cartridge body and a recessed position wherein said at least a portion of said cutting member is below said cartridge deck surface, and wherein said cutting member is retained in said deployed position by a latch feature on said I-beam firing member when said cartridge body is operably seated in said cartridge support.

19. The surgical instrument of claim 18, further comprising:
  an elongate shaft assembly operably coupled to said cartridge support;
  a housing operably attached to said elongate shaft assembly; and
  a motor operably supported by said housing and interfacing with said I-beam firing member to axially drive said I-beam firing member.

20. The surgical instrument of claim 18, wherein said cartridge body further comprises a release feature configured to move said cutting member to said recessed position when said cam assembly is moved to said ending position.

21. The surgical instrument of claim 18, wherein said I-beam firing member is motor driven.

* * * * *